United States Patent
Bayburt et al.

(10) Patent No.: US 8,772,499 B2
(45) Date of Patent: Jul. 8, 2014

(54) TRPV3 MODULATORS

(71) Applicant: AbbVie Inc., North Chicago, IL (US)

(72) Inventors: Erol K. Bayburt, Gurnee, IL (US); Bruce Clapham, Lindenhurst, IL (US); Phil B. Cox, Grayslake, IL (US); Jerome F. Daanen, Racine, WI (US); Michael J. Dart, Highland Park, IL (US); Gregory A. Gfesser, Lindenhurst, IL (US); Arthur Gomtsyan, Vernon Hills, IL (US); Michael E. Kort, Lake Bluff, IL (US); Philip R. Kym, Libertyville, IL (US); Robert G. Schmidt, Antioch, IL (US); Eric A. Voight, Pleasant Prairie, WI (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/658,355

(22) Filed: Oct. 23, 2012

(65) Prior Publication Data

US 2014/0080803 A1 Mar. 20, 2014

(30) Foreign Application Priority Data

Oct. 24, 2011 (WO) ................. PCT/CN2011/001761

(51) Int. Cl.
*C07D 213/00* (2006.01)
*C07D 213/28* (2006.01)
*C07D 211/74* (2006.01)
*C07D 421/00* (2006.01)
*C07D 401/00* (2006.01)

(52) U.S. Cl.
USPC ............... 546/344; 546/278.1; 546/268.1; 514/277; 514/252.03

(58) Field of Classification Search
USPC ....................... 546/278.1; 514/266
See application file for complete search history.

(56) References Cited

U.S. PATENT DOCUMENTS

| | | | |
|---|---|---|---|
| 5,112,828 | A | 5/1992 | Zipperer et al. |
| 6,114,532 | A | 9/2000 | Ries et al. |
| 7,396,910 | B2 | 7/2008 | Bevan et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0093516 | A1 | 4/2009 | Li et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2012/0010190 | A1 | 1/2012 | Bissantz et al. |

FOREIGN PATENT DOCUMENTS

| | | |
|---|---|---|
| CN | 101883772 A | 11/2010 |
| EP | 0400344 A1 | 12/1990 |
| IN | 200900517 A2 | 11/2010 |
| WO | 9429281 A1 | 12/1994 |
| WO | 9504042 A1 | 2/1995 |
| WO | 9507271 A1 | 3/1995 |
| WO | 9710223 A1 | 3/1997 |
| WO | 9940072 A1 | 8/1999 |
| WO | 0222572 A2 | 3/2002 |
| WO | 03086294 A2 | 10/2003 |
| WO | 03086294 A3 | 10/2003 |
| WO | 2004043958 A1 | 5/2004 |
| WO | 2005099353 A2 | 10/2005 |
| WO | 2006008754 A1 | 1/2006 |
| WO | 2006122156 A2 | 11/2006 |
| WO | 2006122156 A3 | 11/2006 |
| WO | 2007056124 A2 | 5/2007 |
| WO | 2010004379 A2 | 1/2010 |
| WO | 2010070452 A1 | 6/2010 |
| WO | 2012019315 A1 | 2/2012 |

(Continued)

OTHER PUBLICATIONS

Drug labelling information for Tylenol® with codeine, dated Aug. 2010, taken from PDR® 3D™ (Digital Drug Database) available at www.pdrnetwork.com.*
Ong, Helen Journal of heterocyclic chemistry, 1981 (18) 815-820.*
Lee-Ruff; Chem. Rev. 2003, 103, 1449-1483.*
Dorwald; "Side Reactions in Organic Synthesis: A Guide to Successful Synthesis Design" 2005 Wiley-VCH Verlag GmbH & Co. KGaA, Wienheim.*
Wermuth; Practice of Medicinal Chemistry, 2008, 3rd Edition, Elsevier.*
Alexander et al., "The Photochemical Synthesis of a Tricyclo[2.2.0. 02,5]hexane," J. American Chem. Soc., 1976, 98(14): 4324-4325.
Aley et al., "Nitric oxide signaling in pain and nociceptor sensitization in the rat," J Neurosci., 1998, 18(17): 7008-7014.
Berge et al., "Pharmaceutical salts," J. Pharm Sci., 1977, 66(1): 1-19.
Beylot et al., "In vivo studies of intrahepatic metabolic pathways," Diabetes Metab., 1997, 23(3): 251-257.

(Continued)

*Primary Examiner* — John Mabry
*Assistant Examiner* — Daniel Carcanague

(57) ABSTRACT

Disclosed herein are modulators of TRPV3 of Formula (I)

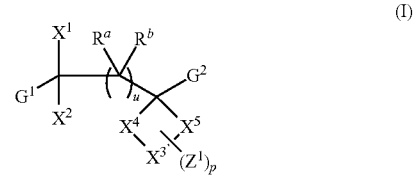

wherein p is 1, 2, 3, or 4, and $G^1$, $X^1$, $X^2$, $X^3$, $X^4$, $X^5$, $G^2$, $Z^1$, $R^a$, $R^b$, and u are as defined in the specification. Compositions comprising such compounds and methods for treating conditions and disorders using such compounds and compositions are also presented.

45 Claims, No Drawings

(56) References Cited

FOREIGN PATENT DOCUMENTS

| WO | WO2012/019315 | * | 2/2012 |
| WO | WO2012019315 | * | 2/2012 |
| WO | 2013062966 A2 | | 5/2012 |

OTHER PUBLICATIONS

Blagojevic et al., "Role of Heavy Water in Boron Neutron Capture Therapy," Topics in Dosimetry & Treatment Planning for Neutron Capture Therapy, R. Zamenhoff, G. Solares, O. Harling, Editors, 1994, Advanced Medical Publishing, Madison Wisconsin pp. 125-134.
Blake et al., "Studies with deuterated drugs," J Pharm Sci., 1975, 64(3): 367-391.
Brickner et al., "Synthesis and antibacterial activity of U-100592 and U-100766, two oxazolidinone antibacterial agents for the potential treatment of multidrug-resistant gram-positive bacterial infections," J Med Chem., 1996, 39(3): 673-679.
Caterina, MJ, "Transient receptor potential ion channels as participants in thermosensation and thermoregulation," Am J Physiol Regul Integr Comp Physiol., 2007, 292(1): R64-R76.
Caterina et al., "A capsaicin-receptor homologue with a high threshold for noxious heat," Nature, 1999, 398(6726): 436-441.
Chung et al., "2-aminoethoxydiphenyl borate activates and sensitizes the heat-gated ion channel TRPV3," J Neurosci. 2004, 24(22):5177-5182.
Chung et al., "Biphasic currents evoked by chemical or thermal activation of the heat-gated ion channel, TRPV3," J Biol Chem., 2005, 280(16): 15928-15941.
Chung et al., "Warm temperatures activate TRPV4 in mouse 308 keratinocytes," J Biol Chem., 2003, 278(34): 32037-32046.
Chung et al., "TRPV3 and TRPV4 mediate warmth-evoked currents in primary mouse keratinocytes," J Biol Chem., 2004, 279(20): 21569-21575.
Coppi et al., "2-Lithiated-2-phenyloxetane: a new attractive synthon for the preparation of oxetane derivatives," Chem. Commun (Camb)., 2011, 47(35): 9918-9920.
Czajka et al., "Effect of deuterium oxide on the reproductive potential of mice," Ann N Y Acad Sci., 1960, 84: 770-779.
Czajka et al., "Physiological effects of deuterium on dogs," Am J Physiol. 1961, 201(2): 357-362.
Dörwald, FZ, "1.3 Hard and Soft Acids and Bases," Side Reactions in Organic Synthesis, 2005, Wiley-VCH, Weinheim, title page, preface (p. IX), and p. 175.
Drug labeling information for Tylenol® with codeine, Revised Aug. 2010, take from PDR® 3D™ (Digital Drug Database) available at www.pdrnetwork.com, printed Mar. 22, 2013 (9 pages).
Facer et al., "Differential expression of the capsaicin receptor TRPV1 and related novel receptors TRPV3, TRPV4 and TRPM8 in normal human tissues and changes in traumatic and diabetic neuropathy," BMC Neurol., 2007, 7: 11-22.
Foster et al., "Deuterium Isotope Effects in the Metabolism of Drugs and Xenobiotics: Implications for Drug Design," Advances in Drug Research, 1985, vol. 14 Academic press, London, pp. 2-36.
Green et al. Editors, Protecting Groups in Organic Synthesis, 3rd Ed., John Wiley & Sons, NY, 1999, 20 pages.
Güler et al., "Heat-evoked activation of the ion channel, TRPV4," J Neurosci., 2002, 22(15): 6408-6414.
Hailes et al., "2.05—Oxetanes and Oxetenes: Monocyclic" Comprehensive Heterocyclic Chemistry III, Elsevier, Oxford, 2008, pp. 321-364.
Harper et al., "1-3,4-Dichlorobenzamidomethyl) cyclohexyldimethylamine and Related Compounds as Potential Analgesics," Journal of Medicinal Chemistry, 1974, 17(11): 1188-1193.
Hattersley et al., "Some Reactions with 4-Cyano-4-phenyltetrahydropyran" Journal of Medicinal Chemistry, 1967, 10(1): 128-129.
Hu et al., "2-aminoethoxydiphenyl borate is a common activator of TRPV1, TRPV2, and TRPV3," J Biol Chem., 2004, 279(34): 35741-35748.
Hu et al., "Potentiation of TRPV3 channel function by unsaturated fatty acids," J Cell Physiol. 2006, 208(1): 201-212.
International Search Report and Written Opinion for PCT/CN2010/001213, mailed May 19, 2011 (11 pages).
International Search Report and Written Opinion for PCT/CN2011/001761, mailed Aug. 2, 2012 (17 pages).
International Search Report for PCT/US2012/061476, mailed Jun. 17, 2013 (6 pages).
International Search Report for PCT/US2012/061478, mailed Jun. 17, 2013 (7 pages).
IUPAC 1974 Recommendations for Section E, Fundamental Stereochemistry, Pure Appl. Chem., 1976, 45: 13-30.
Kato et al., "Synthesis of Deuterated Mosapride Citrate," J Labelled Compd Rad., 1995, 36(10): 927-932.
Kushner et al., "Pharmacological uses and perspectives of heavy water and deuterated compounds," Can J Physiol Pharmacol., 1999, 77(2): 79-88.
Lee et al., "TRPV channels as thermosensory receptors in epithelial cells," Pflugers Arch.—Eur J Physiol. 2005, 451(1): 160-167.
Lee-Ruff et al., "Enantiomerically pure cyclobutane derivatives and their use in organic synthesis," Chem Rev., 2003, 103(4): 1449-1483.
Lizondo et al., "Linezolid. Oxazolidinone Antibacterial," Drugs Fut., 1996, 21(11): 1116-1123.
MacPherson et al., "More than cool: promiscuous relationships of menthol and other sensory compounds" Mol Cell Neurosci. 2006, 32(4): 335-343.
Mallesham et al., "Highly efficient CuI-catalyzed coupling of aryl bromides with oxazolidinones using Buchwald's protocol: a short route to linezolid and toloxatone," Org Lett., 2003, 5(7): 963-965.
Montell, C. "Preventing a Perm with TRPV3," Cell, 2010, 141(2): 218-220.
Moqrich et al., "Impaired thermosensation in mice lacking TRPV3, a heat and camphor sensor in the skin," Science, 2005, 307(5714): 1468-1472.
Moussaieff et al., "Incensole acetate, an incense component, elicits psychoactivity by activating TRPV3 channels in the brain," FASEB J., 2008, 22(8): 3024-3034.
Nilius et al., "Transient receptor potential cation channels in disease," Physiol Rev., 2007, 87(1): 165-217.
Okuhara et al., "Transient receptor potential channels as drug targets," Expert Opin Ther Targets, 2007, 11(3): 391-401.
Ong et al., "Novel Tetracyclic Spiropiperidines. II. Synthesis of 2-Aryl-2,3-dihydrospiro[benzofuran-3,4'-piperidines] (1,2)," Journal of Heterocyclic Chemistry, 1981, 18(4): 815-820.
Peier et al., "A heat-sensitive TRP channel expressed in keratinocytes," Science, 2002, 296(5575): 2046-2049.
Prescott, D.M., Editor, "Methods in Cell Biology," vol. XIV, Academic Press, New York, N.Y. 1976, 12 pages.
Smith et al., "TRPV3 is a temperature-sensitive vanilloid receptor-like protein," Nature 2002, 418(6894): 186-190.
Steinhoff et al., "A TR(I)P to pruritus research: role of TRPV3 in inflammation and itch," J. Invest. Dermatology, 2009, 129(3): 531-535.
Thomson JF, "Physiological effects of D20 in mammals," Ann NY Acad Sci., 1960, 84: 736-744.
Vogt-Eisele et al., "Monoterpenoid agonists of TRPV3," Br J Pharmacol. 2007, 151(4): 530-540.
Wermuth Editor, The Practice of Medicinal Chemistry, 3$^{rd}$ Edition, Elsevier, 2008, pp. 126, 276, 294, 328, 343, 350, 431, 432, 440, 452, 533, 535, 536, 724 and 725.
Wissenbach et al., "TRP channels as potential drug targets," Biology of the Cell., (2004), 96(1): 47-54.
Xu et al., "Camphor activates and strongly desensitizes the transient receptor potential vanilloid subtype 1 channel in a vanilloid-independent mechanism," J Neurosci. 2005, 25(39): 8924-8937.
Xu et al., "Oregano, thyme and clove-derived flavors and skin sensitizers activate specific TRP channels," Nat Neurosci. 2006, 9(5): 628-635.
Xu et al., "TRPV3 is a calcium-permeable temperature-sensitive cation channel," Nature, 2002, 418(6894): 181-186.
Yoshida et al., Editors, "Nitric oxide activates TRP channels by cysteine S-nitrosylation," Nat Chem Biol., 2006, 2(11): 596-607.

(56) References Cited

OTHER PUBLICATIONS

Zhang et al., "Cyclization reactions of 3,3-dimethyl-1-(1H-1,2,4-triazolo-1-yl)-2-butanone or substituted 1-(1H-1,2,4-triazolo-1-yl)acetophenone with dibromide compounds and its biological activities," Gaodeng Xuexiao Huaxue Xuebao, 24(3): 431-435 (retrieved from STN Database accession No. 2003:247751 abstract).
U.S. Appl. No. 13/761,862, filed Feb. 7, 2013, File History.
U.S. Appl. No. 13/658,374, filed Oct. 23, 2012, File History.
Hardouin et al, "BF3•OEt2-Mediated Rearrangement of Cyclopropyl Carbinols: A Concise Route to Polycyclic Cyclobutanes," J. Org. Chem., 66(12): 4450-4452 (2001).
Kanemoto et al., "Novel Synthesis of Monofluorocyclobutanes by the Ring Expansion Fluorination of Cyclopropylmethanols With an Amine-Metal, Fluoride-Pyridinium Poly(Hydrogen Fluoride)-Complex," Tetrahedron Letters, 28(5): 6313-6316 (1987).
McCarty et al., "Central Stimulants. $\alpha$, $\alpha$-Disubstituted 2-Piperidinemethanols and 1,1-Disubstitued Heptahydrooxazolo [3,4-a]pyridines," J. Am. Chem. Soc., 179(2): 472-480 (1957).
Yus et al., "Intramolecular carbolithiation promoted by a DTBB-catalysed chlorine-lithium exchange," Tetrahedron, 59(43):8525-8542 (2003).
Extended European Search Report for Application No. 10855736.4 dated Dec. 4, 2013.

* cited by examiner

TRPV3 MODULATORS

CROSS-REFERENCE TO RELATED PATENT APPLICATIONS

This patent application claims the benefit of International Patent Application No. PCT/CN2011/001761 (filed Oct. 24, 2011). The entire text of that International Patent Application is incorporated by reference into this application.

TECHNICAL FIELD

Compounds that are Transient Receptor Potential Vanilloid 3 (TRPV3) modulators, compositions comprising such compounds, and methods for treating conditions and disorders using such compounds and compositions, are disclosed herein.

BACKGROUND OF THE INVENTION

A subset of the vanilloid channels (TRPV1-4) are referred to as thermoTRPs to reflect the observation that heat elicits channel opening across a continuum of temperatures with thresholds ranging from 25° C. to 52° C. (Caterina, M. J.; Rosen, T. A.; Tominaga, M.; Brake, A. J.; Julius, D., *Nature* 1999, 398, 436-441). TRPV3 characteristically responds to innocuous heat >31° C., exhibits exquisite sensitivity around the physiological temperature of humans, 37° C., and sensitizes dramatically following repetitive heating (Smith, G. D.; Gunthorpe, M. J.; Kelsell, R. E.; Hayes, P. D.; Reilly, P.; Facer, P.; Wright, J. E.; Jerman, J. C.; Walhin, J. P.; Ooi, L.; Egerton, J.; Charles, K. J.; Smart, D.; Randall, A. D.; Anand, P.; Davis, J. B., *Nature* 2002, 418, 186-190; Xu, H.; Ramsey, I. S.; Kotecha, S. A.; Moran, M. M.; Chong, J. A.; Lawson, D.; Ge, P.; Lilly, J.; Silos-Santiago, I.; Xie, Y.; DiStefano, P. S.; Curtis, R.; Clapham, D. E., *Nature* 2002, 418, 181-186; Peier, A. M.; Reeve, A. J.; Andersson, D. A.; Moqrich, A.; Earley, T. J.; Hergarden, A. C.; Story, G. M.; Colley, S.; Hogenesch, J. B.; McIntyre, P.; Bevan, S.; Patapoutian, A., *Science* 2002, 296, 2046-2049).

TRPV3 is a nonselective cation channel with permeability for calcium, but also to other cations, for example sodium. Multiple compounds that have been shown to activate TRPV3, include: monoterpenes, camphor (Peier, A. M. et al., 2002; Moqrich, A.; Hwang, S. W.; Earley, T. J.; Petrus, M. J.; Murray, A. N.; Spencer, K. S.; Andahazy, M.; Story, G. M.; Patapoutian, A., *Science* 2005, 307, 1468-1472; Xu, H.; Blair, N. T.; Clapham, D. E., *J Neurosci.* 2005, 25, 8924-8937), carvacrol, and thymol (Xu, H.; Delling, M.; Jun, J. C.; Clapham, D. E. *Nat. Neurosci.* 2006, 9, 628-635; Vogt-Eisele, A. K.; Weber, K.; Sherkheli, M. A.; Vielhaber, G.; Panten, J.; Gisselmann, G.; Hatt, H., *Br J Pharmacol.* 2007, 151, 530-540; Story, G. M., *Mol Cell Neurosci.* 2006, 32, 335-343; Vogt-Eisele, A. K. et al., 2007); cinnamaldehyde (Macpherson, L. J. et al., 2006); incensole acetate (Moussaieff, A.; Rimmerman, N.; Bregman, T.; Straiker, A.; Felder, C. C.; Shoham, S.; Kashman, Y.; Huang, S. M.; Lee, H.; Shohami, E.; Mackie, K.; Caterina, M. J.; Walker, J. M.; Fride, E.; Mechoulam, R., *FASEB J.* 2008, 22, 3024-3034.); and vanilloid analogs, eugenol and ethyl vanillin (Hu, H. Z.; Gu, Q.; Wang, C.; Colton, C. K.; Tang, J.; Kinoshita-Kawada, M.; Lee, L. Y.; Wood, J. D.; Zhu, M. X., *J Biol. Chem.* 2004, 279, 35741-35748; Vogt-Eisele, A. K. et al., 2007; Xu, H. et al., 2006). Though relatively weak ($EC_{50}$, ~40 μM) and nonspecific across TRPs, 2-aminoethoxydiphenylborate (2-APB) and diphenylboronic anhydride (DPBA) have been widely and productively used to characterize key attributes of TRPV3 in cellular assays and electrophysiology (Hu, H. Z. et al., 2004; Chung, M. K.; Lee, H.; Mizuno, A.; Suzuki, M.; Caterina, M. J. *J Neurosci.* 2004, 24, 5177-5182; Chung, M. K.; Giller, A. D.; Caterina, M. J., *J Biol. Chem.* 2005, 280, 15928-15941). While heat and direct ligand binding are clearly central to TRPV3 pharmacology, accumulating evidence of potentiation by arachidonic acid, other unsaturated fatty acid derivatives (Hu, H. Z.; Xiao, R.; Wang, C.; Gao, N.; Colton, C. K.; Wood, J. D.; Zhu, M. X., *J Cell Physiol.* 2006, 208, 201-212), and nitric oxide (Aley, K. O.; McCarter, G.; Levine, J. D., *J Neurosci.* 1998, 18, 7008-7014; Yoshida, T.; Inoue, R.; Morii, T.; Takahashi, N.; Yamamoto, S.; Hara, Y.; Tominaga, M.; Shimizu, S.; Sato, Y.; Mori, Y., *Nat Chem. Biol.* 2006, 2, 596-607) suggests that authentic activation involves stimulation of G protein-coupled receptors and downstream second messenger signal cascades (e.g., phospholipase C, protein kinase C) that mediate local inflammatory responses and nociceptor sensitization that could enhance TRPV3 function (Xu, H. et al., 2006) in a pathophysiological, as compared to basal state.

Evidence suggests that transcriptional regulation of the TRPV3 gene restricts its basal expression and is responsible for enhanced expression following nerve injury. Levels of TRPV3 mRNA recovered from rat L4 and L5 DRG neurons is elevated in the spinal nerve ligation model of neuropathic pain, as compared to uninjured rats (U.S. Pat. No. 7,396,910). Similar upregulation of TRPV3 has been observed in sensory neurons following peripheral nerve injury in humans (Facer, P.; Casula, M. A.; Smith, G. D.; Benoham, C. D.; Chessell, I. P.; Bountra, C.; Sinisi, M.; Birch, R.; Anand, P., *BMC Neurol.* 2007, 7, 11-22; Smith G. D. et al., 2002).

One feature that distinguishes TRPV3 from the other thermoTRPs is its relatively prominent localization in skin (Peier, A. M. et al., 2002; Xu, H. et al., 2002). TRPV3 is also expressed in dorsal root ganglion, trigeminal ganglion, spinal cord and brain (Xu, H. et al., 2002; Smith G. D. et al., 2002). Its distinctive tissue profile, with significant expression in keratinocytes proximal to nociceptive neurons (Chung, M. K.; Lee, H.; Caterina, M. J., *J Biol. Chem.* 2003, 278, 32037-32046; Chung, M. K.; Lee, H.; Mizuno, A.; Suzuki, M.; Caterina, M. J. *J Biol. Chem.* 2004, 279, 21569-21575; Peier, A. M. et al., 2002; Xu, H. et al., 2002) as well as upregulation of TRPV3 in disease states is consistent with a likely role of TRPV3 in pain (Caterina M J., *Am J Physiol Regul Integr Comp Physiol.* 2007, 292, R64-R76; Lee, H.; Caterina, M. J., *Pflugers Arch.* 2005, 451, 160-167; Güller, A. D.; Lee, H.; Iida, T.; Shimizu, I.; Tominaga, M.; Caterina, M., *J Neurosci.* 2002, 22, 6408-6414; Chung, M. K. et al., 2003; Chung, M. K.; Lee, H.; Mizuno, A.; Suzuki, M.; Caterina, M. J. *J Biol. Chem.* 2004, 279, 21569-21575). In a keratinocyte cell line, stimulation of TRPV3 leads to release of inflammatory mediators including interleukin-1. Thus TRPV3 may also play an important role in regulating inflammation, itch (Steinhoff, M. and Biro, T. *J. Invest. Dermatology,* 2009, 129, 531-535) and pain that results from the release of inflammatory stimuli. In addition, localization of TRPV3 in non-neuronal tissues, especially skin, suggests also that pharmacological modulation of the channel may provide a therapy to treat diseases that impair the skin barrier (Montell, C. *Cell,* 2010, April 16, 218-220) and have additional, as yet unidentified, benefit for disease states beyond pain. Accordingly, compounds that can modulate one or more functions of TRPV3 can have various therapeutic utilities.

SUMMARY

Disclosed herein are compounds of Formula (I):

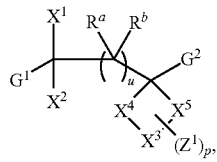

and pharmaceutically acceptable salts, solvates, salts of solvates, or solvates of salts thereof, wherein:

each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is $CH_2$, O, S, $S(O)_2$, or $N(R^{1x})$ wherein $R^{1x}$ is hydrogen, alkyl, —C(O)alkyl, or —C(O)O(alkyl);

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

each $Z^1$ group is an optional substituent on any substitutable carbon atom of the ring containing $X^3$, $X^4$, and $X^5$, and is independently alkyl, $C(O)R^{cz}$, $S(O)_2R^{cz}$, $N(R^{1d})(R^{2d})$, $OR^c$, oxo, $=NOR^{z1}$, $=NNR^{z1}R^{z2}$, $=NR^{z3}$, halogen, haloalkyl, —($C_1$-$C_6$ alkylenyl)-$OR^c$, —($C_1$-$C_6$ alkylenyl)-$C(O)R^{cz}$, —($C_1$-$C_6$ alkylenyl)-$S(O)_2R^{cz}$, or —($C_1$-$C_6$ alkylenyl)-N($R^{1d}$)($R^{2d}$); two $Z^1$ groups that are resided on the same carbon atom, together with the carbon atom to which they are attached optionally form a 4-6 membered monocyclic cycloalkyl or monocyclic heterocycle ring; wherein said ring is optionally substituted with 1, 2, 3, or 4 substituents independently selected from the group consisting of alkyl, haloalkyl, and halogen;

$R^{z1}$, $R^{z2}$, $R^{z3}$ are each independently hydrogen, alkyl, —C(O)(alkyl), —C(O)-$G^d$, or haloalkyl;

$R^{cz}$, at each occurrence, is independently alkyl, haloalkyl, $NH_2$, N(H)(alkyl), or N(alkyl)$_2$;

$R^{1d}$, at each occurrence, is independently hydrogen, alkyl, haloalkyl, C(O)alkyl, or C(O)O(alkyl);

$R^{2d}$ and $R^c$, at each occurrence, are each independently hydrogen, alkyl, or haloalkyl;

p is 0, 1, 2, 3, or 4;

—$X^1$ is —OH and $X^2$ is hydrogen; or —$X^1$ is =O or =$NOR^{10}$ and $X^2$ is absent;

$R^{10}$ is hydrogen, alkyl, or —C(O)alkyl;

$G^1$ is aryl, heteroaryl, cycloalkyl, heterocycle, or cyclaoalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;

$G^2$ is $G^{2d}$ or —$(CR^{1g}R^{2g})_r$-$G^{2d}$ wherein:

r is 1, 2, or 3;

$R^{1g}$ and $R^{2g}$ are the same or different, and are each independently hydrogen, alkyl, halogen, $OR^{1gc}$, $N(R^{1gc})_2$, C(O)alkyl, or haloalkyl; wherein each $R^{1gc}$ is independently hydrogen, alkyl, or haloalkyl;

$G^{2d}$ is aryl, heteroaryl, cycloalkyl, heterocycle, or cyclaoalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$C(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R)C(O)R^f$, —$(CR^{1a}R^{1b})_q$—$N(R)S(O)_2R^c$, —$(CR^{1a}R^{1b})_q$—$N(R^f)C(O)O(R^e)$, —$(CR^{1a}R^{1b})_q$—$N(R)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, halolalkyl, $G^d$, or —$(CR^{1a}R^{1b})_q$-$G^d$;

each occurrence of $R^e$ is independently alkyl, halolalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^j$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$OC(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or haloalkyl; and each occurrence of $R^k$ is independently alkyl or haloalkyl.

Another aspect relates to pharmaceutical compositions comprising therapeutically effective amount of a compound described herein or pharmaceutically acceptable salt, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV3 activity. More particularly, the methods are useful for treating itch and conditions related to pain such as, but not limited to, chronic pain, acute pain, neuropathic pain, nociceptive pain, osteoarthritic pain, inflammatory pain, fibromyalgia, post herpetic neuralgia, cancer pain (e.g. bone cancer pain), lower back pain, post operative pain, migraine, diabetic neuropathy, and eye pain, or combinations thereof.

Further, provided herein are uses of present compounds or pharmaceutically acceptable salts, solvates, or salts of solvates thereof, in the manufacture of medicaments for the treatment of the disease or conditions described above, alone or in combination with a pharmaceutically acceptable carrier, particularly for the treatment of itch or pain such as, but not limited to, chronic pain, acute pain, neuropathic pain, nociceptive pain, osteoarthritic pain, inflammatory pain, fibromyalgia, post herpetic neuralgia, cancer pain (e.g. bone cancer pain), lower back pain, post operative pain, migraine, diabetic neuropathy, and eye pain, or combinations thereof.

The compounds, compositions comprising the compounds, pharmaceutically acceptable salts, solvates, salts of the solvates, or solvates of the salts thereof, and methods for treating or preventing conditions and disorders by administering the compounds or compositions thereof, are further described herein.

These and other objectives are described further in the following paragraphs. These objectives should not be deemed to narrow the scope of the invention.

DETAILED DESCRIPTION OF THE INVENTION

Compounds of Formula (I):

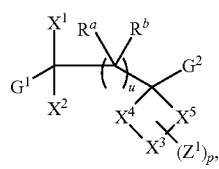

(I)

wherein $G^1$, $X^1$, $X^2$, $X^3$, $X^4$, $X^5$, $G^2$, $Z^1$, $R^a$, $R^b$, u, and p are as defined above in the Summary and below in the Detailed Description, are disclosed. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "$C_x$—$C_y$ alkyl" means a straight or branched chain, saturated hydrocarbon containing x to y carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 6 carbon atoms. The term "$C_1$-$C_6$ alkylenyl" means a divalent group derived from a straight or branched, saturated hydrocarbon chain of 1 to 6 carbon atoms. Examples of alkylene include, but are not limited to, —CH$_2$—, —C(H)(CH$_3$)—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (e.g. 2,3-dihydro-1H-inden-1-yl), indenyl, naphthyl, dihydronaphthalenyl, and tetrahydronaphthalenyl (e.g. 1,2,3,4-tetrahydronaphthalen-1-yl). The aryl groups can be unsubstituted or substituted, and the bicyclic aryl is attached to the parent molecular moiety through any substitutable carbon atom contained within the bicyclic ring system.

The term "cycloalkyl" or "cycloalkane" as used herein, means a monocyclic or a bicyclic. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each consisting of one, two, three, or four carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven-, or eight-carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "heterocycle" or "heterocyclic" as used herein, means a monocyclic heterocycle or a bicyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S, Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include e.g. dihydrochromenyl (e.g. 3,4-dihydro-2H-chromen-4-yl), benzopyranyl, benzothiopyranyl, 2,3-dihydrobenzofuranyl, 2,3-dihydrobenzothienyl, and 2,3-dihydro-1H-indolyl. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic and the bicyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-5H-cyclopenta[b]pyridinyl (e.g. 6,7-dihydro-5H-cyclopenta[b]pyridin-7-yl), 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolinyl (e.g. 5,6,7,8-tetrahydroquinolin-5-yl, 5,6,7,8-tetrahydroquinolin-8-yl). The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "oxo" as used herein, means a =O group.

"Treatment," "treat," or "treating" pain includes acute or chronic pain and refers to: (1) preventing pain, i.e. causing pain not to develop or occur with less intensity in a subject that may be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

b. COMPOUNDS

Compounds of Formula (I) are as described above.

Particular values of variable groups in compounds of Formula (I) are as follows. Such values may be used where appropriate with any of the other values, definitions, claims, or embodiments defined hereinbefore or hereinafter.

$R^a$, $R^b$, and u have values as described in the Summary. For example, in certain embodiments, u is 0 or 1. In certain embodiments, u is 0. In yet other embodiments, u is 1. In conjunction with any of the embodiments described herein above or below, $R^a$ and $R^b$, for example, are hydrogen or alkyl (e.g. methyl), or for example, $R^a$ and $R^b$ are hydrogen.

Examples of compounds of Formula (I) wherein u is 0 can be exemplified by compounds of Formula (I-a)

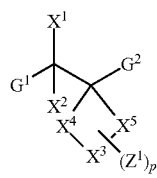
(I-a)

wherein $G^1$, $G^2$, $X^1$, $X^2$, $X^3$, $X^4$, $X^5$, $Z^1$, and p are as disclosed in the Summary and embodiments herein below.

$X^1$ and $X^2$ for Formula (I) and (I-a) have values as described in the Summary and embodiments herein below.

For example, in certain embodiments, —$X^1$ is —OH and $X^2$ is hydrogen, as exemplified by Formula (I-i)

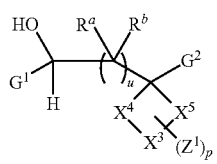
(I-i)

Compounds of Formula (I-i) can exist as stereoisomers wherein asymmetric or chiral centers are present. Thus, contemplated are compounds of Formula (I-i-a), (I-i-b), and mixtures (including racemic mixtures) of various ratios thereof:

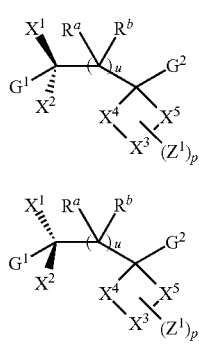
(I-i-a)

(I-i-b)

In certain embodiments, $X^2$ is absent, and —$X^1$ is =O or =$NOR^{10}$ wherein $R^{10}$ is hydrogen, alkyl, or —C(O)alkyl. Thus, included, but not limited to, are compounds of Formula (I-ii):

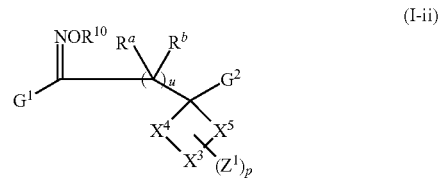
(I-ii)

$G^1$, $G^2$, $X^3$, $X^4$, $X^5$, $Z^1$, $R^{10}$, $R^a$, $R^b$, u, and p for Formula (I-a), (I-i), (I-i-a), (I-i-b), and (I-ii) have values as described in the Summary for Formula (I) and embodiments herein.

In conjunction with any of the embodiments disclosed above and below, $R^{10}$ has values as described in the Summary and herein. For example, in certain embodiments $R^{10}$ is hydrogen.

$X^3$, $X^4$, and $X^5$ for compounds of Formula (I), (I-a), (I-i), (I-i-a), (I-i-b), and (I-ii) are as described in the Summary. $X^3$, for example, is $CH_2$, O, or $N(R^{1x})$. In certain embodiments, $X^3$, for example, is O or $N(R^{1x})$. In certain embodiments, $X^3$, for example, is $CH_2$ or O. In certain embodiments, $X^3$ is O. In certain embodiments, $X^3$ is $CH_2$. In certain embodiments, $X^3$, for example, is $N(R^{1x})$.

In certain embodiments, $X^3$ is O or $N(R^{1x})$, $X^4$ is $(CH_2)_m$, and $X^5$ is $(CH_2)_n$ wherein m is 1, 2, or 3, and n is 1 or 2.

In certain embodiments, $X^3$ is $N(R^{1x})$, $X^4$ is $(CH_2)_m$ and $X^5$ is $(CH_2)_n$ wherein m is 1, 2, or 3, and n is 1 or 2.

In certain embodiments, $X^3$ is $N(R^{1x})$, $X^4$ is a bond, $X^5$ is $(CH_2)_n$, and n is 2, 3, or 4.

In certain embodiments, $X^3$ is O, $X^4$ is $(CH_2)_m$, and $X^5$ is $(CH_2)_n$ wherein m is 1, 2, or 3, and n is 1 or 2.

In certain embodiments, $X^3$ is O, $X^4$ is a bond, $X^5$ is $(CH_2)_n$, and n is 2, 3, or 4.

In certain embodiments, $X^3$ is $CH_2$, $X^4$ is a bond or $(CH_2)_m$, and $X^5$ is $(CH_2)_n$; wherein m and n are each independently 1 or 2.

In conjunction with embodiments herein above and below, $R^{1x}$ has values as described in the Summary. For example, $R^{1x}$ is hydrogen, alkyl (e.g. methyl), or —C(O)O(alkyl) (e.g. —C(O)O(tert-butyl)).

In certain embodiments, $X^3$, $X^4$, and $X^5$ together is

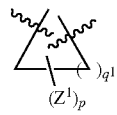
(a)

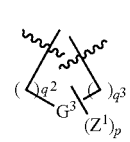
(b)

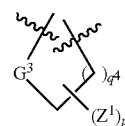
(c)

wherein $G^3$ is O or $N(R^{1x})$, q1 is 1, 2, 3, or 4, q2 and q4, are each independently 1, 2, or 3; q3 is 1 or 2; and the curvy lines represent the points of attachment. In certain embodiments, $X^3$, $X^4$, and $X^5$ together is Formula (a). In still other embodiments, $X^3$, $X^4$, and $X^5$ together is Formula (a), and q1 is 1, 2, or 4. In still other embodiments, $X^3$, $X^4$, and $X^5$ together is Formula (a), and q1 is 2. In yet other embodiments, $X^3$, $X^4$, and $X^5$ together is Formula (b) or Formula (c), wherein $G^3$ is O, and q2, q3, and q4 are each independently 1 or 2.

p is 0, 1, 2, 3, or 4. In certain embodiments, p is 0, 1, or 2. In other embodiments, p is 0 or 1. In yet other embodiments, p is 0. In still other embodiments, p is 1. In still other embodiments, p is 2.

In conjunction with embodiments herein above and below, each $Z^1$ represents optional substituent on any substitutable carbon atom of the ring containing $X^3$, $X^4$, and $X^5$, and has values as disclosed in the Summary. For example, each $Z^1$, when present, is independently alkyl (e.g. methyl), $OR^c$, oxo, or halogen (e.g. F).

In certain embodiments of compounds of Formula (I), (I-a), (I-i), (I-i-a), (I-i-b), and (I-ii), $X^3$ is $CH_2$, p is 1 or 2, and each $Z^1$ is independently alkyl (e.g. methyl) or $OR^c$.

In the embodiments wherein $X^3$, $X^4$, and $X^5$ together is Formula (a), examples of the compounds of Formula (I) include those as depicted in Formula (I-iii)

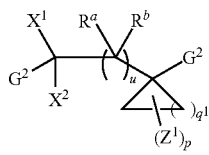

(I-iii)

wherein q1 is 1, 2, 3, or 4. In certain embodiments, q1 is 2.

In the embodiments wherein q1 is 2 in Formula (I-iii), such compounds can be represented by Formula (I-iv)

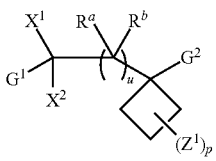

(I-iv)

The variables $G^1$, $G^2$, $X^1$, $X^2$, $R^a$, $R^b$, u, $Z^1$, and p of Formula (I-iii) and (I-iv) are as described in the Summary and the embodiments herein above and below.

In the embodiments wherein the variable, p, in Formula (I-iv) is 2, and that two different $Z^1$ groups are situated on the third carbon atom of the cyclobutyl moiety; or when p is 1 and the $Z^1$ group is situated on the third carbon atom of the cyclobutyl moiety; various geometric isomers resulting from the disposal of these substituents ($Z^1$) around such symmetrical cyclobutyl moiety are contemplated and are within the scope of this invention. For example, Formula (I-iv-a) and (I-iv-b) wherein p is 1 and the $Z^1$ group is $OR^c$, or p is 2, and one of the $Z^1$ groups is alkyl and the other is $OR^c$ represent some of the geometric forms that compounds of Formula (I-iv) possess:

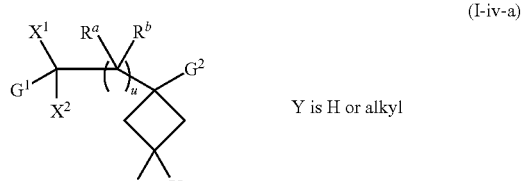

(I-iv-a)

Y is H or alkyl

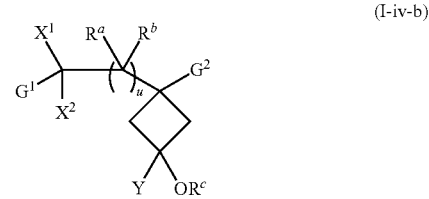

(I-iv-b)

wherein the variables $G^1$, $G^2$, $X^1$, $X^2$, $R^a$, $R^b$, $R^c$, and u of Formula (I-iv-a) and (I-iv-b) are as described in the Summary and the embodiments herein above and below.

In Formula (I-iv-a) the $OR^c$ group is on the same face of the cyclobutane ring as the substituent containing $X^1$ and is assigned the "cis" configuration while Formula (I-iv-b) is assigned the "trans" configuration with the $OR^c$ group on the opposite face of the cyclobutane ring as the substituent containing $X^1$. It is understood that both geometric isomers and mixtures thereof of various ratios are within the scope of the present invention.

When u is 0, for example, the compounds of Formula (I-iv-a) and (I-iv-b) having a "cis" or "trans" configuration can be depicted as shown in Formula (I-iv-c) and Formula (I-iv-d), respectively:

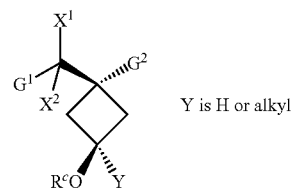

(I-iv-c)

Y is H or alkyl

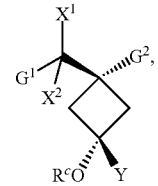

(I-iv-d)

wherein the variables $G^1$, $G^2$, $X^1$, $X^2$, and $R^c$ of Formula (I-iv-c) and (I-iv-d) are as described in the Summary and the embodiments herein above and below.

$G^1$ for Formula (I), (I-a), (I-i), (I-i-a), (I-i-b), (I-ii), (I-iii), (I-iv), (I-iv-a), (I-iv-b), (I-iv-c), and (I-iv-d) are as described in the Summary. In certain embodiments, $G^1$ is heteroaryl or cycloalkyl. In certain embodiments, $G^1$ is heteroaryl. In certain embodiments, $G^1$ is cycloalkyl. Each ring as represented by $G^1$ is optionally substituted as described in the Summary and embodiments herein.

In the embodiments wherein $G^1$ is optionally substituted heteroaryl, $G^1$, for example, is an optionally substituted monocyclic heteroaryl (e.g. pyridinyl, pyrimidinyl, thiazolyl, oxazolyl, or pyrazolyl, each of which is optionally substituted). In yet other embodiments, $G^1$ is an optionally substituted bicyclic heteroaryl (e.g. 6,7-dihydro-5H-cyclopenta[b]pyridinyl, and 5,6,7,8-tetrahydroquinolinyl, each of which is optionally substituted). In the embodiments wherein $G^1$ is an optionally substituted heteroaryl, examples of the heteroaryl group include, but not limited thereto, pyridinyl, pyrimidinyl, thiazolyl, oxazolyl, pyrazolyl, 6,7-dihydro-5H-cyclopenta[b]pyridinyl, and 5,6,7,8-tetrahydroquinolinyl, each of which is optionally substituted as described in the Summary and embodiments herein. In certain embodiments, $G^1$ is optionally substituted pyridinyl. In yet other embodiments, $G^1$ is optionally substituted pyridin-2-yl.

In certain embodiments, $G^1$ is an optionally substituted cycloalkyl. In certain embodiments, $G^1$ is a substituted cycloalkyl. Examples of the cycloalkyl group include, but are not limited to, cyclobutyl, cyclopentyl, and cyclohexyl.

In conjunction with embodiments described herein above and below, examples of the substituents of $G^1$, if present, include, but not limited to, alkyl (e.g. methyl, ethyl), halogen, haloalkyl, and $N(R^{gc})_2$. In the embodiments wherein $G^1$ is a substituted cycloalkyl, the cycloalkyl group, for example, can be substituted with one $N(R^{gc})_2$ group, and is optionally further substituted with one or two substituents selected from alkyl (e.g. methyl, ethyl), halogen, or haloalkyl. In certain embodiments, the $N(R^{gc})_2$ on the cycloalkyl moiety is situated on the carbon atom adjacent to the point of connection. In conjunction with the embodiments herein above and below, $R^{gc}$, for example, is hydrogen or alkyl (e.g. methyl).

$G^2$ for Formula (I), (I-a), (I-i), (I-i-a), (I-i-b), (I-ii), (I-iii), (I-iv), (I-iv-a), (I-iv-b), (I-iv-c), and (I-iv-d) are as described in the Summary. In certain embodiments, $G^2$ is $G^{2d}$ wherein $G^{2d}$ is aryl, heteroaryl, heterocycle, or cycloalkyl; each of which is optionally substituted. In other embodiments, $G^2$ is $G^{2d}$ wherein $G^{2d}$ is optionally substituted aryl or optionally substituted cycloalkyl. In the embodiments wherein $G^2$ is $G^{2d}$ and $G^{2d}$ is optionally substituted aryl, examples of the aryl group include, but are not limited to, phenyl, 2,3-dihydroindenyl, and 1,2,3,4-tetrahydronaphthalenyl, each of which is optionally substituted as described in the Summary and herein. In certain embodiments, $G^2$ is $G^{2d}$ wherein $G^{2d}$ is optionally substituted phenyl. In the embodiments wherein $G^2$ is $G^{2d}$ and $G^{2d}$ is optionally substituted heteroaryl, an example of the optionally substituted heteroaryl includes, but not limited to, optionally substituted pyridinyl. In the embodiments wherein $G^2$ is $G^{2d}$ and $G^{2d}$ is optionally substituted heterocycle, an example of the optionally substituted heterocycle includes, but not limited to, optionally substituted dihydrochromenyl. In the embodiments wherein $G^2$ is $G^{2d}$ and $G^{2d}$ is optionally substituted cycloalkyl, examples of the optionally substituted cycloalkyl include, but not limited to, optionally substituted cyclopentyl and optionally substituted cyclohexyl. The optional substituents of the above mentioned $G^{2d}$ groups (including the exemplary rings) are as described in the Summary and embodiments herein.

In yet other embodiments, $G^2$ is $-(CR^{1g}R^{2g})_r-G^{2d}$ wherein $R^{1g}$, $R^{2g}$, r, and $G^{2d}$ are as described in the Summary and embodiments herein. In certain embodiments, $G^2$ is $-(CR^{1g}R^{2g})_r-G^{2d}$ wherein $G^{2d}$ is aryl (e.g. phenyl) or heteroaryl (e.g. pyridinyl), each of the $G^{2d}$ rings (including the exemplary rings) is optionally substituted as described in the Summary and embodiments herein. In still other embodiments, $G^2$ is $-(CR^{1g}R^{2g})_r-G^{2d}$ wherein $G^{2d}$ is optionally substituted aryl (e.g. optionally substituted phenyl). In yet other embodiments, $G^2$ is $-(CR^{1g}R^{2g})_r-G^{2d}$ wherein $G^{2d}$ is optionally substituted heteroaryl (e.g. optionally substituted monocyclic heteroaryl such as, but not limited to, optionally substituted pyridinyl). In conjunction with the embodiments described herein above and below, $R^{1g}$, $R^{2g}$, and r, and the optional substituents of $G^{2d}$, are as described in the Summary and herein. In certain embodiments, $R^{1g}$ and $R^{2g}$ are, for example, hydrogen. In certain embodiments, one of $R^{1g}$ and $R^{2g}$ is hydrogen, and the other is alkyl (e.g. methyl) or haloalkyl (e.g. trifluoromethyl). In yet other embodiments, one of $R^{1g}$ and $R^{2g}$ is hydrogen, and the other is alkyl (e.g. methyl). In yet other embodiments, one of $R^{1g}$ and $R^{2g}$ is hydrogen, and the other is methyl. r, for example, is 1 or 2. In certain embodiments, r is 1.

In conjunction with the above and below embodiments, examples of the optional substituents of $G^{2d}$ include, but are not limited to, alkyl (e.g. methyl), halogen (e.g. F, Cl), haloalkyl (e.g. trifluoromethyl), CN, $-OR^f$ ($R^f$ is as described in the Summary, for example, $R^f$ is alkyl such as, but not limited to, methyl; haloalkyl such as, but not limited to, trifluoromethyl; or optionally substituted phenyl), $-S(O)_2R^e$ ($R^e$, for example, is $C_1$-$C_4$ alkyl such as, but not limited to, methyl), $G^d$ (e.g. optionally substituted phenyl), $N(R^f)_2$ (each $R^f$, for example, is independently hydrogen, $C_1$-$C_6$ alkyl such as, but not limited to, methyl, ethyl), and $-(CR^{1a}R^{1b})_q-G^d$ (e.g. $CH_2$-phenyl). In certain embodiments, the optional substituents of $G^{2d}$ include, but not limited to, alkyl (e.g. methyl), halogen (e.g. fluorine, chlorine), haloalkyl (e.g. trifluoromethyl), $-O(alkyl)$, or $-O(haloalkyl)$.

It is appreciated that the present invention contemplates compounds of Formula (I), (I-a), (I-i), (I-i-a), (I-i-b), (I-ii), (I-iii), (I-iv), (I-iv-a), (I-iv-b), (I-iv-c), and (I-iv-d) with combinations of the above embodiments, including particular, more particular and preferred embodiments.

Accordingly, one aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is heteroaryl or cycloalkyl, each of which is optionally substituted; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted heteroaryl; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted monocyclic heteroaryl; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $G^{2d}$ wherein $G^{2d}$ is optionally substituted aryl (e.g. optionally substituted phenyl, optionally substituted dihydroindenyl, or optionally substituted tetrahydronaphthalenyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $G^{2d}$ wherein $G^{2d}$ is optionally substituted phenyl. The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $G^{2d}$ wherein $G^{2d}$ is optionally substituted heteroaryl (e.g. optionally substituted pyridinyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $G^{2d}$ wherein $G^{2d}$ is optionally substituted cycloalkyl (e.g. optionally substituted cyclopentyl, optionally substituted cyclohexyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted cycloalkyl; and $G^2$ is $G^{2d}$. In certain embodiments, $G^{2d}$ is optionally substituted aryl. In certain embodiments, $G^{2d}$ is optionally substituted phenyl. The optional substituents and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is substituted cycloalkyl; and $G^2$ is $G^{2d}$. In certain embodiments, $G^{2d}$ is optionally substituted aryl. In certain embodiments, $G^{2d}$ is optionally substituted phenyl. The optional substituents and the exemplary rings of $G^1$ and $G^{2d}$ are as described in the Summary and embodiments herein above.

Yet another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted heteroaryl; and $G^2$ is $-(CR^{1g}R^{2g})_r$-$G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, the optional substituents of $G^1$ and $G^{2d}$, and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted monocyclic heteroaryl; and $G^2$ is $-(CR^{1g}R^{2g})_r$-$G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, the optional substituents of $G^1$ and $G^{2d}$, and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $-(CR^{1g}R^{2g})_r$-$G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, and the optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^2$ is $-(CR^{1g}R^{2g})_r$-$G^{2d}$ wherein $G^{2d}$ is optionally substituted aryl (e.g. optionally substituted phenyl). The optional substituents of $G^1$ and $G^{2d}$, $R^{1g}$, $R^{2g}$, and r, are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), (I-iv-b), (I-iv-c), and (I-iv-d) wherein $G^1$ is optionally substituted pyridinyl (e.g. pyridin-2-yl); and $G^{2d}$ optionally substituted phenyl. The optional substituents of $G^1$ and $G^{2d}$, $R^{1g}$, $R^{2g}$, and r are as described in the Summary and embodiments herein above.

Yet another aspect is directed to a group of compounds of Formula (I), (I-iii), (I-iv), (I-iv-a), (I-iv-b), (I-iv-c), and (I-iv-d) wherein $G^1$ is an optionally substituted heteroaryl (e.g. monocyclic heteroaryl such as, but not limited to, pyridinyl, pyrimidinyl, each of which is optionally substituted as described in the Summary and embodiments herein above), $-X^1$ is $-OH$, $X^2$ is hydrogen, u is 0 or 1, $G^2$ is $G^{2d}$, and $G^{2d}$ is optionally substituted aryl. In certain embodiments, $G^1$ is optionally substituted pyridinyl (e.g. pyridin-2-yl). In yet other embodiments, $G^1$ is optionally substituted pyridinyl (e.g. pyridin-2-yl) and u is 0.

Yet another aspect is directed to a group of compounds of Formula (I), (I-iii), (I-iv), (I-iv-a), (I-iv-b), (I-iv-c), and (I-iv-d) wherein $G^1$ is an optionally substituted heteroaryl (e.g. monocyclic heteroaryl such as, but not limited to, pyridinyl, pyrimidinyl, each of which is optionally substituted as described in the Summary and embodiments herein above), —$X^1$ is —OH, $X^2$ is hydrogen, u is 0 or 1, $G^2$ is $G^{2d}$, and $G^{2d}$ is optionally substituted cycloalkyl (e.g. cyclopentyl, cyclohexyl, each of which is optionally substituted). In certain embodiments, $G^1$ is optionally substituted pyridinyl (e.g. pyridin-2-yl). In yet other embodiments, $G^1$ is optionally substituted pyridinyl (e.g. pyridin-2-yl), and u is 0.

Yet another aspect is directed to a group of compounds of Formula (I), (I-iii), (I-iv), (I-iv-a), (I-iv-b), (I-iv-c), and (I-iv-d) wherein $G^1$ is an optionally substituted heteroaryl (e.g. monocyclic heteroaryl such as, but not limited to, pyridinyl, pyrimidinyl, each of which is optionally substituted as described in the Summary and embodiments herein above), —$X^1$ is —OH, $X^2$ is hydrogen, u is 0 or 1, $G^2$ is —$(CR^{1g}R^{2g})_r$-$G^{2d}$, and $G^{2d}$ is optionally substituted aryl. In certain embodiments, $G^1$ is optionally substituted pyridinyl (e.g. pyridin-2-yl). In yet other embodiments, $G^1$ is optionally substituted pyridinyl (e.g. pyridin-2-yl), and u is 0. $R^{1g}$, $R^{2g}$, and r are as described in the Summary and embodiments herein.

Yet another aspect is directed to a group of compounds of Formula (I), (I-iii), (I-iv), (I-iv-a), (I-iv-b), (I-iv-c), and (I-iv-d) wherein $G^1$ is an optionally substituted cycloalkyl (e.g. cyclobutyl, cyclopentyl, cyclohexyl, each of which is optionally substituted), —$X^1$ is —OH, $X^2$ is hydrogen, u is 0 or 1, $G^2$ is $G^{2d}$, and $G^{2d}$ is optionally substituted phenyl. In certain embodiments, $G^1$ is a substituted cycloalkyl (e.g. cyclobutyl, cyclopentyl, cyclohexyl, each of which is substituted as described in the Summary and embodiments herein above) and u is 0.

Yet another aspect is directed to a group of compounds of Formula (I), (I-iii), (I-iv), (I-iv-a), (I-iv-b), (I-iv-c), and (I-iv-d) wherein $G^1$ is an optionally substituted heteroaryl (e.g. monocyclic heteroaryl such as, but not limited to, pyridinyl, pyrimidinyl, each of which is optionally substituted as described in the Summary and embodiments herein above), —$X^1$ is =$NOR^{10}$, $X^2$ is absent, u is 0 or 1, $G^2$ is $G^{2d}$, and $G^{2d}$ is optionally substituted aryl. In certain embodiments, $G^1$ is optionally substituted pyridinyl (e.g. pyridin-2-yl). In yet other embodiments, $G^1$ is optionally substituted pyridinyl (e.g. pyridin-2-yl) and u is 0. $R^{10}$ is as described in the summary and embodiments herein above.

Within each group of the compounds described above, $X^3$, $X^4$, $X^5$, u. $R^a$, $R^b$, $Z^1$, p, $X^1$, and $X^2$ are as described in the Summary and embodiments herein above. Thus, within each group of the compounds described above, examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is $CH_2$, O, or $N(R^{1x})$.

Examples of another subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is $CH_2$ or O.

Examples of another subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is O.

Other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is $CH_2$.

Other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is $N(R^{1x})$.

Yet other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is O or $N(R^{1x})$, $X^4$ is $(CH_2)_m$, $X^5$ is $(CH_2)_n$, m is 1, 2, or 3, and n is 1 or 2.

Yet other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is O, $X^4$ is $(CH_2)_m$, $X^5$ is $(CH_2)_m$, m is 1, 2, or 3, and n is 1 or 2.

Yet other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is O, $X^4$ is a bond, $X^5$ is $(CH_2)_n$, and n is 2, 3, or 4.

Yet other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$ is $CH_2$, $X^4$ is a bond or $(CH_2)_m$, $X^5$ is $(CH_2)_n$, and m and n are each independently 1 or 2.

Yet other examples of a subgroup of compounds of Formula (I), (I-a), (I-i), (I-i-a), (I-i-b), (I-ii), (I-iii), (I-iv), (I-iv-a), (I-iv-b), (I-iv-c), and (I-iv-d) include, but not limited to, those wherein $X^3$, $X^4$, and $X^5$ together are Formula (a), (b), or (c). In certain embodiments, $X^3$, $X^4$, and $X^5$ together are Formula (a). $X^3$, $X^4$, and $X^5$ together are Formula (b) or Formula (c). In certain embodiments, q1 is 1, 2, or 4. In certain embodiments, q1 is 2. In certain embodiments, $G^3$ is O and q2, q3, and q4 are each independently 1 or 2.

Yet other examples of a subgroup of compounds of Formula (I), (I-i), (I-i-a), (I-i-b), (I-ii), (I-iii), (I-iv), (I-iv-a), (I-iv-b), (I-iv-c), and (I-iv-d) include, but not limited to, those wherein u is 0 or 1.

Yet other examples of a subgroup of compounds of Formula (I), (I-a), (I-iii), (I-iv), (I-iv-a), (I-iv-b), (I-iv-c), and (I-iv-d) include, but not limited to, those wherein —$X^1$ is —OH and $X^2$ is hydrogen.

Yet other examples of a subgroup of compounds of Formula (I), (I-a), (I-iii), (I-iv), (I-iv-a), (I-iv-b), (I-iv-c), and (I-iv-d) include, but not limited to, those wherein —$X^1$ is =$NOR^{10}$ and $X^2$ is absent.

Within each group and subgroup of compounds described in this application, Z1 and p are as described in the Summary and embodiments herein.

Further representative embodiments are set forth below:

(i) Substituted Cyclobutyl Ring

In one embodiment, the invention is directed to compounds of Formula (I) wherein:

each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is $CH_2$;

$X^4$ is $(CH_2)_m$;

$X^5$ is $(CH_2)_n$;

m and n are each 1;

each $Z^1$ group is a substituent on any substitutable carbon atom of the ring containing $X^3$, $X^4$, and $X^5$, and is independently alkyl, $C(O)R^{cz}$, $S(O)_2R^{cz}$, $N(R^{1d})(R^{2d})$, $OR^c$, oxo, =$NOR^{z1}$, =$NNR^{z1}R^{z2}$, =$NR^{z3}$, halogen, haloalkyl, alkylenyl)-$OR^c$, —$(C_1$-$C_6$ alkylenyl)-$C(O)R^{cz}$, alkylenyl)-$S(O)_2R^{cz}$, or —$(C_1$-$C_6$ alkylenyl)-$N(R^{1d})(R^{2d})$; two $Z^1$ groups that are situated on the same carbon atom, together with the carbon atom to which they are attached optionally form a 4-6 membered monocyclic cycloalkyl or monocyclic heterocycle ring; wherein said ring is optionally substituted with 1, 2, 3, or 4 substituents independently selected from the group consisting of alkyl, haloalkyl, and halogen;

$R^{z1}$, $R^{z2}$, $R^{z3}$ are each independently hydrogen, alkyl, —C(O)(alkyl), —C(O)-$G^d$, or haloalkyl;

$R^{cz}$, at each occurrence, is independently alkyl, haloalkyl, $NH_2$, $N(H)(alkyl)$, or $N(alkyl)_2$;

$R^{1d}$, at each occurrence, is independently hydrogen, alkyl, haloalkyl, C(O)alkyl, or C(O)O(alkyl);

$R^{2d}$ and $R^c$, at each occurrence, are each independently hydrogen, alkyl, or haloalkyl;

p is 1, 2, 3, or 4;

$X^1$ is —OH and $X^2$ is hydrogen;

$G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;

$G^2$ is $G^{2d}$ or —$(CR^{1g}R^{2g})_r$-$G^{2d}$ wherein:

r is 1, 2, or 3;

$R^{1g}$ and $R^{2g}$ are the same or different, and are each independently hydrogen, alkyl, halogen, $OR^{1gc}$, $N(R^{1gc})_2$, C(O)alkyl, or haloalkyl; wherein each $R^{1gc}$ is independently hydrogen, alkyl, or haloalkyl;

$G^{2d}$ is aryl, heteroaryl, cycloalkyl, heterocycle, or cycloalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$C(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R)C(O)R^f$, —$(CR^{1a}R^{1b})_q$—$N(R)S(O)_2R^e$, —$(CR^{1a}R^{1b})_q$—$N(R^f)$ $C(O)O(R^e)$, —$(CR^{1a}R^{1b})_q$—$N(R)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, haloalkyl, $G^d$, or —$(CR^{1a}R^{1b})_q$-$G^d$;

each occurrence of $R^e$ is independently alkyl, haloalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^2$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$OC(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)$ $S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or haloalkyl; and each occurrence of $R^k$ is independently alkyl or haloalkyl.

In a preferred embodiment, u is 0 and p is 1 or 2. In further embodiments where u is 0 and p is 1 or 2, the compound has the configuration of Formula (I-i-a):

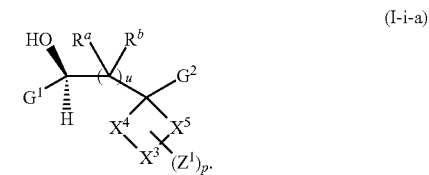

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, oxo, $C_1$-$C_6$-alkyl, or —$OR^c$; or two $Z^1$ groups that are situated on the same carbon atom, together with the carbon atom to which they are attached, form a 4 to 6 membered monocyclic heterocycle ring;

$R^c$ is hydrogen, $C_1$-$C_6$-alkyl, or $C_1$-$C_6$-haloalkyl;

p is 1, 2, 3, or 4;

$X^1$ is —OH and $X^2$ is hydrogen;

$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;

$R^{gc}$ is hydrogen or $C_1$-$C_6$-alkyl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and $R^f$ is $C_1$-$C_6$-alkyl or $C_1$-$C_6$-haloalkyl.

In a further embodiment, p is 1 or 2, and the compound has the configuration of Formula (I-i-a).

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, oxo, $C_1$-$C_4$-alkyl, or —$OR^c$; or two $Z^1$ groups that are situated on the same carbon atom, together with the carbon atom to which they are attached, form a 5-membered monocyclic heterocycle ring comprising two oxygen ring atoms;

$R^c$ is hydrogen or $C_1$-$C_4$-alkyl;

p is 1 or 2;

$X^1$ is —OH and $X^2$ is hydrogen;

$G^1$ is pyridinyl; each of which is optionally substituted with 1 or 2 substituents independently selected from the group consisting of halogen, $C_1$-$C_4$-alkyl, $C_1$-$C_4$-haloalkyl, and $N(R^{gc})_2$;

$R^{gc}$ is hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_4$-alkyl, or —$OR^c$; or two $Z^1$ groups that reside on the same carbon atom, together with the carbon atom to which they are attached, form an unsubstituted 5-membered monocyclic heterocycle ring comprising two oxygen ring atoms;
$R^c$ is hydrogen or $C_1$-$C_4$-alkyl;
p is 1 or 2;
$X^1$ is —OH and $X^2$ is hydrogen;
$G^1$ is unsubstituted pyridinyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_3$-alkyl, or —$OR^c$; or two $Z^1$ groups that are situated on the same carbon atom, together with the carbon atom to which they are attached, form an unsubstituted 5-membered monocyclic heterocycle ring comprising two oxygen ring atoms;
$R^c$ is hydrogen or $C_1$-$C_3$-alkyl;
p is 1 or 2;
$X^1$ is —OH and $X^2$ is hydrogen;
$G^1$ is unsubstituted pyridin-2-yl;
$G^2$ is $G^{2d}$;
$G^{2d}$ is phenyl, pyridinyl, or pyrimidinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_3$-alkyl, or —$OR^c$; or two $Z^1$ groups that are situated on the same carbon atom, together with the carbon atom to which they are attached, form an unsubstituted 5-membered monocyclic heterocycle ring comprising two oxygen ring atoms;
$R^c$ is hydrogen or $C_1$-$C_3$-alkyl;
p is 1 or 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_3$-alkyl, or —$OR^c$; or two $Z^1$ groups that are situated on the same carbon atom, together with the carbon atom to which they are attached, form an unsubstituted 5-membered monocyclic heterocycle ring comprising two oxygen ring atoms;
$R^c$ is hydrogen or $C_1$-$C_3$-alkyl;
p is 1 or 2;
$X^1$ is —OH and $X^2$ is hydrogen;
$G^1$ is unsubstituted pyridin-2-yl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_3$-alkyl, or —$OW$; or two $Z^1$ groups that are situated on the same carbon atom, together with the carbon atom to which they are attached, form an unsubstituted 5-membered monocyclic heterocycle ring comprising two oxygen ring atoms;
$R^c$ is hydrogen or $C_1$-$C_3$-alkyl;
p is 1 or 2;
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;

$X^5$ is $(CH_2)_n$;

m and n are each 1;

the two $Z^1$ groups are situated on the same carbon atom and, together with the carbon atom to which they are attached, form an unsubstituted 5-membered monocyclic heterocycle ring comprising two oxygen ring atoms;

p is 2;

$X^1$ is —OH and $X^2$ is hydrogen;

$G^1$ is unsubstituted pyridin-2-yl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, each $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

the two $Z^1$ groups are situated on the same carbon atom and, together with the carbon atom to which they are attached, form an unsubstituted 5-membered monocyclic heterocycle ring comprising two oxygen ring atoms;

p is 2;

$X^1$ is —OH and $X^2$ is hydrogen;

$G^1$ is unsubstituted pyridin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, each $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, oxo, $C_1$-$C_3$-alkyl, or —$OR^c$;

$R^c$ is hydrogen or $C_1$-$C_3$-alkyl;

p is 1 or 2;

$X^1$ is —OH and $X^2$ is hydrogen;

$G^1$ is unsubstituted pyridin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, each $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

$Z^1$ is oxo;

p is 1;

$X^1$ is —OH and $X^2$ is hydrogen;

$G^1$ is unsubstituted pyridin-2-yl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, the $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

$Z^1$ is oxo;

p is 1;

$X^1$ is —OH and $X^2$ is hydrogen;

$G^1$ is unsubstituted pyridin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, the $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, $C_1$-$C_3$-alkyl, or —OW;

$R^c$ is hydrogen or $C_1$-$C_3$-alkyl;

p is 1 or 2;

$X^1$ is —OH and $X^2$ is hydrogen;

$G^1$ is unsubstituted pyridin-2-yl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a). In a further embodiment, each $Z^1$ group is situated on the $X^3$ carbon atom.

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, $C_1$-$C_3$-alkyl, or —$OR^c$;

$R^c$ is hydrogen or $C_1$-$C_3$-alkyl;
p is 1 or 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, each $Z^1$ group is situated on the $X^3$ carbon atom.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
$Z^1$ is halogen, $C_1$-$C_3$-alkyl, or —$OR^c$;
$R^c$ is hydrogen or $C_1$-$C_3$-alkyl;
p is 1;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, the $Z^1$ group is situated on the $X^3$ carbon atom. In a further embodiment, the $Z^1$ group is situated on the $X^3$ carbon atom and $Z^1$ is $C_1$-$C_3$-alkyl. In a further embodiment, the $Z^1$ group is situated on the $X^3$ carbon atom and $Z^1$ is methyl. In a further embodiment, the $Z^1$ group is situated on the $X^3$ carbon atom, $Z^1$ is —$OR^c$, and $R^c$ is hydrogen. In a further embodiment, the $Z^1$ group is situated on the $X^3$ carbon atom, $Z^1$ is —$OR^c$, and $R^c$ is $C_1$-$C_3$-alkyl. In a further embodiment, the $Z^1$ group is situated on the $X^3$ carbon atom, $Z^1$ is —$OR^c$, and $R^c$ is methyl.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
$Z^1$ is halogen, $C_1$-$C_3$-alkyl, or —$OR^c$;
$R^c$ is hydrogen or $C_1$-$C_3$-alkyl;
p is 1;
$X^1$ is —OH and $X^2$ is hydrogen;
$G^1$ is unsubstituted pyridin-2-yl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, the $Z^1$ group is situated on the $X^3$ carbon atom. In a further embodiment, the $Z^1$ group is situated on the $X^3$ carbon atom and $Z^1$ is $C_1$-$C_3$-alkyl. In a further embodiment, the $Z^1$ group is situated on the $X^3$ carbon atom and $Z^1$ is methyl. In a further embodiment, the $Z^1$ group is situated on the $X^3$ carbon atom, $Z^1$ is —$OR^c$, and $R^c$ is hydrogen. In a further embodiment, the $Z^1$ group is situated on the $X^3$ carbon atom, $Z^1$ is —$OR^c$, and $R^c$ is $C_1$-$C_3$-alkyl. In a further embodiment, the $Z^1$ group is situated on the $X^3$ carbon atom, $Z^1$ is —$OR^c$, and $R^c$ is methyl.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
$Z^1$ is halogen, $C_1$-$C_3$-alkyl, or —$OR^c$;
$R^c$ is hydrogen or $C_1$-$C_3$-alkyl;
p is 1;
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, the $Z^1$ group is situated on the $X^3$ carbon atom. In a further embodiment, the $Z^1$ group is situated on the $X^3$ carbon atom and $Z^1$ is $C_1$-$C_3$-alkyl. In a further embodiment, the $Z^1$ group is situated on the $X^3$ carbon atom and $Z^1$ is methyl. In a further embodiment, the $Z^1$ group is situated on the $X^3$ carbon atom, $Z^1$ is —$OR^c$, and $R^c$ is hydrogen. In a further embodiment, the $Z^1$ group is situated on the $X^3$ carbon atom, $Z^1$ is —$OR^c$, and $R^c$ is $C_1$-$C_3$-alkyl. In a further embodiment, the $Z^1$ group is situated on the $X^3$ carbon atom, $Z^1$ is –$OR^c$, and $R^c$ is methyl.

In one embodiment, the invention is directed to compounds of Formula (I) wherein:
u is 0;
$X^3$ is $CH_2$;
$X^4$ is $(CH_{12})_m$;
$X^5$ is $(CH_{12})_n$;
m and n are each 1;
each $Z^1$ group is independently halogen, $C_1$-$C_3$-alkyl, or —$OR^c$;
$R^c$ is hydrogen or $C_1$-$C_3$-alkyl;
p is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, both $Z^1$ groups are situated on the $X^3$ carbon atom. In a further embodiment, both $Z^1$ groups are situated on the $X^3$ carbon atom and both $Z^1$ groups are halogen. In a further embodiment, both $Z^1$ groups are situated on the $X^3$ carbon atom and both $Z^1$ groups are $C_1$-$C_3$-alkyl. In a further embodiment, both $Z^1$ groups are situated on the $X^3$ carbon atom and both $Z^1$ groups are methyl. In a further embodiment, both $Z^1$ groups are situated on the $X^3$ carbon atom and both $Z^1$ groups are —$OR^c$ wherein $R^c$ is $C_1$-$C_3$-alkyl. In a further embodiment, both $Z^1$ groups are situated on the $X^3$ carbon atom and both $Z^1$ groups are —$OR^c$ wherein $R^c$ is methyl. In a further embodiment, both $Z^1$ groups are situated on the $X^3$ carbon atom, one $Z^1$ group is $C_1$-$C_3$-alkyl, and the other $Z^1$ group is —$OR^c$ wherein $R^c$ is hydrogen. In a further embodiment, both $Z^1$ groups are situated on the $X^3$ carbon atom, one $Z^1$ group is methyl, and the other $Z^1$ group is —$OR^c$ wherein $R^c$ is hydrogen.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, $C_1$-$C_3$-alkyl, or —$OR^c$;
$R^c$ is hydrogen or $C_1$-$C_3$-alkyl;
p is 2;
$X^1$ is —OH and $X^2$ is hydrogen;
$G^1$ is unsubstituted pyridin-2-yl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, both $Z^1$ groups are situated on the $X^3$ carbon atom. In a further embodiment, both $Z^1$ groups are situated on the $X^3$ carbon atom and both $Z^1$ groups are halogen. In a further embodiment, both $Z^1$ groups are situated on the $X^3$ carbon atom and both $Z^1$ groups are $C_1$-$C_3$-alkyl. In a further embodiment, both $Z^1$ groups are situated on the $X^3$ carbon atom and both $Z^1$ groups are methyl. In a further embodiment, both $Z^1$ groups are situated on the $X^3$ carbon atom and both $Z^1$ groups are —$OR^c$ wherein $R^c$ is $C_1$-$C_3$-alkyl. In a further embodiment, both $Z^1$ groups are situated on the $X^3$ carbon atom and both $Z^1$ groups are —$OR^c$ wherein $R^c$ is methyl. In a further embodiment, both $Z^1$ groups are situated on the $X^3$ carbon atom, one $Z^1$ group is $C_1$-$C_3$-alkyl, and the other $Z^1$ group is —OW wherein $R^c$ is hydrogen. In a further embodiment, both $Z^1$ groups are situated on the $X^3$ carbon atom, one $Z^1$ group is methyl, and the other $Z^1$ group is —$OR^c$ wherein $R^c$ is hydrogen.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, $C_1$-$C_3$-alkyl, or —$OR^c$;
p is 2;
$X^1$ is —OH and $X^2$ is hydrogen;
$R^c$ is hydrogen or $C_1$-$C_3$-alkyl;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, both $Z^1$ groups are situated on the $X^3$ carbon atom. In a further embodiment, both $Z^1$ groups are situated on the $X^3$ carbon atom and both $Z^1$ groups are halogen. In a further embodiment, both $Z^1$ groups are situated on the $X^3$ carbon atom and both $Z^1$ groups are $C_1$-$C_3$-alkyl. In a further embodiment, both $Z^1$ groups are situated on the $X^3$ carbon atom and both $Z^1$ groups are methyl. In a further embodiment, both $Z^1$ groups are situated on the $X^3$ carbon atom and both $Z^1$ groups are —$OR^c$ wherein $R^c$ is $C_1$-$C_3$-alkyl. In a further embodiment, both $Z^1$ groups are situated on the $X^3$ carbon atom and both $Z^1$ groups are —$OR^c$ wherein $R^c$ is methyl. In a further embodiment, both $Z^1$ groups are situated on the $X^3$ carbon atom, one $Z^1$ group is $C_1$-$C_3$-alkyl, and the other $Z^1$ group is —$OR^c$ wherein $R^c$ is hydrogen. In a further embodiment, both $Z^1$ groups are situated on the $X^3$ carbon atom, one $Z^1$ group is methyl, and the other $Z^1$ group is —$OR^c$ wherein $R^c$ is hydrogen.

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_4$-alkyl, or —$OR^c$; or two $Z^1$ groups that are situated on the same carbon atom, together with the carbon atom to which they are attached, form a 5-membered monocyclic heterocycle ring comprising two oxygen ring atoms;
$R^c$ is hydrogen or $C_1$-$C_4$-alkyl;
p is 1 or 2;
$X^1$ is —OH and $X^2$ is hydrogen;
$G^1$ is pyrimidinyl which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.
In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;
$X^5$ is $(CH_2)_n$;
m and n are each 1;
each $Z^1$ group is independently halogen, oxo, $C_1$-$C_4$-alkyl, or —OW; or two $Z^1$ groups that reside on the same carbon atom, together with the carbon atom to which they are attached, form an unsubstituted 5-membered monocyclic heterocycle ring comprising two oxygen ring atoms;
$R^c$ is hydrogen or $C_1$-$C_4$-alkyl;
p is 1 or 2;
$X^1$ is —OH and $X^2$ is hydrogen;
$G^1$ is unsubstituted pyrimidinyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.
In a further embodiment, the compound has the configuration of Formula (I-i-a).

In one embodiment, the invention is directed to compounds of Formula (I) wherein:
u is 0;
$X^3$ is $CH_2$;
$X^4$ is $(CH_2)_m$;

$X^5$ is $(CH_2)_n$;

m and n are each 1;

each $Z^1$ group is independently halogen, oxo, $C_1$-$C_3$-alkyl, or —OW; or two $Z^1$ groups that are situated on the same carbon atom, together with the carbon atom to which they are attached, form an unsubstituted 5-membered monocyclic heterocycle ring comprising two oxygen ring atoms;

$R^c$ is hydrogen or $C_1$-$C_3$-alkyl;

p is 1 or 2;

$X^1$ is —OH and $X^2$ is hydrogen;

$G^1$ is unsubstituted pyrimidin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, $C_1$-$C_3$-alkyl, or —$OR^c$;

$R^c$ is hydrogen or $C_1$-$C_3$-alkyl;

p is 1 or 2;

$X^1$ is —OH and $X^2$ is hydrogen;

$G^1$ is unsubstituted pyrimidin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, $C_1$-$C_3$-alkyl, or —$OR^c$;

$R^c$ is hydrogen or $C_1$-$C_3$-alkyl;

p is 1 or 2;

$X^1$ is —OH and $X^2$ is hydrogen;

$G^1$ is unsubstituted pyrimidin-2-yl;

$G^2$ is $G^{2d}$;

$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently halogen, $C_1$-$C_3$-alkyl, or —$OR^c$;

$R^c$ is hydrogen or $C_1$-$C_3$-alkyl;

p is 1 or 2;

$X^1$ is —OH and $X^2$ is hydrogen;

$G^1$ is unsubstituted pyrimidin-2-yl;

$G^2$ is $G^{2d}$;

$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (I-i-a).

In one embodiment, the invention is directed to compounds of Formula (I) wherein:

u is 0;

$X^3$ is $CH_2$;

$X^4$ is $(CH_2)_m$;

$X^5$ is $(CH_2)_n$;

m and n are each 1;

each $Z^1$ group is independently methyl or —$OR^c$;

$R^c$ is hydrogen;

p is 1 or 2;

$X^1$ is —OH and $X^2$ is hydrogen;

$G^1$ is unsubstituted pyrimidin-2-yl;

$G^2$ is $G^{2d}$;

$G^{2d}$ is phenyl or pyridinyl; each of which is optionally substituted with 1, 2, or 3 substituents independently selected from the group consisting of halogen, trifluoromethyl, and —$OR^f$ and $R^f$ is trifluoromethyl.

In a further embodiment, the compound has the configuration of Formula (I-i-a).

In further embodiments, one $Z^1$ substituent is —$OR^c$, and the substituent containing $X^1$ and the —$OR^c$ substituent have a cis configuration (e.g., compounds of Formula I-iv-c).

In further embodiments, one $Z^1$ substituent is —$OR^c$, and the substituent containing $X^1$ and the —$OR^c$ substituent have a trans configuration (e.g., compounds of Formula I-iv-d).

In one embodiment, the invention is directed to compounds of Formula (I) selected from the group consisting of:

[1-(3,4-dichlorophenyl)-3,3-difluorocyclobutyl](pyridin-2-yl)methanol;

(S)-[1-(3,4-dichlorophenyl)-3,3-difluorocyclobutyl](pyridin-2-yl)methanol;

{3,3-difluoro-1-[4-(trifluoromethoxy)phenyl]cyclobutyl}(pyridin-2-yl)-methanol;

{3,3-difluoro-1-[3-(trifluoromethyl)phenyl]cyclobutyl}(pyridin-2-yl)-methanol;

{3,3-difluoro-1-[3-(trifluoromethoxy)phenyl]cyclobutyl}(pyridin-2-yl)-methanol;

3-(3,4-dichlorophenyl)-3-[(S)-hydroxy(pyridin-2-yl)methyl]cyclobutanone;

(trans)-3-(3,4-dichlorophenyl)-3-[(S)-hydroxy(pyridin-2-yl)methyl]-cyclobutanol;

(cis)-3-(3,4-dichlorophenyl)-3-[(S)-hydroxy(pyridin-2-yl)methyl]-cyclobutanol;

(R)-{3,3-difluoro-1-[4-(trifluoromethyl)pyridin-2-yl]cyclobutyl}(pyridin-2-yl)methanol;

(S)-{3,3-difluoro-1-[4-(trifluoromethyl)pyridin-2-yl]cyclobutyl}(pyridin-2-yl)methanol;

(S)-{3,3-difluoro-1-[4-(trifluoromethoxy)phenyl]cyclobutyl}(pyridin-2-yl)-methanol;

{3,3-dimethoxy-1-[4-(trifluoromethoxy)phenyl]cyclobutyl}(pyridin-2-yl)-methanol;

cis-3-[(S)-hydroxy(pyridin-2-yl)methyl]-3-[4-(trifluoromethoxy)phenyl]-cyclobutanol;
(trans)-3-[(S)-hydroxy(pyridin-2-yl)methyl]-3-[4-(trifluoromethoxy)-phenyl]cyclobutanol;
{3,3-difluoro-1-[4-(trifluoromethyl)phenyl]cyclobutyl}(pyridin-2-yl)-methanol;
cis-3-[(S)-hydroxy(pyridin-2-yl)methyl]-1-methyl-3-[4-(trifluoromethoxy)-phenyl]cyclobutanol;
{3,3-difluoro-1-[5-(trifluoromethyl)pyridin-2-yl]cyclobutyl}(pyridin-2-yl)-methanol;
{1-[4-chloro-3-(trifluoromethyl)phenyl]-3,3-difluorocyclobutyl}(pyridin-2-yl)methanol;
{3,3-difluoro-1-[4-fluoro-3-(trifluoromethyl)phenyl]cyclobutyl}(pyridin-2-yl)methanol;
(S)-[cis-1-(3,4-dichlorophenyl)-3-methoxycyclobutyl](pyridin-2-yl)-methanol;
(S)-[1-(3,4-dichlorophenyl)-3-methoxycyclobutyl](pyridin-2-yl)methanol;
(S)-{3,3-difluoro-1-[4-(trifluoromethyl)phenyl]cyclobutyl}(pyridin-2-yl)-methanol;
(R)-{3,3-difluoro-1-[4-(trifluoromethoxy)phenyl]cyclobutyl}(pyridin-2-yl)-methanol;
3-[hydroxy(pyridin-2-yl)methyl]-3-[4-(trifluoromethyl)phenyl]-cyclobutanone;
pyridin-2-yl{2-[4-(trifluoromethyl)phenyl]-5,8-dioxaspiro[3.4]oct-2-yl}-methanol;
3-[(S)-hydroxy(pyridin-2-yl)methyl]-3-[4-(trifluoromethyl)phenyl]-cyclobutanone;
3-[(R)-hydroxy(pyridin-2-yl)methyl]-3-[4-(trifluoromethyl)phenyl]-cyclobutanone;
3-[(S)-hydroxy(pyridin-2-yl)methyl]-3-[4-(trifluoromethyl)phenyl]-cyclobutanol;
3-[(R)-hydroxy(pyridin-2-yl)methyl]-3-[4-(trifluoromethyl)phenyl]-cyclobutanol;
cis-3-[(S)-hydroxy(pyridin-2-yl)methyl]-3-[4-(trifluoromethyl)phenyl]-cyclobutanol;
trans-3-[(S)-hydroxy(pyridin-2-yl)methyl]-3-[4-(trifluoromethyl)phenyl]-cyclobutanol;
pyridin-2-yl{2-[4-(trifluoromethoxy)phenyl]-5,8-dioxaspiro[3.4]oct-2-yl}-methanol;
trans-3-[(S)-hydroxy(pyridin-2-yl)methyl]-1-methyl-3-[4-(trifluoromethoxy)phenyl]cyclobutanol;
cis-3-[(S)-hydroxy(pyridin-2-yl)methyl]-1-methyl-3-[4-(trifluoromethyl)phenyl]cyclobutanol;
trans-3-[(S)-hydroxy(pyridin-2-yl)methyl]-1-methyl-3-[4-(trifluoromethyl)-phenyl]cyclobutanol;
pyridin-2-yl{2-[3-(trifluoromethoxy)phenyl]-5,8-dioxaspiro[3.4]oct-2-yl}-methanol;
cis-3-[(S)-hydroxy(pyridin-2-yl)methyl]-1-methyl-3-[3-(trifluoromethyl)-phenyl]cyclobutanol;
3-[hydroxy(pyridin-2-yl)methyl]-3-[3-(trifluoromethoxy)phenyl]-cyclobutanone;
3-[(S)-hydroxy(pyridin-2-yl)methyl]-3-[3-(trifluoromethyl)phenyl]-cyclobutanone;
pyridin-2-yl{2-[3-(trifluoromethyl)phenyl]-5,8-dioxaspiro[3.4]oct-2-yl}-methanol;
3-[(R)-hydroxy(pyridin-2-yl)methyl]-3-[3-(trifluoromethyl)phenyl]-cyclobutanone;
trans-3-[(S)-hydroxy(pyridin-2-yl)methyl]-1-methyl-3-[3-(trifluoromethyl)-phenyl]cyclobutanol;
3-[hydroxy(pyridin-2-yl)methyl]-3-[3-(trifluoromethyl)phenyl]-cyclobutanone;
cis-3-(3,4-dichlorophenyl)-3-[(R)-hydroxy(pyridin-2-yl)methyl]-cyclobutanol;
(S)-{3-(hydroxyimino)-1-[4-(trifluoromethoxy)phenyl]cyclobutyl}(pyridin-2-yl)methanol;
(S)-{3-(methoxyimino)-1-[4-(trifluoromethoxy)phenyl]cyclobutyl}-(pyridin-2-yl)methanol;
cis-3-[(R)-hydroxy(pyridin-2-yl)methyl]-1-methyl-3-[4-(trifluoromethoxy)-phenyl]cyclobutanol;
3-[(S)-hydroxy(pyridin-2-yl)methyl]-3-[4-(trifluoromethoxy)phenyl]-cyclobutanone;
[2-(3-chloro-4-fluorophenyl)-5,8-dioxaspiro[3.4]oct-2-yl](pyridin-2-yl)-methanol;
3-[(S)-hydroxy(pyridin-2-yl)methyl]-3-[3-(trifluoromethoxy)phenyl]-cyclobutanone;
3-[(R)-hydroxy(pyridin-2-yl)methyl]-3-[3-(trifluoromethoxy)phenyl]-cyclobutanone;
3-(3-chloro-4-fluorophenyl)-3-[hydroxy(pyridin-2-yl)methyl]-cyclobutanone;
cis-3-[(S)-hydroxy(pyridin-2-yl)methyl]-3-[3-(trifluoromethyl)phenyl]-cyclobutanol;
cis-3-[(S)-hydroxy(pyridin-2-yl)methyl]-1-methyl-3-[3-(trifluoromethoxy)-phenyl]cyclobutanol;
trans-3-[(S)-hydroxy(pyridin-2-yl)methyl]-1-methyl-3-[3-(trifluoromethoxy)phenyl]-cyclobutanol;
trans-3-[(S)-hydroxy(pyridin-2-yl)methyl]-3-[3-(trifluoromethyl)-phenyl]cyclobutanol;
(S)-{3-(dimethylhydrazinylidene)-1-[4-(trifluoromethoxy)phenyl]-cyclobutyl}(pyridin-2-yl)methanol;
3-(3-chloro-4-fluorophenyl)-3-[(S)-hydroxy(pyridin-2-yl)methyl]-cyclobutanone;
cis-3-[(S)-hydroxy(pyridin-2-yl)methyl]-3-[3-(trifluoromethoxy)-phenyl]cyclobutanol;
trans-3-[(S)-hydroxy(pyridin-2-yl)methyl]-3-[3-(trifluoromethoxy)-phenyl]cyclobutanol;
3-(3-chloro-4-fluorophenyl)-3-[(S)-hydroxy(pyridin-2-yl)methyl]-cyclobutanol;
3-[(S)-hydroxy(pyridin-2-yl)methyl]-3-[4-(trifluoromethyl)pyridin-2-yl]-cyclobutanone;
3-[(R)-hydroxy(pyridin-2-yl)methyl]-3-[4-(trifluoromethyl)pyridin-2-yl]-cyclobutanone;
cis-3-[(S)-hydroxy(pyridin-2-yl)methyl]-3-[4-(trifluoromethyl)pyridin-2-yl]cyclobutanol;
trans-3-[(S)-hydroxy(pyridin-2-yl)methyl]-3-[4-(trifluoromethyl)pyridin-2-yl]cyclobutanol;
cis-3-[(S)-hydroxy(pyridin-2-yl)methyl]-1-methyl-3-[4-(trifluoromethyl)-pyridin-2-yl]-cyclobutanol;
trans-3-[(S)-hydroxy(pyridin-2-yl)methyl]-3-[4-(trifluoromethyl)pyridin-2-yl]cyclobutanol;
cis-3-[(R)-hydroxy(pyridin-2-yl)methyl]-3-[4-(trifluoromethyl)pyridin-2-yl]cyclobutanol;
3-[(R)-hydroxy(pyridin-2-yl)methyl]-3-[6-methyl-4-(trifluoromethyl)-pyridin-2-yl]-cyclobutanone;
3-[hydroxy(pyridin-2-yl)methyl]-3-[4-(trifluoromethyl)pyridin-2-yl]-cyclobutanone;
3-[(S)-hydroxy(pyridin-2-yl)methyl]-3-[4-(trifluoromethyl)pyridin-2-yl]cyclobutanol;
3-[hydroxy(pyridin-2-yl)methyl]-3-[5-(trifluoromethyl)pyridin-3-yl]-cyclobutanone;
3-[(S)-hydroxy(pyridin-2-yl)methyl]-3-[5-(trifluoromethyl)pyridin-3-yl]-cyclobutanone;
pyridin-2-yl{2-[2-(trifluoromethyl)pyridin-4-yl]-5,8-dioxaspiro[3.4]oct-2-yl}methanol;
3-[hydroxy(pyridin-2-yl)methyl]-3-[2-(trifluoromethyl)pyridin-4-yl]-cyclobutanone;
3-[(S)-hydroxy(pyridin-2-yl)methyl]-3-[2-(trifluoromethyl)pyridin-4-yl]-cyclobutanone;
cis-3-[(S)-hydroxy(pyridin-2-yl)methyl]-1-methyl-3-[2-(trifluoromethyl)-pyridin-4-yl]-cyclobutanol;
cis-3-[(S)-hydroxy(pyridin-2-yl)methyl]-3-[5-(trifluoromethyl)pyridin-3-yl]cyclobutanol;

trans-3-[(S)-hydroxy(pyridin-2-yl)methyl]-3-[5-(trifluoromethyl)pyridin-3-yl]cyclobutanol;
cis-3-[(S)-hydroxy(pyridin-2-yl)methyl]-3-[2-(trifluoromethyl)pyridin-4-yl]-cyclobutanol;
trans-3-[(S)-hydroxy(pyridin-2-yl)methyl]-3-[2-(trifluoromethyl)pyridin-4-yl]cyclobutanol;
trans-3-[(S)-hydroxy(pyridin-2-yl)methyl]-1-methyl-3-[2-(trifluoromethyl)pyridin-4-yl]-cyclobutanol;
cis-3-[(S)-hydroxy(pyridin-2-yl)methyl]-1-methyl-3-[5-(trifluoromethyl)-pyridin-3-yl]-cyclobutanol;
trans-3-[(S)-hydroxy(pyridin-2-yl)methyl]-1-methyl-3-[5-(trifluoromethyl)-pyridin-3-yl]cyclobutanol;
(trans)-3-((S)-hydroxy(pyrimidin-2-yl)methyl)-1-methyl-3-(4-(trifluoromethoxy)phenyl)-cyclobutanol;
(trans)-3-((R)-hydroxy(pyrimidin-2-yl)methyl)-1-methyl-3-(4-(trifluoromethoxy)phenyl)-cyclobutanol;
(trans)-3-(3,4-dichlorophenyl)-3-((S)-hydroxy(pyrimidin-2-yl)methyl)-cyclobutanol; and
(trans)-3-(3,4-dichlorophenyl)-3-((R)-hydroxy(pyrimidin-2-yl)methyl)-cyclobutanol.

In one embodiment, the invention is directed to compounds of Formula (I-iv-e):

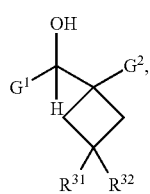

(I-iv-e)

wherein:
$G^1$ is unsubstituted pyridin-2-yl or unsubstituted pyrimidin-2-yl;
$G^2$ is $G^{2d}$;
$G^{2d}$ is phenyl, pyridinyl, or pyrimidinyl; each of which is optionally substituted with 1 or 2 substituents independently selected from the group consisting of halogen, trifluoromethyl, and trifluoromethoxy; and
$R^{31}$ and $R^{32}$ are independently selected from the group consisting of hydrogen, halogen, hydroxy, and methyl.

In one embodiment, the invention is directed to compounds of Formula (I-iv-e) wherein:
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1 or 2 substituents independently selected from the group consisting of halogen, trifluoromethyl, and trifluoromethoxy; and
$R^{31}$ and $R^{32}$ are independently selected from the group consisting of hydrogen, fluoro, hydroxy, and methyl.

In one embodiment, the invention is directed to compounds of Formula (I-iv-c) wherein:
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1 or 2 substituents independently selected from the group consisting of fluoro, trifluoromethyl, and trifluoromethoxy; and
one of $R^{31}$ and $R^{32}$ is hydrogen and the other of $R^{31}$ and $R^{32}$ is hydroxy.

In one embodiment, the invention is directed to compounds of Formula (I-iv-e) wherein:
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1 or 2 substituents independently selected from the group consisting of fluoro, trifluoromethyl, and trifluoromethoxy; and
one of $R^{31}$ and $R^{32}$ is hydrogen and the other of $R^{31}$ and $R^{32}$ is methyl.

In one embodiment, the invention is directed to compounds of Formula (I-iv-e) wherein:
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1 or 2 substituents independently selected from the group consisting of fluoro, trifluoromethyl, and trifluoromethoxy; and
$R^{31}$ and $R^{32}$ are each fluoro.

In one embodiment, the invention is directed to compounds of Formula (I-iv-e) selected from the group consisting of:
3-(3,4-dichlorophenyl)-3-[hydroxy(pyridin-2-yl)methyl]cyclobutanol;
{3,3-difluoro-1-[4-(trifluoromethoxy)phenyl]cyclobutyl}(pyridin-2-yl)-methanol;
3-[hydroxy(pyridin-2-yl)methyl]-3-[4-(trifluoromethoxy)phenyl]-cyclobutanol;
3-[hydroxy(pyridin-2-yl)methyl]-1-methyl-3-[4-(trifluoromethoxy)-phenyl]cyclobutanol;
3-[hydroxy(pyridin-2-yl)methyl]-3-[4-(trifluoromethyl)phenyl]-cyclobutanol;
3-[hydroxy(pyridin-2-yl)methyl]-1-methyl-3-[4-(trifluoromethyl)-phenyl]cyclobutanol;
3-[hydroxy(pyridin-2-yl)methyl]-1-methyl-3-[3-(trifluoromethyl)-phenyl]cyclobutanol;
3-[hydroxy(pyridin-2-yl)methyl]-3-[3-(trifluoromethyl)phenyl]-cyclobutanol;
3-[hydroxy(pyridin-2-yl)methyl]-1-methyl-3-[3-(trifluoromethoxy)-phenyl]cyclobutanol;
3-[hydroxy(pyridin-2-yl)methyl]-3-[3-(trifluoromethoxy)phenyl]-cyclobutanol;
3-[hydroxy(pyridin-2-yl)methyl]-3-[4-(trifluoromethyl)pyridin-2-yl]cyclobutanol;
3-[hydroxy(pyridin-2-yl)methyl]-1-methyl-3-[4-(trifluoromethyl)-pyridin-2-yl]cyclobutanol;
3-[hydroxy(pyridin-2-yl)methyl]-3-[5-(trifluoromethyl)pyridin-3-yl]-cyclobutanol;
3-[hydroxy(pyridin-2-yl)methyl]-3-[2-(trifluoromethyl)pyridin-4-yl]-cyclobutanol; and
3-(3,4-dichlorophenyl)-3-(hydroxy(pyrimidin-2-yl)methyl)-cyclobutanol.

In another embodiment, the invention is directed to compounds of Formula (I-iv-e) wherein:
(trans)-3-(3,4-dichlorophenyl)-3-[(S)-hydroxy(pyridin-2-yl)methyl]-cyclobutanol;
(cis)-3-(3,4-dichlorophenyl)-3-[(S)-hydroxy(pyridin-2-yl)methyl]-cyclobutanol;
(S)-{3,3-difluoro-1-[4-(trifluoromethoxy)phenyl]cyclobutyl}(pyridin-2-yl)-methanol;
cis-3-[(S)-hydroxy(pyridin-2-yl)methyl]-3-[4-(trifluoromethoxy)phenyl]-cyclobutanol;
cis-3-[(S)-hydroxy(pyridin-2-yl)methyl]-1-methyl-3-[4-(trifluoromethoxy)-phenyl]cyclobutanol;
trans-3-[(S)-hydroxy(pyridin-2-yl)methyl]-3-[4-(trifluoromethyl)phenyl]-cyclobutanol;

cis-3-[(S)-hydroxy(pyridin-2-yl)methyl]-1-methyl-3-[4-(trifluoromethyl)-phenyl]cyclobutanol;
cis-3-[(S)-hydroxy(pyridin-2-yl)methyl]-1-methyl-3-[3-(trifluoromethyl)-phenyl]cyclobutanol;
cis-3-[(S)-hydroxy(pyridin-2-yl)methyl]-3-[3-(trifluoromethyl)phenyl]-cyclobutanol;
cis-3-[(S)-hydroxy(pyridin-2-yl)methyl]-1-methyl-3-[3-(trifluoromethoxy)-phenyl]cyclobutanol;
trans-3-[(S)-hydroxy(pyridin-2-yl)methyl]-3-[3-(trifluoromethyl)phenyl]-cyclobutanol;
cis-3-[(S)-hydroxy(pyridin-2-yl)methyl]-3-[3-(trifluoromethoxy)phenyl]-cyclobutanol;
trans-3-[(S)-hydroxy(pyridin-2-yl)methyl]-3-[3-(trifluoromethoxy)phenyl]-cyclobutanol;
cis-3-[(S)-hydroxy(pyridin-2-yl)methyl]-3-[4-(trifluoromethyl)pyridin-2-yl]cyclobutanol;
trans-3-[(S)-hydroxy(pyridin-2-yl)methyl]-3-[4-(trifluoromethyl)pyridin-2-yl]cyclobutanol;
cis-3-[(S)-hydroxy(pyridin-2-yl)methyl]-1-methyl-3-[4-(trifluoromethyl)-pyridin-2-yl]cyclobutanol;
trans-3-[(S)-hydroxy(pyridin-2-yl)methyl]-3-[5-(trifluoromethyl)pyridin-3-yl]cyclobutanol
trans-3-[(S)-hydroxy(pyridin-2-yl)methyl]-3-[2-(trifluoromethyl)pyridin-4-yl]cyclobutanol; and
(trans)-3-(3,4-dichlorophenyl)-3-((S)-hydroxy(pyrimidin-2-yl)methyl)-cyclobutanol.

(ii) Substituted Azetidinyl Ring

In one embodiment, the invention is directed to compounds of Formula (I) wherein:

each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is $N(R^{1x})$, wherein $R^{1x}$ is alkyl, —C(O)alkyl, or —C(O)O(alkyl);

$X^4$ is $(CH_2)_m$;

$X^5$ is $(CH_2)_n$;

m and n are each 1;

each $Z^1$ group is a substituent on any substitutable carbon atom of the ring containing $X^3$, $X^4$, and $X^5$, and is independently alkyl, $C(O)R^{cz}$, $S(O)_2R^{cz}$, $N(R^{1d})(R^{2d})$, $OR^c$, oxo, =$NOR^{z1}$, =$NNR^{z1}R^{z2}$, =$NR^{z3}$, halogen, haloalkyl, —($C_1$-$C_6$ alkylenyl)-$OR^{cz}$, —($C_1$-$C_6$ alkylenyl)-$C(O)R^{cz}$, —($C_1$-$C_6$ alkylenyl)-$S(O)_2R^{cz}$, or —($C_1$-$C_6$ alkylenyl)-$N(R^{1d})(R^{2d})$; two $Z^1$ groups that are situated on the same carbon atom, together with the carbon atom to which they are attached optionally form a 4-6 membered monocyclic cycloalkyl or monocyclic heterocycle ring; wherein said ring is optionally substituted with 1, 2, 3, or 4 substituents independently selected from the group consisting of alkyl, haloalkyl, and halogen;

$R^{z1}$, $R^{z2}$, $R^{z3}$ are each independently hydrogen, alkyl, —C(O)(alkyl), —C(O)-$G^d$, or haloalkyl;

$R^{cz}$, at each occurrence, is independently alkyl, haloalkyl, $NH_2$, $N(H)(alkyl)$, or $N(alkyl)_2$;

$R^{1d}$, at each occurrence, is independently hydrogen, alkyl, haloalkyl, C(O)alkyl, or C(O)O(alkyl);

$R^{2d}$ and $R^c$, at each occurrence, are each independently hydrogen, alkyl, or haloalkyl;

p is 0;

$X^1$ is —OH and $X^2$ is hydrogen;

$G^{2d}$ is aryl, heteroaryl, cycloalkyl, heterocycle, or cycloalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, —$(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN;

$G^2$ is $G^{2d}$ or —$(CR^{1g}R^{2g})_r$-$G^{2d}$ wherein:

r is 1, 2, or 3;

$R^{1g}$ and $R^{2g}$ are the same or different, and are each independently hydrogen, alkyl, halogen, $OR^{1gc}$, $N(R^{1gc})_2$, C(O)alkyl, or haloalkyl; wherein each $R^{1gc}$ is independently hydrogen, alkyl, or haloalkyl;

$G^{2d}$ is aryl, heteroaryl, cycloalkyl, heterocycle, or cycloalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R)_2$, —$N(R^f)_2$, —$N(R^f)C(O)R^f$, —$N(R^f)S(O)_2R^e$, —$N(R^f)C(O)O(R^e)$, —$N(R^f)C(O)N(R)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$C(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R)C(O)R^f$, —$(CR^{1a}R^{1b})_q$—$N(R^f)S(O)_2R^e$, —$(CR^{1a}R^{1b})_q$—$N(R)C(O)O(R^e)$, —$(CR^{1a}R^{1b})_q$—$N(R^f)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, haloalkyl, $G^d$, or —$(CR^{1a}R^{1b})_q$-$G^d$;

each occurrence of $R^e$ is independently alkyl, haloalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^j$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$C(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or haloalkyl; and each occurrence of $R^k$ is independently alkyl or haloalkyl.

In a preferred embodiment, u is 0. In further embodiments where u is 0, the compound has the configuration of Formula (I-i-a):

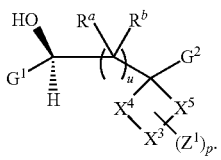

(I-i-a)

In one embodiment, the invention is directed to compounds of Formula (I) wherein:
u is 0;
$X^3$ is $N(R^{1x})$, wherein $R^{1x}$ is alkyl, —C(O)alkyl, or —C(O)O(alkyl);
$X^4$ is $(CH_2)_m$;
$X^5$ is $(CH_2)_n$;
m and n are each 1;
p is 0;
$X^1$ is —OH and $X^2$ is hydrogen;
$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;
$R^{gc}$ is hydrogen or $C_1$-$C_6$-alkyl;
$G^2$ is $G^{2d}$;
$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and
$R^f$ is $C_1$-$C_6$-alkyl or $C_1$-$C_6$-haloalkyl.
In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O-$C_1$-$C_4$-alkyl;
$X^4$ is $(CH_2)_m$;
$X^5$ is $(CH_2)_n$;
m and n are each 1;
p is 0;
$X^1$ is —OH and $X^2$ is hydrogen;
$G^1$ is pyridinyl; each of which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_6$-alkyl, $C_1$-$C_6$-haloalkyl, and —$OR^f$; and
$R^f$ is $C_1$-$C_4$-alkyl or $C_1$-$C_4$-haloalkyl.
In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 1;
p is 0;
$X^1$ is —OH and $X^2$ is hydrogen;
$G^1$ is unsubstituted pyridinyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.
In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 1;
p is 0;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, $R^{1x}$ is $C_1$-$C_4$-alkyl. In a further embodiment, $R^{1x}$ is methyl. In a further embodiment, $R^{1x}$ is —C(O)—$C_1$-$C_4$-alkyl. In a further embodiment, $R^{1x}$ is —C(O)O—$C_1$-$C_4$-alkyl. In a further embodiment, $R^{1x}$ is tert-butoxycarbonyl.

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 1;
p is 0;
$X^1$ is —OH and $X^2$ is hydrogen;
$G^1$ is unsubstituted pyridin-2-yl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (I-i-a). In a further embodiment, $R^{1x}$ is $C_1$-$C_4$-alkyl. In a further embodiment, $R^{1x}$ is methyl. In a further embodiment, $R^{1x}$ is —C(O)—$C_1$-$C_4$-alkyl. In a further embodiment, $R^{1x}$ is —C(O)O—$C_1$-$C_4$-alkyl. In a further embodiment, $R^{1x}$ is tert-butoxycarbonyl.

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 1;
p is 0;
$X^1$ is —OH and $X^2$ is hydrogen;
$G^1$ is unsubstituted pyridin-2-yl;
$G^2$ is $G^{2d}$;

$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —OR$^f$; and R$^f$ is $C_1$-$C_3$-alkyl or $C_1$-$C_3$-haloalkyl.

In a further embodiment, the compound has the configuration of Formula (I-i-a). In a further embodiment, R$^{1x}$ is $C_1$-$C_4$-alkyl. In a further embodiment, R$^{1x}$ is methyl. In a further embodiment, R$^{1x}$ is —C(O)—$C_1$-$C_4$-alkyl. In a further embodiment, R$^{1x}$ is —C(O)O—$C_1$-$C_4$-alkyl. In a further embodiment, R$^{1x}$ is tert-butoxycarbonyl.

In one embodiment, the compound of Formula (I) is selected from the group consisting of:

tert-butyl 3-[hydroxy(pyridin-2-yl)methyl]-3-[4-(trifluoromethyl)phenyl]azetidine-1-carboxylate; and {1-methyl-3-[4-(trifluoromethyl)phenyl]azetidin-3-yl}(pyridin-2-yl)methanol (iii) Substituted Piperidinyl Ring In one embodiment, the invention is directed to compounds of Formula (I) wherein:

each occurrence of R$^a$ and R$^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

X$^3$ is N(R$^{1x}$), wherein R$^{1x}$ is alkyl, —C(O)alkyl, or —C(O)O(alkyl);

X$^4$ is (CH$_2$)$_m$;

X$^5$ is (CH$_2$)$_n$;

m and n are each 2;

each Z$^1$ group is a substituent on any substitutable carbon atom of the ring containing X$^3$, X$^4$, and X$^5$, and is independently alkyl, C(O)R$^{cz}$, S(O)$_2$R$^{cz}$, N(R$^{1d}$)(R$^{2d}$), OR$^c$, oxo, =NOR$^{z1}$, =NNR$^{z1}$R$^{z2}$, =NR$^{z3}$, halogen, haloalkyl, —(C$_1$-C$_6$ alkylenyl)-OR$^c$, —(C$_1$-C$_6$ alkylenyl)-C(O)R$^{cz}$, —(C$_1$-C$_6$ alkylenyl)-S(O)$_2$R$^{cz}$, or —(C$_1$-C$_6$ alkylenyl)-N(R$^{1d}$)(R$^{2d}$);

two Z$^1$ groups that are situated on the same carbon atom, together with the carbon atom to which they are attached optionally form a 4-6 membered monocyclic cycloalkyl or monocyclic heterocycle ring; wherein said ring is optionally substituted with 1, 2, 3, or 4 substituents independently selected from the group consisting of alkyl, haloalkyl, and halogen;

R$^{z1}$, R$^{z2}$, R$^{z3}$ are each independently hydrogen, alkyl, —C(O)(alkyl), —C(O)-G$^d$, or haloalkyl;

R$^{cz}$, at each occurrence, is independently alkyl, haloalkyl, NH$_2$, N(H)(alkyl), or N(alkyl)$_2$;

R$^{1d}$, at each occurrence, is independently hydrogen, alkyl, haloalkyl, C(O)alkyl, or C(O)O(alkyl);

R$^{2d}$ and R$^c$, at each occurrence, are each independently hydrogen, alkyl, or haloalkyl;

p is 0;

X$^1$ is —OH and X$^2$ is hydrogen;

G$^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, OR$^{gc}$, N(R$^{gc}$)$_2$, N(R$^{gc}$)C(O)alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each R$^{gc}$ is independently hydrogen, alkyl, or haloalkyl;

G$^2$ is G$^{2d}$ or —(CR$^{1g}$R$^{2g}$)$_r$-G$^{2d}$ wherein:

r is 1, 2, or 3;

R$^{1g}$ and R$^{2g}$ are the same or different, and are each independently hydrogen, alkyl, halogen, OR$^{1gc}$, N(R$^{1gc}$)$_2$, C(O)alkyl, or haloalkyl; wherein each R$^{1gc}$ is independently hydrogen, alkyl, or haloalkyl;

G$^{2d}$ is aryl, heteroaryl, cycloalkyl, heterocycle, or cycloalkenyl, each of which is optionally substituted with 1, 2, 3, 4, or 5 substituents independently selected from the group consisting of G$^d$, alkyl, alkenyl, alkynyl, halogen, haloalkyl, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—C(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O(R$^e$), —(CR$^{1a}$R$^{1b}$)$_q$—N(R)C(O)N(R$^f$)$_2$, and —(CR$^{1a}$R$^{1b}$)$_q$—CN;

R$^{1a}$ and R$^{1b}$, are the same or different, and at each occurrence are each independently hydrogen, halogen, alkyl, or haloalkyl;

each occurrence of R$^f$ is independently hydrogen, alkyl, haloalkyl, G$^d$, or —(CR$^{1a}$R$^{1b}$)$_q$-G$^d$;

each occurrence of R$^e$ is independently alkyl, haloalkyl, G$^d$, or —(CR$^{1a}$R$^{1b}$)$_q$-G$^d$;

q, at each occurrence, is independently 1, 2, or 3;

each occurrence of G$^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —OW, —OC(O)R$^j$, —OC(O)N(R$^j$)$_2$, —S(O)$_2$R$^k$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^j$, —N(R$^j$)S(O)$_2$R$^k$, —N(R$^j$)C(O)O(R$^k$), —N(R$^j$)C(O)N(R$^j$)$_2$, —(CR$^{1a}$R$^{1b}$)$_q$—OR$^j$, —(CR$^{1a}$R$^{1b}$)$_q$—OC(O)R$^j$, —(CR$^{1a}$R$^{1b}$)$_q$—OC(O)N(R$^j$)$_2$, —(CR$^{1a}$R$^{1b}$)$_q$—S(O)$_2$R$^k$, —(CR$^{1a}$R$^{1b}$)$_q$—S(O)$_2$N(R$^j$)$_2$, —(CR$^{1a}$R$^{1b}$)$_q$—C(O)R$^j$, —(CR$^{1a}$R$^{1b}$)$_q$—C(O)OR$^j$, —(CR$^{1a}$R$^{1b}$)$_q$—C(O)N(R$^j$)$_2$, —(CR$^{1a}$R$^{1b}$)$_q$—N(R$^j$)$_2$, —(CR$^{1a}$R$^{1b}$)$_q$—N(R$^j$)C(O)R$^j$, —(CR$^{1a}$R$^{1b}$)$_q$—N(R$^j$)S(O)$_2$R$^k$, —(CR$^{1a}$R$^{1b}$)$_q$—N(R$^j$)C(O)O(R$^k$), —(CR$^{1a}$R$^{1b}$)$_q$—N(R$^j$)C(O)N(R$^j$)$_2$, and —(CR$^{1a}$R$^{1b}$)$_q$—CN;

each occurrence of R$^j$ is independently hydrogen, alkyl, or haloalkyl; and each occurrence of R$^k$ is independently alkyl or haloalkyl.

In a preferred embodiment, u is 0. In further embodiments where u is 0, the compound has the configuration of Formula (I-i-a):

(I-i-a)

In one embodiment, the invention is directed to compounds of Formula (I) wherein:

u is 0;

X$^3$ is N(R$^{1x}$), wherein R$^{1x}$ is alkyl, —C(O)alkyl, or —C(O)O(alkyl);

X$^4$ is (CH$_2$)$_m$;

X$^5$ is (CH$_2$)$_n$;

m and n are each 2;
p is 0;
$X^1$ is —OH and $X^2$ is hydrogen;
$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;
$R^{gc}$ is hydrogen or $C_1$-$C_6$-alkyl;
$G^2$ is $G^{2d}$;
$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and
$R^f$ is $C_1$-$C_6$-alkyl or $C_1$-$C_6$-haloalkyl.

In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 2;
p is 0;
$X^1$ is —OH and $X^2$ is hydrogen;
$G^1$ is pyridinyl; each of which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_6$-alkyl, $C_1$-$C_6$-haloalkyl, and —$OR^f$; and
$R^f$ is $C_1$-$C_4$-alkyl or $C_1$-$C_4$-haloalkyl.

In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 2;
p is 0;
$X^1$ is —OH and $X^2$ is hydrogen;
$G^1$ is unsubstituted pyridinyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

In a further embodiment, the compound has the configuration of Formula (I-i-a).

In one embodiment, the invention is directed to compounds of Formula (I) wherein:
u is 0;
$X^3$ is $N(R^{1x})$, wherein $R^{1x}$ is $R^{1x}$ is $C_1$-$C_4$-alkyl, —C(O)—$C_1$-$C_4$-alkyl, or —C(O)O-$C_1$-$C_4$-alkyl;
$X^4$ is $(CH_2)_m$;
$X^5$ is $(CH_2)_n$;
m and n are each 2;
p is 0;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a). In a further embodiment, $R^{1x}$ is $C_1$-$C_4$-alkyl. In a further embodiment, $R^{1x}$ is methyl. In a further embodiment, $R^{1x}$ is —C(O)—$C_1$-$C_4$-alkyl. In a further embodiment, $R^{1x}$ is —C(O)O—$C_1$-$C_4$-alkyl. In a further embodiment, $R^{1x}$ is tert-butoxycarbonyl.

In one embodiment, the invention is directed to compounds of Formula (I) wherein:
u is 0;
$X^3$ is $N(R^{1x})$, wherein $R^{1x}$ is $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 2;
p is 0;
$X^1$ is —OH and $X^2$ is hydrogen;
$G^1$ is unsubstituted pyridin-2-yl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a). In a further embodiment, $R^{1x}$ is $C_1$-$C_4$-alkyl. In a further embodiment, $R^{1x}$ is methyl. In a further embodiment, $R^{1x}$ is —C(O)—$C_1$-$C_4$-alkyl. In a further embodiment, $R^{1x}$ is —C(O)O—$C_1$-$C_4$-alkyl. In a further embodiment, $R^{1x}$ is tert-butoxycarbonyl.

In one embodiment, the invention is directed to compounds of Formula (I) wherein:
u is 0;
$X^3$ is $N(R^{1x})$, wherein $R^{1x}$ is $R^{1x}$ is $C_1$-$C_4$-alkyl, —C(O)—$C_1$-$C_4$-alkyl, or —C(O)O—$C_1$-$C_4$-alkyl;
$X^4$ is $(CH_2)_m$;
$X^5$ is $(CH_2)_n$;
m and n are each 2;
p is 0;
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (I-i-a). In a further embodiment, $R^{1x}$ is $C_1$-$C_4$-alkyl. In a further embodiment, $R^{1x}$ is methyl. In a further embodiment, $R^{1x}$ is —C(O)—$C_1$-$C_4$-alkyl. In a further embodiment, $R^{1x}$ is —C(O)O—$C_1$-$C_4$-alkyl. In a further embodiment, $R^{1x}$ is tert-butoxycarbonyl.

In one embodiment, the invention is directed to compounds of Formula (I) selected from the group consisting of:
[4-(3,4-dichlorophenyl)-1-methylpiperidin-4-yl](pyridin-2-yl)methanol;
{1-methyl-4-[4-(trifluoromethyl)phenyl]piperidin-4-yl}(pyridin-2-yl)-methanol;

{1-methyl-4-[4-(trifluoromethoxy)phenyl]piperidin-4-yl}(pyridin-2-yl)-methanol;
{1-methyl-4-[3-(trifluoromethoxy)phenyl]piperidin-4-yl}(pyridin-2-yl)-methanol;
{1-methyl-4-[2-(trifluoromethoxy)phenyl]piperidin-4-yl}(pyridin-2-yl)-methanol;
tert-butyl 4-[hydroxy(pyridin-2-yl)methyl]-4-[3-(trifluoromethoxy)-phenyl]-piperidine-1-carboxylate;
tert-butyl 4-[hydroxy(pyridin-2-yl)methyl]-4-[4-(trifluoromethyl)phenyl]-piperidine-1-carboxylate; and
tert-butyl 4-[hydroxy(pyridin-2-yl)methyl]-4-[4-(trifluoromethoxy)phenyl]-piperidine-1-carboxylate.

In one embodiment, the invention is directed to compounds of Formula (I) selected from the group consisting of:
[1-(3,4-dichlorophenyl)-3,3-difluorocyclobutyl](pyridin-2-yl)methanol;
(S)-[1-(3,4-dichlorophenyl)-3,3-difluorocyclobutyl](pyridin-2-yl)-methanol;
{3,3-difluoro-1-[4-(trifluoromethoxy)phenyl]cyclobutyl}(pyridin-2-yl)-methanol;
{3,3-difluoro-1-[3-(trifluoromethyl)phenyl]cyclobutyl}(pyridin-2-yl)-methanol;
{3,3-difluoro-1-[3-(trifluoromethoxy)phenyl]cyclobutyl}(pyridin-2-yl)-methanol;
3-(3,4-dichlorophenyl)-3-[(S)-hydroxy(pyridin-2-yl)methyl]cyclobutanone;
(trans)-3-(3,4-dichlorophenyl)-3-[(S)-hydroxy(pyridin-2-yl)methyl]-cyclobutanol;
(cis)-3-(3,4-dichlorophenyl)-3-[(S)-hydroxy(pyridin-2-yl)methyl]-cyclobutanol;
(R)-{3,3-difluoro-1-[4-(trifluoromethyl)pyridin-2-yl]cyclobutyl}(pyridin-2-yl)methanol;
(S)-{3,3-difluoro-1-[4-(trifluoromethyl)pyridin-2-yl]cyclobutyl}(pyridin-2-yl)methanol;
(S)-{3,3-difluoro-1-[4-(trifluoromethoxy)phenyl]cyclobutyl}(pyridin-2-yl)-methanol;
{3,3-dimethoxy-1-[4-(trifluoromethoxy)phenyl]cyclobutyl}(pyridin-2-yl)-methanol;
cis-3-[(S)-hydroxy(pyridin-2-yl)methyl]-3-[4-(trifluoromethoxy)phenyl]-cyclobutanol;
(trans)-3-[(S)-hydroxy(pyridin-2-yl)methyl]-3-[4-(trifluoromethoxy)-phenyl]cyclobutanol;
{3,3-difluoro-1-[4-(trifluoromethyl)phenyl]cyclobutyl}(pyridin-2-yl)-methanol;
cis-3-[(S)-hydroxy(pyridin-2-yl)methyl]-1-methyl-3-[4-(trifluoromethoxy)-phenyl]cyclobutanol;
{3,3-difluoro-1-[5-(trifluoromethyl)pyridin-2-yl]cyclobutyl}(pyridin-2-yl)-methanol;
{1-[4-chloro-3-(trifluoromethyl)phenyl]-3,3-difluorocyclobutyl}(pyridin-2-yl)methanol;
{3,3-difluoro-1-[4-fluoro-3-(trifluoromethyl)phenyl]cyclobutyl}(pyridin-2-yl)methanol;
[4-(3,4-dichlorophenyl)-1-methylpiperidin-4-yl](pyridin-2-yl)methanol;
{1-methyl-4-[4-(trifluoromethyl)phenyl]piperidin-4-yl}(pyridin-2-yl)-methanol;
{1-methyl-4-[4-(trifluoromethoxy)phenyl]piperidin-4-yl}(pyridin-2-yl)-methanol;
{1-methyl-4-[3-(trifluoromethoxy)phenyl]piperidin-4-yl}(pyridin-2-yl)-methanol;
{1-methyl-4-[2-(trifluoromethoxy)phenyl]piperidin-4-yl}(pyridin-2-yl)-methanol;
(S)-[cis-1-(3,4-dichlorophenyl)-3-methoxycyclobutyl] (pyridin-2-yl)-methanol;
(S)-[1-(3,4-dichlorophenyl)-3-methoxycyclobutyl](pyridin-2-yl)methanol;
tert-butyl 3-[hydroxy(pyridin-2-yl)methyl]-3-[4-(trifluoromethyl)-phenyl]azetidine-1-carboxylate;
(S)-{3,3-difluoro-1-[4-(trifluoromethyl)phenyl]cyclobutyl}(pyridin-2-yl)-methanol;
{1-methyl-3-[4-(trifluoromethyl)phenyl]azetidin-3-yl}(pyridin-2-yl)-methanol;
tert-butyl 4-[hydroxy(pyridin-2-yl)methyl]-4-[4-(trifluoromethyl)-phenyl]piperidine-1-carboxylate;
tert-butyl 4-[hydroxy(pyridin-2-yl)methyl]-4-[4-(trifluoromethoxy)-phenyl]piperidine-1-carboxylate;
tert-butyl 4-[hydroxy(pyridin-2-yl)methyl]-4-[3-(trifluoromethoxy)-phenyl]piperidine-1-carboxylate;
(R)-{3,3-difluoro-1-[4-(trifluoromethoxy)phenyl]cyclobutyl}(pyridin-2-yl)methanol;
3-[hydroxy(pyridin-2-yl)methyl]-3-[4-(trifluoromethyl)phenyl]-cyclobutanone;
pyridin-2-yl{2-[4-(trifluoromethyl)phenyl]-5,8-dioxaspiro[3.4]oct-2-yl}-methanol;
3-[(S)-hydroxy(pyridin-2-yl)methyl]-3-[4-(trifluoromethyl)phenyl]-cyclobutanone;
3-[(R)-hydroxy(pyridin-2-yl)methyl]-3-[4-(trifluoromethyl)phenyl]-cyclobutanone;
3-[(S)-hydroxy(pyridin-2-yl)methyl]-3-[4-(trifluoromethyl)phenyl]-cyclobutanol;
3-[(R)-hydroxy(pyridin-2-yl)methyl]-3-[4-(trifluoromethyl)phenyl]-cyclobutanol;
cis-3-[(S)-hydroxy(pyridin-2-yl)methyl]-3-[4-(trifluoromethyl)phenyl]-cyclobutanol;
trans-3-[(S)-hydroxy(pyridin-2-yl)methyl]-3-[4-(trifluoromethyl)phenyl]-cyclobutanol;
pyridin-2-yl{2-[4-(trifluoromethoxy)phenyl]-5,8-dioxaspiro[3.4]oct-2-yl}-methanol;
trans-3-[(S)-hydroxy(pyridin-2-yl)methyl]-1-methyl-3-[4-(trifluoromethoxy)phenyl]cyclobutanol;
cis-3-[(S)-hydroxy(pyridin-2-yl)methyl]-1-methyl-3-[4-(trifluoromethyl)-phenyl]cyclobutanol;
trans-3-[(S)-hydroxy(pyridin-2-yl)methyl]-1-methyl-3-[4-(trifluoromethyl)-phenyl]cyclobutanol;
pyridin-2-yl{2-[3-(trifluoromethoxy)phenyl]-5,8-dioxaspiro[3.4]oct-2-yl}-methanol;
cis-3-[(S)-hydroxy(pyridin-2-yl)methyl]-1-methyl-3-[3-(trifluoromethyl)-phenyl]cyclobutanol;
3-[hydroxy(pyridin-2-yl)methyl]-3-[3-(trifluoromethoxy)phenyl]-cyclobutanone;
3-[(S)-hydroxy(pyridin-2-yl)methyl]-3-[3-(trifluoromethyl)phenyl]-cyclobutanone;
pyridin-2-yl{2-[3-(trifluoromethyl)phenyl]-5,8-dioxaspiro[3.4]oct-2-yl}-methanol;
3-[(R)-hydroxy(pyridin-2-yl)methyl]-3-[3-(trifluoromethyl)phenyl]-cyclobutanone;
trans-3-[(S)-hydroxy(pyridin-2-yl)methyl]-1-methyl-3-[3-(trifluoromethyl)-phenyl]cyclobutanol;
3-[hydroxy(pyridin-2-yl)methyl]-3-[3-(trifluoromethyl)phenyl]-cyclobutanone;
cis-3-(3,4-dichlorophenyl)-3-[(R)-hydroxy(pyridin-2-yl)methyl]-cyclobutanol;
(S)-{3-(hydroxyimino)-1-[4-(trifluoromethoxy)phenyl]cyclobutyl}(pyridin-2-yl)methanol;
(S)-{3-(methoxyimino)-1-[4-(trifluoromethoxy)phenyl]cyclobutyl}(pyridin-2-yl)methanol;
cis-3-[(R)-hydroxy(pyridin-2-yl)methyl]-1-methyl-3-[4-(trifluoromethoxy)-phenyl]cyclobutanol;
3-[(S)-hydroxy(pyridin-2-yl)methyl]-3-[4-(trifluoromethoxy)phenyl]-cyclobutanone;
[2-(3-chloro-4-fluorophenyl)-5,8-dioxaspiro[3.4]oct-2-yl](pyridin-2-yl)-methanol;

3-[(S)-hydroxy(pyridin-2-yl)methyl]-3-[3-(trifluoromethoxy)phenyl]-cyclobutanone;
3-[(R)-hydroxy(pyridin-2-yl)methyl]-3-[3-(trffluoromethoxy)phenyl]-cyclobutanone;
3-(3-chloro-4-fluorophenyl)-3-[hydroxy(pyridin-2-yl)methyl]-cyclobutanone;
cis-3-[(S)-hydroxy(pyridin-2-yl)methyl]-3-[3-(trifluoromethyl)phenyl]-cyclobutanol;
cis-3-[(S)-hydroxy(pyridin-2-yl)methyl]-1-methyl-3-[3-(trifluoromethoxy)-phenyl]cyclobutanol;
trans-3-[(S)-hydroxy(pyridin-2-yl)methyl]-1-methyl-3-[3-(trifluoromethoxy)phenyl]cyclobutanol;
trans-3-[(S)-hydroxy(pyridin-2-yl)methyl]-3-[3-(trifluoromethyl)-phenyl]cyclobutanol;
(S)-{3-(dimethylhydrazinylidene)-1-[4-(trifluoromethoxy)phenyl]-cyclobutyl}(pyridin-2-yl)methanol;
3-(3-chloro-4-fluorophenyl)-3-[(S)-hydroxy(pyridin-2-yl)methyl]-cyclobutanone;
cis-3-[(S)-hydroxy(pyridin-2-yl)methyl]-3-[3-(trifluoromethoxy)-phenyl]cyclobutanol;
trans-3-[(S)-hydroxy(pyridin-2-yl)methyl]-3-[3-(trifluoromethoxy)-phenyl]cyclobutanol;
3-(3-chloro-4-fluorophenyl)-3-[(S)-hydroxy(pyridin-2-yl)methyl]-cyclobutanol;
3-[(S)-hydroxy(pyridin-2-yl)methyl]-3-[4-(trifluoromethyl)pyridin-2-yl]-cyclobutanone;
3-[(R)-hydroxy(pyridin-2-yl)methyl]-3-[4-(trifluoromethyl)pyridin-2-yl]-cyclobutanone;
cis-3-[(S)-hydroxy(pyridin-2-yl)methyl]-3-[4-(trifluoromethyl)pyridin-2-yl]cyclobutanol;
trans-3-[(S)-hydroxy(pyridin-2-yl)methyl]-3-[4-(trifluoromethyl)pyridin-2-yl]cyclobutanol;
cis-3-[(S)-hydroxy(pyridin-2-yl)methyl]-1-methyl-3-[4-(trifluoromethyl)-pyridin-2-yl]cyclobutanol;
trans-3-[(S)-hydroxy(pyridin-2-yl)methyl]-3-[4-(trifluoromethyl)pyridin-2-yl]cyclobutanol;
cis-3-[(R)-hydroxy(pyridin-2-yl)methyl]-3-[4-(trifluoromethyl)pyridin-2-yl]cyclobutanol;
3-[(R)-hydroxy(pyridin-2-yl)methyl]-3-[6-methyl-4-(trifluoromethyl)-pyridin-2-yl]cyclobutanone;
3-[hydroxy(pyridin-2-yl)methyl]-3-[4-(trifluoromethyl)pyridin-2-yl]-cyclobutanone;
3-[(S)-hydroxy(pyridin-2-yl)methyl]-3-[4-(trifluoromethyl)pyridin-2-yl]-cyclobutanone;
3-[hydroxy(pyridin-2-yl)methyl]-3-[5-(trifluoromethyl)pyridin-3-yl]-cyclobutanone;
3-[(S)-hydroxy(pyridin-2-yl)methyl]-3-[5-(trifluoromethyl)pyridin-3-yl]-cyclobutanone;
pyridin-2-yl{2-[2-(trifluoromethyl)pyridin-4-yl]-5,8-dioxaspiro[3.4]oct-2-yl}methanol;
3-[hydroxy(pyridin-2-yl)methyl]-3-[2-(trifluoromethyl)pyridin-4-yl]-cyclobutanone;
3-[(S)-hydroxy(pyridin-2-yl)methyl]-3-[2-(trifluoromethyl)pyridin-4-yl]-cyclobutanone;
cis-3-[(S)-hydroxy(pyridin-2-yl)methyl]-1-methyl-3-[2-(trifluoromethyl)-pyridin-4-yl]cyclobutanol;
cis-3-[(S)-hydroxy(pyridin-2-yl)methyl]-3-[5-(trifluoromethyl)pyridin-3-yl]cyclobutanol;
trans-3-[(S)-hydroxy(pyridin-2-yl)methyl]-3-[5-(trifluoromethyl)pyridin-3-yl]cyclobutanol;
cis-3-[(S)-hydroxy(pyridin-2-yl)methyl]-3-[2-(trifluoromethyl)pyridin-4-yl]cyclobutanol;
trans-3-[(S)-hydroxy(pyridin-2-yl)methyl]-3-[2-(trifluoromethyl)pyridin-4-yl]cyclobutanol;
trans-3-[(S)-hydroxy(pyridin-2-yl)methyl]-1-methyl-3-[2-(trifluoromethyl)-pyridin-4-yl]cyclobutanol;
cis-3-[(S)-hydroxy(pyridin-2-yl)methyl]-1-methyl-3-[5-(trifluoromethyl)-pyridin-3-yl]cyclobutanol;
trans-3-[(S)-hydroxy(pyridin-2-yl)methyl]-1-methyl-3-[5-(trifluoromethyl)-pyridin-3-yl]cyclobutanol;
(trans)-3-((S)-hydroxy(pyrimidin-2-yl)methyl)-1-methyl-3-(4-(trifluoromethoxy)phenyl)cyclobutanol;
(trans)-3-((R)-hydroxy(pyrimidin-2-yl)methyl)-1-methyl-3-(4-(trifluoromethoxy)phenyl)cyclobutanol;
(trans)-3-(3,4-dichlorophenyl)-3-((S)-hydroxy(pyrimidin-2-yl)methyl)-cyclobutanol; and
(trans)-3-(3,4-dichlorophenyl)-3-((R)-hydroxy(pyrimidin-2-yl)methyl)-cyclobutanol.

The present compounds may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Various stereoisomers of the present compounds and mixtures thereof are included within the scope of this application. Stereoisomers include enantiomers and diastereomers, and mixtures of enantiomers or diastereomers. Individual stereoisomers may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}$H, $^{3}$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^{2}$H), tritium ($^{3}$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of TRPV3 modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to TRPV3 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

c. BIOLOGICAL DATA (i) In Vitro Antagonism of Recombinant Human TRPV3 Activation.

Test compounds were evaluated for ability to antagonize the activation of recombinant human TRPV3 using FLIPR® Tetra cellular screening. Specifically, on the day prior to the experiment recombinant HEK293 cells that stably express human TRPV3 were removed from tissue culture flasks and plated in growth medium at 20,000 cells/well into Poly-d-lysine coated black/clear 384-well Plate (Corning, 3845) using a Multidrop® dispenser (ThermoScientific, Waltham, Mass.). Prior to the start of the assay, the medium was removed by aspiration, and cells were loaded with 30 μL no-wash FLIPR® Calcium-4 dye ($\lambda_{EX}$=470-495 nm, $\lambda_{EM}$=515-575 nm; Molecular Devices, Sunnyvale, Calif.). The cells were then incubated for 90-120 minutes in the dark prior to addition of the test compound.

A double-addition protocol was used. The test compound (i.e., the TRPV3 antagonist) was added at the 10 second time point, followed by the addition of a TRPV3 agonist three minutes later. Each test compound evaluated was first dissolved in DMSO to prepare a 10 mM stock solution. A solution (5×) of the test compound was then prepared in DPBS (Dulbecco's Phosphate Buffered Saline) and 10 μl, of that solution was added to the cells at a delivery rate of 40 μL/sec. The TRPV3 agonist used to activate human TRPV3 expressed by the HEK3 cells was 2-aminoethoxy-diphenyl borate (2-APB; Tocris Cookson, Ellisville, Mo.) at 80 μM. Final assay volume was 50 μl, Total length of an experimental run was 10 minutes.

Changes in fluorescence were measured over time using the FLIPR® instrument. The intensity of the fluorescence was captured and digitally transferred to an interfaced computer. The maximum response minus minimum response was calculated and expressed as the percentage of the maximum 2-APB response in the absence of antagonist. The concentration of 2-APB corresponds to its $EC_{80}$.

Table 1 reports the $IC_{50}$ values measured for the test compounds as human TRPV3 antagonists. As used in Table 1, "A" refers to an $IC_{50}$ value of greater than 20 μM, "B" refers to an $IC_{50}$ value in range of 5.1 μM to 20 μM, "C" refers to an $IC_{50}$ value in range of 1.1 μM to 5 μM, "D" refers to an $IC_{50}$ value in range of 501 nM to 1,000 nM, and "E" refers to an $IC_{50}$ value in range of 50 nM to 500 nM. Actual measured values are shown parenthetically after the reported range. In most cases, the values reported are average values from at least two runs (i.e., n≥2).

TABLE 1

| EXAMPLE | IC50 (μM) |
| --- | --- |
| 1 | C (1.5) |
| 2 | E (0.32) |
| 3 | D (0.79) |
| 4 | E (0.46) |
| 5 | B (5.22) |
| 6 | E (0.35) |
| 7 | B (17.5) |
| 8 | E (0.38) |

TABLE 1-continued

| EXAMPLE | IC50 (µM) |
|---|---|
| 9 | C (1.51) |
| 10 | C (1.1) |
| 11 | E (0.4) |
| 12 | E (0.42) |
| 13 | D (0.6) |
| 14 | A (>20) |
| 15 | E (0.31) |
| 16 | A (>20) |
| 17 | C (1.1) |
| 18 | D (0.74) |
| 19 | A (>20) |
| 20 | A (>20) |
| 21 | A (>20) |
| 22 | A (>20) |
| 23 | D (0.93) |
| 24 | C (4.7) |
| 25 | C (1.18) |
| 26 | E (0.31) |
| 27 | C (1.4) |
| 28 | E (0.44) |
| 29 | C (2.54) |
| 30 | C (1.72) |
| 31 | C (3.08) |
| 32 | A (>20) |
| 33 | B (8.5) |
| 34 | A (>20) |
| 35 | B (10.2) |
| 36 | B (5.18) |
| 37 | D (0.83) |
| 38 | E (0.06*) |
| 39 | D (0.74) |
| 40 | B (13.3) |
| 41 | >10 |
| 42 | >10 |
| 43 | E (0.66) |
| 44 | B (8) |
| 45 | C (2.22) |
| 46 | B (13.7) |
| 47 | C (2.22) |
| 48 | B (5.68) |
| 49 | C (3.27) |
| 50 | C (2.42) |
| 51 | B (8.25) |
| 52 | C (5.02) |
| 53 | C (1.75) |
| 54 | A (22) |
| 55 | B (7.12) |
| 56 | C (1.07) |
| 57 | B (9.29) |
| 58 | C (3.63) |
| 59 | C (1.79) |
| 60 | B (7.55) |
| 61 | B (7.54) |
| 62 | B (11.8) |
| 63 | B (7.17) |
| 64 | C (2.34) |
| 65 | C (2.26) |
| 66 | C (1.52) |
| 67 | C (2.6) |
| 68 | C (3.68) |
| 69 | C (4.97) |
| 70 | B (12) |
| 71 | C (2.13) |
| 72 | C (2.24) |
| 73 | C (1.94) |
| 74 | E (0.41) |
| 75 | D (0.94) |
| 76 | D (0.65) |
| 77 | D (0.76) |
| 78 | C (3.56) |
| 79 | A (>20) |
| 80 | C (1.78) |
| 81 | A (>20) |
| 82 | D (0.78) |
| 83 | A (>20) |
| 84 | A (>20) |
| 85 | B (5.61) |
| 86 | C (3.56) |
| 87 | A (>20) |
| 88 | E (0.37) |
| 89 | C (2) |
| 90 | E (0.46) |
| 91 | E (0.33) |
| 92 | E (0.1) |
| 93 | D (0.59) |
| 94 | E (0.36) |
| 95 | C (1.85) |
| 96 | C (1.22) |
| 97 | E (0.3) |
| 98 | E (0.11) |
| 99 | C (1.24) |
| 100 | D (0.83) |
| 101 | A (>20) |
| 102 | A (>20) |
| 103 | C (2) |
| 104 | E (0.28) |
| 105 | B (7.57) |
| 106 | E (0.21) |
| 107 | C (2.93) |
| 108 | D (0.61) |
| 109 | B (5.81) |
| 110 | E (0.5) |
| 111 | E (0.19) |
| 112 | E (0.3) |
| 113 | E (0.26) |
| 114 | E (0.23) |
| 115 | B (19.4) |
| 116 | D (0.75) |
| 117 | C (2.42) |
| 118 | E (0.22) |
| 119 | D (0.57) |
| 120 | A (>20) |
| 121 | A (>20) |
| 122 | A (>20) |
| 123 | E (0.39) |
| 124 | A (>20) |
| 125 | B (18.6) |
| 126 | D (0.82) |
| 127 | B (11.6) |
| 128 | E (0.11) |
| 129 | E (0.33) |
| 130 | C (3.11) |
| 131 | C (0.82) |
| 132 | B (9.33) |
| 133 | E (0.12) |
| 134 | D (0.86) |
| 135 | D (1.01) |
| 136 | E (0.39) |
| 137 | C (4.87) |
| 138 | D (0.83) |
| 139 | D (0.75) |
| 140 | A (>20) |
| 141 | A (>20) |
| 142 | A (>20) |
| 143 | A (>20) |
| 144 | A (>20) |
| 145 | C (1.77) |
| 146 | B (12.8) |
| 147 | A (>20) |
| 148 | C (3.1) |
| 149 | B (6.2) |
| 150 | C (1.69) |
| 151 | C (1.24) |
| 152 | B (19.7) |
| 153 | B (8.01) |
| 154 | E (0.23) |
| 155 | B (17) |
| 156 | A (>20) |
| 157 | A (>20) |
| 158 | A (>20) |
| 159 | C (1.98) |
| 160 | B (6.11) |
| 161 | C (3.27) |
| 162 | C (3.88) |

TABLE 1-continued

| EXAMPLE | IC50 (μM) |
|---|---|
| 163 | C (4.9) |
| 164 | C (2.61) |
| 165 | B (16.6) |
| 166 | B (5.94) |
| 167 | A (>20) |
| 168 | B (9.14) |
| 169 | B (5.82) |
| 170 | A (>20) |
| 171 | A (>20) |
| 172 | A (>20) |
| 173 | A (>20) |
| 174 | A (>20) |
| 175 | A (>20) |
| 176 | A (>20) |
| 177 | C (3.38) |
| 178 | A (>20) |
| 179 | C (2.95) |
| 180 | A (>20) |
| 181 | C (1.98) |
| 182 | A (>20) |
| 183 | C (1.4) |
| 184 | A (>20) |
| 185 | A (>20) |
| 186 | A (>20) |
| 187 | A (>20) |
| 188 | A (>20) |
| 189 | A (>20) |
| 190 | A (>20) |
| 191 | >7.4 |
| 192 | A (>20) |
| 173 | A (>20) |
| 194 | A (>20) |
| 195 | A (>20) |
| 196 | A (>20) |
| 197 | A (>20) |
| 198 | A (>20) |
| 199 | A (>20) |
| 200 | B (5.25) |
| 201 | B (6.01) |
| 202 | B (5.17) |
| 203 | B (13.8) |
| 204 | C (1.6) |
| 205 | C (3.87) |
| 206 | C (2.63) |
| 207 | C (3.99) |
| 208 | C (2.06) |
| 209 | C (4.6) |
| 210 | C (3.31) |
| 211 | B (6.17) |
| 212 | C (2.87) |
| 213 | C (3.24) |
| 214 | C (1.22) |
| 215 | D (0.77) |
| 216 | C (2.26) |
| 217 | C (3.99) |
| 218 | C (1.73) |
| 219 | C (3.07) |
| 220 | D (0.65) |
| 221 | C (1.8) |
| 222 | C (2.35) |
| 223 | C (2.07) |
| 224 | C (4.84) |
| 225 | C (2.82) |
| 226 | D (0.79) |
| 227 | E (0.5) |
| 228 | C (2.52) |
| 229 | C (4.58) |
| 230 | >10 |
| 231 | D (0.54) |
| 232 | C (1.95) |
| 233 | B (10.8) |
| 234 | B (5.36) |
| 235 | C (3.32) |
| 236 | D (0.76) |
| 237 | C (3.66) |
| 238 | C (3.91) |
| 239 | ND |

TABLE 1-continued

| EXAMPLE | IC50 (μM) |
|---|---|
| 240 | D (0.71) |
| 241 | C (1.67) |
| 242 | B (5.1) |
| 243 | B (18.5) |
| 244 | C (3.6) |
| 245 | C (3.65) |
| 246 | A (>20) |
| 247 | C (4.31) |
| 248 | C (1.17) |
| 249 | C (3.93) |
| 250 | B (9.23) |
| 251 | C (1.97) |
| 252 | A (>20) |
| 253 | C (3.4) |
| 254 | C (4.22) |
| 255 | B (5.49) |
| 256 | C (2.24) |
| 257 | B (9.51) |
| 258 | B (11) |
| 259 | E (0.47) |
| 260 | B (5.32) |
| 261 | C (1.27) |
| 262 | D (0.63) |
| 263 | C (2.8) |
| 264 | E (0.23) |
| 265 | B (5.64) |
| 266 | C (2.31) |
| 267 | C (2.41) |
| 268 | C (2.13) |
| 269 | B (11.2) |
| 270 | C (3.94) |
| 271 | C (2.19) |
| 272 | E (0.19) |
| 273 | E (0.09) |
| 274 | C (3.11) |
| 275 | B (19) |
| 276 | E (0.2) |
| 277 | C (1.97) |
| 278 | B (6.6) |
| 279 | B (7.5) |
| 280 | C (1.95) |
| 281 | B (7.69) |
| 282 | D (0.74) |
| 283 | D (0.69) |
| 284 | A (>20) |
| 285 | D (1) |
| 286 | C (1.47) |
| 287 | A (>20) |
| 288 | B (14.6) |
| 289 | A (>20) |
| 290 | A (>20) |
| 291 | B (17.3) |
| 292 | D (0.56) |
| 293 | A (>20) |
| 294 | A (>20) |
| 295 | A (>20) |
| 296 | A (>20) |
| 297 | A (>20) |
| 298 | A (>20) |
| 299 | A (>20) |
| 300 | C (4.92) |
| 301 | B (6.04) |
| 302 | D (0.95) |
| 303 | D (0.53) |
| 304 | E (0.25) |
| 305 | E (0.29) |
| 306 | E (0.14) |
| 307 | B (8.23) |
| 308 | D (1) |
| 309 | C (3.05) |
| 310 | A (>20) |
| 311 | A (>20) |
| 312 | C (1.96) |
| 313 | A (>20) |

ND = not determined (ii) In Vitro Metabolic Stability (Human and Rat Microsomal Stability)

Test compounds were evaluated for metabolic stability in an in vitro rat microsomal stability assay using rat liver microsomes (Sprague-Dawley, from BD Biosciences) and/or an in vitro human microsomal stability assay using human liver microsomes (Xenotech). Incubations were conducted using a 0.5 µM substrate concentration in dimethyl sulfoxide (DMSO) and 0.25 mg/mL microsomal protein in 50 mM phosphate buffer at pH 7.4. Incubations were carried out at 37° C. with a final incubation volume of 135 µL. Time-zero samples were prepared by transferring 13.5 µL of compound-microsomal mixture to the quench plates containing 45 µL of quench solution consisting of 50 nM carbutamide as internal standard in 1:1 methanol:acetonitrile. A 1.5 µL aliquot of reduced nicotine adenine disphosphonucleotide (NADPH) (Chem-Impex Int'L Inc., Lot 12532024) was also added to the time-zero plates. The reaction was initiated by the addition of 13.5 µL NADPH to the compound-microsomal mixture and then quenched after 30 minutes by addition of 15 µL of incubation mixture to 45 µL of quench solution. The percent of parent compound remaining after the 30-minute microsomal incubation was ascertained by HPLC-MS/MS and is reported in the table.

TABLE 2

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 1 | 0.38 | 0.48 |
| 2 | 17 | 0.64 |
| 3 | 28 | 3.8 |
| 4 | 19 | 4.2 |
| 5 | 0.27 | 0.06 |
| 6 | 1.2 | 2.3 |
| 7 | 0.15 | 0.32 |
| 8 | 0.13 | 0.73 |
| 9 | 0.12 | 0.18 |
| 10 | 0.42 | 0.62 |
| 11 | 0.72 | 0.80 |
| 12 | 24 | 11 |
| 13 | 7.4 | 19 |
| 15 | 5.6 | 1.2 |
| 17 | 21 | 13 |
| 18 | ND | 0.27 |
| 19 | >85 | 76 |
| 20 | 80 | 81 |
| 21 | 71 | 52 |
| 23 | 0.12 | 0.69 |
| 24 | 20 | 17 |
| 25 | 21 | 1.3 |
| 26 | 6.3 | 1.0 |
| 27 | 13 | 15 |
| 28 | 12 | 13 |
| 29 | 5.3 | 45 |
| 30 | 1.5 | 0.98 |
| 37 | ND | 7.7 |
| 38 | ND | 9.5 |
| 39 | 51 | 11 |
| 40 | 68 | 5.6 |
| 41 | 54 | 21 |
| 42 | 50 | 40 |
| 43 | 1.8 | 0.31 |
| 45 | 0.03 | 0.02 |
| 46 | 11 | 0.23 |
| 49 | 15 | 0.13 |
| 50 | 0.08 | 0.18 |
| 52 | 1.7 | 0.05 |
| 54 | ND | 0.21 |
| 55 | 1.6 | 0.29 |
| 56 | 0.42 | 1.1 |
| 57 | 16 | 10 |
| 58 | 36 | 33 |

TABLE 2-continued

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 59 | 45 | 12 |
| 66 | 31 | 23 |
| 67 | 58 | 47 |
| 74 | 6.8 | 0.45 |
| 75 | 44 | 0.74 |
| 76 | 39 | 0.47 |
| 77 | 11 | 0.94 |
| 82 | 35 | 16 |
| 85 | 82 | 76 |
| 87 | 47 | 8.6 |
| 88 | 38 | 7.0 |
| 89 | 70 | 4.3 |
| 90 | 35 | <0.01 |
| 91 | 46 | 1.0 |
| 92 | 2.7 | 0.23 |
| 93 | 12 | 0.33 |
| 94 | 55 | 3.8 |
| 95 | 57 | 0.61 |
| 96 | 0.68 | 0.15 |
| 97 | 6.4 | 0.16 |
| 98 | 7.6 | 0.020 |
| 99 | 30 | 0.17 |
| 100 | 26 | 2.9 |
| 101 | 40 | 0.17 |
| 102 | 45 | 0.55 |
| 103 | 73 | 0.012 |
| 104 | 15 | 0.42 |
| 105 | 42 | 0.040 |
| 106 | 3.9 | 1.6 |
| 107 | 31 | 0.23 |
| 108 | 13 | 4.9 |
| 109 | 45 | 0.74 |
| 110 | 8.0 | 2.8 |
| 111 | 52 | 23 |
| 112 | 75 | 75 |
| 113 | 24 | 18 |
| 114 | 6.9 | 11 |
| 115 | >85 | 81 |
| 116 | 37 | 25 |
| 117 | 18 | 50 |
| 118 | >85 | 74 |
| 119 | >85 | 69 |
| 120 | 1.6 | <0.01 |
| 121 | 41 | 0.18 |
| 122 | 28 | 26 |
| 123 | 21 | 11 |
| 124 | 1.6 | <0.01 |
| 125 | 53 | 8.8 |
| 126 | 21 | 7.7 |
| 127 | 51 | 1.1 |
| 128 | 59 | 67 |
| 129 | 46 | 0.01 |
| 130 | 4.0 | <0.01 |
| 131 | >85 | 50 |
| 132 | 81 | 72 |
| 133 | 73 | 61 |
| 134 | 78 | 72 |
| 135 | 33 | 3.4 |
| 136 | 24 | 9.5 |
| 137 | 77 | >85 |
| 138 | 41 | 18 |
| 139 | 41 | 26 |
| 140 | >85 | 37 |
| 141 | >85 | 59 |
| 142 | >85 | 37 |
| 143 | >85 | 80 |
| 144 | >85 | 51 |
| 145 | 68 | 42 |
| 146 | 84 | 8.9 |
| 147 | >85 | 79 |
| 148 | >85 | 53 |
| 149 | >85 | 62 |
| 150 | 42 | <0.01 |
| 151 | 32 | <0.01 |
| 152 | >85 | >85 |

TABLE 2-continued

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 153 | 49 | 21 |
| 154 | 56 | 78 |
| 155 | >85 | 76 |
| 156 | 26 | 0.08 |
| 157 | 28 | 0.93 |
| 158 | 3.7 | 0.04 |
| 159 | 45 | 65 |
| 160 | >85 | 60 |
| 161 | 61 | <0.01 |
| 162 | 0.02 | <0.01 |
| 163 | 0.11 | <0.01 |
| 164 | 71 | 81 |
| 165 | 83 | 77 |
| 166 | >85 | >85 |
| 167 | 9.5 | <0.01 |
| 168 | 5.6 | <0.01 |
| 169 | <0.01 | <0.01 |
| 170 | <0.01 | <0.01 |
| 171 | 2.7 | <0.01 |
| 172 | 2.4 | <0.01 |
| 173 | 45 | <0.01 |
| 174 | 26 | <0.01 |
| 175 | 29 | <0.01 |
| 176 | 20 | <0.01 |
| 177 | 0.12 | <0.01 |
| 178 | 9.2 | <0.01 |
| 179 | <0.01 | <0.01 |
| 180 | <0.01 | <0.01 |
| 181 | <0.01 | <0.01 |
| 182 | <0.01 | <0.01 |
| 183 | <0.01 | <0.01 |
| 184 | 0.46 | <0.01 |
| 1>85 | 0.39 | <0.01 |
| 186 | 0.18 | <0.01 |
| 187 | <0.01 | <0.01 |
| 188 | 0.16 | <0.01 |
| 189 | 0.65 | <0.01 |
| 190 | 3.7 | <0.01 |
| 191 | <0.01 | <0.01 |
| 192 | <0.01 | <0.01 |
| 193 | 0.02 | <0.01 |
| 194 | 0.08 | <0.01 |
| 195 | <0.01 | <0.01 |
| 196 | <0.01 | <0.01 |
| 197 | 0.26 | <0.01 |
| 198 | 0.05 | <0.01 |
| 199 | >85 | >85 |
| 200 | >85 | >85 |
| 201 | 73 | >85 |
| 202 | 73 | <0.01 |
| 203 | >85 | 74 |
| 204 | >85 | >85 |
| 205 | >85 | >85 |
| 206 | 83 | 62 |
| 208 | ND | 36 |
| 212 | >85 | 3.9 |
| 213 | >85 | 72 |
| 216 | >85 | 41 |
| 217 | 73 | 68 |
| 220 | >85 | 67 |
| 221 | 83 | 56 |
| 222 | >85 | 59 |
| 223 | >85 | 65 |
| 224 | >85 | 70 |
| 225 | >85 | 34 |
| 226 | >85 | <0.01 |
| 227 | >85 | 42 |
| 228 | 70 | 25 |
| 229 | >85 | 80 |
| 230 | 33 | 30 |
| 231 | 4.0 | 17 |
| 232 | 80 | 67 |
| 233 | >85 | 67 |
| 234 | 19 | 23 |
| 235 | 20 | <0.01 |
| 236 | 54 | 41 |
| 237 | 51 | 50 |
| 238 | 7.1 | 21 |
| 239 | 57 | 0.072 |
| 240 | 50 | 38 |
| 241 | 66 | 59 |
| 242 | 45 | <0.01 |
| 243 | 64 | 55 |
| 244 | 80 | 77 |
| 245 | 57 | 72 |
| 246 | 71 | 59 |
| 247 | 62 | >85 |
| 248 | 70 | 29 |
| 249 | 61 | 3.2 |
| 250 | 70 | 70 |
| 253 | 0.21 | 0.017 |
| 254 | 1.1 | 0.57 |
| 255 | 54 | <0.01 |
| 256 | 44 | 55 |
| 257 | 42 | 57 |
| 258 | 70 | 53 |
| 259 | 76 | 73 |
| 260 | 12 | <0.01 |
| 261 | 0.01 | <0.01 |
| 262 | 48 | 57 |
| 263 | ND | >85 |
| 264 | 56 | 59 |
| 265 | 43 | 0.059 |
| 266 | 46 | 0.14 |
| 267 | 64 | 10 |
| 268 | 66 | 82 |
| 269 | 40 | 12 |
| 270 | 17 | 0.48 |
| 271 | 62 | 8.6 |
| 272 | 54 | 48 |
| 273 | 42 | 65 |
| 274 | 55 | 10 |
| 275 | 67 | 5.7 |
| 276 | 72 | 73 |
| 277 | >85 | >85 |
| 278 | 83 | >85 |
| 279 | 22 | <0.01 |
| 280 | 9.0 | <0.01 |
| 281 | >85 | 0.054 |
| 282 | >85 | >85 |
| 283 | >85 | >85 |
| 284 | >85 | 16 |
| 2>85 | 83 | 69 |
| 286 | >85 | 70 |
| 287 | 15 | <0.01 |
| 288 | <0.01 | <0.01 |
| 289 | 4.2 | <0.01 |
| 290 | >85 | 71 |
| 291 | >85 | 53 |
| 292 | 19 | 5.4 |
| 293 | 78 | 69 |
| 294 | >85 | >85 |
| 295 | 70 | 8.2 |
| 296 | 67 | 12 |
| 297 | >85 | 2.0 |
| 298 | 80 | 59 |
| 299 | >85 | >85 |
| 300 | 35 | 0.020 |
| 301 | 57 | 22 |
| 303 | 80 | 32 |
| 304 | >85 | 44 |
| 305 | 63 | 49 |
| 306 | >85 | >85 |
| 307 | 73 | >85 |
| 308 | 41 | 13 |
| 309 | >85 | ND |
| 310 | >85 | >85 |
| 311 | >85 | >85 |

TABLE 2-continued

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 312 | >85 | >85 |
| 313 | 81 | >85 |

ND = not determined
*Microsomal stability was not determined for those Examples not listed in Table 2.

(iii) In Vivo Efficacy Against Neuropathic Pain

Test compounds were evaluated for analgesic effect in an in vivo chronic constriction injury (CCI) model of neuropathic pain. CD1 mice (Charles River) were used for these studies. Prior to testing (2-4 weeks) animals underwent a surgical procedure consisting of approximately 3 loose ligatures around the sciatic nerve. Following sterilization procedures, under isofluorane anesthetic, a 1.5 cm incision was made dorsal to the pelvis. The biceps femoris and gluteous superficialis (right side) were separated and the sciatic nerve exposed, isolated, and 2-4 loose ligatures (5-0 chromic gut) with less than 1 mm spacing were placed around it. Following hemostasis, the wound was sutured (layer of muscle closed with 5-0 nylon suture, and the wound closed with surgical staples) and coated with iodine. The mice were allowed to recover on a warming plate and were returned to their home cages (soft bedding) when able to walk on their own.

Two to four weeks after the surgery, test compound was administered orally (PO) in these mice, and mechanical allodynia was evaluated 1 hour after oral dosing where the threshold to response was assessed using calibrated von Frey monofilaments. The von Frey monofilaments were applied to the hind paw at increasing forces until the animal responded by lifting its paw. Normally, the force of the von Frey monofilament was innocuous and only in the altered state (allodynia or hyperalgesia) did the animals respond to this stimulation. Test compounds were evaluated to determine the degree to which they showed analgesic activity by prolonging the latency to respond to thermal stimulation or increasing the grams of force needed to elicit a withdrawal response. At the end of the experiment, after behavioral testing, plasma (and in some instances brain tissue) was taken for exposure analysis.

Each test compound was evaluated in eight different mice. The data reported in Table 3 represent the average value of the approximate percent effect of each compound in relieving neuropathic pain in mice receiving 100 mg/kg oral dose of the test compound. The grams of force needed to elicit a withdrawal response from the injured mouse that was challenged with vehicle was assigned a 0% effect, while the grams of force needed to elicit a withdrawal response from the control was given a 100% effect.

TABLE 3

| EXAMPLE | % EFFECT |
|---|---|
| 118 | 89 |
| 119 | 16 |
| 128 | 78 |
| 134 | 98 |
| 136 | 52 |
| 201 | 64 |
| 228 | 52 |
| 232 | 65 |
| 236 | 33 |
| 250 | 57 |
| 262 | 45 |
| 283 | 49 |
| 285 | 59 |
| 306 | 0 |

(iv) Additional In Vivo Pain Models

There are a number of additional animal models that can be employed for studying pain. Generally, these pain models mimic one of the mechanisms of pain (e.g., nociceptive, inflammatory, or neuropathic pain), rather than the pain associated with any one disease or injury. Such models provide evidence of whether a drug or therapy will be effective in treating any of a number of injuries, diseases, or conditions that generate pain via a particular mechanism. In addition to the Chronic Constriction Injury Model (CCI) discussed above, other animal models of pain that can be used to evaluate test compounds include, but are not limited to, the Chung model, the carageenan induced hyperalgesia model, and the Freund's complete adjuvant (CFA) induced hyperalgesia model.

(v) In Vivo Efficacy Against Itch

Test compounds were evaluated for efficacy against itch in an in vivo mouse model of itch. Specifically, CD1 male mice (about 30 g) were shaved on the back of their neck about 18 hours before testing. Test compound in 10% DMSO/PEG 400 was administered orally. 60 Minutes after oral administration of the test compound, chloroquine (400 µg/50 µL) was injected with a Hamilton syringe. Within a minute of injection the mice were observed for 10 minutes and the episodes of scratching were recorded.

d. METHODS OF USING THE COMPOUNDS

Data in Table 1 demonstrate that the present compounds are modulators of TRPV3 receptors, and thus are useful in the treatment of diseases, conditions, and/or disorders modulated by TRPV3. The relationship between therapeutic effect and inhibition of TRPV3 has been shown in WO2007/056124; Wissenbach, U. et al., Biology of the cell (2004), 96, 47-54; Nilius, B. et al., Physiol Rev (2007), 87, 165-217; Okuhara, D.Y. et al., Expert Opinion on Therapeutic Targets (2007), 11, 391-401; Hu, H. Z. et al., Journal of Cellular Physiology (2006), 208, 201-212.

One embodiment is therefore directed to a method for treating a disease, condition, and/or disorder modulated by TRPV3 in a subject in need thereof, said method comprises administering to the subject a therapeutically effective amount of a compound, or pharmaceutically acceptable salt, solvate, salt of a solvate or solvate of a salt thereof, optionally with a pharmaceutically acceptable carrier.

Diseases, conditions, and/or disorders that are modulated by TRPV3 include, but are not limited to, migraine, arthralgia, cardiac pain arising from an ischemic myocardium, acute pain, chronic pain, nociceptive pain, neuropathic pain, postoperative pain, pain due to neuralgia (e.g., post-herpetic neuralgia, traumatic neuralgia, fibromyalgia, trigeminal neuralgia), pain due to diabetic neuropathy, dental pain and cancer pain, inflammatory pain conditions (e.g. arthritis and osteoarthritis).

Diseases, conditions, and/or disorders that are modulated by TRPV3 also include, but are not limited to, pain such as neuropathic pain, nociceptive pain, dental pain, HIV pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, itch, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

One embodiment provides methods for treating pain (for example, migraine, inflammatory pain, acute pain, chronic pain, neuropathic pain, nociceptive pain, arthritic pain, osteoarthritic pain, post-operative pain, cancer pain, lower back pain, diabetic neuropathy, eye pain) in a subject (including human) in need of such treatment.

Certain embodiments provides methods for treating itch in a subject (including human) in need of such treatment.

The methods comprise administering to the subject therapeutically effective amount of a compound as described herein, or a pharmaceutically acceptable salt, solvate, salt of a solvate, or solvate of a salt thereof, optionally with a pharmaceutically acceptable carrier. The method further comprises administration of the present compound as a single dose. The method also comprises repeated or chronic administration of the present compound over a period of days, weeks, months, or longer. In certain embodiments, the method comprises administering to the subject a therapeutically effective amount of a compound as described herein, or a pharmaceutically acceptable salt, solvate, salt of a solvate, or solvate of a salt thereof, in combination with one or more additional agents appropriate for the particular disease, condition, or disorder being treated.

When combinations of a TRPV3 inhibitor and one or more other compounds or agents are administered, the invention contemplates administration via the same route of administration or via differing routes of administration.

Another embodiment provides method for increasing the therapeutic effectiveness or potency of compounds described herein by repeated or chronic administration over a period of days, weeks, or months.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, other drugs, compounds and/or materials used in combination with the particular compound employed, the age, sex, weight, condition, general health and prior medical history of the patient being treated, the severity of the condition being treated, and like factors well known in the medical arts.

A physician or veterinarian having ordinary skill in the art can readily determine and prescribe the effective amount of the pharmaceutical composition required. For example, the physician or veterinarian could start doses of the compounds employed in the pharmaceutical compositions at levels lower than required to achieve the desired therapeutic effect and gradually increase the dosage until the desired effect is achieved. In the treatment of certain medical conditions, repeated or chronic administration of the compounds may be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest, or pharmaceutically acceptable salts, solvates, or salts of solvates thereof, in combination with one or more pharmaceutically acceptable carriers. The phrase "therapeutically effective amount" of a compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

The compounds may be administered alone, or in combination with one or more other compounds described herein, or in combination (i.e. co-administered) with one or more additional pharmaceutical agents. For example, one or more compounds, or pharmaceutically acceptable salts, solvates, salts of solvates, or solvates of salts thereof, may be administered in combination with one or more analgesic such as, but not limited to, acetaminophen, salicylates, glucocorticosteroids, opioids such as, but not limited to, morphine; and non-steroidal anti-inflammatory drugs (NSAIDs), or combinations thereof. In certain embodiments, the analgesic is opioid (e.g. morphine) or nonsteroidal anti-inflammatory drugs (NSAIDs). In one certain embodiments, a compound of the invention is co-administered with nonsteroidal anti-inflammatory drugs (NSAIDs).

Non-limiting examples of NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, the compounds and one or more additional pharmaceutical agents may be administered at essentially the same time (e.g., concurrently) or at separately staggered times (e.g., sequentially).

e. PHARMACEUTICAL COMPOSITIONS

Further provided herein is a pharmaceutical composition that comprises a compound or a pharmaceutically acceptable salt, solvate, salt of a solvate, or solvate of a salt thereof, formulated together with a pharmaceutically acceptable carrier.

Another aspect provides pharmaceutical composition comprising a compound or a pharmaceutically acceptable salt, solvate, salt of a solvate, or solvate of a salt thereof, in combination with an analgesic (e.g. acetaminophen or opioid such as morphine or other related opioids), or in combination with a nonsteroidal anti-inflammatory drugs (NSAIDs), or a combination thereof, formulated together with a pharmaceutically acceptable carrier.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of the compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds can be prepared by a variety of processes well known for the preparation of compounds of this class.

For example, the compounds described herein wherein the groups $G^1$, $X^1$, $X^2$, $X^3$, $X^4$, $X^5$, $G^2$, $G^{2d}$, $R^{z1}$, $R^{z2}$, $R^{1g}$, $R^{10}$, u, p, and $Z^1$ have the meanings as set forth in the summary section unless otherwise noted, can be synthesized as shown in Schemes 1-9.

Abbreviations which have been used in the descriptions of the Schemes and the Examples that follow are: $(Boc)_2O$ for di-tert-butyl dicarbonate, DAST for (diethylamino)sulfur trifluoride; DIBAL of DIBAL-H for diisobutylaluminum hydride, DIPEA for diisopropylethyl amine, DMAP for 4-(dimethylamino)pyridine, DMF for N,N-dimethylformamide, DMSO for dimethyl sulfoxide, EtOAc for ethyl acetate, EtOH for ethanol, HATU for O-(7-azabenzotriazol-1-yl)-N, N,N',N'-tetramethyluronium hexafluorophosphate, HMDS for hexamethyl disilylazide, HMPA for hexamethylphosphoramide, IPA for isopropanol, LCMS or LC-MS for liquid chromatography-mass spectroscopy, LDA for lithium diisopropylamide; MeOH for methanol; MTBE for methyl tertbutyl ether, n-BuLi for n-butyl lithium, Prep-HPLC for preparative high performance liquid chromatography, prep-TLC for preparatory thick layer chromatography, SFC for supercritical fluid chromatography, TBAF for tetrabutyl ammonium fluoride, TFA for trifluoroacetic acid, THF for tetrahydrofuran, and TsOH for p-toluenesulfonic acid.

Compounds of Formula (I) wherein u is 0 can be prepared using general procedures as illustrated in Scheme 1.

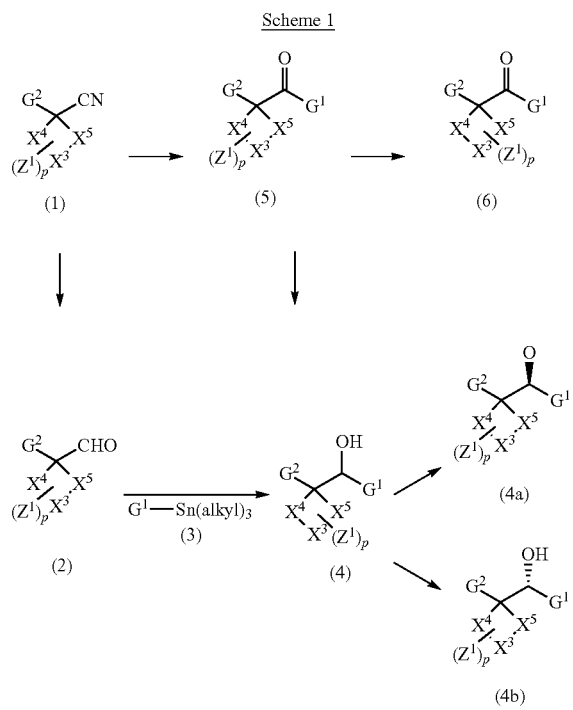

Reduction of nitriles of Formula (I) with a reducing agent such as, but not limited to, diisobutylaluminum hydride, at a temperature of about –78° C., and in a solvent such as, but not limited to, dichloromethane, produces aldehydes of Formula (2). Treatment of the aldehydes (2) with trialkylstannyl of Formula (3) in the presence of n-butyllithium and in a solvent such as, but not limited to, tetrahydrofuran, provides alcohols of Formula (4). The reaction is generally conducted at low temperature, such as at about –78° C. to about –100° C.

Conversion of (2) to (4) may also be achieved by treatment of (2) with $G^1$-Li (prepared in situ from the reaction of $G^1$-H or $G^1$-Br with a base such as n-butyllithium or lithium hexamethyl disilylazide in a solvent such as THF or diethyl ether at about –78° C.) at about room temperature.

Alternatively, compounds of Formula (4) may be prepared from the nitriles of Formula (I) by (a) treatment with a bromide of formula $G^1$-Br in the presence of n-butyllithium and at about –78° C.; and (b) treating the intermediate from step (a) with sulfuric acid at about 40 to about 60° C.; to provide ketones of Formula (5); and subsequently reducing the ketones with a reducing agent such as, but not limited to, sodium borohydride at about room temperature, in a solvent such as, but not limited to, methanol.

The nitriles of Formula (I) may be prepared from reaction of nitriles of Formula (16) with halides of Formula $G^2$-$R^{101}$ wherein $R^{101}$ is Br or F, in the presence of a base such as lithium, sodium, or potassium hexamethyl disilazide, or lithium diisopropylamide, and in a solvent such as, for example, toluene, at about room temperature to about 60° C.

Chiral alcohols of Formula (4a) and (4b) can be obtained by separation of the enantiomers using chiral columns or by chiral reduction of the ketones of Formula (5), for example, by reducing (5) in the presence of a chiral agent such as, but not limited to, (S,S)—N-(p-toluenesulfonyl)-1,2-diphenylethanediamine(chloro)(p-cumene)ruthenium (II), and a hydrogen source such as, but not limited to, formic acid, ammonium formate, or gaseous hydrogen.

Oximes of Formula (6) can be prepared by treatment of the ketones (5) with compounds of Formula $H_2NOR^{10}$ using reaction conditions that are known to one skilled in the art.

Nitriles of Formula (I) may be purchased or prepared using general procedures known in the art such as those illustrated in Scheme 2:

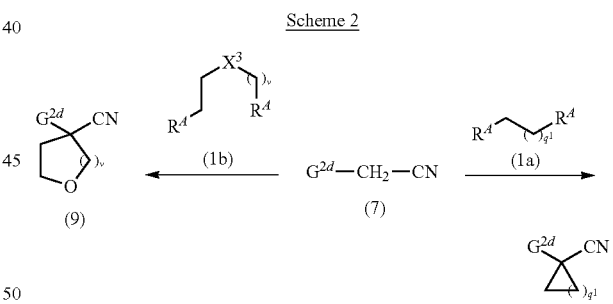

Nitriles of Formula (7) can be treated with compounds of Formula (Ia) wherein q1 is 1, 2, 3, 4, 5, or 6, or Formula (Ib) wherein $X^3$ is O, v is 1 or 2, and each $R^A$ in Formula (1a) and (1b) is the same or different, and is chloro, bromo, mesylate, or tosylate, to provide nitriles of Formula (8) and (9) respectively. The reaction is generally conducted in the presence of a base such as, but not limited to, sodium hydride, and in an aprotic solvent such as, but not limited to, DMSO, and at a temperature ranging from about 0° C. to about 50° C., typically at about room temperature. Alternatively, the conversion can be achieved utilizing lithium diisopropyl amide as a base, and at a temperature of about –78° C.

Scheme 3 further illustrates synthetic methods for the preparation of the intermediate nitriles used in Scheme 1.

Scheme 3

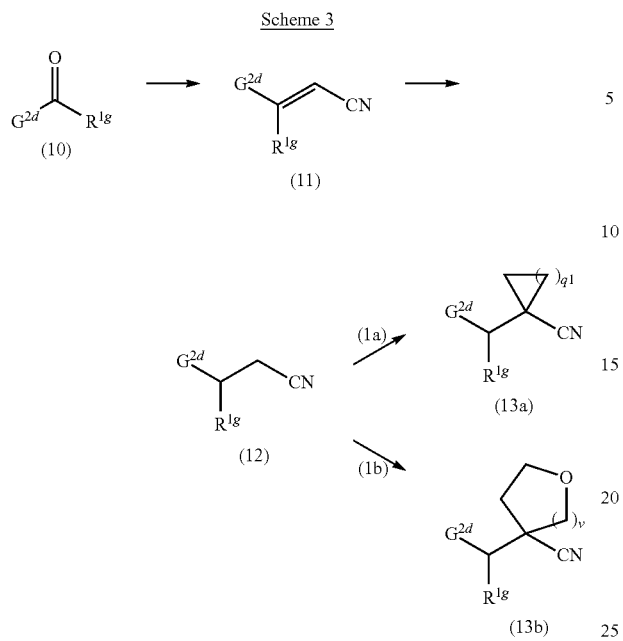

Reaction of ketones of Formula (10) with diethyl cyanomethylphosphonate in the presence of a base such as, but not limited to, sodium hydride at about room temperature provides alkenes of Formula (11). Reduction of the alkenes to compounds of Formula (12) can be accomplished by hydrogenation in the presence of Pd/C catalyst. Alternatively, the reduction reaction can be conducted in the presence of a reducing agent such as, but not limited to, sodium borohydride, in methanol, at about room temperature. Treatment of compounds of Formula (12) with (1a) or (1b) utilizing conditions as described in Scheme 2 provide the intermediate nitrile of Formula (13a) or (13b) respectively.

Scheme 4

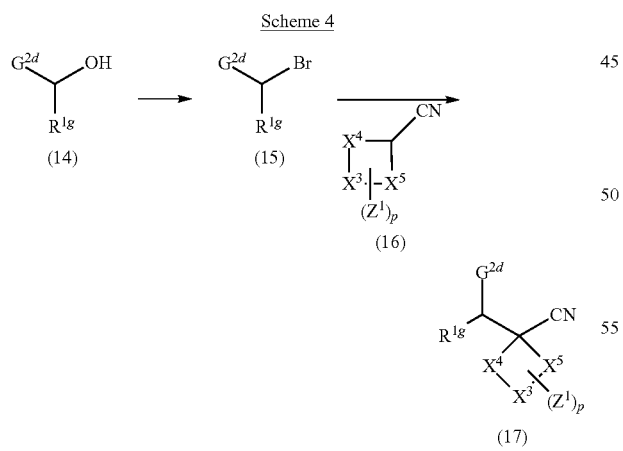

Nitriles of Formula (17) can be prepared from alcohols of Formula (14) via a two-step reactions. The alcohols are first treated with tribromophosphine at about room temperature, followed by the reaction of the resulting bromides of Formula (15) with nitriles of Formula (16) in the presence of lithium diisopropyl amide at about −78° C.

Compounds of Formula (I) wherein u is 0, $X^1$ is OH, $X^2$ is hydrogen, $X^3$ is O, $X^4$ and $X^5$ are $CH_2$, and $G^2$ is $G^{2d}$ can be prepared using general procedure as shown in Scheme 5.

Scheme 5

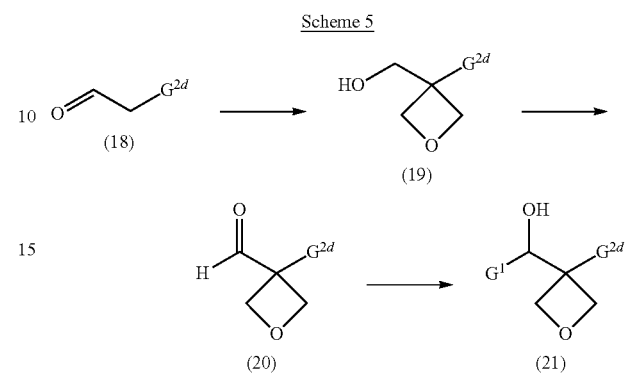

Aldehydes of Formula (18) can be treated with paraformaldehyde and calcium hydroxide to form oxenatyl alcohols of Formula (19). Swern oxidation of (19) provides aldehydes of Formula (20). Treatment of (20) with bromides of Formula $G^1$-Br in the presence of n-butyllithium provides compounds of Formula (21).

Aldehydes of Formula (2) and ketones of Formula (5) may be prepared utilizing reaction conditions known to one skilled in the art. For example, as illustrated in Scheme 6, esters of Formula (22) may be treated with $G^1$-Li (prepared in situ from the reaction of $G^1$-H or $G^1$-Br with n-butyl lithium, and in a solvent such as, for example, THF or diethyl ether, at about −78° C.) at about room temperature to provide ketones (5). Reduction of esters (22) by treatment with a reducing agent such as, for example, lithium aluminum hydride, and in a solvent such as, for example, THF, at about room temperature provides the primary alcohols (23). Swern oxidation of (23) provides aldehydes (2).

Scheme 6

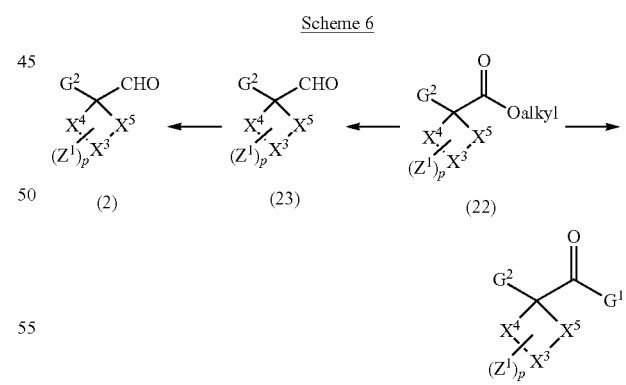

Scheme 7 illustrates general procedures for the synthesis of nitriles of Formula (I) wherein $G^2$ is $G^{2d}$, $X^3$, $X^4$, and $X^5$ are $CH_2$, p is 1 or 2 and $Z^1$ is F, OH, O(alkyl) (e.g. $OCH_3$), or oxo, or two $Z^1$ together form a ring such as 1,3-dioxolanyl; and the preparation of esters of Formula (22) wherein $G^2$ is $G^{2d}$, $X^3$, $X^4$, and $X^5$ are $CH_2$, and p is 1 and $Z^1$ is oxo, or p is 2 and both $Z^1$ is F, or p is 2 and both $Z^1$ is $OCH_3$.

Scheme 7

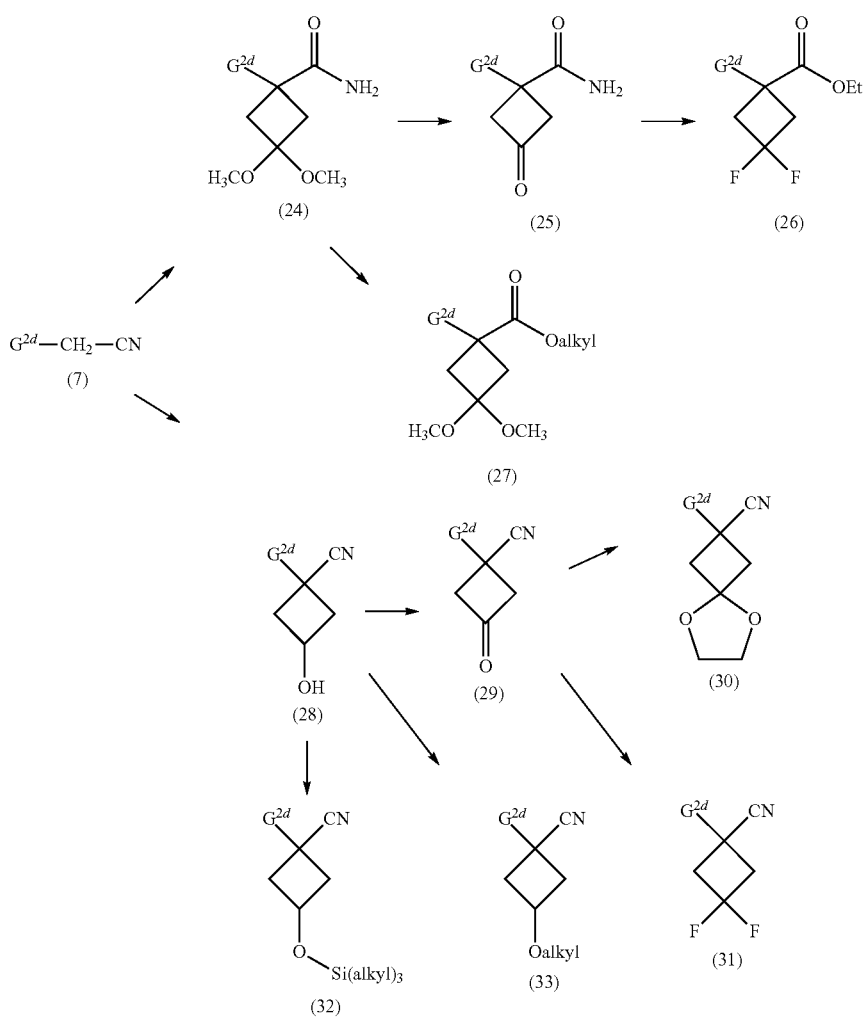

Nitriles (7) may be converted to compounds (24) by reacting with 1,3-dibromo-2,2-dimethoxypropane and a base such as, for example, sodium or potassium tert-butoxide and in a solvent such as, for example, DMSO, at elevated temperature (e.g. about 100 to about 130° C.). Refluxing (24) with concentrated sulfuric acid in ethanol provides the esters (25). Reaction of (25) with (diethylamino)sulfur trifluoride in a solvent such as, for example, dichloromethane, at room temperature provides compounds (26).

Reaction of (24) with acetyl chloride in methanol or ethanol provides the esters of Formula (27).

Transformation of nitriles of Formula (7) to compounds (28) may be achieved by (a) treating (7) with methyllithium at about −78° C., (b) treating the intermediate formed in step (a) with epibromohydrin in a solvent such as, for example, THF, at about −78° C.; and (c) treating with methyl magnesium bromide at about room temperature. Oxidation of (28) with an oxidizing agent such as, for example, Dess-Martin periodinane provides the ketones (29). (29) may be converted to (30) by reaction with 1,2-bis(trimethylsilyloxy)ethane or 1,2-ethanediol in a solvent such as, for example, dichloromethane, at about room temperature. Reaction of (29) with (diethylamino)sulfur trifluoride in a solvent such as, for example, dichloromethane, at room temperature provides compounds (31).

The hydroxy group of the cyclobutane ring may be protected using methodologies known in the art, for example, by treatment of (28) with trialkylsilyl chloride (e.g. tert-butylchlorodimethylsilane) in the presence of a base such as, for example, triethylamine or diisopropylethyl amine, in a solvent such as, for example, acetonitrile, and at about room temperature. Alkylation of (28) to afford compounds (33) may be accomplished by treatment of (28) with an alkyl halide (e.g. methyl iodide) in the presence of a base such as, for example, sodium hydride, in a solvent such as, for example, THF or diethyl ether, at about room temperature.

Nitriles (7) may be commercially available or may be prepared using synthesis analogous to those known in the art. For example, the nitriles (7) may be prepared from the corresponding acids or ester as outlined in Scheme 8.

Scheme 8

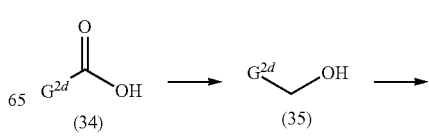

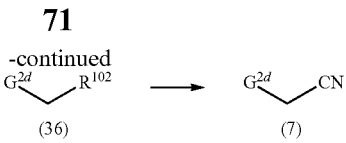

The acids (34) may be converted to the corresponding mixed anhydrides by reacting with suitable chloroformates (e.g. ethyl chloroformates) in a solvent such as, for example, THF in the presence of a base such as, for example, triethylamine or diisopropylethyl amine, at about 0° C. to about 10° C. Without isolation, the resulting mixed anhydrides obtained may be reduced to alcohols (35) in the presence of a reducing agent such as, for example, sodium borohydride, at about −78° C. Alternatively, the acids may be (a) converted to esters using methodologies known to one skilled in the art, and (b) reduced the resulting esters with a reducing agent such as, for example, sodium borohydride, in a solvent such as, methanol, at about 60° C. to provide alcohols (35).

Conversion of (35) to chlorides (36) wherein $R^{102}$ is Cl may be accomplished by treatment of (35) with phosphorous oxychloride in a solvent such as, for example, DMF, at about room temperature.

(35) may also be converted to tosylates or methanesulfonates (36) wherein $R^{102}$ is tosylate or methanesulfonate by treating alcohols (35) with p-toluenesulofonyl chloride or methanesulfonyl chloride respectively, in the presence of a base such as, for example, triethylamine, in a solvent such as, for example, dichloromethane. Displacement reaction of the tosylates, methanesulfonates, and chlorides (36) respectively with KCN in a solvent such as, for example, DMSO, or a mixture of ethanol and water, at about room temperature to about 60° C. provides nitriles (7).

Compounds of Formula (4) wherein $X^3$, $X^4$, and $X^5$ are $CH_2$, p is 1 or 2, and $Z^1$ is $OCH_3$, $CH_3$, $=NOR^{z1}$, or $NN(R^{z2})_2$, may be prepared as shown in Scheme 9.

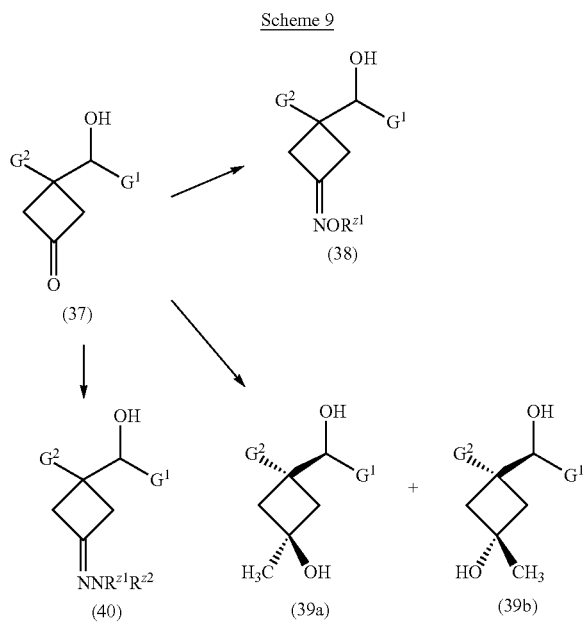

Scheme 9

Compounds of Formula (37) may be transformed to compounds of Formula (38) using reaction conditions known to one skilled in the art. For example, (37) may be treated with compounds of Formula $R^{z1}ONH_2$, or the hydrochloride salts thereof, in a solvent such as, for example, methanol, and in the presence of a base such as, for example, methylmorpholine, at about 60° C., to provide oximes of Formula (38).

Hydrazones (40) may be obtained from the reaction of (37) with hydrazines of Formula $R^{z1}R^{z2}NNH_2$ in the presence of acetic acid, and in a solvent such as, for example, THF, at about 60° C.

Tertiary alcohols (39a) and (39b) may be obtained from the reaction of (37) with methyl lithium at about room temperature, in a solvent such as, for example, 2-methyltetrahydrofuran. The isomers obtained may be separated by methodologies known to one skilled in the art, for example, by chromatography.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

Generally, LCMS measurement were run on Agilent 1200 HPLC/6100 SQ System using the follow condition: Mobile Phase: A: Water(0.05% TFA) B: Acetonitirle (0.05% TFA); Gradient Phase: 5%-95% in 1.3 min; Flow rate: 1.6 mL/min; Column: XBridge, 2.5 min; Oven temp: 50° C.

The preparation of Examples 1-77 is reported in International Application No. PCT/CN2010/001213 filed Aug. 10, 2010 (WIPO Interernational Publication No. WO12/19315 published Feb. 16, 2012).

Example 1

[1-(2-fluorophenyl)cyclobutyl](pyridin-2-yl)methanol

Example 2

[1-(3-fluorophenyl)cyclobutyl](pyridin-2-yl)methanol

Example 3

[1-(4-fluorophenyl)cyclobutyl](pyridin-2-yl)methanol

Example 4

[1-(3,4-difluorophenyl)cyclobutyl](pyridin-2-yl)methanol

Example 5 pyridin-2-yl{1-[2-(trifluoromethyl)phenyl]cyclobutyl}methanol

Example 6 pyridin-2-yl{1-[3-(trifluoromethyl)phenyl]cyclobutyl}methanol

Example 7

[1-(2-methylphenyl)cyclobutyl](pyridin-2-yl)methanol

Example 8

[1-(3-methylphenyl)cyclobutyl](pyridin-2-yl)methanol

Example 9

[1-(4-methylphenyl)cyclobutyl](pyridin-2-yl)methanol

Example 10 pyridin-2-yl{1-[2-(trifluoromethoxy)phenyl]cyclobutyl}methanol

Example 11 pyridin-2-yl{1-[3-(trifluoromethoxy)phenyl]cyclobutyl}methanol

Example 12 pyridin-2-yl{1-[4-(trifluoromethoxy)phenyl]cyclobutyl}methanol

Example 13

{1-[3,5-bis(trifluoromethyl)phenyl]cyclobutyl}(pyridin-2-yl)methanol

Example 14

{1-[3-fluoro-5-(trifluoromethyl)phenyl]cyclobutyl}(pyridin-2-yl)methanol

Example 15

{1-[4-fluoro-3-(trifluoromethyl)phenyl]cyclobutyl}(pyridin-2-yl)methanol

Example 16

{1-[4-(methylsulfonyl)phenyl]cyclobutyl}(pyridin-2-yl)methanol

Example 17

1-[3-fluoro-4-(trifluoromethyl)phenyl]cyclobutyl}(pyridin-2-yl)methanol

Example 18

{1-[4-(diethylamino)phenyl]cyclobutyl}(pyridin-2-yl)methanol

Example 19 pyridin-2-yl(1-pyridin-2-ylcyclobutyl)methanol

Example 20 pyridin-2-yl(1-pyridin-3-ylcyclobutyl)methanol

Example 21 pyridin-2-yl(1-pyridin-4-ylcyclobutyl)methanol

Example 22

[1-(1,1'-biphenyl-4-yl)cyclobutyl](pyridin-2-yl)methanol

Example 23

[1-(3-phenoxyphenyl)cyclobutyl](pyridin-2-yl)methanol

Example 24

[1-(4-phenoxyphenyl)cyclobutyl](pyridin-2-yl)methanol

Example 25

[1-(4-benzylphenyl)cyclobutyl](pyridin-2-yl)methanol

Example 26

(S)-[1-(3,4-dichlorophenyl)cyclobutyl](pyridin-2-yl)methanol

Example 27

(S)-{1-[2-fluoro-4-(trifluoromethyl)phenyl]cyclobutyl}(pyridin-2-yl)-methanol

Example 28

(S)-pyridin-2-yl{1-[4-(trifluoromethyl)phenyl]cyclobutyl}methanol

Example 29

(S)-{1-[3-fluoro-4-(trifluoromethyl)phenyl]cyclobutyl}(pyridin-2-yl)-methanol

Example 30

(S)-[1-(3,4-dichlorophenyl)cyclobutyl] (3-methylpyridin-2-yl)methanol

Example 31 pyrimidin-2-yl{1-[4-(trifluoromethoxy)phenyl]cyclobutyl}methanol

Example 32

[1-(2-fluorophenyl)cyclobutyl](pyrimidin-2-yl)methanol

Example 33

[1-(3-fluorophenyl)cyclobutyl](pyrimidin-2-yl)methanol

Example 34

[1-(4-fluorophenyl)cyclobutyl](pyrimidin-2-yl)methanol

Example 35

[1-(3,4-difluorophenyl)cyclobutyl](pyrimidin-2-yl)methanol

Example 36 pyrimidin-2-yl{1-[2-(trifluoromethoxy)phenyl]cyclobutyl}methanol

Example 37 pyrimidin-2-yl{1-[3-(trifluoromethoxy)phenyl]cyclobutyl}methanol

Example 38

[1-(3,4-dichlorophenyl)cyclobutyl] (pyrimidin-2-yl)methanol

Example 39

(S)-[1-(3,4-dichlorophenyl)cyclobutyl](pyrimidin-2-yl)methanol

Example 40

(R)-[1-(3,4-dichlorophenyl)cyclobutyl](pyrimidin-2-yl)methanol

Example 41

(S)-pyrimidin-2-yl{1-[4-(trifluoromethyl)phenyl]cyclobutyl}methanol

Example 42

(R)-pyrimidin-2-yl{1-[4-(trifluoromethyl)phenyl]cyclobutyl}methanol

Example 43

[1-(3,4-dichlorophenyl)cyclohexyl](pyridin-2-yl)methanol

Example 44

{1-[1-(3-chlorophenyl)ethyl]cyclobutyl}(pyridin-2-yl)methanol

Example 45

{1-[1-(2-methylphenyl)ethyl]cyclobutyl}(pyridin-2-yl)methanol

Example 46

{1-[1-(4-fluorophenyl)ethyl]cyclobutyl}(pyridin-2-yl)methanol

Example 47

{1-[1-(3-fluorophenyl)ethyl]cyclobutyl}(pyridin-2-yl)methanol

Example 48

{1-[1-(2-fluorophenyl)ethyl]cyclobutyl}(pyridin-2-yl)methanol

Example 49

{1-[1-(4-chlorophenyl)ethyl]cyclobutyl}(pyridin-2-yl)methanol

Example 50

{1-[1-(2-chlorophenyl)ethyl]cyclobutyl}(pyridin-2-yl)methanol

Example 51

[1-(1-phenylethyl)cyclobutyl](pyridin-2-yl)methanol

Example 52

[1-(4-methylbenzyl)cyclobutyl](pyridin-2-yl)methanol

Example 53 pyridin-2-yl(1-{1-[4-(trifluoromethyl)phenyl]ethyl}cyclobutyl)methanol

Example 54 pyridin-2-yl(1-{1-[3-(trifluoromethyl)phenyl]ethyl}cyclobutyl)methanol

Example 55

[1-(2,3-dihydro-1H-inden-1-yl)cyclobutyl](pyridin-2-yl)methanol

Example 56 pyridin-2-yl[1-(1,2,3,4-tetrahydronaphthalen-1-yl)cyclobutyl]methanol

Example 57

[1-(3,4-dihydro-2H-chromen-4-yl)cyclobutyl](pyridin-2-yl)methanol

Example 58 pyridin-2-yl[1-(2,2,2-trifluoro-1-phenylethyl)cyclobutyl]methanol

Example 59

[4-(3,4-dichlorophenyl)tetrahydro-2H-pyran-4-yl](pyridin-2-yl)methanol

Example 60

(4-phenyltetrahydro-2H-pyran-4-yl)(pyridin-2-yl)methanol

Example 61

[4-(3-fluorophenyl)tetrahydro-2H-pyran-4-yl](pyridin-2-yl)methanol

Example 62

[4-(4-fluorophenyl)tetrahydro-2H-pyran-4-yl](pyridin-2-yl)methanol

Example 63

[4-(3,4-difluorophenyl)tetrahydro-2H-pyran-4-yl](pyridin-2-yl)methanol

Example 64

[4-(4-chlorophenyl)tetrahydro-2H-pyran-4-yl](pyridin-2-yl)methanol

Example 65 pyridin-2-yl{4-[4-(trifluoromethyl)phenyl]tetrahydro-2H-pyran-4-yl}-methanol

Example 66 pyridin-2-yl{4-[3-(trifluoromethoxy)phenyl]tetrahydro-2H-pyran-4-yl}-methanol

Example 67 pyridin-2-yl{4-[4-(trifluoromethoxy)phenyl]tetrahydro-2H-pyran-4-yl}-methanol

Example 68

2-(1-phenylcyclobutyl)-1-(pyridin-2-yl)ethanol

Example 69

2-[1-(4-chlorophenyl)cyclobutyl]-1-(pyridin-2-yl)ethanol

Example 70

2-[1-(4-fluorophenyl)cyclobutyl]-1-(pyridin-2-yl)ethanol

Example 71

2-[1-(3-fluorophenyl)cyclobutyl]-1-(pyridin-2-yl)ethanol

Example 72

2-[1-(3-chlorophenyl)cyclobutyl]-1-(pyridin-2-yl)ethanol

Example 73

2-[1-(3,4-dichlorophenyl)cyclobutyl]-1-(pyridin-2-yl)ethanol

Example 74

1-(pyridin-2-yl)-2-{1-[3-(trifluoromethyl)phenyl]cyclobutyl}ethanol

Example 75

1-(pyridin-2-yl)-2-{1-[4-(trifluoromethyl)phenyl]cyclobutyl}ethanol

Example 76

1-(pyridin-2-yl)-2-{1-[4-(trifluoromethoxy)phenyl]cyclobutyl}ethanol

Example 77

1-(pyridin-2-yl)-2-{1-[3-(trifluoromethoxy)phenyl]cyclobutyl}ethanol

Example 78 pyridin-2-yl{3-[4-(trifluoromethyl)phenyl]tetrahydrofuran-3-yl}methanol

Example 79

4-{3-[hydroxy(pyridin-2-yl)methyl]tetrahydrofuran-3-yl}benzonitrile

Example 80 pyridin-2-yl{3-[3-(trifluoromethoxy)phenyl]tetrahydrofuran-3-yl}methanol

Example 81

3-{3-[hydroxy(pyridin-2-yl)methyl]tetrahydrofuran-3-yl}benzonitrile

Example 82

[1-(3,4-dichlorophenyl)-3,3-difluorocyclobutyl](pyridin-2-yl)methanol

Example 82A 1-(3,4-dichlorophenyl)-3,3-dimethoxycyclobutanecarboxamide 3,4-Dichlorophenylacetonitrile (9.30 g, 50 mmol), 1,3-dibromo-2,2-dimethoxypropane (13.10 g, 50 mmol), and sodium tert-butoxide (10.57 g, 110 mmol) in DMSO (100 mL) and water (5 mL) were heated at 125° C. for 1 hour, then stirred at ambient temperature for 20 hours. The reaction mixture was diluted with water and extracted three times with diethyl ether. The organic layers were combined, washed with brine, dried with MgSO$_4$, filtered, and concentrated. The crude product was triturated with 1:1 diethyl ether/hexanes, and the solid collected by filtration was Example 82A (7.16 g, 23.54 mmol, 47.1% yield). $^1$H NMR (300 MHz, DMSO-d$_6$) δ 7.61-7.55 (m, 2H), 7.37 (s, 1H), 7.29 (dd, J=8.4, 2.2 Hz, 1H), 6.95 (s, 1H), 3.05 (s, 3H), 2.99 (s, 3H), 2.97-2.89 (m, 2H), 2.46-2.37 (m, 2H).

Example 82B ethyl 1-(3,4-dichlorophenyl)-3-oxocyclobutanecarboxylate

Example 82A (9.73 g, 32.0 mmol) was dissolved in ethanol (160 mL) and concentrated sulfuric acid (40 mL), and refluxed for 2 hours. The reaction mixture was cooled, diluted with water (100 mL) and stirred for 30 minutes. The mixture was poured onto a mixture of ice and 10N sodium hydroxide (75 mL), and extracted twice with diethyl ether. The organic layers were combined, washed with brine, dried with MgSO$_4$, filtered, and concentrated to give Example 82B (5.25 g, 18.28 mmol, 57.2% yield). MS (DCI$^+$): m/z 304.0 (M+NH$_4$). $^1$H NMR (300 MHz, DMSO-d$_6$) δ 7.68-7.63 (m, 2H), 7.37 (dd, J=8.4, 2.3 Hz, 1H), 4.10 (q, J=7.1 Hz, 2H), 3.82-3.60 (m, 4H), 1.12 (t, J=7.1 Hz, 3H).

Example 82C ethyl 1-(3,4-dichlorophenyl)-3,3-difluorocyclobutanecarboxylate

Example 82B (3.96 g, 13.79 mmol) was dissolved in dichloromethane (50 mL) and cooled to 0° C. DAST (3.64 mL, 27.6 mmol) in dichloromethane (10 mL) was added dropwise. The reaction mixture was allowed to warm to ambient temperature and stirred overnight. The reaction was quenched with saturated NaHCO$_3$ solution. The mixture was extracted twice with dichloromethane, and the combined organic layers washed with saturated NH$_4$Cl solution, dried with MgSO$_4$, filtered, and concentrated. The residue was chromatographed on an AnaLogix SF40-120 g column with 0-15% EtOAc in hexanes to give Example 82C (3.06 g, 9.90 mmol, 71.8% yield). $^1$H NMR (300 MHz, DMSO-d$_6$) δ 7.70-7.60 (m, 2H), 7.35 (dd, J=8.4, 2.3 Hz, 1H), 4.09 (q, J=7.1 Hz, 2H), 3.47-3.34 (m, 2H), 3.29-3.11 (m, 2H), 1.11 (t, J=7.0 Hz, 3H).

Example 82D

[1-(3,4-dichlorophenyl)-3,3-difluorocyclobutyl](pyridin-2-yl)methanone 2.5M n-Butyllithium (9.86 mL, 24.65 mmol) in hexanes was added to diethyl ether (60 mL) and cooled to −78° C. in a dry ice/acetone bath. 2-Bromopyridine (2.484 mL, 25.5 mmol) was added slowly, and the reaction was stirred for 30 minutes. Example 82C (5.08 g, 16.43 mmol) in diethyl ether (15 mL) was added dropwise over 10 minutes. The reaction was then warmed to ambient temperature by removing the cooling bath. The reaction was quenched by the addition of saturated NH$_4$Cl solution, and extracted twice with diethyl ether. The combined organic layers were dried with MgSO$_4$, filtered, and concentrated. The residue was chromatographed on an AnaLogix SF40-120 g column ane eluted with 20-35% dichloromethane in hexanes to give Example 82D (5.00 g, 14.61 mmol, 89% yield). MS (DCI$^+$): m/z 342.0 (M+H). $^1$H NMR (300 MHz, DMSO-d$_6$) δ 8.61 (dt, J=4.7, 1.2 Hz, 1H), 8.03-7.93 (m, 2H), 7.74 (d, J=2.2 Hz, 1H), 7.62-7.53 (m, 2H), 7.44 (dd, J=8.5, 2.3 Hz, 1H), 3.68-3.48 (m, 2H), 3.46-3.32 (m, 2H).

Example 82E

[1-(3,4-dichlorophenyl)-3,3-difluorocyclobutyl](pyridin-2-yl)methanol

Example 82D (0.07 g, 0.205 mmol) was dissolved in ethanol (5 mL). Sodium borohydride (0.019 g, 0.511 mmol) was added and the reaction was stirred at ambient temperature for 1.5 hours. The reaction mixture was quenched with 1N hydrochloric acid (1.5 mL), made basic with NaHCO$_3$ solution, diluted with water and extracted with diethyl ether. The organic layers were washed with brine, dried with MgSO$_4$, filtered, and concentrated to give Example 82E (0.039 g, 0.113 mmol, 55.4% yield) as an oil. MS (ESI$^+$): m/z 344.0 (M+H). $^1$H NMR (300 MHz, DMSO-d$_6$) δ 8.44 (ddd, J=4.8, 1.7, 0.9 Hz, 1H), 7.57 (td, J=7.7, 1.8 Hz, 1H), 7.39 (d, J=8.3 Hz, 1H), 7.20 (ddd, J=7.5, 4.8, 1.1 Hz, 1H), 7.00 (d, J=2.2 Hz, 1H), 6.81-6.73 (m, 2H), 6.07 (d, J=4.7 Hz, 1H), 4.84 (d, J=4.7 Hz, 1H), 3.60-3.34 (m, 2H), 2.99-2.75 (m, 2H).

Example 83

[3-(4-methoxyphenyl)tetrahydrofuran-3-yl](pyridin-2-yl)methanol

Example 84

[3-(3,4-dimethoxyphenyl)tetrahydrofuran-3-yl](pyridin-2-yl)methanol

Example 85 pyridin-2-yl{1-[6-(trifluoromethyl)pyridin-3-yl]cyclobutyl}methanol

Example 86

[3-(3-chlorophenyl)oxetan-3-yl](pyridin-2-yl)methanol

Example 87

[3-(3,4-dichlorophenyl)oxetan-3-yl](pyridin-2-yl)methanol

Example 88

(anti)-pyridin-2-yl{2-[4-(trifluoromethyl)phenyl]tetrahydrofuran-2-yl}methanol

Example 89

(syn)-pyridin-2-yl{2-[4-(trifluoromethyl)phenyl]tetrahydrofuran-2-yl}methanol

Example 90

[2-(2-methylphenyl)tetrahydrofuran-2-yl](pyridin-2-yl)methanol

Example 91

[2-(3-methylphenyl)tetrahydrofuran-2-yl](pyridin-2-yl)methanol

Example 92

(anti)-pyridin-2-yl{2-[3-(trifluoromethoxy)phenyl]tetrahydrofuran-2-yl}methanol

Example 93

(syn)-pyridin-2-yl{2-[3-(trifluoromethoxy)phenyl]tetrahydrofuran-2-yl}methanol

Example 94

(anti)-pyridin-2-yl{2-[4-(trifluoromethoxy)phenyl]tetrahydrofuran-2-yl}methanol

Example 95

(syn)-pyridin-2-yl{2-[4-(trifluoromethoxy)phenyl]tetrahydrofuran-2-yl}methanol

Example 96

(anti)-pyridin-2-yl{2-[2-(trifluoromethoxy)phenyl]tetrahydrofuran-2-yl}-methanol

Example 97

(syn)-pyridin-2-yl{2-[2-(trifluoromethoxy)phenyl]tetrahydrofuran-2-yl}-methanol

Example 98

(anti)-2-(3,4-dichlorophenyl)tetrahydrofuran-2-yl](pyridin-2-yl)methanol

Example 99

(syn)-[2-(3,4-dichlorophenyl)tetrahydrofuran-2-yl](pyridin-2-yl)methanol

Example 100

(anti)-[2-(3-fluorophenyl)tetrahydrofuran-2-yl](pyridin-2-yl)methanol

Example 101

(syn)-[2-(3-fluorophenyl)tetrahydrofuran-2-yl](pyridin-2-yl)methanol

Example 102

(anti)-[2-fluorophenyl)tetrahydrofuran-2-yl](pyridin-2-yl)methanol

Example 103

(syn)-[2-(2-fluorophenyl)tetrahydrofuran-2-yl](pyridin-2-yl)methanol

Example 104

(anti)-[2-(3-chlorophenyl)tetrahydrofuran-2-yl](pyridin-2-yl)methanol

Example 105

(syn)-[2-(3-chlorophenyl)tetrahydrofuran-2-yl](pyridin-2-yl)methanol

Example 106

(anti)-pyridin-2-yl{2-[3-(trifluoromethyl)phenyl]tetrahydrofuran-2-yl}-methanol

Example 107

(syn)-pyridin-2-yl{2-[3-(trifluoromethyl)phenyl]tetrahydrofuran-2-yl}-methanol

Example 108

(anti)-[2-(3,4-difluorophenyl)tetrahydrofuran-2-yl](pyridin-2-yl)methanol

Example 109

(syn)-[2-(3,4-difluorophenyl)tetrahydrofuran-2-yl](pyridin-2-yl)methanol

Example 110 pyridin-2-yl{1-[5-(trifluoromethyl)pyridin-3-yl]cyclobutyl}methanol

Example 111

(S)-[1-(3,4-dichlorophenyl)-3,3-difluorocyclobutyl](pyridin-2-yl)methanol hydrochloride Example 82D (5 g, 14.61 mmol) was dissolved in formic acid (2.410 mL, 62.8 mmol) and triethylamine (5.09 mL, 36.5 mmol). (S,S)—N-(p-toluenesulfonyl)-1,2-diphenylethanediamine(chloro)(p-cymene)ruthenium(II) (0.093 g, 0.146 mmol) was added and the reaction mixture was stirred overnight at 35° C. The reaction mixture was cooled, diluted with dichloromethane, and washed with saturated NaHCO$_3$ solution. The organic layer was dried with MgSO$_4$, filtered, and concentrated. The residue was chromatographed on an AnaLogix SF40-80 g column and eluted with 100% dichloromethane. The fractions collected were concentrated, dissolved in 2N hydrogen chloride in methanol and concentrated to give the HCl salt of Example 111 (4.60 g, 12.08 mmol, 83% yield). MS (DCI$^+$): m/z 344.1 (M+H). $^1$H NMR (300 MHz, DMSO-d$_6$) δ 8.54 (d, J=5.2 Hz, 1H), 8.13-7.95 (m, 1H), 7.65-7.51 (m, 1H), 7.41 (d, J=8.4 Hz, 1H), 7.22 (d, J=6.7 Hz, 1H), 7.15 (d, J=2.0 Hz, 1H), 6.82 (dd, J=8.4, 2.2 Hz, 1H), 5.10 (s, 1H), 3.62-3.24 (m, 2H), 3.04-2.78 (m, 2H). [α]$_D$=−35.6° (c 0.715, MeOH). Calculated for C$_{16}$H$_{13}$Cl$_2$F$_2$NO.HCl: C, 50.49%; H, 3.71%; N, 3.68%. Found: C, 50.65%; H, 3.69%; N, 3.59%.

Example 112

{3,3-difluoro-1-[4-(trifluoromethoxy)phenyl]cyclobutyl}(pyridin-2-yl)-methanol

The title compound was prepared using procedures analogous to that described for the synthesis of Example 114, substituting 2-(4-(trifluoromethoxy)phenyl)-acetonitrile for 2-(3-(trifluoromethoxy)phenyl)acetonitrile. LC-MS: m/z (M+H) 360.1. $^1$H NMR (400 MHz, CDCl$_3$): δ 8.36-8.37 (d, J=4.8 Hz, 1H), 7.42-7.85 (m, 2H), 7.13-7.17 (m, 1H), 7.03-7.05 (d, J=8 Hz, 2H), 6.84-6.86 (d, J=8.4 Hz, 2H), 6.52-6.54 (d, J=7.6 Hz, 1H), 4.85 (s, 1H), 4.60 (br, 1H), 3.26-3.52 (m, 2H), 2.70-2.88 (m, 2H).

Example 113

{3,3-difluoro-1-[3-(trifluoromethyl)phenyl]cyclobutyl}(pyridin-2-yl)-methanol

The title compound was prepared using procedures analogous to that described for the synthesis of Example 114, substituting 2-(3-(trifluoromethyl)phenyl)-acetonitrile for 2-(3-(trifluoromethoxy)phenyl)acetonitrile. LC-MS: m/z (M+H) 344.1. $^1$H NMR (400 MHz, CDCl$_3$): δ 8.35-8.36 (d, J=4.4 Hz, 1H), 7.45-7.50 (m, 2H), 7.33-7.37 (t, J=7.6 Hz, 1H), 7.11-7.11 (m, 2H), 6.88 (s, 1H), 6.55-6.57 (d, J=8 Hz, 1H), 4.87 (s, 1H), 4.60 (br, 1H), 3.31-3.52 (m, 2H), 2.75-2.90 (m, 2H).

Example 114

{3,3-difluoro-1-[3-(trifluoromethoxy)phenyl]cyclobutyl}(pyridin-2-yl)-methanol

Example 114A 3,3-dimethoxy-1-(3-(trifluoromethoxy)phenyl)cyclobutanecarboxamide

The mixture of 1,3-dibromo-2,2-dimethoxypropane (1310 mg, 5.00 mmol), sodium tert-butoxide (1057 mg, 11 mmol) and 2-(3-(trifluoromethoxy)phenyl)acetonitrile (1006 mg, 5 mmol) in DMSO (12 mL) was stirred at 25° C. for about 16 hours, then heated at about 125° C. for about 30 minutes. The solution was cooled to room temperature, diluted with water, and extracted with ether three times. The organic phase was washed with saturated NH$_4$Cl. The combined organic layers were dried over MgSO$_4$, filtered, and concentrated. The crude mixture was purified by silica gel chromatography (50% Hexanes/EtOAc to 100% EtOAc) to afford the product (450 mg, 28.2%). LC-MS: m/z (M+H) 288. $^1$H NMR (400 MHz, DMSO-d$_6$): δ 7.44-7.48 (t, J=8 Hz, 1H), 7.41 (s, 1H), 7.34-7.36 (d, J=7.6 Hz, 1H), 7.30 (s, 1H), 7.22-7.24 (d, J=8 Hz, 1H), 6.95 (s, 1H), 3.05 (s, 3H), 3.00 (s, 3H), 3.00-2.95 (d, J=14 Hz, 2H), 2.43-2.40 (d, J=12.8 Hz, 2H).

Example 114B ethyl 3-oxo-1-(3-(trifluoromethoxy)phenyl)cyclobutanecarboxylate

To a solution of Example 114A (450 mg, 1.409 mmol) in EtOH (30 mL) was added concentrated H$_2$SO$_4$ (6 mL, 113 mmol); and mixture heated at about 90° C. for about 1 hour. The reaction mixture was cooled to room temperature, diluted with water, and extracted with ether (3×75 mL). The combined organic layers were washed with brine, dried over Na$_2$SO$_4$, filtered, and concentrated under reduced pressure to give residue which was used directly for the next step without further purification. (400 mg, 94%). LC-MS: m/z (M+H) 303.1.

Example 114C ethyl 3,3-difluoro-1-(3-(trifluoromethoxy)phenyl)cyclobutanecarboxylate To a solution of Example 114B (400 mg, 1.3 mmol) in dichloromethane (10 mL) was added a solution of DAST (0.350 mL, 2.65 mmol) in dichloromethane (5 mL) at 0° C. The mixture was warmed to room temperature and stirred for about 16 hours. The mixture was quenched by saturated aqueous sodium bicarbonate and extracted twice with dichloromethane. The combined organic layers were washed with brine, dried with magnesium sulfate, filtered, and the solvent removed under vacuum. The resulting mixture chromatographed on silica gel (hexanes/EtOAc) to give desired product (135 mg, 31.5%).
LC-MS: m/z (M+H) 325.1

Example 114D (3,3-difluoro-1-(3-(trifluoromethoxy)phenyl)cyclobutyl)methanol

To a solution of Example 114C (500 mg, 1.5 mmol) in THF (30 mL) was added LiAlH$_4$ (123 mg, 3.24 mmol) at 0° C. The mixture was warmed to room temperature and stirred for about 16 hours. The reaction mixture was quenched by saturated aqueous Na$_2$SO$_4$ solution, filtered, and washed twice with EtOAc. The combined organic layers were dried over MgSO$_4$, filtered, and concentrated to give the product as yellow oil (400 mg, 92%).

Example 114E 3,3-difluoro-1-(3-(trifluoromethoxy)phenyl)cyclobutanecarbaldehyde

To a mixture of the product from Example 114D (400 mg, 1.4 mmol) and sodium bicarbonate (1.2 g, 14.17 mmol) in dichloromethane (30 mL) was added Dess-Martin Periodinane (782 mg, 1.8 mmol) portionwise and the reaction was stirred for about 16 hours at room temperature. The mixture was quenched by saturated aqueous NaS$_2$O$_3$, and extracted twice with dichloromethane. The combined organic layers were washed with brine, dried with magnesium sulfate, filtered, and the solvent removed under vacuum. The resulting mixture was used directly in the next step without further purification (380 mg, 96%).

Example 114F

{3,3-difluoro-1-[3-(trifluoromethoxy)phenyl]cyclobutyl}(pyridin-2-yl)methanol

To a solution of 2-bromopyridine (321 mg, 2.034 mmol) in THF (20 mL) was added n-butyllithium (1.356 mL, 2.170 mmol) at −78° C. under nitrogen. The mixture was stirred for about 20 minutes at −78° C. Then a solution of Example 114E (380 mg, 1.356 mmol) in THF (5 mL) was added and the resulting mixture was stirred for another 30 minutes at the same temperature. The reaction mixture was quenched by saturated aqueous NH$_4$Cl, and extracted twice with EtOAc. The combined organic layers were washed with brine, dried with magnesium sulfate, filtered, and the solvent removed under vacuum. The resulting mixture was purified by Prep-HPLC (50-80% acetonitrile in water) to afford the title compound (111.3 mg, 22.8%). LC-MS: m/z (M+H) 360.1. $^1$H NMR (400 MHz, CDCl$_3$): δ 8.37-8.38 (d, J=4.4 Hz, 1H), 7.44-7.48 (m, 1H), 7.26-7.27 (d, J=6.4 Hz, 1H), 7.13-7.16 (m, 1H), 7.05-7.07 (d, J=8.4 Hz, 1H), 6.89-6.91 (d, J=7.6 Hz, 1H), 6.55 (s, 1H), 6.50-6.52 (d, J=8 Hz, 1H), 4.85 (s, 1H), 4.60 (br, 1H), 3.27-3.52 (m, 2H), 2.68-2.88 (m, 2H).

Example 115 pyridin-2-yl{1-[5-(trifluoromethyl)pyridin-2-yl]cyclobutyl}methanol

Example 116 pyridin-2-yl{1-[4-(trifluoromethyl)pyridin-2-yl]cyclobutyl}methanol

Example 117

3-(3,4-dichlorophenyl)-3-[(S)-hydroxy(pyridin-2-yl)methyl]cyclobutanone

Example 117A methyl 1-(3,4-dichlorophenyl)-3,3-dimethoxycyclobutanecarboxylate Concentrated sulfuric acid (25 mL, 469 mmol) was dissolved in MeOH (100 mL), and the solution was added to Example 82A (7.16 g, 23.54 mmol). The reaction was heated at reflux overnight, then cooled to ambient temperature and poured onto ice-water in which sodium hydroxide (30 g) had been dissolved. The mixture was extracted twice with diethyl ether. The combined organic layers were washed with brine, dried with $MgSO_4$, filtered, and concentrated. The residue was chromatographed on an AnaLogix SF40-150 g column and eluted with 10-20% EtOAc in hexanes to give Example 117A (4.29 g, 13.44 mmol, 57.1% yield). MS ($DCI^+$): m/z 336.1 ($M+NH_4$). $^1$H NMR (300 MHz, DMSO-$d_6$) δ 7.61 (d, J=8.4 Hz, 1H), 7.52 (d, J=2.2 Hz, 1H), 7.28 (dd, J=8.4, 2.2 Hz, 1H), 3.59 (s, 3H), 3.06 (s, 3H), 3.01 (s, 3H), 2.99-2.91 (m, 2H), 2.62-2.53 (m, 2H).

Example 117B 3-(3,4-dichlorophenyl)-3-picolinoylcyclobutanone 2.5M n-Butyllithium (8.06 mL, 20.16 mmol) in hexanes was added to diethyl ether (25 mL), and cooled to −78° C. in a dry ice/acetone bath. 2-Bromopyridine (2.032 mL, 20.83 mmol) was added, and the reaction was stirred for 30 minutes. Example 117A (4.29 g, 13.44 mmol) in diethyl ether (25 mL) was added dropwise over 10 minutes, and the reaction warmed to ambient temperature. The reaction was quenched with water and stirred overnight. 3N Hydrochloric acid (25 mL) was added, and the reaction stirred at ambient temperature for 1.5 hours. The reaction mixture was neutralized with 3N sodium hydroxide (25 mL), and extracted three times with EtOAc. The organic layers were washed with brine, dried with $MgSO_4$, filtered, and concentrated. TLC showed a mixture of intermediate (ketone/ketal) and product (ketone/ketone). The residue was dissolved in acetone (50 mL), and 12N hydrochloric acid (10 mL) was added. The reaction was stirred for 45 minutes, and concentrated. The residue was made basic with 3N sodium hydroxide, and extracted three times with EtOAc. The organic layers were washed with brine, dried with $MgSO_4$, filtered, and concentrated. The residue was chromatographed on an AnaLogix SF40-150 g column and eluted with 15% EtOAc in hexanes to give Example 117B (3.03 g, 9.46 mmol, 70.4% yield). MS ($DCI^+$): m/z 320.0 (M+H). $^1$H NMR (300 MHz, DMSO-$d_6$) δ 8.59 (ddd, J=4.7, 1.6, 1.0 Hz, 1H), 8.06-7.93 (m, 2H), 7.74 (d, J=2.2 Hz, 1H), 7.60-7.52 (m, 2H), 7.42 (dd, J=8.5, 2.3 Hz, 1H), 4.13-3.98 (m, 2H), 3.78-3.65 (m, 2H).

Example 117C 3-(3,4-dichlorophenyl)-3-[(S)-hydroxy(pyridin-2-yl)methyl]cyclobutanone Example 117B (0.3 g, 0.937 mmol), formic acid (0.155 mL, 4.03 mmol), triethylamine (0.326 mL, 2.343 mmol), and (S,S)—N-(p-toluenesulfonyl)-1,2-diphenyl-ethanediamine (chloro)(p-cymene)ruthenium(II) (5.97 mg, 9.37 µmol) were dissolved in THF (10 mL) and heated overnight at 35° C. The reaction mixture was diluted with saturated $NaHCO_3$ solution and extracted twice with dichloromethane. The organic layers were dried with $MgSO_4$ filtered, and concentrated. The residue was triturated with diethyl ether and the solids removed by filtration. The filtrate was chromatographed on an AnaLogix SF10-4 g column and eluted with 20% EtOAc in hexanes. The compound isolated was dissolved in 2N hydrogen chloride in methanol, followed by removal of solvent to give Example 117C as HCl salt (0.126 g, 0.351 mmol, 37.5% yield). MS ($DCI^+$): m/z 322.2 (M+H). $^1$H NMR (300 MHz, DMSO-$d_6$) δ 8.53 (dt, J=4.7, 1.3 Hz, 1H), 7.97-7.91 (m, 2H), 7.57-7.46 (m, 3H), 7.22 (dd, J=8.4, 2.2 Hz, 1H), 3.34-3.23 (m, 2H), 2.47-2.38 (m, 2H). $[α]_D$=−0.6° (c 0.640, MeOH).

Example 118

(trans)-3-(3,4-dichlorophenyl)-3-[(S)-hydroxy(pyridin-2-yl)methyl]cyclobutanol

Example 118A 3-(tert-butyldimethylsilyloxy)-1-(3,4-dichlorophenyl)cyclobutane-carbonitrile Example 150A (33.6 g, 139 mmol) and tert-butylchlorodimethylsilane (22.9 g, 152 mmol) were dissolved into anhydrous acetonitrile (140 mL), treated with DIPEA (36 mL, 207 mmol), and stirred overnight at room temperature. The reaction mixture was concentrated, dissolved into $CH_2Cl_2$ (200 mL), and washed twice with water. Each aqueous phase was back-extracted with $CH_2Cl_2$. The combined organic phases were washed with brine, dried ($Na_2SO_4$), filtered, and concentrated. The residue was chromatographed on silica gel (20-50% $CH_2Cl_2$ in hexanes) to give Example 118A (34.3 g, 96 mmol, 69.4% yield) as a white solid, a mixture of geometric isomers by proton NMR.

Example 118B

A solution of 2.5M n-butyllithium (58 mL, 145 mmol) in hexanes was added to anhydrous diethyl ether (90 mL) and cooled in a dry ice/acetone bath. Then 2-bromopyridine (14.6 mL, 150 mmol) in diethyl ether (80 mL) was added dropwise over 50 minutes, and the mixture was stirred for another hour. Then a solution of Example 118A (34.3 g, 96 mmol) in diethyl ether (100 mL) was added dropwise over about 25 minutes, and the resulting mixture was warmed to room temperature slowly overnight before being chilled with a water ice bath and kept at 10° C. or less as 3M aqueous HCl (100 mL) was added dropwise. The biphasic mixture was stirred cold for another 40 minutes and then slowly basified with 3M aqueous NaOH (150 mL). The aqueous phase was separated and extracted twice with EtOAc, and the combined organic phases were washed with brine, dried ($Na_2SO_4$), concentrated, and filtered through basic alumina with a 1:1 $CH_2Cl_2$/hexanes rinse. The filtrate was concentrated and chromatographed on silica (20-50% $CH_2Cl_2$ in hexanes). Impure fractions were chromatographed on silica (15-50% $CH_2Cl_2$ in hexanes) for further separation. Impure fractions of the second column were also chromatographed on silica (15-55% $CH_2Cl_2$ in hexanes). All lots of the first eluting isomer were combined to give Example 118B (11.41 g, 26.1 mmol, 27.2% yield) as a pale oil. MS (ESI): m/z 436 (M+H). $^1$H NMR (500 MHz, $CD_3CN$) δ 8.47 (ddd, J=4.7, 1.7, 0.9 Hz, 1H), 7.94 (ddd, J=7.8, 1.2, 0.9 Hz, 1H), 7.83 (ddd, J=7.8, 7.6, 1.7 Hz, 1H), 7.55 (d, J=2.2 Hz, 1H), 7.40 (ddd, J=7.6, 4.7, 1.2 Hz, 1H), 7.36 (d, J=8.4 Hz, 1H), 7.25 (dd, J=8.4, 2.2 Hz, 1H), 4.24 (tt, J=7.1, 7.1 Hz, 1H), 3.44-3.38 (m, 2H), 2.50-2.45 (m, 2H), 0.85 (s, 9H), 0.02 (s, 6H).

Example 118C

Example 118B (11.3 g, 25.9 mmol) was dissolved into anhydrous $CH_2Cl_2$ (100 mL) and methanol (10 mL), and the flask was placed in a water bath before solid sodium borohydride (1.03 g, 27.2 mmol) was added in one portion. The mixture was stirred overnight at room temperature, then concentrated and partitioned between EtOAc (100 mL) and water (50 mL). The aqueous phase was separated and extracted with more EtOAc, and the combined organic phases were washed with brine, dried ($Na_2SO_4$), filtered, and concentrated to give Example 118C (10.52 g, 23.99 mmol, 93% yield) as a white powder. MS (ESI): m/z 438 (M+H). $^1H$ NMR (300 MHz, DMSO-$d_6$) δ 8.43 (ddd, J=4.7, 1.7, 0.7 Hz, 1H), 7.59 (td, J=7.7, 1.8 Hz, 1H), 7.36 (d, J=8.3 Hz, 1H), 7.20 (ddd, J=7.5, 4.9, 1.1 Hz, 1H), 6.93-6.86 (m, 2H), 6.69 (dd, J=8.3, 2.1 Hz, 1H), 5.67 (d, J=3.4 Hz, 1H), 4.71 (d, J=3.1 Hz, 1H), 4.10 (p, J=7.0 Hz, 1H), 3.19-3.05 (m, 2H), 1.97 (dd, J=12.3, 7.1 Hz, 2H), 0.79 (s, 9H), −0.04 (s, 6H).

Example 118D

The enantiomers of Example 118C (2.7 g, 6.158 mmol) were separated by chiral preparative SFC on a Whelk-0 (S,S) column (21×250 mm, 5 micron). The second eluting peak was collected and concentrated to give Example 118D (1.18 g, 2.69 mmol) as a white solid. MS (ESI$^+$): m/z 438 (M+H). $^1H$ NMR (300 MHz, DMSO-$d_6$) δ 8.44 (ddd, J=4.8, 1.8, 0.9 Hz, 1H), 7.59 (td, J=7.7, 1.8 Hz, 1H), 7.36 (d, J=8.3 Hz, 1H), 7.20 (ddd, J=7.5, 4.8, 1.1 Hz, 1H), 6.93-6.86 (m, 2H), 6.69 (dd, J=8.3, 2.1 Hz, 1H), 5.68 (d, J=2.2 Hz, 1H), 4.71 (s, 1H), 4.17-4.04 (m, 1H), 3.19-3.05 (m, 2H), 1.97 (dd, J=12.5, 6.9 Hz, 2H), 0.79 (s, 9H), −0.04 (s, 6H). $[α]_D$=−51.9° (c 1.0, MeOH).

Example 118E (trans)-3-(3,4-dichlorophenyl)-3-[(S)-hydroxy(pyridin-2-yl)methyl]-cyclobutanol Example 118D (1.18 g, 2.69 mmol) was dissolved into anhydrous THF (5 mL), treated with 1M TBAF (3.2 mL, 3.2 mmol) in THF, and stirred at room temperature for 5 hours. The reaction mixture was diluted with EtOAc (50 mL), stirred with water (0.1 mL), concentrated under vacuum to a sludge, and stirred in MTBE with a little EtOAc overnight. The product had solidified and was collected by filtration, rinsed with more MTBE, and dissolved into EtOAc (110 mL). This solution was diluted with hexanes (20 mL) and washed with water. The aqueous phase was extracted once with 3:1 EtOAc/hexanes. The combined organic phases were dried ($Na_2SO_4$), filtered, and concentrated to a white powder. This was dissolved into methanol/$CH_2Cl_2$, passed through silica gel with 10% MeOH in $CH_2Cl_2$, and concentrated to give Example 118E (719 mg, 2.218 mmol, 82% yield) as a white powder. MS (ESI$^+$): m/z 324 (M+H). $^1H$ NMR (300 MHz, DMSO-$d_6$) δ 8.43 (ddd, J=4.9, 1.8, 0.9 Hz, 1H), 7.58 (td, J=7.7, 1.8 Hz, 1H), 7.37 (d, J=8.3 Hz, 1H), 7.20 (ddd, J=7.5, 4.8, 1.1 Hz, 1H), 6.88 (d, J=2.1 Hz, 1H), 6.83 (d, J=7.9 Hz, 1H), 6.67 (dd, J=8.4, 2.1 Hz, 1H), 5.64 (d, J=4.7 Hz, 1H), 4.90 (d, J=6.8 Hz, 1H), 4.72 (d, J=4.7 Hz, 1H), 4.10-3.94 (m, 1H), 3.15-2.98 (m, 2H), 2.03-1.87 (m, 2H).

$[α]_D$=−92.3° (c 1.0, MeOH).

Example 119

(cis)-3-(3,4-dichlorophenyl)-3-[(S)-hydroxy(pyridin-2-yl)methyl]-cyclobutanol

Example 117B (3.6 g, 11.24 mmol), triethylamine (3.92 mL, 28.1 mmol), formic acid (1.854 mL, 48.3 mmol), and (S,S)—N-(p-toluenesulfonyl)-1,2-diphenyl-ethanediamine (chloro)(p-cymene)ruthenium(II) (0.072 g, 0.112 mmol) were combined and heated overnight at 35° C. The reaction mixture was cooled to ambient temperature, diluted with saturated $NaHCO_3$ solution, extracted with EtOAc, and concentrated. The geometric isomers were separated by SFC. The fractions collected were dissolved in 2N hydrogen chloride in methanol, and concentrated to give Example 118E (0.406 g, 1.126 mmol, HCl salt) and Example 119 as HCl salt (0.650 g, 1.802 mmol). MS (DCI$^+$): m/z 324.0 (M+H).

$^1H$ NMR (300 MHz, DMSO-$d_6$) δ 8.51 (d, J=5.0 Hz, 1H), 8.29-8.10 (m, 1H), 7.76-7.59 (m, 1H), 7.49-7.36 (m, 2H), 7.20 (d, J=1.8 Hz, 1H), 6.86 (dd, J=8.4, 2.2 Hz, 1H), 5.10 (s, 1H), 2.66-2.53 (m, 3H), 2.41 (dd, J=11.4, 8.0 Hz, 1H). $[α]_D$=−14.9° (c 0.465, MeOH).

Example 120

(3-aminopyridin-2-yl) {1-[3-(trifluoromethyl)phenyl]cyclobutyl}methanol

Example 121

(3-aminopyridin-2-yl) {1-[4-(trifluoromethoxy)phenyl]cyclobutyl}methanol

Example 122

(R)-pyridin-2-yl{1-[4-(trifluoromethyl)pyridin-2-yl]cyclobutyl}methanol

Example 123

(S)-pyridin-2-yl{1-[4-(trifluoromethyl)pyridin-2-yl]cyclobutyl}methanol

Example 124

(3-aminopyridin-2-yl) {1-[3-(trifluoromethoxy)phenyl]cyclobutyl}methanol

Example 125

(R)-{3,3-difluoro-1-[4-(trifluoromethyl)pyridin-2-yl]cyclobutyl}(pyridin-2-yl)-methanol

Example 125A 3-oxocyclobutanecarbonitrile

A mixture of 3-methylenecyclobutanecarbonitrile (9.39 g, 101 mmol), dichloromethane (200 mL), water (300 mL), acetonitrile (200 mL), and ruthenium(III) chloride hydrate (0.500 g, 2.218 mmol) was cooled to <5° C., followed by portionwise addition of sodium periodate (88 g, 413 mmol) at <20° C., and stirred for 10 minutes. The mixture was diluted with dichloromethane and partitioned. The organic phase was filtered through a silica pad, dried ($Na_2SO_4$), filtered, concentrated, and passed through a silica plug again, eluting with 200 mL dichloromethane to provide Example 125A (8.21 g, 86 mmol, 86% yield) as a white solid. $^1H$ NMR (300 MHz, CDCl$_3$) δ 3.60-3.22 (m, 5H).

Example 125B 3,3-difluorocyclobutanecarbonitrile

Example 125A (8.21 g, 86 mmol) in dichloromethane (135 mL) was stirred at room temperature, cooled to <10° C., added DAST (11.41 mL, 86 mmol), warmed to room temperature, and stirred for 2 hours. The mixture was poured into saturated aqeuous $NaHCO_3$ (200 mL) and partitioned. The aqueous phase was extracted with 2×50 mL dichloromethane. The combined organic phase was dried ($Na_2SO_4$), filtered, and concentrated to give Example 125B (9.14 g, 78 mmol, 90% yield) as a brown oil. $^1$H NMR (400 MHz, $CDCl_3$) δ 3.06-2.91 (m, 5H).

Example 125C 3,3-difluoro-1-(4-(trifluoromethyl)pyridin-2-yl)cyclobutanecarbonitrile Example 125B and 2-fluoro-4-(trifluoromethyl)pyridine (0.900 mL, 7.39 mmol) were dissolved in toluene (2.4 mL), cooled to <5° C. and added KHMDS (29.6 mL, 14.78 mmol) dropwise, allowed to warm slowly to room temperature and stirred for 90 minutes. The mixture was diluted with MTBE and washed with water (2×). The organic phase was dried ($Na_2SO_4$), filtered, and concentrated. The residue was chromatographed on silica gel (0-25% EtOAc/hexanes) to provide Example 125C (1.22 g, 4.65 mmol, 63.0% yield). $^1$H NMR (300 MHz, DMSO-$d_6$) δ 9.00-8.94 (m, 1H), 8.04-7.99 (m, 1H), 7.88 (ddd, J=5.1, 1.6, 0.8 Hz, 1H), 3.68-3.48 (m, 5H).

Example 125D (3,3-difluoro-1-(4-(trifluoromethyl)pyridin-2-yl)cyclobutyl)(pyridin-2-yl)-methanone A mixture of 2-bromopyridine (0.679 mL, 6.98 mmol) in THF (10 mL) was cooled to <−70° C. and added n-BuLi (2.79 mL, 6.98 mmol) dropwise at <−70° C. After 5 minutes, Example 125C (1.22 g, 4.65 mmol) in THF (1+0.5+0.5 mL) was dropwise at <−70° C., followed by addition of 2N HCl (12 mL) and the mixture heated to 50° C. for 15 minutes. The mixture was cooled, diluted with MTBE, and washed with brine. The organic phase was dried ($Na_2SO_4$), filtered, and concentrated to provide crude Example 125D (1.69 g,). MS (DCI$^+$) M/Z 343 (M+H). $^1$H NMR (300 MHz, DMSO-$d_6$) δ 8.64 (dd, J=5.1, 0.9 Hz, 1H), 8.41 (ddd, J=4.7, 1.7, 0.9 Hz, 1H), 8.11-7.92 (m, 3H), 7.60 (ddd, J=5.1, 1.6, 0.8 Hz, 1H), 7.50 (ddd, J=7.5, 4.7, 1.4 Hz, 1H), 3.61-3.40 (m, 4H).

Example 125E (R)-{3,3-difluoro-1-[4-(trifluoromethyl)pyridin-2-yl]cyclobutyl}(pyridin-2-yl)methanol A solution of Example 125D (1592 mg, 4.65 mmol), triethylamine (1620 μL, 11.63 mmol), and formic acid (767 μL, 20.00 mmol) was cooled to 35° C. after an exotherm to 50° C. following formic acid addition. (S,S)—N—(P-toluenesulfonyl)-1,2-diphenylethanediamine(chloro)(p-cumene)ruthenium(II) (29.6 mg, 0.047 mmol) was added and the reaction was stirred at 35° C. for 24 hours and 14 hours at room temperature. The mixture was diluted with dichloromethane, washed with saturated aqueous $NaHCO_3$, and partitioned. The aqueous layer was extracted with dichloromethane. The combined organic layers were dried ($Na_2SO_4$), filtered, and concentrated. The residue was chromatographed on silica gel (10-50% EtOAc/hexanes) to give about 1.5 g of 70% ee product which was separated on AD-H column (3/1 hexanes/isopropanol) to provide Example 125E (187 mg, 0.543 mmol, 11.68% yield) and Example 126 (1.08 g, 3.14 mmol, 67.5% yield). MS (DCI$^+$) M/Z 345 (M+H). $^1$H NMR (300 MHz, DMSO-$d_6$) δ 8.64 (d, J=5.1 Hz, 1H), 8.32 (dd, J=4.9, 1.6 Hz, 1H), 7.62-7.53 (m, 2H), 7.36 (s, 1H), 7.17 (ddd, J=7.5, 4.8, 1.1 Hz, 1H), 6.88 (d, J=7.9 Hz, 1H), 6.15 (d, J=4.7 Hz, 1H), 4.90 (d, J=4.7 Hz, 1H), 3.20-2.96 (m, 2H).

Example 126

(S)-{3,3-difluoro-1-[4-(trifluoromethyl)pyridin-2-yl]cyclobutyl}(pyridin-2-yl)methanol A solution of Example 125D (1592 mg, 4.65 mmol), triethylamine (1620 μL, 11.63 mmol), and formic acid (767 μL, 20.00 mmol) was cooled to 35° C. after an exotherm to 50° C. following formic acid addition. (S,S)—N—(P-toluenesulfonyl)-1,2-diphenylethanediamine(chloro)(p-cumene)ruthenium(II) (29.6 mg, 0.047 mmol) was added and the reaction was stirred at 35° C. for 24 hours and 14 hours at room temperature. The mixture was diluted with dichloromethane, washed with saturated aqueous $NaHCO_3$, and partitioned. The aqueous layer was extracted with dichloromethane. The combined organic layers were dried ($Na_2SO_4$), filtered, and concentrated. The residue was chromatographed on silica gel (10-50% EtOAc/hexanes) to give about 1.5 g of 70% ee product which was separated on AD-H column (3/1 hexanes/isopropanol) to provide Example 125E (187 mg, 0.543 mmol, 11.68% yield) and Example 126 (1.08 g, 3.14 mmol, 67.5% yield). MS (DCI$^+$) M/Z 345 (M+H). $^1$H NMR (300 MHz, DMSO-$d_6$) δ 8.64 (d, J=5.2 Hz, 1H), 8.32 (ddd, J=4.8, 1.8, 0.9 Hz, 1H), 7.57 (dd, J=15.3, 1.8 Hz, 2H), 7.57 (t, J=2.0 Hz, 1H), 7.38-7.33 (m, 1H), 7.17 (ddd, J=7.5, 4.8, 1.2 Hz, 1H), 6.88 (d, J=7.9 Hz, 1H), 6.15 (s, 1H), 4.90 (bs, 1H), 3.24-2.97 (m, 2H).

Example 127

(3-aminopyridin-2-yl){1-[4-(trifluoromethyl)phenyl]cyclobutyl}methanol

Example 128

(S)-{3,3-difluoro-1-[4-(trifluoromethoxy)phenyl]cyclobutyl}(pyridin-2-yl)-methanol

Example 128A 3-hydroxy-1-[4-(trifluoromethoxy)phenyl]cyclobutanecarbonitrile 2-[4-(Trifluoromethoxy)phenyl]acetonitrile (5.0 g, 24.86 mmol) was dissolved in THF (40 mL) and chilled to −75° C. 1.6M Methyllithium (15.54 mL, 24.86 mmol) in diethyl ether was added dropwise, and the yellow solution was stirred at −75° C. for 1 hour. Epibromohydrin (2.057 mL, 24.86 mmol) in THF (10 mL) was added slowly, and the reaction was stirred at −75° C. for 1 hour. 3.0M methyl magnesium bromide (8.29 mL, 24.86 mmol) in diethyl ether was added dropwise, and the reaction was warmed to ambient temperature and stirred overnight. The reaction was quenched with 50 mL water, treated with 100 mL 3N hydrochloric acid, extracted twice with 200 mL EtOAc, washed with brine, dried over $Na_2SO_4$, filtered, and concentrated. The residue was chromatographed on a Grace Reveleris 80 g column, eluted with 0-100% EtOAc in heptane (35 mL/min) to provide the title compound (6.377 g, 24.79 mmol, 100% yield) as a yellow oil. MS (DCI$^+$): m/z 275.0 (M+$NH_4$).

Example 128B 3-oxo-1-[4-(trifluoromethoxy)phenyl]cyclobutanecarbonitrile

Example 128A (6.377 g, 24.79 mmol) was dissolved in dichloromethane (100 mL), and then Dess-Martin periodinane (15.77 g, 37.2 mmol) was added. The yellow solution was stirred overnight at ambient temperature, and concentrated. The residue was chromatographed on a Grace Reveleris 80 g column, eluted with 100% dichloromethane (30 mL/min) to provide the title compound (5.752 g, 22.54 mmol, 91% yield) as a pale yellow solid. $^1$H NMR (300 MHz, DMSO-d$_6$) δ 7.77-7.70 (m, 2H), 7.54-7.46 (m, 2H), 4.17-4.07 (m, 2H), 3.97-3.86 (m, 2H).

Example 128C 3,3-difluoro-1-[4-(trifluoromethoxy)phenyl]cyclobutanecarbonitrile A solution of Example 128B (5.752 g, 22.54 mmol) in dichloromethane (40 mL) was chilled to 0° C., followed by the slow addition of DAST (7.5 mL, 56.8 mmol) in dichloromethane (20 mL). The orange solution was stirred for 2 days at ambient temperature and quenched with 200 mL saturated NaHCO$_3$ solution. The reaction mixture was extracted with 200 mL dichloromethane, washed with 200 mL saturated NaHCO$_3$ solution, dried over Na$_2$SO$_4$, filtered, and concentrated. The residue was chromatographed on a Grace Reveleris 80 g column, eluted with 0-30% EtOAc in heptane (35 mL/min) to provide the title compound (5.245 g, 18.92 mmol, 84% yield) as an orange liquid. $^1$H NMR (300 MHz, DMSO-d$_6$) δ 7.71-7.64 (m, 2H), 7.53-7.45 (m, 2H), 3.66-3.50 (m, 2H), 3.50-3.34 (m, 2H).

Example 128D

{3,3-difluoro-1-[4-(trifluoromethoxy)phenyl]cyclobutyl}(pyridin-2-yl)methanone

A solution of 2.5M n-butyllithium (11.35 mL, 28.4 mmol) in hexanes and diethyl ether (25 mL) was chilled to −70° C., followed by the dropwise addition of 2-bromopyridine (2.86 mL, 29.3 mmol) in diethyl ether (25 mL), and stirred for 40 minutes. Example 128C (5.245 g, 18.92 mmol) in diethyl ether (25 mL) was added dropwise, and the mixture was slowly warmed to 0° C. over a period of 3 hours. The mixture was quenched with 200 mL 3N hydrochloric acid, followed by addition of 100 mL diethyl ether. The biphasic mixture was stirred for 90 minutes at ambient temperature, followed by addition of 250 mL 3N sodium hydroxide, extracted twice with 200 mL EtOAc, washed with 200 mL brine, dried over Na$_2$SO$_4$, filtered, and concentrated. The residue was chromatographed on a Grace Reveleris 80 g column, eluted with 0-30% EtOAc in hexanes (35 mL/min) to provide the title compound (5.667 g, 15.86 mmol, 84% yield) as a dark yellow oil. (ESI): m/z 358.0 (M+H). $^1$H NMR (300 MHz, DMSO-d$_6$) δ 8.64-8.57 (m, 1H), 8.02-7.91 (m, 2H), 7.66-7.59 (m, 2H), 7.59-7.53 (m, 1H), 7.30 (dd, J=8.9, 0.9 Hz, 2H), 3.70-3.52 (m, 2H), 3.42-3.25 (m, 2H).

Example 128E (S)-{3,3-difluoro-1-[4-(trifluoromethoxy)phenyl]cyclobutyl}(pyridin-2-yl)methanol Example 128D (5.667 g, 15.86 mmol) was dissolved in a mixture of formic acid (5.23 mL, 136 mmol) and triethylamine (10.99 mL, 79 mmol), then (S,S)—N-(p-toluenesulfonyl)-1,2-diphenylethanediamine(chloro)(p-cymene)ruthenium(II) (0.253 g, 0.397 mmol) was added. The yellow solution was heated overnight at 35° C., followed by the addition of 300 mL dichloromethane. The mixture was washed with 300 mL saturated NaHCO$_3$ solution, dried over Na$_2$SO$_4$, filtered, and concentrated. The residue was chromatographed on a Grace Reveleris 120 g column, eluted with 0-100% EtOAc in hexanes (40 mL/min) to provide the title compound (5.537 g, 15.41 mmol, 97% yield) as a yellow oil. The yellow oil (4.34 g, 12.08 mmol) was dissolved in methanol (40 mL), and then 1.25 M hydrogen chloride in methanol (50 mL, 62.5 mmol) was added. The solution was concentrated to yield the HCl salt of the title compound (4.50 g, 11.37 mmol, 94% yield) as an off-white solid. (ESI): m/z 360.0 (M+H). $^1$H NMR (300 MHz, CD$_3$OD) δ 8.48-8.38 (m, 2H), 7.94-7.85 (m, 1H), 7.70 (d, J=8.0 Hz, 1H), 7.14 (dd, J=8.8, 0.7 Hz, 2H), 7.05 (d, J=8.8 Hz, 2H), 5.33 (s, 1H), 3.55-3.35 (m, 2H), 3.09-2.89 (m, 2H). [α]$_D$=−24.6° (c 1.0, MeOH). Calculated for C$_{17}$H$_{14}$F$_5$NO$_2$.HCl: C, 51.59%; H, 3.82%; N, 3.54%. Found: C, 51.55%; H, 3.91%; N, 3.49%.

Example 129

{3,3-dimethoxy-1-[4-(trifluoromethoxy)phenyl]cyclobutyl}(pyridin-2-yl)-methanol

Example 129A 3,3-dimethoxy-1-[4-(trifluoromethoxy)phenyl]cyclobutanecarboxamide 2-[4-(Trifluoromethoxy)phenyl]acetonitrile (7.86 mL, 50 mmol), 1,3-dibromo-2,2-dimethoxypropane (13.10 g, 50.0 mmol), and sodium tert-butoxide (10.57 g, 110 mmol) were dissolved in DMSO (100 mL) and water (5 mL), and the mixture was heated for 1 hour at 125° C. The reaction was cooled to ambient temperature and stirred overnight. The reaction mixture was diluted with water and extracted three times with diethyl ether. The combined organic layers were washed with brine, dried with MgSO$_4$, filtered, and concentrated to give the title compound (17.02 g, 53.3 mmol, 107% yield). MS (DCI$^+$): m/z 320.1 (M+H), 337.1 (M+NH$_4$). $^1$H NMR (300 MHz, DMSO-d$_6$) δ 7.44 (d, J=8.8 Hz, 2H), 7.34 (s, 1H), 7.31 (d, J=8.8 Hz, 2H), 6.90 (s, 1H), 3.05 (s, 3H), 3.02-2.93 (m, 5H), 2.41 (d, J=13.4 Hz, 2H).

Example 129B methyl 3,3-dimethoxy-1-[4-(trifluoromethoxy)phenyl]cyclobutane-carboxylate Example 129A (17.02 g, 49.6 mmol) was dissolved in methanol (200 mL). Acetyl chloride (20 mL, 281 mmol) was added slowly, and the reaction mixture heated overnight at 70° C., then cooled and stirred for 7 days at ambient temperature. The reaction mixture was concentrated, the residue partitioned between diethyl ether and water, and the aqueous layer extracted with diethyl ether. The organic layers were combined, washed with brine, dried with MgSO$_4$, filtered, and concentrated. The residue was chromatographed on an AnaLogix SF65-400 g column and eluted with 3-6% EtOAc in hexanes to give the title compound (6.55 g, 19.59 mmol, 39.5% yield). MS (DCI$^+$): m/z 352.1 (M+NH$_4$). $^1$H NMR (300 MHz, DMSO-d$_6$) δ 7.45-7.38 (m, 2H), 7.38-7.30 (m, 2H), 3.58 (s, 3H), 3.07 (s, 3H), 3.04-2.95 (m, 5H), 2.58-2.52 (m, 2H).

Example 129C

{3,3-dimethoxy-1-[4-(trifluoromethoxy)phenyl]cyclobutyl}
(pyridin-2-yl)-methanol 2.5M n-Butyllithium (11.67 mL, 29.2 mmol) in hexanes was added to diethyl ether (40 mL) and cooled to −78° C. in a dry ice/acetone bath. 2-Bromopyridine (2.94 mL, 30.1 mmol) was added slowly via syringe, and the reaction was stirred for 40 minutes. Example 129B (6.50 g, 19.44 mmol) in diethyl ether (30 mL) was added dropwise over 15 minutes. The reaction was warmed to ambient temperature and stirred overnight. The reaction mixture was quenched with water and extracted twice with EtOAc. The combined organic layers were washed with brine, dried with $MgSO_4$, filtered, and concentrated. The residue was chromatographed on an AnaLogix SF40-240 g column with 10% EtOAc in hexanes to give Example 131A (2.29 g, 6.01 mmol, 30.9% yield). The column was eluted with 50% EtOAc in hexanes to give Example 129C (2.50 g, 6.52 mmol, 33.5% yield). MS ($DCI^+$): m/z 384.1 (M+H). $^1$H NMR (300 MHz, DMSO-$d_6$) δ 8.41 (ddd, J=4.8, 1.7, 0.9 Hz, 1H), 7.44 (td, J=7.7, 1.8 Hz, 1H), 7.14 (ddd, J=7.5, 4.8, 1.2 Hz, 1H), 7.07 (dd, J=8.7, 0.9 Hz, 2H), 6.82 (d, J=8.8 Hz, 2H), 6.54 (d, J=7.9 Hz, 1H), 5.69 (d, J=4.6 Hz, 1H), 4.90 (d, J=4.5 Hz, 1H), 3.16-3.07 (m, 4H), 2.96 (s, 3H), 2.92 (dd, J=12.8, 3.1 Hz, 1H), 2.35 (d, J=12.4 Hz, 1H), 2.22 (d, J=12.9 Hz, 1H).

Example 130

(3-aminopyridin-2-yl)[1-(3,4-dichlorophenyl)cyclobutyl]methanol

Example 131 cis-3-[(S)-hydroxy(pyridin-2-yl)methyl]-3-[4-(trifluoromethoxy)phenyl]-cyclobutanol

Example 131A

{3,3-dimethoxy-1-[4-(trifluoromethoxy)phenyl]cyclobutyl}(pyridin-2-yl)-methanone 2.5M n-Butyllithium (11.67 mL, 29.2 mmol) in hexanes was added to diethyl ether (40 mL) and cooled to −78° C. in a dry ice/acetone bath. 2-Bromopyridine (2.94 mL, 30.1 mmol) was added slowly via syringe, and the reaction was stirred for 40 minutes. Example 129B (6.50 g, 19.44 mmol) in diethyl ether (30 mL) was added dropwise over 15 minutes. The reaction was warmed to ambient temperature and stirred overnight. The reaction mixture was quenched with water and extracted twice with EtOAc.

The combined organic layers were washed with brine, dried with $MgSO_4$, filtered, and concentrated. The residue was chromatographed on an AnaLogix SF40-240 g column with 10% EtOAc in hexanes to give desired Example 131A (2.29 g, 6.01 mmol, 30.9% yield) MS ($DCI^+$): m/z 382.1 (M+H). $^1$H NMR (300 MHz, DMSO-$d_6$) δ 8.59 (dt, J=4.7, 1.2 Hz, 1H), 7.97-7.92 (m, 2H), 7.58-7.49 (m, 3H), 7.26 (d, J=8.7 Hz, 2H), 3.18 (d, J=13.5 Hz, 2H), 3.04 (s, 3H), 3.00 (s, 3H), 2.78 (d, J=13.6 Hz, 2H).

Example 131B (S)-3-[hydroxy(pyridin-2-yl)methyl]-3-[4-(trifluoromethoxy)phenyl]-cyclobutanol Example 131A (2.29 g, 6.01 mmol) was dissolved in triethylamine (2.09 mL, 15.01 mmol) and formic acid (0.99 mL, 25.8 mmol). (S,S)—N-(p-toluenesulfonyl)-1,2-diphenylethanediamine(chloro)(p-cymene)ruthenium(II) (0.038 g, 0.060 mmol) was added, and the reaction was heated at 55° C. for 5 days. Additional catalyst was added during that time, but the reaction remained sluggish. Additional triethylamine (2 mL) and formic acid (1 mL) were added, and the reaction continued for 3 days. The reaction mixture was cooled to ambient temperature, diluted with $NaHCO_3$ solution, and extracted twice with dichloromethane. The organic layers were combined, dried with $MgSO_4$, filtered, and concentrated. The residue was dissolved in acetone and stirred overnight with 12N hydrochloric acid (10 mL) to remove the ketal. The mixture was basified with 3N sodium hydroxide and extracted twice with diethyl ether. The organic layers were washed with brine, dried with $MgSO_4$, filtered, and concentrated. The residue was chromatographed on an AnaLogix SF40-120 g column with 20-80% EtOAc in hexanes to give Example 134B (0.22 g, 0.652 mmol, 10.9% yield) and desired Example 131B (0.92 g, 2.711, mmol, 45.1% yield) as a mixture of geometric isomers by proton NMR. MS ($DCI^+$): m/z 340.1 (M+H).

Example 131C (cis)-3-[(S)-hydroxy(pyridin-2-yl)methyl]-3-[4-(trifluoromethoxy)phenyl]-cyclobutanol The geometric isomers of Example 131B (0.92 g, 2.711, mmol) were separated by chromatography on Analogix SF40-120 g column (EtOAc-Hexane, 20% to 80%), and the collected fractions were combined and concentrated. The residue was dissolved in 2N hydrogen chloride in methanol, followed by removal of solvent to give Example 131C as HCl salt (0.43 g, 1.144 mmol). MS ($DCI^+$): m/z 340.0 (M+H). $^1$H NMR (500 MHz, DMSO-$d_6$) δ 8.52 (dd, J=5.7, 0.8 Hz, 1H), 8.34 (t, J=7.3 Hz, 1H), 7.81 (t, J=6.4 Hz, 1H), 7.50 (d, J=7.8 Hz, 1H), 7.18-7.09 (m, 4H), 5.20 (s, 1H), 2.66-2.53 (m, 3H), 2.45 (dd, J=11.2, 8.1 Hz, 1H). $[α]_D$=−2.3° (c 0.535, MeOH).

Example 132

(trans)-3-[(S)-hydroxy(pyridin-2-yl)methyl]-3-[4-(trifluoromethoxy)-phenyl]cyclobutanol The geometric isomers of Example 131B (0.92 g, 2.711, mmol) were separated by chromatography on Analogix SF40-120 g column (EtOAc-Hexane, 20% to 80%), and the collected fractions were combined and concentrated. The residue was dissolved in 2N hydrogen chloride in methanol, followed by removal of solvent to give the HCl salt of Example 132 (0.31 g, 0.825 mmol). MS ($DCI^+$): m/z 340.1 (M+H). $^1$H NMR (300 MHz, DMSO-$d_6$) δ 8.53 (d, J=5.1 Hz, 1H), 8.22-7.99 (m, 1H), 7.76-7.56 (m, 1H), 7.39-7.22 (m, 1H), 7.15 (d, J=8.2 Hz, 2H), 6.87 (d, J=8.6 Hz, 2H), 5.03 (s, 1H), 3.10-2.96 (m, 2H), 2.05 (dd, J=10.8, 7.6 Hz, 2H). $[α]_D$=−4.0° (c 0.515, MeOH).

Example 133

{3,3-difluoro-1-[4-(trifluoromethyl)phenyl]cyclobutyl}(pyridin-2-yl)-methanol

Example 133A 3-oxocyclobutanecarbonitrile

To a solution of 3-methylenecyclobutanecarbonitrile (5.2 g, 55.8 mmol) and ruthenium(III) chloride (0.255 g, 1.228 mmol) in dichloromethane (150 mL), acetonitrile (150 mL) and water (225 mL) was added sodium periodate (49.0 g, 229 mmol) within 30 minutes at 0° C. The reaction temperature was slowly elevated to room temperature. The reaction mixture was stirred for another 18 hours. The solid was removed by filtration and the organic layer was separated, and the aqueous layer was extracted with EtOAc. The combined organic layers were washed with water, dried over MgSO$_4$, and filtered. The solvent was removed under reduced pressure to afford a light yellow crystals. The product was used directly for the next step (4.5 g, 85%). $^1$H NMR (400 MHz, CDCl$_3$): δ 3.50 (d, J=8.0 Hz, 4H), 3.18-3.26 (m, 1H).

Example 133B 5,8-dioxaspiro[3.4]octane-2-carbonitrile

Example 133A (6.0 g, 63.1 mmol) and 4-methylbenzenesulfonic acid (0.543 g, 3.15 mmol) were added sequentially to a 50 mL flask, followed by the addition of toluene (200 mL). The mixture was refluxed overnight and the water produced during the reaction was removed by Dean-Stark apparatus. After cooling to room temperature, the mixture was washed with aqueous NaHCO$_3$ (3×50 mL). The organic phase was dried over Na$_2$SO$_4$, filtered, and concentrated under vacuo. The residue was purified by a silica gel chromatography (dichloromethane) to afford the title compound (8.6 g, 98%). $^1$H NMR (400 MHz, CDCl$_3$): δ 3.91 (s, 4H), 2.87-2.91 (m, 1H), 2.72-2.74 (m, 2H).

Example 133C 2-(4-(trifluoromethyl)phenyl)-5,8-dioxaspiro[3.4]octane-2-carbonitrile In a 50 mL nitrogen inlet adapter, Example 133B (1.390 g, 10 mmol), 1-fluoro-4-(trifluoromethyl)benzene (1.640 g, 10 mmol) and KHMDS (1.64 g, 10 mmol) in toluene (20 mL) were mixed together. The resulting mixture was stirred at about 60° C. for about 24 hours. The solution was diluted with ethyl acetate, and washed with saturated NH$_4$Cl and water. The organic layer was dried over Na$_2$SO$_4$, filtered and concentrated. The residue was chromatographed on a silica gel column (15% EtOAc/Heptane) to provide the title compound as a white solid (1.2 g, 42%). $^1$H NMR (400 MHz, CDCl$_3$): δ 7.68 (s, 4H), 4.01-4.04 (m, 2H), 3.91-3.97 (m, 2H), 3.29-3.32 (m, 2H), 2.98-3.02 (m, 2H).

Example 133D 3-oxo-1-(4-(trifluoromethyl)phenyl)cyclobutanecarbonitrile

To Example 133C (1.0 g, 3.5 mmol) was added 2,2,2-trifluoroacetic acid (10.06 g, 88 mmol) and the mixture was stirred at about 25° C. for about 24 hours. The solution was diluted with ethyl acetate, and washed with saturated NaHCO$_3$ and water. The organic layer was dried over Na$_2$SO$_4$, filtered and concentrated. The crude product was used in the next reaction without further purification (0.65 g, 77%). LC-MS: MS (M+H): 240.0.

Example 133E

To a solution of Example 133D (0.45 g, 1.881 mmol) in dichloromethane (20 mL) was added DAST (0.497 mL, 3.76 mmol) dropwise at 0° C. in 10 minutes. The reaction temperature was slowly elevated to room temperature and stirred at the same temperature for another 18 hours. The reaction solution was poured into saturated aqueous NaHCO$_3$ (200 mL) and stirred for 10 minutes. The organic layer was separated, and the aqueous layer was extracted with dichloromethane (3×10 mL). The combined organic layers were washed with water (2×25 mL). dried over MgSO$_4$, filtered and concentrated. The residue was purified on silica gel column (5% EtOAc/Heptane) to give Example 133E as an oil (0.33 g, 67%). LC-MS:MS (M+H): 262.3.

Example 133F (3,3-difluoro-1-(4-(trifluoromethyl)phenyl)cyclobutyl)(pyridin-2-yl)methanone To a solution of 2-bromopyridine (0.181 g, 1.149 mmol) in 5 mL of dry THF was added n-butyllithium, (2.5 M in hexane, 0.6 mL, 1.149 mmol) at −78° C. After stirring for 30 minutes, the solution of Example 133E (0.200 g, 0.766 mmol) in THF (1 mL) was added. The mixture was stirred at −78° C. for 45 minutes and aqueous NH$_4$Cl was added. The aqueous phase was separated and extracted with EtOAc. The combined organic phase was washed with water, brine, dried over Na$_2$SO$_4$, filtered, and concentrated. The residue was purified on silica gel column (10% EtOAc/Heptane) to give Example 133F as a white solid (0.12 g, 46%). LC-MS:MS (M+H): 342.1.

Example 133G

{3,3-difluoro-1-[4-(trifluoromethyl)phenyl]cyclobutyl}(pyridin-2-yl)-methanol

To a solution of Example 133F (120 mg, 0.352 mmol) in 10 mL of dry MeOH was added NaBH$_4$ (13.30 mg, 0.352 mmol) at 0° C. After stirring for 5 minutes, the temperature was elevated to 20° C. for 10 minutes and 10 mL of water was added slowly. The aqueous phase was separated and extracted with EtOAc. The combined organic phase was washed with water, brine, dried over Na$_2$SO$_4$, filtered, and concentrated to give the title compound as a white solid (67 mg, 56%). LC-MS:MS (M+H): 344.1; $^1$H NMR (400 MHz, CDCl$_3$): δ 8.30 (d, J=4.8 Hz, 1H), 7.38-7.44 (m, 3H), 7.07-7.19 (m, 1H), 6.89 (d, J=8.0 Hz, 2H), 6.49 (d, J=8.0 Hz, 1H), 4.82 (d, J=5.6 Hz, 1H), 4.49 (d, J=7.2 Hz, 1H), 3.37-3.46 (m, 1H), 3.23-3.30 (m, 1H), 2.67-2.83 (m, 2H).

Example 134 cis-3-[(S)-hydroxy(pyridin-2-yl)methyl]-1-methyl-3-[4-(trifluoromethoxy)-phenyl]cyclobutanol Example 134A 3-[hydroxy(pyridin-2-yl)methyl]-3-[4-(trifluoromethoxy)phenyl]-cyclobutanone Example 202C (17.0 g, 44.6 mmol) was dissolved in acetone (250 mL), treated with 6M aqueous HCl (25 mL), and stirred at room temperature overnight. The solution was concentrated and the resulting oil was made basic with 3M aqueous NaOH (60 mL) and extracted twice with EtOAc. The combined organic phases were washed with brine, dried (Na$_2$SO$_4$), and concentrated to give Example 134A (15.06 g, 44.6 mmol, 100% yield) as a white powder. MS (ESI$^+$): m/z 338 (M+H). $^1$H NMR (300 MHz, DMSO-d$_6$) δ 8.41-8.37 (m, 1H), 7.55 (ddd, J=7.7, 7.7, 1.8 Hz, 1H), 7.22-7.12 (m, 3H), 7.05-6.98 (m, 2H), 6.84 (d, J=7.9 Hz, 1H), 5.99 (d, J=4.5 Hz, 1H), 4.87 (d, J=4.5 Hz, 1H), 3.82-3.67 (m, 2H), 3.33-3.24 (m, 2H).

Example 134B (S)-3-[hydroxy(pyridin-2-yl)methyl]-3-[4-(trifluoromethoxy)phenyl]-cyclobutanone The enantiomers of Example 134A (15.06 g, 44.6 mmol) were separated on a Chiralpak AD DAC column (5 cm ID×30 cm, 20 micron) and eluted with 80/4/16 hexanes/EtOH/MeOH at 100 mL/min. The first eluting peak was collected and concentrated to provide Example 134B (7.52 g, 22.3 mmol) as a white powder. MS (ESI$^+$): m/z 338 (M+H). $^1$H NMR (400 MHz, CD$_3$CN) δ 8.43 (ddd, J=4.8, 1.4, 0.9 Hz, 1H), 7.49 (td, J=7.7, 1.8 Hz, 1H), 7.20 (ddd, J=7.5, 4.9, 1.0 Hz, 1H), 7.13 (d, J=8.7 Hz, 2H), 7.04 (d, J=8.8 Hz, 2H), 6.62 (d, J=7.9 Hz, 1H), 4.97 (d, J=5.7 Hz, 1H), 4.47 (d, J=6.0 Hz, 1H), 3.78 (ddd, J=17.0, 6.0, 2.5 Hz, 1H), 3.63 (ddd, J=17.3, 6.0, 2.4 Hz, 1H), 3.28 (ddd, J=17.0, 3.6, 2.4 Hz, 1H), 3.20 (ddd, J=17.3, 3.5, 2.5 Hz, 1H). [α]$_D$=−18.8° (c 1, MeOH).

Example 134C cis-3-[(S)-hydroxy(pyridin-2-yl)methyl]-1-methyl-3-[4-(trifluoromethoxy)-phenyl]cyclobutanol Example 134B (6.94 g, 20.5 mmol) was dissolved into anhydrous THF (100 mL) and chilled with a dry ice/acetone bath. 1.6M Methyllithium in diethyl ether (28.3 mL, 45 mmol) was added slowly, and the temperature was permitted to rise to 0° C. overnight. The cold bath was removed and the solution was stirred for another 30 minutes before the flask was placed in a water bath and the reaction was quenched dropwise with 1M aqueous KH$_2$PO$_4$ (50 mL). The solids were filtered off and washed with EtOAc, and the aqueous phase of the filtrate was separated and extracted with EtOAc. The combined organic phases were washed with brine, dried (Na$_2$SO$_4$), filtered, and concentrated. The residue was chromatographed on silica (30 to 100% EtOAc/hexanes, then 1 to 5% MeOH/EtOAc) to provide two geometric isomers: Example 203 (0.77 g, 1.96 mmol, 9.5% yield) as a gum (first peak) and Example 134C (3.8 g, 9.68 mmol, 47% yield) as a syrup (second peak). Example 134C (3.8 g, 9.68 mmol) was dissolved in excess hydrogen chloride in methanol, followed by removal of solvent to give the HCl salt of Example 134C (3.62 g, 9.29 mmol, 96% yield) as a white powder. MS (ESI$^+$): m/z 354 (M+H). $^1$H NMR (300 MHz, DMSO-d$_6$) δ 8.44 (d, J=5.0 Hz, 1H), 8.27-8.00 (m, 1H), 7.78-7.54 (m, 1H), 7.50-7.24 (m, 1H), 7.12 (d, J=8.2 Hz, 2H), 6.94 (d, J=8.7 Hz, 2H), 5.21 (s, 1H), 2.82 (dd, J=37.5, 11.9 Hz, 2H), 2.35 (ddd, J=24.5, 12.2, 3.5 Hz, 2H), 0.90 (s, 3H). [α]$_D$=−15.2° (c 1.0, MeOH).

Example 135

(R)-[(2S)-2-(3,4-dichlorophenyl)oxetan-2-yl](pyridin-2-yl)methanol

Example 136

(R)-[(2R)-2-(3,4-dichlorophenyl)oxetan-2-yl](pyridin-2-yl)methanol

Example 137

{3,3-difluoro-1-[5-(trifluoromethyl)pyridin-2-yl]cyclobutyl}(pyridin-2-yl)-methanol The title compound was prepared using procedures analogous to that described for the synthesis of Example 133, substituting 2-fluoro-5-(trifluoromethyl)-pyridine for 1-fluoro-4-(trifluoromethyl)benzene in Example 133C. LC-MS:MS (M+H): 345.1. $^1$H NMR (400 MHz, CDCl$_3$): δ 8.62 (t, J=1.2 Hz, 1H), 8.30 (d, J=4.4 Hz, 1H), 7.73-7.75 (m, 1H), 7.42-7.46 (m, 1H), 7.15-7.19 (m, 1H), 7.06-7.09 (m, 1H), 6.68 (d, J=8.0 Hz, 1H), 5.01 (s, 1H), 4.76 (s, 1H), 3.21-3.37 (m, 2H), 3.02-3.08 (m, 1H), 2.81-2.87 (m, 1H).

Example 138

{1-[4-chloro-3-(trifluoromethyl)phenyl]-3,3-difluorocyclobutyl}(pyridin-2-yl)methanol

Example 138A 1-(4-chloro-3-(trifluoromethyl)phenyl)-3-hydroxycyclobutanecarbonitrile To a solution of 2-(4-chloro-3-(trifluoromethyl)phenyl)acetonitrile (440 mg, 2.0 mmol) in THF (8 mL) was added 3 M methyllithium in ether (0.67 mL, 2.0 mmol) dropwise at −78° C. The mixture was stirred for about 1 hour, then added the solution of 2-(bromomethyl)oxirane (274 mg, 2.0 mmol) in THF (2 mL); and the final mixture was stirred at −78° C. for another 1.5 hours. 3M Methylmagnesium iodide in ether (0.67 mL, 2.0 mmol) was added to the mixture and the mixture was warmed to room temperature slowly and stirred overnight. The mixture was quenched with 2N aqueous HCl (5 mL) and extracted with ethyl acetate (20 mL×2). The combined organic phases was washed with brine, dried over Na$_2$SO$_4$, filtered, and concentrated. The residue was purified on silica gel (EtOAc-Hexane, 0-100%) to obtain the Example 138A as a reddish oil (0.41 g, 74.2%). LC-MS: 276.0 (M+H). $^1$H NMR (400 MHz, CDCl$_3$): δ 7.73 (d, J=4.8 Hz, 1H), 7.57-7.55 (m, 2H), 4.83-4.74 (m, 0.34H), 4.54-4.47 (m, 0.68H), 3.26-3.20 (m, 0.66H), 3.02-2.92 (m, 3H), 2.55-2.49 (m, 0.69H), 2.25 (br, 1H).

Example 138B 1-(4-chloro-3-(trifluoromethyl)phenyl)-3-oxocyclobutanecarbonitrile To a solution of Example 138A (0.41 g, 1.49 mmol) in dichloromethane (10 mL) was added Dess-Martin periodinane (0.82 g, 1.93 mmol), NaHCO$_3$ (1.25 g, 14.9 mmol) and the mixture was stirred at room temperature overnight. The reaction mixture was quenched by saturated Na$_2$S$_2$O$_3$ (10 mL), washed with brine, dried over Na$_2$SO$_4$, filtered, and concentrated to obtain Example 138B as a yellow solid (0.32 g, 87%). $^1$H NMR (400 MHz, CDCl$_3$): δ 7.80 (s, 1H), 7.63 (m, 2H), 4.15-4.09 (m, 2H), 3.80-3.69 (m, 2H).

Example 138C 1-(4-chloro-3-(trifluoromethyl)phenyl)-3,3-difluorocyclobutanecarbonitrile A solution of DAST (0.42 g, 2.57 mmol) in dichloromethane (2 mL) was added to a solution of Example 138B (0.32 g, 1.17 mmol) in dichloromethane (10 mL) and the solution was stirred at room temperature overnight. The reaction mixture was washed with saturated sodium bicarbonate, washed with brine, dried over Na$_2$SO$_4$, filtered and concentrated to obtain Example 138C (0.27 g, 78%).

Example 138D (1-(4-chloro-3-(trifluoromethyl)phenyl)-3,3-difluorocyclobutyl)(pyridin-2-yl)methanone To a solution of 2-bromopyridine (0.26 g, 1.63 mmol) in THF (10 mL) was added 2.5M n-BuLi in hexane (0.76 mL, 1.89 mmol) dropwise at −78° C. Solution was stirred for about half an hour; then a solution Example 138C (0.4 g, 1.35 mmol) in THF (2 mL) was added in one portion and stirring continued for about 45 min. The mixture was quenched by addition of 2N $H_2SO_4$ (2 mL). The mixture was refluxed for about one hour, quenched by saturated sodium bicarbonate and extracted with ethyl acetate (30 mL×2). The organic phase was washed with brine, dried over $Na_2SO_4$, filtered, and concentrated to provide Example 138D (0.27 g, 53.5%). LC-MS:MS (M+H):376.

Example 138E

{1-[4-chloro-3-(trifluoromethyl)phenyl]-3,3-difluorocyclobutyl}(pyridin-2-yl)methanol To a solution of Example 138D (272 mg, 0.72 mmol) in methanol (10 mL) was added $NaBH_4$ (82 mg, 2.17 mmol) and the mixture was stirred at rt for about one hour. The reaction mixture was quenched by $NH_4Cl$ and extracted with ethyl acetate (30 mL). The organic phase was washed with brine, dried over $Na_2SO_4$, filtered and concentrated. The residue was purified by HPLC (Column: BOSTON −C18 20×250 mm 10 μm, eluent: water (0.05% $NH_4HCO_3$): acetonitrile, 1:1 to 1:4) to obtain Example 138E (162 mg, 59.2%). LC-MS: MS (M+H): 378. $^1$H NMR (400 MHz, $CDCl_3$): δ 8.37 (d, J=5.2 Hz, 1H), 7.58-7.54 (m, 1H), 7.35 (d, J=8.4 Hz, 1H), 7.20-7.17 (m, 1H), 7.00 (d, J=8.0 Hz, 1H), 6.93 (d, J=2.0 Hz, 1H), 6.74 (d, J=8.0 Hz, 1H), 4.89 (s, 1H), 4.46 (br, 1H), 3.48-3.32 (m, 2H), 2.87-2.74 (m, 2H).

Example 139

{3,3-difluoro-1-[4-fluoro-3-(trifluoromethyl)phenyl]cyclobutyl}(pyridin-2-yl)methanol The title compound was prepared using procedures analogous to that described for the synthesis of Example 138, substituting 2-(4-fluoro-3-(trifluoromethyl)-phenyl)acetonitrile for 2-(4-chloro-3-(trifluoromethyl)phenyl)acetonitrile in Example 138A. LC-MS: MS (M+H): 362. $^1$H NMR (400 MHz, $CDCl_3$): δ 8.37 (d, J=5.2 Hz, 1H), 7.56-7.52 (m, 1H), 7.19-7.16 (m, 1H), 7.06-7.03 (m, 2H), 6.85 (d, J=6.8 Hz, 1H), 6.73 (d, J=7.6 Hz, 1H), 4.88 (s, 1H), 4.48 (br, 1H), 3.46-3.32 (m, 2H), 2.87-2.74 (m, 2H).

Example 140

[4-(3,4-dichlorophenyl)piperidin-4-yl](pyridin-2-yl)methanol

Example 141

[4-(3,4-dichlorophenyl)-1-methylpiperidin-4-yl](pyridin-2-yl)methanol

Example 141A tert-butyl 4-cyano-4-(3,4-dichlorophenyl)piperidine-1-carboxylate

To a solution of 1,2-dichloro-4-fluorobenzene (1.64 g, 10 mmol) in toluene (25 mL) was added tert-butyl 4-cyanopiperidine-1-carboxylate (2.10 g, 10 mmol) and KHMDS (0.5 M in toluene) (2.99 g, 15.00 mmol). The reaction mixture was stirred at 60° C. for 16 hours and cooled to room temperature. After the addition of 1N HCl (25 mL), the reaction mixture was extracted with EtOAc (3×20 mL). The combined organic extracts were washed with brine (100 mL), dried over $MgSO_4$, filtered, and concentrated. The residue was purified by Prep-TLC (eluted with ethyl acetate:petroleum ether=1:5) to provide Example 141A. LCMS: 255 [M-100]$^+$.

Example 141B tert-butyl 4-(3,4-dichlorophenyl)-4-picolinoylpiperidine-1-carboxylate To a solution of 2-bromopyridine (0.768 g, 4.86 mmol) in dry THF (20 mL) was added n-butyllithium (2.5 M in hexane, 0.6 mL, 4.86 mmol) at −78° C. After stirring for 30 minutes, the solution of Example 141A (1.2 g, 3.24 mmol) in THF (5 mL) was added. The mixture was stirred at −78° C. for 30 minutes, diluted with saturated $NH_4Cl$ (2×20 mL) and extracted with EtOAc (2×20 mL). The combined organic layers were dried over $Na_2SO_4$, filtered, and concentrated. The resulting residue was purified by column chromatography on silica gel (petroleum ether/EtOAc=10/1) to give Example 141B.

Example 141C tert-butyl 4-(3,4-dichlorophenyl)-4-(hydroxy(pyridin-2-yl)methyl)-piperidine-1-carboxylate To a solution of Example 141B (500 mg, 1.11 mmol) in dry MeOH (5 mL) was added $NaBH_4$ (84 mg, 2.22 mmol) at 0° C. The mixture was stirred at 25° C. for 1 hour and water (10 mL) was added slowly. The aqueous phase was separated and extracted with dichloromethane (2×20 mL). The combined organic phases were washed with water, brine, dried over $Na_2SO_4$, filtered, and concentrated in vacuo. The resulting residue was purified by column chromatography on silica gel (petroleum ether/EtOAc=1/1) to give Example 141C.

Example 141D

[4-(3,4-dichlorophenyl)piperidin-4-yl](pyridin-2-yl)methanol

To a solution of Example 141C (390 mg, 0.866 mmol) in MeOH (2 mL) was added HCl/MeOH (2 M, 2 mL, 4 mmol) at room temperature. The reaction mixture was stirred at ambient temperature overnight. The solvent was removed in vacuo. The resulting residue was partitioned between EtOAc (20 mL) and saturated $NaHCO_3$ (20 mL). The organic layer was separated, dried over $Na_2SO_4$, filtered, and concentrated. Crude product was purified by Prep-HPLC (Column: Waters X-bridge ODS C 18 21.2×250 mm, water (0.05% TFA): acetonitrile 45-85%) to give Example 141D. LCMS: 450[M+1]. $^1$H NMR (400 MHz, DMSO-$d_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 141E

[4-(3,4-dichlorophenyl)-1-methylpiperidin-4-yl](pyridin-2-yl)methanol

The mixture of Example 141D (155 mg, 0.440 mmol), formaldehyde (13.33 μL, 0.484 mmol) and formic acid (42.2 μL, 1.100 mmol) were heated at 90° C. for 18 hours. After addition of concentrated HCl (1 mL), the volatiles were removed under reduced pressure and the resulting residue was dissolved in $H_2O$ (5 mL). The aqueous solution was adjusted to pH=8 with 30% NaOH and extracted with diethyl ether (3×10 mL). The combined organic phases were dried ($Na_2SO_4$), filtered, concentrated. The crude product was purified by prep-HPLC (Column: Waters X-bridge ODS C 18 21.2×250 mm, water (0.05% TFA): acetonitrile 45-85%) to give Example 141E. $^1$H NMR (400 MHz, DMSO-$d_6$): δ 12.81

(s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 142 pyridin-2-yl{4-[2-(trifluoromethoxy)phenyl]piperidin-4-yl}methanol

Example 143

{1-methyl-4-[4-(trifluoromethyl)phenyl]piperidin-4-yl}(pyridin-2-yl)-methanol

Example 143A pyridin-2-yl{4-[4-(trifluoromethyl)phenyl]piperidin-4-yl}methanol The title compound was prepared using procedures analogous to that described for the synthesis of Example 141D, substituting 1-fluoro-4-(trifluoromethyl)-benzene for 1,2-dichloro-4-fluorobenzene in Example 141A. $^1$H NMR (400 MHz, DMSO-d$_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 143B

{1-methyl-4-[4-(trifluoromethyl)phenyl]piperidin-4-yl}(pyridin-2-yl)-methanol

The title compound was prepared using procedures analogous to that described for the synthesis of Example 141E, substituting Example 143A for Example 141D. $^1$H NMR (400 MHz, DMSO-d$_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 144 pyridin-2-yl{4-[4-(trifluoromethoxy)phenyl]piperidin-4-yl}methanol

Example 145

{1-methyl-4-[4-(trifluoromethoxy)phenyl]piperidin-4-yl}(pyridin-2-yl)-methanol

Example 145A pyridin-2-yl{4-[4-(trifluoromethoxy)phenyl]piperidin-4-yl}methanol The title compound was prepared using procedures analogous to that described for the synthesis of Example 141D, substituting 1-fluoro-4-(trifluoromethoxy)-benzene for 1,2-dichloro-4-fluorobenzene in Example 141A. LCMS: 353[M+1]. $^1$H NMR (400 MHz, DMSO-d$_6$): δ 8.37 (d, J=5.2 Hz, 1H), 7.51-7.55 (m, 1H), 7.13-7.24 (m, 5H), 6.67 (d, J=8.4 Hz, 1H), 4.68 (s, 1H), 2.94-2.97 (m, 2H), 2.50-2.61 (m, 3H), 2.17-2.21 (m, 1H), 1.99-2.10 (m, 2H).

Example 145B

{1-methyl-4-[4-(trifluoromethoxy)phenyl]piperidin-4-yl}(pyridin-2-yl)-methanol

The title compound was prepared using procedures analogous to that described for the synthesis of Example 141E, substituting Example 145A for Example 141D. LCMS: 367 [M+1]. $^1$H NMR (400 MHz, DMSO-d$_6$): δ 8.34 (d, J=4.8 Hz, 1H), 7.49-7.53 (m, 1H), 7.10-7.21 (m, 5H), 6.68 (d, J=8.0 Hz, 1H), 4.68 (s, 1H), 2.71-2.76 (m, 2H), 2.54-2.67 (m, 1H), 2.14 (s, 3H), 2.07-2.20 (m, 5H).

Example 146

{1-methyl-4-[3-(trifluoromethoxy)phenyl]piperidin-4-yl}(pyridin-2-yl)-methanol

Example 146A pyridin-2-yl{4-[3-(trifluoromethoxy)phenyl]piperidin-4-yl}methanol The title compound was prepared using procedures analogous to that described for the synthesis of Example 141D, substituting 1-fluoro-3-(trifluoromethoxy)-benzene for 1,2-dichloro-4-fluorobenzene in Example 141A. LCMS: 353[M+1]. $^1$H NMR (400 MHz, DMSO-d$_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 146B

{1-methyl-4-[3-(trifluoromethoxy)phenyl]piperidin-4-yl}(pyridin-2-yl)-methanol

The title compound was prepared using procedures analogous to that described for the synthesis of Example 141E, substituting Example 146A for Example 141D. LCMS: 367 [M+1]. $^1$H NMR (400 MHz, DMSO-d$_6$): δ 8.36 (d, J=4.0 Hz, 1H), 7.53 (s, 1H), 7.29-7.34 (m, 1H), 7.13-7.21 (m, 4H), 6.75 (s, 1H), 5.49 (s, 1H), 2.78-2.81 (m, 2H), 2.64-2.67 (m, 4H), 2.14 (s, 3H), 1.97-2.21 (m, 5H).

Example 147 pyridin-2-yl{4-[4-(trifluoromethyl)phenyl]piperidin-4-yl}methanol

Example 148 pyridin-2-yl{4-[3-(trifluoromethoxy)phenyl]piperidin-4-yl}methanol

Example 149

{1-methyl-4-[2-(trifluoromethoxy)phenyl]piperidin-4-yl}(pyridin-2-yl)-methanol

Example 149A pyridin-2-yl{4-[2-(trifluoromethoxy)phenyl]piperidin-4-yl}methanol The title compound was prepared using procedures analogous to that described for the synthesis of Example 141D, substituting 1-fluoro-2-(trifluoromethoxy)-benzene for 1,2-dichloro-4-fluorobenzene in Example 141A. LCMS: 353 [M+1]; $^1$H NMR (400 MHz, DMSO-d$_6$): δ 8.38 (d, J=4.8 Hz, 1H), 7.53-7.57 (m, 1H), 7.32-7.36 (m, 1H), 7.16-7.25 (m, 4H), 6.80 (s, 1H), 4.68 (s, 1H), 2.95-2.99 (m, 2H), 2.50-2.66 (m, 4H), 1.99-2.15 (m, 2H).

Example 149B

{1-methyl-4-[2-(trifluoromethoxy)phenyl]piperidin-4-yl}(pyridin-2-yl)-methanol

The title compound was prepared using procedures analogous to that described for the synthesis of Example 141E, substituting Example 149A for Example 141D. LCMS: 367 [M+1]. $^1$H NMR (400 MHz, DMSO-d$_6$): δ 8.36 (d, J=4.0 Hz, 1H), 7.53 (s, 1H), 7.29-7.34 (m, 1H), 7.13-7.21 (m, 4H), 6.75 (s, 1H), 5.49 (s, 1H), 2.78-2.81 (m, 2H), 2.64-2.67 (m, 4H), 2.14 (s, 3H), 1.97-2.21 (m, 5H).

Example 150

(S)-[cis-1-(3,4-dichlorophenyl)-3-methoxycyclobutyl](pyridin-2-yl)-methanol

Example 150A 1-(3,4-dichlorophenyl)-3-hydroxycyclobutanecarbonitrile 3,4-Dichlorophenylacetonitrile (18.60 g, 100 mmol) was dissolved in THF (30 mL) and chilled to −78° C. in a dry ice/acetone bath. 1.6M Methyllithium (62.5 mL, 100 mmol) in diethyl ether was added dropwise over 20 minutes, and the reaction stirred at −78° C. for 1 hour. Epibromohydrin (8.28 mL, 100 mmol) was added and the reaction stirred for 1 hour at −78° C. 3M Methyl magnesium bromide (33.3 mL, 100 mmol) in diethyl ether was then added dropwise over 5 minutes and the reaction was warmed to ambient temperature and stirred overnight. The reaction was quenched with water, made acidic with 3N hydrochloric acid (50 mL), and extracted twice with diethyl ether. The combined organic layers were washed with brine, dried with MgSO$_4$, filtered, and concentrated to give Example 150A (17.43 g, 72 mmol, 72% yield), a mixture of geometric isomers by proton NMR. MS (DCI$^+$): m/z 259.0 (M+NH$_4$).

Example 150B 1-(3,4-dichlorophenyl)-3-methoxycyclobutanecarbonitrile

Example 150A (4.84 g, 20 mmol) in THF (70 mL) was added 60% sodium hydride (0.880 g, 22.00 mmol) in mineral oil. Hydrogen gas evolution was observed. After 1 hour, methyl iodide (1.376 mL, 22.00 mmol) was added, and the reaction was allowed to stir at ambient temperature for 4 days. The reaction mixture was quenched with water, and extracted twice with diethyl ether. The combined organic layers were washed with brine, dried with MgSO$_4$, and concentrated. The residue was chromatographed on an AnaLogix SF40-150 g column and eluted with 20% EtOAc in hexanes to give Example 150B (3.93 g, 15.34 mmol, 77% yield), a mixture of geometric isomers. MS (DCI$^+$): m/z 273.1 (M+NH$_4$).

Example 150C 2.5M n-Butyllithium (7.37 mL, 18.41 mmol) in hexanes was added to diethyl ether (30 mL), and cooled to −78° C. in a dry ice/acetone bath. 2-Bromopyridine (1.945 mL, 19.95 mmol) was added, and the reaction stirred at −78° C. for 40 minutes. Example 150B (3.93 g, 15.34 mmol) was added dropwise, and the reaction was warmed to ambient temperature. The reaction was quenched with 3N hydrochloric acid (25 mL) and stirred over the weekend. The reaction mixture was made basic with 3N sodium hydroxide and extracted twice with diethyl ether. The organic layers were combined, washed with brine, dried with MgSO$_4$, and concentrated. The residue was chromatographed on an AnaLogix SF40-120 g column with 15% EtOAc in hexanes to give crude product (4.44 g, 13.2 mmol, 86% yield). This material was chromatographed on an AnaLogix SF40-150 g column and eluted with 0-1% EtOAc in dichloromethane to give Example 150C (1.38 g, 4.70 mmol), a single geometric isomer by proton NMR, and Example 151A (2.50 g, 7.44 mmol), a mixture of geometric isomers. MS (DCI$^+$): m/z 336.0 (M+H). $^1$H NMR (500 MHz, DMSO-d$_6$) δ 8.58 (dt, J=4.5, 1.1 Hz, 1H), 7.99-7.91 (m, 2H), 7.69 (d, J=2.2 Hz, 1H), 7.58-7.50 (m, 2H), 7.41 (dd, J=8.5, 2.2 Hz, 1H), 3.90 (p, J=7.0 Hz, 1H), 3.12 (s, 3H), 3.04-2.95 (m, 2H), 2.72-2.62 (m, 2H).

Example 150D (S)-[cis-1-(3,4-dichlorophenyl)-3-methoxycyclobutyl](pyridin-2-yl)-methanol A solution of Example 150C (1.357 g, 4.04 mmol), triethylamine (1.406 mL, 10.09 mmol), formic acid (0.666 mL, 17.36 mmol), and (S,S)—N-(p-toluenesulfonyl)-1,2-diphenylethanediamine(chloro)(p-cymene)ruthenium(II) (0.026 g, 0.040 mmol) in THF (5 mL) was heated overnight at 35° C. The reaction was incomplete, mostly starting ketone, and was heated at 55° C. for another 24 hours. The reaction was still incomplete. Additional chiral ruthenium catalyst (0.026 g, 0.040 mmol) was added, and the reaction was heated at 75° C. for 4 hours, then cooled to ambient temperature and stirred for one week. The reaction was then heated overnight at 75° C. The reaction was cooled to ambient temperature, diluted with dichloromethane, washed with saturated NaHCO$_3$ solution, dried with MgSO$_4$, filtered, and concentrated. The residue was chromatographed on an AnaLogix SF25-40 g column and eluted with 50% EtOAc in hexanes to give Example 150D (0.33 g, 0.976 mmol, 24.2% yield). MS (DCI$^+$): m/z 338.0 (M+H). $^1$H NMR (300 MHz, DMSO-d$_6$) δ 8.38 (ddd, J=4.8, 1.7, 0.9 Hz, 1H), 7.56 (td, J=7.7, 1.8 Hz, 1H), 7.36 (d, J=8.4 Hz, 1H), 7.16 (ddd, J=7.5, 4.8, 1.1 Hz, 1H), 7.05 (d, J=2.2 Hz, 1H), 6.85 (dd, J=8.4, 2.2 Hz, 1H), 6.79 (d, J=7.9 Hz, 1H), 5.72 (d, J=4.3 Hz, 1H), 4.78 (d, J=4.0 Hz, 1H), 3.61-3.48 (m, 1H), 3.11 (s, 3H), 2.69-2.52 (m, 2H), 2.48-2.39 (m, 1H). [α]$_D$=+10.1° (c 0.555, MeOH).

Example 151

(S)-[1-(3,4-dichlorophenyl)-3-methoxycyclobutyl](pyridin-2-yl)methanol

Example 151A

[1-(3,4-dichlorophenyl)-3-methoxycyclobutyl](pyridin-2-yl)methanone 2.5M n-Butyllithium (7.37 mL, 18.41 mmol) in hexanes was added to diethyl ether (30 mL), and cooled to −78° C. in a dry ice/acetone bath. 2-Bromopyridine (1.945 mL, 19.95 mmol) was added, and the reaction stirred at −78° C. for 40 minutes. Example 150B (3.93 g, 15.34 mmol) was added dropwise, and the reaction was warmed to ambient temperature. The reaction was quenched with 3N hydrochloric acid (25 mL) and stirred overnight. The reaction mixture was made basic with 3N sodium hydroxide and extracted twice with diethyl ether. The organic layers were combined, washed with brine, dried with MgSO$_4$, filtered, and concentrated. The residue was chromatographed on an AnaLogix SF40-120 g column with 15% EtOAc in hexanes to give crude product (4.44 g, 13.2 mmol, 86% yield). This material was chromatographed on an AnaLogix SF40-150 g column and eluted with 0-1% EtOAc in dichloromethane to give Example 150C (1.38 g, 4.70 mmol), a single geometric isomer, and Example 151A (2.50 g, 7.44 mmol), a mixture of geometric isomers by proton NMR. MS (DCI$^+$): m/z 336.0 (M+H).

Example 151B (S)-[1-(3,4-dichlorophenyl)-3-methoxycyclobutyl](pyridin-2-yl)methanol Example 151A (2.50 g, 7.44 mmol) was dissolved in triethylamine (12.95 mL, 93 mmol) and formic acid (6.13 mL, 160 mmol). (S,S)—N-(p-toluenesulfonyl)-1,2-diphenylethanediamine(chloro)(p-cymene)ruthenium(II) (0.237 g, 0.372 mmol) was added, and the reaction was heated overnight at 55° C. The reaction was cooled, diluted with dichloromethane, washed with saturated NaHCO₃ solution, dried with MgSO₄, filtered, and concentrated. The residue was chromatographed on an AnaLogix SF40-80 g column and eluted with 50% EtOAc in hexanes to give Example 151B (1.38 g, 4.08 mmol, 54.9% yield), a 2:1 mixture of geometric isomers. MS (DCI⁺): m/z 338.0 (M+H). ¹H NMR (300 MHz, DMSO-d₆) δ 8.45-8.41 (m, 1½H), 8.40-8.36 (m, 1H), 7.61-7.53 (m, 1½H), 7.39-7.34 (m, 1½H), 7.23-7.14 (m, 1½H), 7.05 (d, J=2.1 Hz, 1H), 6.87 (dd, J=2.0, 1.6 Hz, 1H), 6.85-6.77 (m, 2H), 6.66 (dd, J=8.3, 2.1 Hz, 1½H), 5.75 (d, J=4.7 Hz, 1½H), 5.72 (d, J=4.7 Hz, 1H), 4.78 (d, J=4.7 Hz, 1H), 4.74 (d, J=4.7 Hz, ½H), 3.87 (p, J=6.9 Hz, ½H), 3.55 (p, J=7.1 Hz, 1H), 3.11 (s, 3H), 3.19-3.03 (m, 1½H), 3.08 (s, 1½H), 2.69-2.53 (m, 2H), 2.5-2.41 (m, 1½H), 2.03-1.92 (m, 1H).

Example 152 pyridin-2-yl{3-[4-(trifluoromethyl)phenyl]azetidin-3-yl}methanol

Example 153 tert-butyl 3-[hydroxy(pyridin-2-yl)methyl]-3-[4-(trifluoromethyl)phenyl]-azetidine-1-carboxylate The title compound was prepared using procedures analogous to that described for the synthesis of Example 141C, substituting 1-fluoro-4-(trifluoromethyl)-benzene for 1,2-dichloro-4-fluorobenzene and substituting tert-butyl 3-cyanoazetidine-1-carboxylate for tert-butyl 4-cyanopiperidine-1-carboxylate in Example 141A. LCMS: 409[M+1]. ¹H NMR: (400 MHz, CD₃OD): δ 8.31 (s, 1H), 7.41-7.37 (m, 3H), 7.10-7.07 (m, 1H), 6.81 (d, J=8.0 Hz, 2H), 6.60 (s, 1H), 4.94 (s, 1H), 4.55-4.45 (m, 3H), 4.06-4.02 (m, 2H), 1.36 (s, 9H).

Example 154

(S)-{3,3-difluoro-1-[4-(trifluoromethyl)phenyl]cyclobutyl}(pyridin-2-yl)-methanol Example 133F (2.609 g, 7.64 mmol) was dissolved in formic acid (2.52 mL, 65.7 mmol) and triethylamine (5.30 mL, 38.2 mmol), followed by the addition of (S,S)—N-(p-toluenesulfonyl)-1,2-diphenylethanediamine(chloro)(p-cymene)ruthenium(II) (0.122 g, 0.191 mmol). The orange solution was heated overnight at 35° C., followed by the addition of 300 mL dichloromethane, washed with 300 mL saturated NaHCO₃ solution, dried over Na₂SO₄, filtered, and concentrated. The residue was chromatographed on a Grace Reveleris 80 g column, eluted with 0-100% EtOAc in hexanes (35 mL/min) to provide Example 154 (2.423 g, 7.06 mmol, 92% yield) as a white solid. MS (ESL): m/z: 344.0 (M+H). ¹H NMR (300 MHz, DMSO-d₆) δ 8.42 (ddd, J=4.8, 1.7, 0.9, 1H), 7.56-7.43 (m, 3H), 7.18 (ddd, J=7.5, 4.8, 1.2, 1H), 7.04 (d, J=8.1, 2H), 6.71 (d, J=7.9, 1H), 6.05 (s, 1H), 4.87 (s, 1H), 3.65-3.48 (m, 1H), 3.48-3.32 (m, 1H), 3.00-2.75 (m, 2H). [α]$_D$=−76.0° (c 1.0, MeOH). Calculated for C₁₇H₁₄F₅NO: C, 59.48%; H, 4.11%; N, 4.08%. Found: C, 59.58%; H, 3.96%; N, 3.97%.

Example 155

{1-methyl-3-[4-(trifluoromethyl)phenyl]azetidin-3-yl}(pyridin-2-yl)-methanol

Example 155A pyridin-2-yl{3-[4-(trifluoromethyl)phenyl]azetidin-3-yl}methanol The title compound was prepared using procedures analogous to that described for the synthesis of Example 141D, substituting 1-fluoro-4-(trifluoromethyl)-benzene for 1,2-dichloro-4-fluorobenzene and substituting tert-butyl 3-cyanoazetidine-1-carboxylate for tert-butyl 4-cyanopiperidine-1-carboxylate, in Example 141A. LCMS: 309 [M+1]. ¹H NMR (400 MHz, DMSO-d₆): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 155B

{1-methyl-3-[4-(trifluoromethyl)phenyl]azetidin-3-yl}(pyridin-2-yl)-methanol

The title compound was prepared using procedures analogous to that described for the synthesis of Example 141E, substituting Example 155A for Example 141D. ¹H NMR (400 MHz, DMSO-d₆): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 156 tert-butyl 4-[hydroxy(pyridin-2-yl)methyl]-4-[4-(trifluoromethyl)phenyl]-piperidine-1-carboxylate The title compound was prepared using procedures analogous to that described for the synthesis of Example 141C, substituting 1-fluoro-4-(trifluoromethyl)-benzene for 1,2-dichloro-4-fluorobenzene in Example 141A. LCMS: 437[M+1]. ¹H NMR: (400 MHz, CD₃OD): δ 8.36 (d, J=4.0 Hz, 1H), 7.54-7.52 (m, 3H), 7.30 (d, J=8.4 Hz, 2H), 7.23-7.20 (t, J=6.0 Hz, 1H), 6.67 (d, J=7.6 Hz, 1H), 3.92 (d, J=9.4 Hz, 1H), 3.90 (s, 1H), 2.73 (m, 2H), 2.72 (m, 2H), 2.56 (d, J=14.0 Hz, 2H), 2.22 (d, J=13.6 Hz 1H), 2.02-1.90 (m, 2H), 1.43 (s, 9H).

Example 157 tert-butyl 4-[hydroxy(pyridin-2-yl)methyl]-4-[4-(trifluoromethoxy)phenyl]-piperidine-1-carboxylate The title compound was prepared using procedures analogous to that described for the synthesis of Example 141C, substituting 1-fluoro-4-(trifluoromethoxy)-benzene for 1,2-dichloro-4-fluorobenzene in Example 141A. LCMS: 453[M+1]. ¹H NMR: (400 MHz, CD₃OD): δ 8.35 (d, J=4.4 Hz, 1H), 7.53-7.49 (m, 1H), 7.21-7.11 (m, 5H), 6.64 (d, J=8.0 Hz, 1H), 4.65 (s, 1H), 3.90 (d, J=14.0 Hz, 2H), 2.73 (s, 2H), 2.50 (d, J=12.8 Hz, 1H), 2.16 (d, J=13.6 Hz 1H), 2.01-1.90 (m, 2H), 1.41 (s, 9H).

Example 158 tert-butyl 4-[hydroxy(pyridin-2-yl)methyl]-4-[3-(trifluoromethoxy)phenyl]-piperidine-1-carboxylate The title compound was prepared using procedures analogous to that described for the synthesis of Example 141C, substituting 1-fluoro-3-(trifluoromethoxy)-benzene for 1,2-dichloro-4-fluorobenzene in Example 141A. LCMS: 453[M+1]. $^1$H NMR: (400 MHz, CD$_3$OD: δ 8.36 (d, J=4.0 Hz, 1H), 7.49 (t, J=8.0 Hz, 1H), 7.34 (t, J=8.0 Hz, 1H), 7.21-7.11 (m, 3 Hz), 6.90 (s, 1H), 6.62 (d, J=8.4 Hz, 1H), 4.66 (s, 1H), 3.89-3.92 (m, J=14.0 Hz, 2H), 2.73 (s, 2H), 2.47 (d, J=14.0 Hz, 1H), 2.11 (m, 1H), 2.00-1.92 (m, 2H), 1.43 (s, 9H).

Example 159

(R)-{3,3-difluoro-1-[4-(trifluoromethoxy)phenyl]cyclobutyl}(pyridin-2-yl)-methanol Example 128D (1.206 g, 3.38 mmol) was dissolved in formic acid (1.113 mL, 29.0 mmol) and triethylamine (2.340 mL, 16.88 mmol), followed by the addition of (R,R)—N-(p-toluenesulfonyl)-1,2-diphenylethanediamine(chloro)(p-cymene)ruthenium(II) (0.054 g, 0.084 mmol). The yellow solution was heated overnight at 35° C., followed by the addition of 200 mL dichloromethane, washed with 200 mL saturated NaHCO$_3$ solution, dried over Na$_2$SO$_4$, filtered, and concentrated. The residue was chromatographed on a Grace Reveleris 80 g column, eluted with 0-100% EtOAc in hexanes (35 mL/min) to provide Example 159 (1.157 g, 3.22 mmol, 95% yield) as a pale yellow oil which partially crystallized overnight.

Example 159 (1.157 g, 3.22 mmol) was dissolved in methanol (20 mL), followed by the addition of 1.25M hydrogen chloride in methanol (35 mL, 43.8 mmol). The solution was concentrated to yield the HCl salt of Example 159 (1.225 g, 3.10 mmol, 96% yield) as a white solid. (ESI$^+$): m/z 360.0 (M+H). $^1$H NMR (300 MHz, CD$_3$OD) δ 8.48-8.38 (m, 2H), 7.94-7.85 (m, 1H), 7.70 (d, J=8.0 Hz, 1H), 7.14 (dd, J=8.9, 0.9 Hz, 2H), 7.05 (d, J=9.0 Hz, 2H), 5.33 (s, 1H), 3.55-3.35 (m, 2H), 3.08-2.89 (m, 2H). [α]$_D$=+27.2° (c 1.0, MeOH). Calculated for C$_{17}$H$_{14}$F$_5$NO$_2$.HCl: C, 51.59%; H, 3.82%; N, 3.54%. Found: C, 51.69%; H, 3.43%; N, 3.49%.

Example 160

3-[hydroxy(pyridin-2-yl)methyl]-3-[4-(trifluoromethyl)phenyl]-cyclobutanone

A mixture of Example 161B (7.562 g, 20.70 mmol), acetone (150 mL), water (15 mL) and 12M hydrochloric acid (15 mL) was stirred overnight at ambient temperature, followed by the addition of 200 mL 3N sodium hydroxide, extracted twice with 300 mL EtOAc, washed with 200 mL brine, dried over Na$_2$SO$_4$, filtered, and concentrated. The residue was chromatographed on a Grace Reveleris 120 g column, eluted with 0-100% EtOAc in heptane (40 mL/min) to provide Example 160 (6.94 g, 21.60 mmol, 104% yield) as a colorless oil which solidified upon cooling. (ESI$^+$): m/z 322.0 (M+H). $^1$H NMR (300 MHz, DMSO-d$_6$) δ 8.40 (ddd, J=4.8, 1.8, 0.8 Hz, 1H), 7.61-7.49 (m, 3H), 7.19 (ddd, J=7.5, 4.8, 1.1 Hz, 1H), 7.13 (d, J=8.0 Hz, 2H), 6.88 (d, J=7.9 Hz, 1H), 6.03 (s, 1H), 4.90 (s, 1H), 3.87-3.69 (m, 2H), 3.39-3.25 (m, 2H).

Example 161 pyridin-2-yl{2-[4-(trifluoromethyl)phenyl]-5,8-dioxaspiro[3.4]oct-2-yl}-methanol

Example 161A pyridin-2-yl{2-[4-(trifluoromethyl)phenyl]-5,8-dioxaspiro[3.4]octan-2-yl}-methanone A solution of 2.5M n-butyllithium (14.05 mL, 35.1 mmol) in hexanes and diethyl ether (40 mL) was chilled to −70° C., followed by dropwise addition of 2-bromo-pyridine (5.73 g, 36.3 mmol) in diethyl ether (25 mL) and stirred for 45 minutes. Example 133C (6.633 g, 23.42 mmol) in diethyl ether (25 mL) was added dropwise to the reaction mixture, allowing the temperature to slowly warm to 0° C. over a period of 2.5 hours. The mixture was quenched with 100 mL 1N hydrochloric acid, and the biphasic mixture was stirred for 40 minutes at ambient temperature, followed by the addition of 100 mL 3N sodium hydroxide, and extracted twice with 200 mL EtOAc. The organic phase was washed with brine (200 mL), dried over Na$_2$SO$_4$, filtered, and concentrated. The residue was chromatographed on a Grace Reveleris 120 g column, eluted with 0-30% EtOAc in hexanes (40 mL/min) to provide Example 161A (7.722 g, 21.25 mmol, 91% yield) as a yellow oil which solidified overnight. (ESI$^+$): m/z 364.0 (M+H). $^1$H NMR (300 MHz, DMSO-d$_6$) δ 8.58-8.53 (m, 1H), 8.01-7.90 (m, 2H), 7.64 (s, 4H), 7.52 (ddd, J=6.8, 4.7, 2.0 Hz, 1H), 3.86-3.74 (m, 4H), 3.34-3.24 (m, 2H), 3.02-2.93 (m, 2H).

Example 161B pyridin-2-yl{2-[4-(trifluoromethyl)phenyl]-5,8-dioxaspiro[3.4]oct-2-yl}-methanol To a solution of Example 161A (7.494 g, 20.63 mmol) in dichloromethane (80 mL) and methanol (8 mL) was added sodium borohydride (0.858 g, 22.69 mmol). The mixture was stirred for 2.5 hours at ambient temperature, followed by the addition of 200 mL 3N sodium hydroxide, and extracted twice with 300 mL EtOAc. The organic phase was washed with brine (200 mL), dried over Na$_2$SO$_4$, filtered, and concentrated. The residue was chromatographed on a Grace Reveleris 120 g column, eluted with 0-100% EtOAc in hexanes (40 mL/min) to provide Example 161B (7.595 g, 20.79 mmol, 101% yield) as a colorless oil. (ESI$^+$): m/z 366.1 (M+H). $^1$H NMR (300 MHz, DMSO-d$_6$) δ 8.41 (ddd, J=4.7, 1.7, 0.8 Hz, 1H), 7.51-7.42 (m, 3H), 7.15 (ddd, J=7.4, 4.8, 1.1 Hz, 1H), 6.95 (d, J=8.0 Hz, 2H), 6.59 (d, J=7.9 Hz, 1H), 5.78 (d, J=4.6 Hz, 1H), 5.00 (d, J=4.5 Hz, 1H), 3.91-3.83 (m, 2H), 3.80-3.70 (m, 2H), 3.26 (dd, J=9.9, 2.7 Hz, 1H), 3.07 (dd, J=13.0, 3.4 Hz, 1H), 2.56 (dd, J=13.1, 2.1 Hz, 1H), 2.44 (dd, J=12.9, 2.2 Hz, 1H).

Example 162

(1-cyclohexylcyclobutyl)(pyridin-2-yl)methanol

Example 163

(1-cyclopentylcyclobutyl)(pyridin-2-yl)methanol

Example 164

3-[(S)-hydroxy(pyridin-2-yl)methyl]-3-[4-(trifluoromethyl)phenyl]-cyclobutanone

The enantiomers of Example 160 (3.198 g, 9.95 mmol) were separated on a Chiralpak AD column (5 cm ID×30 cm, 20 micron) and eluted with 25-40% isopropyl alcohol in hexanes at 40 mL/min (2/30/10 min run time) and injected with a sample solution of 100 mg in 5 mL ethanol per run. The first eluting peak was collected and concentrated to afford Example 164 (1.320 g, 4.11 mmol) as a colorless oil which solidified overnight. (ESI$^+$): m/z 322.1 (M+H). $^1$H NMR (300 MHz, DMSO-d$_6$) δ 8.40 (ddd, J=4.8, 1.7, 0.8 Hz, 1H), 7.62-7.49 (m, 3H), 7.19 (ddd, J=7.5, 4.9, 1.0 Hz, 1H), 7.13 (d, J=8.0 Hz, 2H), 6.88 (d, J=7.9 Hz, 1H), 6.03 (d, J=4.8 Hz, 1H), 4.90 (d, J=4.8 Hz, 1H), 3.87-3.69 (m, 2H), 3.38-3.25 (m, 2H). [α]$_D$=−25.3° (c 1.0, MeOH).

Example 165

3-[(R)-hydroxy(pyridin-2-yl)methyl]-3-[4-(trifluoromethyl) phenyl]-cyclobutanone The enantiomers of Example 160 (3.198 g, 9.95 mmol) were separated on a Chiralpak AD column (5 cm ID×30 cm, 20 micron), eluted with 25-40% isopropyl alcohol in hexanes at 40 mL/min (2/30/10 min run time), and injected with a sample solution of 100 mg in 5 mL ethanol per run. The second eluting peak was collected and concentrated to afford Example 165 (1.426 g, 4.44 mmol) as a yellow oil. (ESL): m/z 322.0 (M+H). $^1$H NMR (300 MHz, DMSO-d$_6$) δ 8.40 (ddd, J=4.8, 1.6, 0.8 Hz, 1H), 7.61-7.49 (m, 3H), 7.19 (ddd, J=7.5, 4.9, 1.0 Hz, 1H), 7.13 (d, J=8.0 Hz, 2H), 6.88 (d, J=7.9 Hz, 1H), 6.03 (d, J=4.8 Hz, 1H), 4.90 (d, J=4.8 Hz, 1H), 3.86-3.69 (m, 2H), 3.38-3.25 (m, 2H). MD=+20.0° (c 1.0, MeOH).

Example 166

3-[(S)-hydroxy(pyridin-2-yl)methyl]-3-[4-(trifluoromethyl) phenyl]-cyclobutanol

Example 164 (718 mg, 2.235 mmol) was dissolved in dichloromethane (20 mL) and methanol (2 mL), and then sodium borohydride (178 mg, 4.69 mmol) was added to the colorless solution. The reaction was complete after stirring for 90 minutes at ambient temperature. To the reaction mixture was added 200 mL 1N sodium hydroxide, and the mixture was extracted twice with 200 mL EtOAc. The combined organic phases was washed with 200 mL brine, dried over Na$_2$SO$_4$, filtered, and concentrated. The residue was chromatographed on a Grace Reveleris 40 g column and eluted with 1-10% methanol in EtOAc (30 mL/min) to provide Example 166 (655 mg, 2.026 mmol, 91% yield) as a white solid, about 1:1 mixture of geometric isomers by proton NMR. (ESL): m/z 324.1 (M+H). $^1$H NMR (300 MHz, DMSO-d$_6$) δ 8.42 (ddd, J=4.8, 1.7, 0.9 Hz, 0.5H), 8.35 (ddd, J=4.9, 1.8, 0.9 Hz, 0.5H), 7.59-7.42 (m, 3H), 7.23-7.08 (m, 2H), 6.95 (d, J=8.0 Hz, 1H), 6.81 (d, J=7.9 Hz, 0.5H), 6.74 (d, J=7.9 Hz, 0.5H), 5.62 (dd, J=6.9, 4.9 Hz, 1H), 5.01 (d, J=6.1 Hz, 0.5H), 4.87 (d, J=6.9 Hz, 0.5H), 4.82 (d, J=3.8 Hz, 0.5H), 4.74 (d, J=4.1 Hz, 0.5H), 3.99 (dd, J=14.3, 7.2 Hz, 0.5H), 3.73 (dd, J=13.5, 7.2 Hz, 0.5H), 3.19-3.05 (m, 1H), 2.70-2.55 (m, 1H), 2.55-2.41 (m, 1H), 2.05-1.93 (m, 1H).

Example 167

(anti)-[1-(3,4-dichlorophenyl)cyclobutyl][6,7-dihydro-5H-cyclopenta[b]-pyridin-7-yl]methanol Example 168

(syn)-[1-(3,4-dichlorophenyl)cyclobutyl][6,7-dihydro-5H-cyclopenta[b]-pyridin-7-yl]methanol Example 169

(anti)-[1-(3,4-difluorophenyl)cyclobutyl][5,6,7,8-tetrahydroquinolin-8-yl]-methanol Example 170

(syn)-[1-(3,4-difluorophenyl)cyclobutyl][5,6,7,8-tetrahydroquinolin-8-yl]-methanol Example 171

(anti)-[1-(3,4-difluorophenyl)cyclobutyl][6,7-dihydro-5H-cyclopenta[b]-pyridin-7-yl]methanol Example 172

(syn)-[1-(3,4-difluorophenyl)cyclobutyl][6,7-dihydro-5H-cyclopenta[b]-pyridin-7-yl]methanol Example 173

(anti)-6,7-dihydro-5H-cyclopenta[b]pyridin-7-yl{1-[4-(trifluoromethyl)-phenyl]cyclobutyl}methanol Example 174

(syn)-6,7-dihydro-5H-cyclopenta[b]pyridin-7-yl{1-[4-(trifluoromethyl)-phenyl]cyclobutyl}methanol Example 175

(anti)-6,7-dihydro-5H-cyclopenta[b]pyridin-7-yl{1-[4-(trifluoromethoxy)-phenyl]cyclobutyl}methanol Example 176

(syn)-6,7-dihydro-5H-cyclopenta[b]pyridin-7-yl{1-[4-(trifluoromethoxy)-phenyl]cyclobutyl}methanol Example 177

(anti)-5,6,7,8-tetrahydroquinolin-8-yl{1-[4-(trifluoromethoxy)phenyl]-cyclobutyl}methanol Example 178

(syn)-5,6,7,8-tetrahydroquinolin-8-yl{1-[4-(trifluoromethoxy)phenyl]-cyclobutyl}methanol Example 179

(anti)-5,6,7,8-tetrahydroquinolin-8-yl{1-[3-(trifluoromethyl)phenyl]-cyclobutyl}methanol Example 180

(syn)-5,6,7,8-tetrahydroquinolin-8-yl{1-[3-(trifluoromethyl)phenyl]-cyclobutyl}methanol Example 181

(anti)-[1-(3,4-dichlorophenyl)cyclobutyl][5,6,7,8-tetrahydroquinolin-8-yl]-methanol Example 182

(syn)-[1-(3,4-dichlorophenyl)cyclobutyl][5,6,7,8-tetrahydroquinolin-8-yl]-methanol Example 183

(anti)-5,6,7,8-tetrahydroquinolin-8-yl{1-[4-(trifluoromethyl)phenyl]cyclobutyl}methanol

Example 184

(syn)-5,6,7,8-tetrahydroquinolin-8-yl{1-[4-(trifluoromethyl)phenyl]-cyclobutyl}methanol

Example 185

(anti)-6,7-dihydro-5H-cyclopenta[b]pyridin-7-yl{1-[3-(trifluoromethyl)-phenyl]cyclobutyl}methanol

Example 186

(syn)-6,7-dihydro-5H-cyclopenta[b]pyridin-7-yl{1-[3-(trifluoromethyl)-phenyl]cyclobutyl}methanol

Example 187

(anti)-5,6,7,8-tetrahydroquinolin-8-yl{1-[3-(trifluoromethoxy)phenyl]-cyclobutyl}methanol

Example 188

(syn)-5,6,7,8-tetrahydroquinolin-8-yl{1-[3-(trifluoromethoxy)phenyl]-cyclobutyl}methanol

Example 180

(anti)-6,7-dihydro-5H-cyclopenta[b]pyridin-7-yl{1-[3-(trifluoromethoxy)-phenyl]cyclobutyl}methanol

Example 190

(syn)-6,7-dihydro-5H-cyclopenta[b]pyridin-7-yl{1-[3-(trifluoromethoxy)-phenyl]cyclobutyl}methanol

Example 191

(anti)-5,6,7,8-tetrahydroquinolin-8-yl{1-[2-(trifluoromethoxy)phenyl]-cyclobutyl}methanol

Example 192

(syn)-5,6,7,8-tetrahydroquinolin-8-yl{1-[2-(trifluoromethoxy)phenyl]-cyclobutyl}methanol

Example 193

(anti)-6,7-dihydro-5H-cyclopenta[b]pyridin-7-yl{1-[2-(trifluoromethoxy)-phenyl]cyclobutyl}methanol

Example 194

(syn)-6,7-dihydro-5H-cyclopenta[b]pyridin-7-yl{1-[2-(trifluoromethoxy)-phenyl]cyclobutyl}methanol

Example 195

(anti)-5,6,7,8-tetrahydroquinolin-8-yl{1-[2-(trifluoromethyl)phenyl]-cyclobutyl}methanol

Example 196

(syn)-5,6,7,8-tetrahydroquinolin-8-yl{1-[2-(trifluoromethyl)phenyl]-cyclobutyl}methanol

Example 197

(anti)-6,7-dihydro-5H-cyclopenta[b]pyridin-7-yl{1-[2-(trifluoromethyl)-phenyl]cyclobutyl}methanol

Example 198

(syn)-6,7-dihydro-5H-cyclopenta[b]pyridin-7-yl{1-[2-(trifluoromethyl)-phenyl]cyclobutyl}methanol

Example 199

3-[(R)-hydroxy(pyridin-2-yl)methyl]-3-[4-(trifluoromethyl)phenyl]-cyclobutanol

Example 165 (1.379 g, 4.29 mmol) was dissolved in dichloromethane (30 mL) and methanol (3 mL), and then sodium borohydride (0.341 g, 9.01 mmol) was added to the colorless solution. The reaction was stirred overnight at ambient temperature. Added 200 mL 1N sodium hydroxide and extracted twice with 200 mL EtOAc. The combined organic phases was washed with 200 mL brine, dried over $Na_2SO_4$, filtered, and concentrated. The residue was supported on silica gel, chromatographed on a Grace Reveleris 40 g column, eluted with 1-10% methanol in EtOAc (30 mL/min) to provide Example 199 (1.164 g, 3.60 mmol, 84% yield) as a white solid, about 1:1 mixture of geometric isomers by proton NMR. (ESI$^+$): m/z 324.1 (M+H). $^1$H NMR (300 MHz, DMSO-$d_6$) δ 8.42 (ddd, J=4.8, 1.7, 0.9 Hz, 0.5H), 8.35 (ddd, J=4.9, 1.8, 0.8 Hz, 0.5H), 7.59-7.42 (m, 3H), 7.22-7.09 (m, 2H), 6.96 (d, J=7.9 Hz, 1H), 6.81 (d, J=7.9 Hz, 0.5H), 6.74 (d, J=7.9 Hz, 0.5H), 5.62 (dd, J=7.3, 4.8 Hz, 1H), 5.01 (d, J=6.1 Hz, 0.5H), 4.87 (d, J=6.8 Hz, 0.5H), 4.82 (d, J=4.5 Hz, 0.5H), 4.74 (d, J=4.7 Hz, 0.5H), 3.99 (dd, J=14.2, 7.2 Hz, 0.5H), 3.73 (dd, J=13.9, 7.3 Hz, 0.5H), 3.19-3.05 (m, 1H), 2.69-2.55 (m, 1H), 2.55-2.41 (m, 1H), 2.06-1.94 (m, 1H).

Example 200 cis-3-[(S)-hydroxy(pyridin-2-yl)methyl]-3-[4-(trifluoromethyl)phenyl]-cyclobutanol The geometric isomers of Example 166 (660 mg, 2.041 mmol) were separated by chiral preparative SFC on a Chiralpak Whelk-0 (S,S) column (21×250 mm, 5 micron). The second eluting peak was collected and concentrated to afford Example 200 (231 mg, 0.714 mmol) as a white solid. (ESL): m/z 324.0 (M+H). $^1$H NMR (501 MHz, DMSO-$d_6$) δ 8.41 (d, J=4.1 Hz, 1H), 7.53 (td, J=7.7, 1.6 Hz, 1H), 7.47 (d, J=8.2 Hz, 2H), 7.17 (dd, J=6.9, 5.3 Hz, 1H), 6.95 (d, J=8.0 Hz, 2H), 6.81 (d, J=7.9 Hz, 1H), 5.60 (s, 1H), 4.87 (d, J=6.5 Hz, 1H), 4.74 (s, 1H), 4.04-3.93 (m, 1H), 3.15-3.05 (m, 2H), 2.05-1.93 (m, 2H). $[α]_D$=−68.0° (c 1.0, MeOH). Calculated for $C_{17}H_{16}F_3NO_2$.0.27 $CH_3OH$: C, 62.49%; H, 5.19%; N, 4.22%. Found: C, 62.39%; H, 4.82%; N, 4.17%.

Example 201 trans-3-[(S)-hydroxy(pyridin-2-yl)methyl]-3-[4-(trifluoromethyl)phenyl]-cyclobutanol The geometric isomers of Example 166 (660 mg, 2.041 mmol) were separated by chiral preparative SFC on a Chiralpak Whelk-0 (S,S) column (21×250 mm, 5 micron). The first eluting peak was collected and concentrated to afford Example 201 (190 mg, 0.588 mmol) as a white solid. (ESI$^+$): m/z 324.1 (M+H). $^1$H NMR (300 MHz, DMSO-$d_6$) δ 8.35 (ddd, J=4.8, 1.7, 0.8 Hz, 1H), 7.52 (td, J=7.7, 1.8 Hz, 1H), 7.46 (d, J=8.1 Hz, 2H), 7.18-7.10 (m, 3H), 6.74 (d, J=7.9 Hz, 1H), 5.64 (s, 1H), 5.01 (d, J=5.9 Hz, 1H), 4.82 (s, 1H), 3.81-3.65 (m, 1H), 2.70-2.56 (m, 2H), 2.55-2.41 (m, 2H). $[\alpha]_D$=−41.6° (c 1.0, MeOH). Calculated for $C_{12}H_{16}F_3NO_2 \cdot 0.18$ $CH_3OH$: C, 62.70%; H, 5.12%; N, 4.26%. Found: C, 62.61%; H, 4.76%; N, 4.23%.

Example 202 pyridin-2-yl{2-[4-(trifluoromethoxy)phenyl]-5,8-dioxaspiro [3.4]oct-2-yl}-methanol Example 202A 2-[4-(trifluoromethoxy)phenyl]-5,8-dioxaspiro[3.4]octane-2-carbonitrile Example 128B (30 g, 0.12 moles), ethylene glycol (8.4 mL, 0.15 moles), and 4-toluenesulfonic acid hydrate (685 mg, 3.6 mmol) were refluxed in anhydrous toluene (240 mL) with distillation into a Dean-Stark trap for 90 minutes. Trimethyl orthoformate (5.0 mL, 46 mmol) was added and the solution was stirred for 3 hours at room temperature and then warmed to 100° C. where it was kept for about 100 minutes before additional ethylene glycol (1.7 mL, 0.03 moles) was added. The solution was heated at 100° C. overnight, the flask was removed from the hot bath and allowed to cool, and the reaction mixture was washed three times with 0.5M aqueous $K_2HPO_4$, dried ($Na_2SO_4$), filtered, and concentrated. The residue was chromatographed on silica (10 to 25% EtOAc/hexanes) to give Example 202A (28.55 g, 95 mmol, 81% yield) as a pale oil, an inseparable mixture of the ketal and remaining starting material, and was used without further purification.

Example 202B pyridin-2-yl{2-[4-(trifluoromethoxy)phenyl]-5,8-dioxaspiro [3.4]octan-2-yl}methanone A solution of 2.5M n-butyllithium (59 mL, 148 mmol) in hexanes was added to anhydrous diethyl ether (90 mL) and cooled in a dry ice/acetone bath. Then 2-bromopyridine (14.8 mL, 152 mmol) in diethyl ether (80 mL and a rinse) was added dropwise over nearly 30 minutes, and the mixture was stirred for about another 45 minutes. Then a solution of Example 202A (28.5 g, 95 mmol) in diethyl ether (100 mL) was added dropwise over at least 20 minutes, and the cold solution was permitted to warm to room temperature slowly overnight. The reaction mixture was chilled and kept at or below 5° C. as 3M aqueous HCl (100 mL) was added dropwise. The biphasic mixture warmed to room temperature as it was stirred for 3 hours, and then was basified with 3M aqueous NaOH (150 mL). The aqueous phase was separated and extracted twice with EtOAc. The combined organic phases were washed with brine. The aqueous phase was separated and extracted with EtOAc, and the combined organic phases were dried ($Na_2SO_4$), filtered, concentrated, and chromatographed on silica (0 to 5% EtOAc in 2:3 $CH_2Cl_2$/hexanes) to give Example 202B (22 g, 58 mmol, 60.8% yield). MS (ESI$^+$): m/z 380 (M+H). $^1$H NMR (300 MHz, DMSO-d$_6$) δ 8.59-8.55 (m, 1H), 7.98-7.91 (m, 2H), 7.58-7.50 (m, 3H), 7.29-7.23 (m, 2H), 3.82 (dd, J=9.9, 3.8 Hz, 2H), 3.77 (dd, J=9.9, 3.8 Hz, 2H), 3.3-3.23 (m, 2H), 2.99-2.91 (m, 2H).

Example 202C pyridin-2-yl{2-[4-(trifluoromethoxy)phenyl]-5,8-dioxaspiro [3.4]octan-2-yl}methanol Example 202B (21.8 g, 57 mmol) was dissolved into anhydrous $CH_2Cl_2$ (200 mL) and methanol (20 mL), and the flask was placed in a water bath before solid sodium borohydride (2.3 g, 61 mmol) was added in one portion. The mixture was stirred overnight at room temperature, concentrated and partitioned between EtOAc (200 mL) and water (50 mL). The aqueous phase was separated and extracted with more EtOAc. The combined organic phases were washed with brine, dried ($Na_2SO_4$), filtered, and concentrated. The residue was chromatographed on silica (20 to 40% EtOAc/$CH_2Cl_2$) to give Example 202C (17.05 g, 44.7 mmol, 78% yield) as a white powder. MS (ESI$^+$): m/z 382 (M+H). $^1$H NMR (300 MHz, DMSO-d$_6$) δ 8.40 (ddq, J=4.8, 1.7, 0.8 Hz, 1H), 7.44 (ddd, J=7.7, 7.7, 1.8 Hz, 1H), 7.14 (ddd, J=7.5, 4.8, 1.1 Hz, 1H), 7.10-7.04 (m, 2H), 6.85-6.79 (m, 2H), 6.55 (d, J=7.9 Hz, 1H), 5.74 (d, J=4.2 Hz, 1H), 4.96 (d, J=4.2 Hz, 1H), 3.90-3.83 (m, 2H), 3.78-3.71 (m, 2H), 3.22 (dd, J=12.9, 3.4 Hz, 1H), 3.04 (dd, J=12.9, 3.4 Hz, 1H), 2.57-2.5 (m, 1H), 2.41 (dd, J=13.0, 2.3 Hz, 1H).

Example 203 trans-3-[(S)-hydroxy(pyridin-2-yl)methyl]-1-methyl-3-[4-(trifluoromethoxy)phenyl]cyclobutanol Example 134B (6.94 g, 20.5 mmol) was dissolved into anhydrous THF (100 mL) and chilled with a dry ice/acetone bath. 1.6M Methyllithium in diethyl ether (28.3 mL, 45 mmol) was added slowly, and the temperature was permitted to rise to 0° C. overnight. The cold bath was removed and the solution was stirred for another 30 minutes before the flask was placed in a water bath and the reaction was quenched dropwise with 1M aqueous $KH_2PO_4$ (50 mL). The solids were filtered off and washed with EtOAc, and the aqueous phase of the filtrate was separated and extracted with EtOAc. The combined organic phases were washed with brine, dried ($Na_2SO_4$), concentrated, and chromatographed on silica (30 to 100% EtOAc/hexanes, then 1 to 5% MeOH/EtOAc) to give two geometric isomers: Example 203 (0.77 g, 1.96 mmol, 9.5% yield) as a gum (first peak) and Example 134C (3.8 g, 9.68 mmol, 47% yield) as a syrup (second peak). Example 203 (0.77 g, 1.96 mmol) was dissolved in excess hydrogen chloride in methanol, followed by removal of solvent to give the HCl salt of Example 203 (0.71 g, 1.82 mmol, 92.9% yield) as a pale foam. MS (ESL): m/z 354 (M+H). $^1$H NMR (300 MHz, DMSO-d$_6$) δ 8.46 (d, J=4.9 Hz, 1H), 8.21-7.95 (m, 1H), 7.74-7.50 (m, 1H), 7.37-7.15 (m, 1H), 7.11 (d, J=8.1 Hz, 2H), 6.87 (d, J=8.7 Hz, 2H), 5.10 (s, 1H), 2.89 (dd, J=19.8, 12.6 Hz, 2H), 2.31 (dd, J=19.1, 12.3 Hz, 2H), 1.38 (s, 3H). $[\alpha]_D$= −19.2° (c 1.0, MeOH).

Example 204

(2-aminocyclopentyl){1-[3-(trifluoromethyl)phenyl] cyclobutyl}methanol

Example 205

(2-aminocyclopentyl){1-[4-(trifluoromethyl)phenyl] cyclobutyl}methanol

Example 206

(2-aminocyclopentyl){1-[4-(trifluoromethoxy)phenyl] cyclobutyl}methanol

Example 207

(2-aminocyclohexyl){1-[4-(trifluoromethyl)phenyl] cyclobutyl}methanol

Example 208

(2-aminocyclopentyl){1-[3-(trifluoromethoxy)phenyl]cyclobutyl}methanol

Example 209

(2-aminocyclohexyl){1-[4-(trifluoromethoxy)phenyl]cyclobutyl}methanol

Example 210

(2-aminocyclohexyl){1-[3-(trifluoromethoxy)phenyl]cyclobutyl}methanol

Example 211

(2-aminocyclohexyl)[1-(3,4-dichlorophenyl)cyclobutyl]methanol

Example 212

(2-aminocyclohexyl){1-[3-(trifluoromethyl)phenyl]cyclobutyl}methanol

Example 213

(2-aminocyclobutyl){1-[3-(trifluoromethyl)phenyl]cyclobutyl}methanol

Example 214

(2-aminocyclopentyl){1-[2-(trifluoromethoxy)phenyl]cyclobutyl}methanol

Example 215

(2-aminocyclopentyl)[1-(3,4-dichlorophenyl)cyclobutyl]methanol

Example 216

(R)-[(1S,2R)-2-aminocyclopentyl][1-(3,4-dichlorophenyl)cyclobutyl]-methanol

Example 217

(S)-[(1R,2S)-2-aminocyclopentyl][1-(3,4-dichlorophenyl)cyclobutyl]-methanol

Example 218

(R)-[(1R,2S)-2-aminocyclopentyl][1-(3,4-dichlorophenyl)cyclobutyl]-methanol

Example 219

(S)-[(1S,2S)-2-aminocyclopentyl][1-(3,4-dichlorophenyl)cyclobutyl]-methanol

Example 220

(R)-[(1R,2R)-2-aminocyclopentyl][1-(3,4-dichlorophenyl)cyclobutyl]-methanol

Example 221

(R)-[(1S,2R)-2-aminocyclopentyl]{1-[4-(trifluoromethoxy)phenyl]-cyclobutyl}methanol

Example 222

(S)-[(1S,2S)-2-aminocyclopentyl]{1-[4-(trifluoromethoxy)phenyl]-cyclobutyl}methanol

Example 223

(R)-[(1R,2R)-2-aminocyclopentyl]{1-[4-(trifluoromethoxy)phenyl]-cyclobutyl}methanol

Example 224

(R)-[(1R,2R)-2-aminocyclopentyl][1-(4-chlorophenyl)cyclobutyl]methanol

Example 225

(S)-[(1S,2S)-2-aminocyclopentyl][1-(4-chlorophenyl)cyclobutyl]methanol

Example 226

(R)-[(1R,2S)-2-aminocyclopentyl][1-(2-fluorophenyl)cyclobutyl]methanol

Example 227

(R)-[(1R,2R)-2-aminocyclopentyl]{1-[3-(trifluoromethyl)phenyl]-cyclobutyl}methanol

Example 228

(R)-[1-(3,4-dichlorophenyl)cyclobutyl][(1R,2R)-2-(methylamino)-cyclopentyl]methanol

Example 229

(R)-[(1R,2S)-2-aminocyclopentyl]{1-[4-(trifluoromethoxy)phenyl]-cyclobutyl}methanol

Example 230

(Z)-[1-(3,4-dichlorophenyl)cyclobutyl](pyridin-2-yl)methanone oxime

Example 231

(S)-[1-(3,4-dichlorophenyl)cyclopropyl](pyridin-2-yl)methanol

Example 232 cis-3-[(S)-hydroxy(pyridin-2-yl)methyl]-1-methyl-3-[4-(trifluoromethyl)-phenyl]cyclobutanol Example 164 (2.21 g, 6.88 mmol) was dissolved in anhydrous THF (35 mL) and chilled with a dry ice/acetone bath. 1.6M Methyl lithium (10 mL, 16 mmol) in diethyl ether was added slowly, and the reaction was permitted to warm to ambient temperature overnight. The reaction was quenched with 1M aqueous $KH_2PO_4$ (40 mL), added water (200 mL), and extracted with EtOAc (200 mL). The organic phase was washed with brine, dried over $Na_2SO_4$, filtered, and concentrated. The residue was chromatographed on silica (0-10%

MeOH in EtOAc) to give the two geometric isomers: Example 233 (0.229 g, 0.679 mmol, 9.87% yield) as a yellow oil (first peak) and Example 232 (1.141 g, 3.38 mmol, 49.2% yield) as a yellow solid (second peak). MS (ESI+): m/z 338 (M+H). $^1$H NMR (300 MHz, DMSO-$d_6$) δ 8.37 (ddd, J=4.8, 1.8, 0.9 Hz, 1H), 7.51-7.40 (m, 3H), 7.13 (ddd, J=7.5, 4.8, 1.2 Hz, 1H), 6.99 (d, J=8.1 Hz, 2H), 6.59 (d, J=7.9 Hz, 1H), 5.64 (d, J=4.5 Hz, 1H), 4.98 (d, J=4.5 Hz, 1H), 4.95 (s, 1H), 2.97 (d, J=12.2 Hz, 1H), 2.77 (d, J=12.0 Hz, 1H), 2.39 (dd, J=12.1, 3.6 Hz, 1H), 2.24 (dd, J=12.1, 3.5 Hz, 1H), 0.87 (s, 3H). $[α]_D$=−45.0° (c 1.0, MeOH).

Example 233 trans-3-[(S)-hydroxy(pyridin-2-yl)methyl]-1-methyl-3-[4-(trifluoromethyl)-phenyl]cyclobutanol Example 164 (2.21 g, 6.88 mmol) was dissolved in anhydrous THF (35 mL) and chilled with a dry ice/acetone bath. 1.6M Methyl lithium (10 mL, 16 mmol) in diethyl ether was added slowly, and the reaction was permitted to warm to ambient temperature overnight. The reaction was quenched with 1M aqueous $KH_2PO_4$ (40 mL), added water (200 mL), and extracted with EtOAc (200 mL). The organic phase was washed with brine, dried over $Na_2SO_4$, filtered, and concentrated. The residue was chromatographed on silica (0-10% MeOH in EtOAc) to give the two geometric isomers: Example 233 (0.229 g, 0.679 mmol, 9.87% yield) as a yellow oil (first peak) and Example 232 (1.141 g, 3.38 mmol, 49.2% yield) as a yellow solid (second peak). MS (ESI+): m/z 338 (M+H). $^1$H NMR (300 MHz, DMSO-$d_6$) δ 8.41 (ddd, J=4.8, 1.8, 0.9 Hz, 1H), 7.51-7.39 (m, 3H), 7.15 (ddd, J=7.4, 4.9, 1.0 Hz, 1H), 6.93 (d, J=8.0 Hz, 2H), 6.57 (d, J=7.9 Hz, 1H), 5.64 (d, J=4.6 Hz, 1H), 4.88 (d, J=4.6 Hz, 1H), 4.69 (s, 1H), 3.02 (d, J=12.2 Hz, 1H), 2.88 (dd, J=12.5, 1.4 Hz, 1H), 2.34 (d, J=12.4 Hz, 1H), 2.22 (d, J=12.4 Hz, 1H), 1.35 (s, 3H). $[α]_D$=−61.1° (c 1.0, MeOH).

Example 234 pyridin-2-yl{1-[6-(trifluoromethyl)pyridin-2-yl]cyclobutyl}methanol

Example 235 pyridin-2-yl{2-[3-(trifluoromethoxy)phenyl]-5,8-dioxaspiro[3.4]oct-2-yl}-methanol

Example 235A 3-hydroxy-1-[3-(trifluoromethoxy)phenyl]cyclobutanecarbonitrile 2-[3-(Trifluoromethoxy)phenyl]acetonitrile (10.280 g, 51.1 mmol) was dissolved in anhydrous THF (80 mL) and chilled to −75° C. 1.6M Methyl lithium (31.9 mL, 51.1 mmol) in diethyl ether was added dropwise and the yellow solution was stirred at −75° C. for 1 hour. Epibromohydrin (4.23 mL, 51.1 mmol) in THF (15 mL) was added slowly and the reaction was stirred at −75° C. for 1 hour. 3.0M Methyl magnesium bromide (17.04 mL, 51.1 mmol) in diethyl ether was added dropwise, and the reaction was permitted to warm to ambient temperature overnight. The reaction was quenched with water (50 mL), followed by the addition of 3N hydrochloric acid (100 mL), and extraction with EtOAc (2×100 mL). The organic phase was washed with brine, dried over $Na_2SO_4$, filtered, and concentrated. The residue was chromatographed on silica (0-100% EtOAc in heptane) to give Example 235A (11.970 g, 46.5 mmol, 91% yield) as a yellow oil. MS (DCI+): m/z 275 (M+$NH_4$).

Example 235B 3-oxo-1-[3-(trifluoromethoxy)phenyl]cyclobutanecarbonitrile

Example 235A (11.970 g, 46.5 mmol) was dissolved in dichloromethane (200 mL), and then Dess-Martin Periodinane (29.6 g, 69.8 mmol) was added. The yellow solution was stirred overnight at ambient temperature. The reaction was filtered through a pad of silica, rinsed with dichloromethane, and the filtrate was concentrated. The resulting residue was chromatographed on silica (100% dichloromethane) to give Example 235B (11.318 g, 44.4 mmol, 95% yield) as a yellow oil. $^1$H NMR (300 MHz, DMSO-$d_6$) δ 7.68-7.59 (m, 3H), 7.49-7.40 (m, 1H), 4.17-4.05 (m, 2H), 3.99-3.87 (m, 2H).

Example 235C

2-[3-(trifluoromethoxy)phenyl]-5,8-dioxaspiro[3.4]octane-2-carbonitrile

To a solution of Example 235B (11.318 g, 44.4 mmol) and 1,2-bis-(trimethylsilyloxy)ethane (17 mL, 69.2 mmol) in dichloromethane (100 mL) was added trimethylsilyl trifluoromethanesulfonate (1.0 mL, 5.53 mmol). The yellow solution was stirred overnight at ambient temperature. The reaction was quenched with triethylamine (1.2 mL, 8.66 mmol), washed twice with saturated $NaHCO_3$ solution, dried over $Na_2SO_4$, filtered, and concentrated. The residue was chromatographed on silica (0-100% EtOAc in heptane) to give Example 235C (12.851 g, 42.9 mmol, 97% yield) as a yellow liquid. $^1$H NMR (300 MHz, DMSO-$d_6$) δ 7.65-7.52 (m, 2H), 7.48 (s, 1H), 7.44-7.36 (m, 1H), 4.00-3.92 (m, 2H), 3.90-3.81 (m, 2H), 3.23-3.13 (m, 2H), 3.03-2.92 (m, 2H).

Example 235D pyridin-2-yl{2-[3-(trifluoromethoxy)phenyl]-5,8-dioxaspiro[3.4]octan-2-yl}methanone A solution of 2.5M n-butyl lithium (25.8 mL, 64.4 mmol) in hexanes and anhydrous diethyl ether (90 mL) was chilled to −75° C., followed by the dropwise addition of 2-bromopyridine (6.35 mL, 66.6 mmol) in diethyl ether (40 mL). The resulting orange-red solution was stirred for 1.5 hours, followed by dropwise addition of Example 235C (12.851 g, 42.9 mmol) in diethyl ether (40 mL). The reaction mixture was slowly warmed to 0° C. while stirring for 3.5 hours. The reaction was quenched with 1N hydrochloric acid (150 mL) and the biphasic mixture was stirred for 45 minutes at ambient temperature, followed by the addition of 3N sodium hydroxide (150 mL), and extraction with EtOAc (2×300 mL). The organic phase was washed with brine, dried over $Na_2SO_4$, filtered, and concentrated. The residue was chromatographed on silica (0-50% EtOAc in heptane) to give Example 235D (12.470 g, 32.9 mmol, 77% yield) as a yellow oil. MS (ESI+): m/z 380 (M+H). $^1$H NMR (500 MHz, $CD_3CN$) δ 8.50 (dd, J=4.5, 0.4 Hz, 1H), 7.95 (d, J=7.9 Hz, 1H), 7.84 (td, J=7.8, 1.7 Hz, 1H), 7.52 (s, 1H), 7.44-7.38 (m, 2H), 7.33 (t, J=8.0 Hz, 1H), 7.10-7.05 (m, 1H), 3.87-3.78 (m, 4H), 3.37-3.30 (m, 2H), 3.01-2.94 (m, 2H).

Example 235E pyridin-2-yl{2-[3-(trifluoromethoxy)phenyl]-5,8-dioxaspiro[3.4]oct-2-yl}-methanol Example 235D (12.470 g, 32.9 mmol) was dissolved in dichloromethane (100 mL) and MeOH (10 mL), then sodium borohydride (1.368 g, 36.2 mmol) was added to the yellow solution. The reaction was stirred overnight at ambient temperature, followed by the addition of 3N sodium hydroxide (200 mL), and extraction with EtOAc (2×300 mL). The organic phase was washed with brine, dried over $Na_2SO_4$, filtered, and concentrated. The resulting residue was chromatographed on silica (0-100% EtOAc in hexanes) to give Example 235E (12.364 g, 32.4 mmol, 99% yield) as a yellow oil. MS (ESI+): m/z 382 (M+H). $^1$H NMR (501 MHz, $CD_3CN$) δ 8.32 (d, J=4.8 Hz, 1H), 7.50 (td, J=7.7, 1.7 Hz, 1H), 7.22 (t, J=8.0 Hz, 1H), 7.14 (dd, J=7.5, 4.9 Hz, 1H), 7.06-7.02 (m, 1H), 6.91 (d, J=7.8 Hz, 1H), 6.79 (d, J=7.9 Hz, 1H), 6.64 (s, 1H), 5.00 (d, J=6.1 Hz, 1H), 4.18 (d, J=6.1 Hz, 1H), 3.93-3.86 (m, 2H), 3.81-3.75 (m, 2H), 3.18 (dd, J=12.9, 3.2 Hz, 1H), 3.03 (dd, J=13.0, 3.2 Hz, 1H), 2.58 (dd, J=13.0, 3.1 Hz, 1H), 2.53 (dd, J=12.9, 3.1 Hz, 1H).

Example 236 cis-3-[(S)-hydroxy(pyridin-2-yl)methyl]-1-methyl-3-[3-(trifluoromethyl)-phenyl]cyclobutanol Example 241 (2.011 g, 6.26 mmol) was dissolved in anhydrous THF (35 mL) and chilled with a dry ice/acetone bath. 1.6M Methyl lithium (9 mL, 14.4 mmol) in diethyl ether was added slowly, and the reaction was permitted to warm to ambient temperature overnight. The reaction was quenched with 1M aqueous $KH_2PO_4$ (50 mL), added water (200 mL), extracted with EtOAc (200 mL), washed with brine, dried over $Na_2SO_4$, filtered, and concentrated. The residue was chromatographed on silica (0-10% MeOH in EtOAc) to give two geometric isomers: Example 244 (0.312 g, 0.925 mmol, 14.78% yield) as a yellow oil (first peak) and Example 236 (1.176 g, 3.49 mmol, 55.7% yield) as a yellow solid (second peak). MS (ESI+): m/z 338 (M+H). $^1$H NMR (500 MHz, $CD_3CN$) δ 8.29 (d, J=4.8 Hz, 1H), 7.50 (td, J=7.7, 1.7 Hz, 1H), 7.42 (d, J=7.7 Hz, 1H), 7.33 (t, J=7.8 Hz, 1H), 7.19-7.10 (m, 2H), 6.99 (s, 1H), 6.73 (d, J=7.9 Hz, 1H), 4.94 (d, J=3.9 Hz, 1H), 4.43 (d, J=5.3 Hz, 1H), 3.41 (s, 1H), 2.93 (d, J=12.0 Hz, 1H), 2.78 (d, J=12.2 Hz, 1H), 2.50-2.40 (m, 2H), 0.99 (s, 3H). $[α]_D$=−48.6° (c 1.0, MeOH).

Example 237

3-[hydroxy(pyridin-2-yl)methyl]-3-[3-(trifluoromethoxy)phenyl]-cyclobutanone

A solution of Example 235E (12.364 g, 32.4 mmol) in acetone (200 mL), water (20 mL) and 12N hydrochloric acid (25 mL) was stirred overnight at ambient temperature. Mixture was concentrated to about half of the original volume, followed by the addition of 3N sodium hydroxide (150 mL), and extraction with EtOAc (2×300 mL). The organic phase was washed with brine, dried over $Na_2SO_4$, filtered, and concentrated. The residue was chromatographed on silica (0-100% EtOAc in heptane) to give Example 237 (10.815 g, 32.1 mmol, 99% yield) as a colorless oil which solidified upon cooling. MS (ESI+): m/z 338 (M+H). $^1$H NMR (400 MHz, $CD_3CN$) δ 8.43 (d, J=4.7 Hz, 1H), 7.49 (td, J=7.7, 1.7 Hz, 1H), 7.34 (t, J=8.0 Hz, 1H), 7.19 (dd, J=7.4, 4.9, 0.9 Hz, 1H), 7.17-7.11 (m, 1H), 7.05 (dd, J=7.8, 0.6 Hz, 1H), 6.79 (s, 1H), 6.60 (d, J=7.9 Hz, 1H), 4.97 (d, J=6.2 Hz, 1H), 4.49 (d, J=6.2 Hz, 1H), 3.79 (ddd, J=17.1, 6.0, 2.4 Hz, 1H), 3.64 (ddd, J=17.4, 6.0, 2.4 Hz, 1H), 3.29 (ddd, J=17.1, 3.5, 2.5 Hz, 1H), 3.20 (ddd, J=17.4, 3.4, 2.6 Hz, 1H).

Example 238

(S)-pyridin-2-yl{1-[6-(trifluoromethyl)pyridin-2-yl]cyclobutyl}methanol

Example 239 pyridin-2-yl[1-(tetrahydro-2H-pyran-4-yl)cyclobutyl]methanol

Example 240

(S)-pyridin-2-yl{1-[2-(trifluoromethyl)pyridin-4-yl]cyclobutyl}methanol

Example 241

3-[(S)-hydroxy(pyridin-2-yl)methyl]-3-[3-(trifluoromethyl)phenyl]-cyclobutanone

Mixture of the enantiomers of Example 245 (9.93 g, 30.9 mmol) were separated on a Chiralpak AD-H column (3 cm ID×25 cm, 5 micron), and eluted with 10% EtOH in hexanes at 45 mL/min. The mixture was injected at 190 mg in 1.9 mL 1:1 EtOH-hexanes per run. The title compound was collected as the first eluting peak (4.52 g, 14.07 mmol) as a white solid. MS (ESI+): m/z 322 (M+H). $^1$H NMR (500 MHz, $CD_3CN$) δ 8.45-8.40 (m, 1H), 7.53 (dd, J=7.7, 0.5 Hz, 1H), 7.49 (td, J=7.7, 1.7 Hz, 1H), 7.42 (t, J=7.8 Hz, 1H), 7.27 (d, J=7.7 Hz, 1H), 7.20 (ddd, J=7.5, 4.8, 1.0 Hz, 1H), 7.14 (s, 1H), 6.61 (d, J=7.8 Hz, 1H), 4.98 (s, 1H), 4.47 (br s, 1H), 3.81 (ddd, J=17.1, 6.0, 2.5 Hz, 1H), 3.67 (ddd, J=17.4, 6.1, 2.4 Hz, 1H), 3.32 (ddd, J=17.1, 3.6, 2.5 Hz, 1H), 3.25 (ddd, J=17.4, 3.5, 2.6 Hz, 1H). $[α]_D$=−34.3° (c 1.0, MeOH).

Example 242 pyridin-2-yl{2-[3-(trifluoromethyl)phenyl]-5,8-dioxaspiro[3.4]oct-2-yl}-methanol

Example 242A 3-hydroxy-1-[3-(trifluoromethyl)phenyl]cyclobutanecarbonitrile

2-[3-(Trifluoromethyl)phenyl]acetonitrile (10.249 g, 55.4 mmol) was dissolved in anhydrous THF (80 mL) and chilled to −75° C. 1.6M Methyl lithium (34.6 mL, 55.4 mmol) in diethyl ether was added dropwise and the yellow solution was stirred at −75° C. for 1 hour. Epibromohydrin (4.58 mL, 55.4 mmol) in THF (15 mL) was added slowly and the reaction was stirred at −75° C. for 1 hour. 3.0M Methyl magnesium bromide (18.45 mL, 55.4 mmol) in diethyl ether was added dropwise, and the reaction was permitted to warm to ambient temperature overnight. The reaction was quenched with water (50 mL), added 3N hydrochloric acid (100 mL), and extracted twice with EtOAc (200 mL). The organic phase was washed with brine, dried over $Na_2SO_4$, filtered, and concentrated. The residue was chromatographed on silica (0-100% EtOAc in heptane) to give Example 242A (12.207 g, 50.6 mmol, 91% yield) as a yellow oil. MS (DCI+): m/z 259 (M+$NH_4$).

Example 242B 3-oxo-1-[3-(trifluoromethyl)phenyl]cyclobutanecarbonitrile

Example 242A (12.207 g, 50.6 mmol) was dissolved in dichloromethane (200 mL), and Dess-Martin Periodinane (32.2 g, 76 mmol) was added. The yellow solution was stirred overnight at ambient temperature, filtered through a pad of silica, rinsed with dichloromethane, and the filtrate was concentrated. The residue was chromatographed on silica (100% dichloromethane) to give Example 242B (11.364 g, 47.5 mmol, 94% yield) as a yellow oil.

MS (DCI+): m/z 257 (M+NH$_4$). $^1$H NMR (300 MHz, DMSO-d$_6$) δ 7.98-7.89 (m, 2H), 7.85-7.70 (m, 2H), 4.18-4.06 (m, 2H), 4.05-3.93 (m, 2H).

Example 242C

2-[3-(trifluoromethyl)phenyl]-5,8-dioxaspiro[3.4]octane-2-carbonitrile

Example 242B (11.364 g, 47.5 mmol) and 1,2-bis(trimethylsilyloxy)ethane (18 mL, 73.2 mmol) were dissolved in dichloromethane (100 mL), followed by the addition of trimethylsilyl trifluoromethanesulfonate (1.0 mL, 5.53 mmol). The yellow solution was stirred overnight at ambient temperature, quenched with triethylamine (1.2 mL, 8.66 mmol), and washed twice with saturated NaHCO$_3$ solution. The organic phase was dried over Na$_2$SO$_4$, filtered, and concentrated. The mixture was chromatographed on silica (0-100% EtOAc in heptane) to give Example 242C (13.323 g, 47.0 mmol, 99% yield) as a yellow liquid. $^1$H NMR (300 MHz, DMSO-d$_6$) δ 7.87-7.79 (m, 2H), 7.79-7.66 (m, 2H), 4.04-3.92 (m, 2H), 3.91-3.82 (m, 2H), 3.25-3.15 (m, 2H), 3.06-2.96 (m, 2H).

Example 242D pyridin-2-yl{2-[3-(trifluoromethyl)phenyl]-5,8-dioxaspiro [3.4]octan-2-yl}-methanone A solution of 2.5M n-butyl lithium (28.2 mL, 70.6 mmol) in hexanes plus anhydrous diethyl ether (100 mL) was chilled to −75° C., followed by th dropwise addition of 2-bromopyridine (6.95 mL, 72.9 mmol) in diethyl ether (40 mL). The orange-red solution was stirred for 1.5 hours, followed by the dropwise addition of Example 242C (13.323 g, 47.0 mmol) in diethyl ether (40 mL). The mixture was slowly warmed to 0° C. while stirring for 3 hours. The reaction was quenched with 1N hydrochloric acid (150 mL) and the biphasic mixture was stirred for 50 minutes at ambient temperature, followed by the addition of 3N sodium hydroxide (150 mL) and extraction with EtOAc (2×300 mL). The organic phase was washed with brine, dried over Na$_2$SO$_4$, filtered, and concentrated. The residue was chromatographed on silica (0-50% EtOAc in heptane) to give Example 242D (13.020 g, 35.8 mmol, 76% yield) as a yellow oil. MS (ESI+): m/z 364 (M+H). $^1$H NMR (500 MHz, CD$_3$CN) δ 8.51 (d, J=4.6 Hz, 1H), 7.96 (d, J=7.8 Hz, 1H), 7.88-7.81 (m, 2H), 7.73 (d, J=7.3 Hz, 1H), 7.50-7.39 (m, 3H), 3.87-3.79 (m, 4H), 3.36 (d, J=13.7 Hz, 2H), 3.02 (d, J=13.6 Hz, 2H).

Example 242E pyridin-2-yl{2-[3-(trifluoromethyl)phenyl]-5,8-dioxaspiro [3.4]oct-2-yl}-methanol Example 242D (13.020 g, 35.8 mmol) was dissolved in dichloromethane (110 mL) and MeOH (11 mL), then sodium borohydride (1.491 g, 39.4 mmol) was added to the yellow solution. The reaction was stirred overnight at ambient temperature, followed by the addition of 3N sodium hydroxide (200 mL), and extraction with EtOAc (2×300 mL). The organic phase was washed with brine, dried over Na$_2$SO$_4$, filtered, and concentrated. The residue was chromatographed on silica (0-100% EtOAc in hexanes) to give Example 242E (12.386 g, 33.9 mmol, 95% yield) as a yellow oil. MS (ESI+): m/z 366 (M+H). $^1$H NMR (400 MHz, CD$_3$CN) δ 8.34-8.29 (m, 1H), 7.50 (td, J=7.7, 1.7 Hz, 1H), 7.43 (d, J=7.7 Hz, 1H), 7.32 (t, J=7.8 Hz, 1H), 7.18-7.10 (m, 2H), 6.97 (s, 1H), 6.79 (d, J=7.9 Hz, 1H), 5.02 (d, J=6.0 Hz, 1H), 4.15 (d, J=6.0 Hz, 1H), 3.94-3.87 (m, 2H), 3.82-3.75 (m, 2H), 3.20 (dd, J=12.9, 3.2 Hz, 1H), 3.05 (dd, J=13.0, 3.3 Hz, 1H), 2.64 (ddd, J=13.1, 3.2, 0.7 Hz, 1H), 2.55 (dd, J=12.9, 3.1 Hz, 1H).

Example 243

3-[(R)-hydroxy(pyridin-2-yl)methyl]-3-[3-(trifluoromethyl) phenyl]-cyclobutanone Mixture of enantiomers of Example 245 (9.93 g, 30.9 mmol) was separated on a Chiralpak AD-H column (3 cm ID×25 cm, 5 micron) and eluted with 10% EtOH in hexanes at 45 mL/min. For each run, the mixture was injected as a solution of 190 mg of material in 1.9 mL of 1:1 EtOH-hexanes. The title compound was collected as the second eluting peak (4.48 g, 13.94 mmol) as an off-white solid. MS (ESI+): m/z 322 (M+H). $^1$H NMR (500 MHz, CD$_3$CN) δ 8.42 (d, J=4.6 Hz, 1H), 7.53 (d, J=7.8 Hz, 1H), 7.49 (td, J=7.7, 1.6 Hz, 1H), 7.42 (t, J=7.8 Hz, 1H), 7.27 (d, J=7.8 Hz, 1H), 7.20 (dd, J=7.3, 5.0 Hz, 1H), 7.14 (s, 1H), 6.61 (d, J=7.8 Hz, 1H), 4.98 (s, 1H), 4.46 (br s, 1H), 3.81 (ddd, J=17.1, 6.0, 2.4 Hz, 1H), 3.67 (ddd, J=17.4, 6.0, 2.3 Hz, 1H), 3.36-3.29 (m, 1H), 3.29-3.21 (m, 1H). [α]$_D$=+34.8° (c 1.0, MeOH).

Example 244 trans-3-[(S)-hydroxy(pyridin-2-yl)methyl]-1-methyl-3-[3-(trifluoromethyl)-phenyl]cyclobutanol Example 241 (2.011 g, 6.26 mmol) was dissolved in anhydrous THF (35 mL) and chilled with a dry ice/acetone bath. 1.6M Methyl lithium (9 mL, 14.4 mmol) in diethyl ether was added slowly, and the reaction was permitted to warm to ambient temperature overnight. The reaction was quenched with 1M aqueous KH$_2$PO$_4$ (50 mL), followed by the addition of water (200 mL), and extraction with EtOAc (200 mL). The organic phase was washed with brine, dried over Na$_2$SO$_4$, filtered, and concentrated. The residue was chromatographed on silica (0-10% MeOH in EtOAc) to give two geometric isomers: Example 244 (0.312 g, 0.925 mmol, 14.78% yield) as a yellow oil (first peak) and Example 236 (1.176 g, 3.49 mmol, 55.7% yield) as a yellow solid (second peak). MS (ESI+): m/z 338 (M+H). $^1$H NMR (500 MHz, CD$_3$CN) δ 8.31 (dd, J=4.8, 0.4 Hz, 1H), 7.49 (td, J=7.7, 1.7 Hz, 1H), 7.41 (d, J=7.8 Hz, 1H), 7.32 (t, J=7.8 Hz, 1H), 7.17-7.11 (m, 2H), 6.98 (s, 1H), 6.74 (d, J=7.9 Hz, 1H), 4.90 (s, 1H), 4.16 (br s, 1H), 3.06-3.00 (m, 1H), 2.92-2.86 (m, 1H), 2.83 (t, J=6.9 Hz, 1H), 2.40 (d, J=12.9 Hz, 1H), 2.34 (d, J=12.7 Hz, 1H), 1.41 (s, 3H). [α]$_D$=−64.2° (c 1.0, MeOH).

Example 245

3-[hydroxy(pyridin-2-yl)methyl]-3-[3-(trifluoromethyl)phenyl]-cyclobutanone

A solution of Example 242E (12.386 g, 33.9 mmol) in acetone (200 mL), water (20 mL) and 12N hydrochloric acid (25 mL) was stirred overnight at ambient temperature. Concentrated to the half of the original volume, added 3N sodium hydroxide (150 mL), extracted twice with EtOAc (300 mL), washed with brine, and dried over Na$_2$SO$_4$. Chromatographed on silica (0-100% EtOAc in 1:1 heptane:dichloromethane) to give Example 245 (10.037 g, 31.2 mmol, 92% yield) as a white solid. MS (ESI+): m/z 322 (M+H). $^1$H NMR (500 MHz, CD$_3$CN) δ 8.42 (d, J=4.8 Hz, 1H), 7.53 (d, J=7.7 Hz, 1H), 7.49 (td, J=7.7, 1.7 Hz, 1H), 7.42 (t, J=7.8 Hz, 1H), 7.27 (d, J=7.8 Hz, 1H), 7.22-7.17 (m, 1H), 7.14 (s, 1H), 6.61 (d, J=7.9 Hz, 1H), 4.98 (d, J=6.1 Hz, 1H), 4.46 (d, J=6.1 Hz, 1H), 3.81 (ddd, J=17.1, 6.0, 2.5 Hz, 1H), 3.67 (ddd, J=17.4, 6.1, 2.4 Hz, 1H), 3.36-3.29 (m, 1H), 3.29-3.22 (m, 1H).

Example 246

3-{1-[hydroxy(pyridin-2-yl)methyl]cyclobutyl}tetrahydrofuran-3-ol

Example 247 cis-3-(3,4-dichlorophenyl)-3-[(R)-hydroxy(pyridin-2-yl)methyl]-cyclobutanol

Example 247A 1-(3,4-dichlorophenyl)-3-hydroxycyclobutanecarbonitrile

A solution of 2-(3,4-dichlorophenyl)acetonitrile (26.42 g, 142.0 mmol) in anhydrous THF (220 mL) was cooled in a dry ice/acetone bath, followed by the dropwise addition of 1.6 M methyllithium in diethyl ether (about 90 mL, 144 mmol). The mixture was stirred cold for an hour. A solution of epibromohydrin (12.3 mL, 144 mmol) in anhydrous THF (50 mL) was added dropwise and the reaction mixture was stirred cold for 70 minutes, followed by the addition of 3 M methyl magnesium chloride in diethyl ether (47 mL, 142 mmol). The reaction mixture was stirred and allowed to warm to room temperature overnight. The solution was cooled with a water/ice bath and quenched slowly with water (150 mL) and then dropwise with 3 M aqueous HCl (80 mL). The aqueous phase was separated and extracted twice with EtOAc. The combined organic phases were washed with brine, dried (Na$_2$SO$_4$), filtered, and concentrated. The residue was chromatographed on silica (1 to 3% CH$_3$CN/CH$_2$Cl$_2$) to provide the title compound (33.6 g) as a crude syrup. MS (ESI) m/z=240 (M−H)$^-$.

Example 247B 3-(tert-butyldimethylsilyloxy)-1-(3,4-dichlorophenyl)cyclobutane-carbonitrile The crude Example 248A (33.6 g, 138 mmol) and tert-butyldimethylsilyl chloride (22.9 g, 152 mmol) were dissolved in anhydrous CH$_3$CN (140 mL), treated with N,N-diisopropylethylamine (36 mL, 207 mmol), and stirred overnight at room temperature. The reaction mixture was concentrated, and the residue dissolved in CH$_2$Cl$_2$ (200 mL), and washed twice with water. Each aqueous phase was back-extracted with CH$_2$Cl$_2$. The combined organic phases were washed with brine, dried (Na$_2$SO$_4$), filtered, and concentrated. The residue was chromatographed on silica (20 to 50% CH$_2$Cl$_2$/hexanes) to provide the title compound (34.3 g) as a syrup which solidified to a white solid overnight.

Example 247C trans-3-(tert-butyldimethylsilyloxy)-1-(3,4-dichlorophenyl)cyclobutyl)-(pyridin-2-yl)methanone A solution of 2.5 M n-butyllithium in hexanes (58 mL, 145 mmol) was added to anhydrous diethyl ether (90 mL) and cooled in a dry ice/acetone bath. Then 2-bromopyridine (14.6 mL, 150 mmol) in diethyl ether (80 mL) was added dropwise over 50 minutes, followed by the addition of a solution of Example 247B (34.3 g, 96 mmol) in diethyl ether (100 mL) over about 25 minutes, and the cold solution was permitted to warm to room temperature very slowly overnight. The reaction mixture was chilled with a water ice bath and the internal temperature was kept at no more than 10° C. as 3 M aqueous HCl (100 mL) was added dropwise. The biphasic mixture was stirred cold for another 40 minutes and then slowly basified with 3 M aqueous NaOH (150 mL). The aqueous phase was separated and extracted twice with EtOAc, and the combined organic phases were washed with brine, dried (Na$_2$SO$_4$), filtered, concentrated, and filtered through basic alumina with a 1:1 CH$_2$Cl$_2$/hexanes rinse. The filtrate was concentrated and chromatographed on silica (20 to 50% CH$_2$Cl$_2$/hexanes) to provide the title compound (11.4 g) and Example 247D (20.2 g). MS (ESI) m/z=436 (M+H)$^+$. $^1$H NMR (500 MHz, CD$_3$CN) δ 8.47 (ddd, J=4.7, 1.7, 0.9 Hz, 1H), 7.94 (ddd, J=7.8, 1.2, 0.9 Hz, 1H), 7.83 (ddd, J=7.8, 7.6, 1.7 Hz, 1H), 7.55 (d, J=2.2 Hz, 1H), 7.40 (ddd, J=7.6, 4.7, 1.2 Hz, 1H), 7.36 (d, J=8.4 Hz, 1H), 7.25 (dd, J=8.4, 2.2 Hz, 1H), 4.24 (tt, J=7.1, 7.1 Hz, 1H), 3.44-3.38 (m, 2H), 2.50-2.45 (m, 2H), 0.85 (s, 9H), 0.02 (s, 6H).

Example 247D cis-3-(tert-butyldimethylsilyloxy)-1-(3,4-dichlorophenyl)cyclobutyl)-(pyridin-2-yl)methanone The second eluting peak from the chromatographic separation of Example 247C was collected and concentrated to provide the title compound (20.2 g). MS (ESI) m/z=436 (M+H)$^+$. $^1$H NMR (400 MHz, CD$_3$CN) δ 8.51 (ddd, J=4.7, 1.7, 0.9 Hz, 1H), 7.92 (ddd, J=7.9, 1.2, 0.9 Hz, 1H), 7.83 (ddd, J=7.8, 7.7, 1.7 Hz, 1H), 7.69 (dd, J=1.6, 0.7 Hz, 1H), 7.44-7.38 (m, 3H), 4.33 (tt, J=7.3, 7.2 Hz, 1H), 3.08-3.01 (m, 2H), 2.74-2.66 (m, 2H), 0.85 (s, 9H), 0.02 (s, 6H).

Example 247E cis-(R)-3-(tert-butyldimethylsilyloxy)-1-(3,4-dichlorophenyl)cyclobutyl)-(pyridin-2-yl)methanol Example 247D (20.0 g, 45.8 mmol) was dissolved into anhydrous CH$_2$Cl$_2$ (160 mL) and methanol (16 mL), and the flask was placed in a water bath before solid sodium borohydride (1.82 g, 48.1 mmol) was added in one portion. The mixture was stirred overnight at room temperature. The mixture was concentrated and partitioned between EtOAc (240 mL) and water (60 mL), and the aqueous phase was separated and extracted with more EtOAc. The combined organic phases were washed with brine, dried (Na$_2$SO$_4$), filtered, and concentrated to 19.82 g of a white powder. The enantiomers were separated by Chiralpak AD-H (5 micron, 3.0 cm ID×25 cm, with supercritical CO$_2$ and 15% isopropanol, flow rate of 100 gm/mL and back pressure of 100 bar) to give Example 247E (>99% ee). [α]$_D$=+40.1 (c=1, MeOH); MS (ESI) m/z=438 (M+H)$^+$. $^1$H NMR (300 MHz, DMSO-d$_6$) δ 8.37 (ddd, J=4.8, 1.8, 0.8 Hz, 1H), 7.56 (ddd, J=7.8, 7.5, 1.8 Hz, 1H), 7.36 (d, J=8.4 Hz, 1H), 7.16 (ddd, J=7.5, 4.8, 1.1 Hz, 1H), 7.07 (d, J=2.1 Hz, 1H), 6.87 (dd, J=8.4, 2.1 Hz, 1H), 6.84-6.79 (m, 1H), 5.69 (d, J=3.6 Hz, 1H), 4.75 (d, J=3.2 Hz, 1H), 3.93 (tt, J=7.5 Hz, 1H), 2.69-2.52 (m, 4H), 0.84 (s, 9H), −0.01 (s, 6H).

Example 247F cis-3-(3,4-dichlorophenyl)-3-[(R)-hydroxy(pyridin-2-yl)methyl]-cyclobutanol Example 247E (154 mg, 0.35 mmol) was dissolved into anhydrous THF (700 μL), treated with 1 M tetra-N-butylammonium fluoride in THF (420 μL, 0.42 mmol), and stirred at room temperature overnight. Water (200 μL) was added to the solution and a powder began to precipitate. The suspension was stirred for about 90 minutes and the solids were collected by filtration, rinsed thoroughly with diethyl ether and dried under vacuum to give 94 mg of title compound. MS (ESI) m/z=324 (M+H)$^+$. $^1$H NMR (300 MHz, DMSO-d$_6$) δ 8.37 (ddd, J=4.9, 1.7, 0.8 Hz, 1H), 7.55 (ddd, J=7.7, 7.7, 1.7 Hz, 1H), 7.35 (d, J=8.4 Hz, 1H), 7.16 (ddd, J=7.5, 4.9, 1.1 Hz, 1H), 7.04 (d, J=2.1 Hz, 1H), 6.85 (dd, J=8.4, 2.1 Hz, 1H), 6.80-6.75 (m, 1H), 5.65 (bs, 1H), 5.03 (bs, 1H), 4.79 (s, 1H), 3.74 (tt, J=7.5, 7.5 Hz, 1H), 2.65-2.52 (m, 2H), 2.48-2.36 (m, 2H).

Example 248

(S)-{3-(hydroxyimino)-1-[4-(trifluoromethoxy)phenyl]cyclobutyl}(pyridin-2-yl)methanol A mixture of Example 134B (34 mg, 0.10 mmol), hydroxylamine hydrochloride (about 8.3 mg, 0.12 mmol), and methylmorpholine (13.5 mL, 0.12 mmol) were heated in methanol (400 mL) at 55° C. for two hours. The solution was brought to room temperature and partitioned between 1:1 EtOAc/hexanes (2 mL) and 0.5 M aqueous KH$_2$PO$_4$ (1 mL). The aqueous phase was separated and extracted twice with more 1:1 EtOAc/hexanes solution. The combined organic phases were washed with water. This wash was also back-extracted with 1:1 EtOAc/hexanes solution. The combined organic phases were washed with brine, dried (Na$_2$SO$_4$), and passed through a plug of alumina (EtOAc). The filtrate was concentrated to provide the title compound (14 mg) as an off-white powder. MS (ESI) m/z=353 (M+H)$^+$. $^1$H NMR (300 MHz, DMSO-d$_6$) δ 10.26-10.24 (m, 1H), 8.43-8.40 (m, 1H), 7.54-7.47 (m, 1H), 7.21-7.15 (m, 1H), 7.15-7.10 (m, 2H), 6.94 (d, J=8.7 Hz, 2H), 6.74-6.68 (m, 1H), 5.89-5.85 (m, 1H), 4.80-4.76 (m, 1H), 3.74-3.47 (m, 2H), 3.09-2.85 (m, 2H).

Example 249

(S)-{3-(methoxyimino)-1-[4-(trifluoromethoxy)phenyl]cyclobutyl}(pyridin-2-yl)methanol Example 134B (34 mg, 0.10 mmol), methoxylamine hydrochloride (10 mg, 0.12 mmol), and methylmorpholine (13.5 μL, 0.12 mmol) were heated in methanol (400 mL) at 55° C. for two hours. The solution was brought to room temperature and partitioned between 1:1 EtOAc/hexanes (2 mL) and 0.5 M aqueous KH$_2$PO$_4$ (1 mL). The aqueous phase was separated and extracted with more 1:1 solution and the combined organic phases were washed with water. This wash was also back-extracted with 1:1 solution, and the combined organic phases were washed with brine, dried (Na$_2$SO$_4$), and passed through a plug of alumina (1:1 to 2:1 EtOAc/hexanes). The filtrate was concentrated to provide the title compound (33 mg) as a white powder. MS (ESI) m/z=367 (M+H)$^+$. $^1$H NMR (300 MHz, DMSO-d$_6$) δ 8.43-8.39 (m, 1H), 7.55-7.48 (m, 1H), 7.21-7.16 (m, 1H), 7.16-7.10 (m, 2H), 6.94 (d, J=8.5 Hz, 2H), 6.77-6.70 (m, 1H), 5.93-5.89 (m, 1H), 4.80-4.75 (m, 1H), 3.77-3.50 (m, 2H), 3.70-3.69 (m, 3H), 3.12-2.90 (m, 2H).

Example 250 cis-3-[(R)-hydroxy(pyridin-2-yl)methyl]-1-methyl-3-[4-(trifluoromethoxy)-phenyl]cyclobutanol

Example 250A (R)-3-(hydroxy(pyridin-2-yl)methyl)-3-(4-(trifluoromethoxy)phenyl)-cyclobutanone The enantiomers of Example 134A (15.06 g, 44.6 mmol) were separated on a Chiralpak AD DAC column (5 cm ID×30 cm, 20 micron) and eluted with 80/4/16 hexanes/EtOH/MeOH at 100 mL/min. The second eluting peak was collected and concentrated to provide the title compound as a white powder. [α]$_D$=+26.0 (c=1, MeOH). MS (ESI$^+$): m/z 338 (M+H). $^1$H NMR (400 MHz, CD$_3$CN) δ 8.43 (ddd, J=4.8, 1.4, 0.9 Hz, 1H), 7.49 (td, J=7.7, 1.8 Hz, 1H), 7.20 (ddd, J=7.5, 4.9, 1.0 Hz, 1H), 7.13 (d, J=8.7 Hz, 2H), 7.04 (d, J=8.8 Hz, 2H), 6.62 (d, J=7.9 Hz, 1H), 4.97 (d, J=5.7 Hz, 1H), 4.47 (d, J=6.0 Hz, 1H), 3.78 (ddd, J=17.0, 6.0, 2.5 Hz, 1H), 3.63 (ddd, J=17.3, 6.0, 2.4 Hz, 1H), 3.28 (ddd, J=17.0, 3.6, 2.4 Hz, 1H), 3.20 (ddd, J=17.3, 3.5, 2.5 Hz, 1H).

Example 250B cis-3-[(R)-hydroxy(pyridin-2-yl)methyl]-1-methyl-3-[4-(trifluoromethoxy)-phenyl]cyclobutanol Example 250A (1.01 g, 3.0 mmol) was dissolved into anhydrous THF (15 mL) and cooled with a dry ice/acetone bath. Then the solution was slowly treated with 1.6 M MeLi in THF (4.1 mL, 6.6 mmol) and the bath was permitted to warm to 0° C. over 70 minutes. Then it was removed and the reaction was stirred at room temperature for another 5 hours before the flask was placed in a water bath and the reaction was quenched dropwise with 1 M aqueous KH$_2$PO$_4$ (4.5 mL). The solids were filtered off and washed with EtOAc. The aqueous phase of the filtrate was separated and extracted with EtOAc, and the combined organic phases were washed with brine, dried (Na$_2$SO$_4$), concentrated, and chromatographed on silica (5 to 35% CH$_3$CN/CH$_2$Cl$_2$ then to 5% MeOH/30% CH$_3$CN/65% CH$_2$Cl$_2$) to give title compound (632 mg). MS (ESI) m/z=354 (M+H)$^+$. $^1$H NMR (300 MHz, DMSO-d$_6$) δ 8.36 (dq, J=4.9, 0.8 Hz, 1H), 7.45 (ddd, J=7.7, 7.7, 1.8 Hz, 1H), 7.12 (ddd, J=7.5, 4.8, 1.1 Hz, 1H), 7.09-7.03 (m, 2H), 6.87 (d, J=8.8 Hz, 2H), 6.56 (d, J=7.9 Hz, 1H), 5.58 (d, J=4.6 Hz, 1H), 4.94 (d, J=4.6 Hz, 1H), 4.92 (s, 1H), 2.92 (d, J=12.1 Hz, 1H), 2.74 (d, J=12.1 Hz, 1H), 2.35 (dd, J=12.1, 3.5 Hz, 1H), 2.20 (dd, J=12.1, 3.5 Hz, 1H), 0.89 (s, 3H).

The HCl salt of the title compound was prepared by reacting with excess HCl in MeOH. [α]$_D$=+12.7 (c=1, MeOH).

Example 251

3-[(S)-hydroxy(pyridin-2-yl)methyl]-3-[4-(trifluoromethoxy)phenyl]-cyclobutanone The enantiomers of Example 134A (15.06 g, 44.6 mmol) were separated on a Chiralpak AD DAC column (5 cm ID×30 cm, 20 micron) and eluted with 80/4/16 hexanes/EtOH/MeOH at 100 mL/min. The first eluting peak was collected and concentrated to provide the title compound (7.52 g, 22.3 mmol) as a white powder. MS (ESI$^+$): m/z 338 (M+H). $^1$H NMR (400 MHz, CD$_3$CN) δ 8.43 (ddd, J=4.8, 1.4, 0.9 Hz, 1H), 7.49 (td, J=7.7, 1.8 Hz, 1H), 7.20 (ddd, J=7.5, 4.9, 1.0 Hz, 1H), 7.13 (d, J=8.7 Hz, 2H), 7.04 (d, J=8.8 Hz, 2H), 6.62 (d, J=7.9 Hz, 1H), 4.97 (d, J=5.7 Hz, 1H), 4.47 (d, J=6.0 Hz, 1H), 3.78 (ddd, J=17.0, 6.0, 2.5 Hz, 1H), 3.63 (ddd, J=17.3, 6.0, 2.4 Hz, 1H), 3.28 (ddd, J=17.0, 3.6, 2.4 Hz, 1H), 3.20 (ddd, J=17.3, 3.5, 2.5 Hz, 1H). [α]$_D$=−18.8° (c=1, MeOH).

Example 252

[1-(3,6-dihydro-2H-pyran-4-yl)cyclobutyl](pyridin-2-yl)methanol

Example 253

[1-(2-methylbenzyl)cyclobutyl](pyridin-2-yl)methanol

Example 254

[1-(3-fluorobenzyl)cyclobutyl](pyridin-2-yl)methanol

Example 255

[2-(3-chloro-4-fluorophenyl)-5,8-dioxaspiro[3.4]oct-2-yl](pyridin-2-yl)-methanol

Example 255A 1-(3-chloro-4-fluorophenyl)-3-hydroxycyclobutanecarbonitrile 2-(3-Chloro-4-fluorophenyl)acetonitrile (10.265 g, 60.5 mmol) was dissolved in anhydrous THF (90 mL) and chilled to −75° C. 1.6M Methyl lithium (37.8 mL, 60.5 mmol) in diethyl ether was added dropwise and the yellow solution was stirred at −75° C. for 1 hour. Epibromohydrin (5.01 mL, 60.5 mmol) in THF (20 mL) was added slowly and the reaction was stirred at −75° C. for 1 hour. 3.0M Methyl magnesium bromide (20.18 mL, 60.5 mmol) in diethyl ether was added dropwise and the reaction was permitted to warm to ambient temperature overnight. The reaction was quenched with water (50 mL), followed by the addition of 3N hydrochloric acid (100 mL), and extracted twice with EtOAc (200 mL). The combined organic phases was washed with brine, dried over Na$_2$SO$_4$, filtered, and concentrated. The residue was chromatographed on silica (0-100% EtOAc in heptane) to give Example 255A (13.508 g, 59.9 mmol, 99% yield) as a yellow oil. MS (DCI$^+$): m/z 243 (M+NH$_4$).

Example 255B 1-(3-chloro-4-fluorophenyl)-3-oxocyclobutanecarbonitrile

Example 255A (13.508 g, 59.9 mmol) was dissolved in dichloromethane (230 mL), and then Dess-Martin Periodinane (38.1 g, 90 mmol) was added. The yellow solution was stirred overnight at ambient temperature. The reaction mixture was filtered through a pad of silica, rinsed with dichloromethane, and the filtrate was concentrated. The residue was chromatographed on silica (100% dichloromethane) to give Example 255B (12.457 g, 55.7 mmol, 93% yield) as a yellow oil. MS (DCI+): m/z 241 (M+NH$_4$). $^1$H NMR (500 MHz, CD$_3$CN) δ 7.69 (dd, J=6.7, 2.5 Hz, 1H), 7.52 (ddd, J=8.6, 4.3, 2.6 Hz, 1H), 7.34 (t, J=8.9 Hz, 1H), 4.04-3.96 (m, 2H), 3.81-3.73 (m, 2H).

Example 255C 2-(3-chloro-4-fluorophenyl)-5,8-dioxaspiro[3.4]octane-2-carbonitrile Example 255B (12.457 g, 55.7 mmol) and 1,2-bis(trimethylsilyloxy)ethane (21 mL, 85 mmol) were dissolved in dichloromethane (120 mL), followed by the addition of trimethylsilyl trifluoromethanesulfonate (1.2 mL, 6.64 mmol). The yellow solution was stirred overnight at ambient temperature. The reaction was quenched with triethylamine (1.5 mL, 10.82 mmol), added dichloromethane (100 mL), and washed twice with saturated NaHCO$_3$ solution (200 mL). The organic phase was dried over Na$_2$SO$_4$, filtered, and concentrated. The residue was chromatographed on silica (0-100% EtOAc in heptane) to give Example 255C (13.041 g, 48.7 mmol, 87% yield) as a yellow oil. MS (DCI+): m/z 285 (M+NH$_4$). $^1$H NMR (500 MHz, CD$_3$CN) δ 7.60 (dd, J=6.9, 2.4 Hz, 1H), 7.44 (ddd, J=8.5, 4.4, 2.5 Hz, 1H), 7.30 (t, J=8.9 Hz, 1H), 3.98 (t, J=6.5 Hz, 2H), 3.88 (t, J=6.3 Hz, 2H), 3.19-3.13 (m, 2H), 2.98-2.91 (m, 2H).

Example 255D

[2-(3-chloro-4-fluorophenyl)-5,8-dioxaspiro[3.4]octan-2-yl](pyridin-2-yl)-methanone A solution of 2.5M n-butyl lithium (29.2 mL, 73.1 mmol) in hexanes plus anhydrous diethyl ether (120 mL) was chilled to −75° C., followed by the dropwise addition of 2-bromopyridine (7.20 mL, 76 mmol) in diethyl ether (40 mL). The orange-red solution was stirred for 1 hour, followed by the dropwise addition of Example 255C (13.041 g, 48.7 mmol) in diethyl ether (40 mL). The mixture was slowly warmed to 0° C. while stirring for 2 hours. The reaction was quenched with 1N hydrochloric acid (160 mL) and the biphasic mixture was stirred for 1 hour at ambient temperature. Added 3N sodium hydroxide (160 mL) and extracted twice with EtOAc (300 mL). The combined organic phases were washed with brine, dried over Na$_2$SO$_4$, filtered, and concentrated. The residue was chromatographed on silica (0-50% EtOAc in heptane) to give Example 255D (13.080 g, 37.6 mmol, 77% yield) as a yellow oil. MS (ESI+): m/z 348 (M+H). $^1$H NMR (500 MHz, CD$_3$CN) δ 8.53 (d, J=4.6 Hz, 1H), 7.96 (d, J=7.9 Hz, 1H), 7.85 (td, J=7.8, 1.6 Hz, 1H), 7.64 (dd, J=7.1, 2.4 Hz, 1H), 7.46-7.38 (m, 2H), 7.12 (t, J=9.0 Hz, 1H), 3.87-3.78 (m, 4H), 3.35-3.28 (m, 2H), 2.99-2.92 (m, 2H).

Example 255E

[2-(3-chloro-4-fluorophenyl)-5,8-dioxaspiro[3.4]oct-2-yl](pyridin-2-yl)-methanol Example 255D (13.020 g, 37.4 mmol) was dissolved in dichloromethane (110 mL) and MeOH (11 mL), then sodium borohydride (1.558 g, 41.2 mmol) was added to the yellow solution. The reaction was stirred overnight at ambient temperature. Added 3N sodium hydroxide (200 mL), extracted twice with EtOAc (300 mL), washed with brine, and dried over Na$_2$SO$_4$. Chromatographed on silica (0-100% EtOAc in heptane) to give Example 255E (13.154 g, 37.6 mmol, 100% yield) as a yellow oil. MS (ESI+): m/z 350 (M+H). $^1$H NMR (500 MHz, CD$_3$CN) δ 8.35 (d, J=4.8 Hz, 1H), 7.53 (td, J=7.7, 1.7 Hz, 1H), 7.16 (dd, J=7.3, 4.9 Hz, 1H), 6.97 (t, J=9.0 Hz, 1H), 6.86 (dd, J=7.2, 2.3 Hz, 1H), 6.82 (d, J=7.9 Hz, 1H), 6.74 (ddd, J=8.5, 4.7, 2.3 Hz, 1H), 4.98 (d, J=6.0 Hz, 1H), 4.18 (d, J=6.0 Hz, 1H), 3.92-3.86 (m, 2H), 3.81-3.74 (m, 2H), 3.15 (dd, J=12.9, 3.2 Hz, 1H), 3.00 (dd, J=13.0, 3.2 Hz, 1H), 2.57 (dd, J=13.0, 3.1 Hz, 1H), 2.49 (dd, J=12.9, 3.2 Hz, 1H).

Example 256

3-[(S)-hydroxy(pyridin-2-yl)methyl]-3-[3-(trifluoromethoxy)phenyl]-cyclobutanone Mixture of enantiomers of Example 237 (10.2 g, 30.2 mmol) was separated on a Chiralpak AD-H column (3 cm ID×25 cm, 5 micron) and eluted with 10% EtOH in hexanes at 45 mL/min. The sample was injected at 100 mg in 0.5 mL 1:1 EtOH-hexanes per run. The first eluting peak was collected and concentrated to provide the title compound (4.0 g, 11.86 mmol) as a yellow oil. MS (ESI+): m/z 338 (M+H). $^1$H NMR (500 MHz, CD$_3$CN) δ 8.43 (d, J=4.8 Hz, 1H), 7.49 (td, J=7.7, 1.7 Hz, 1H), 7.34 (t, J=8.0 Hz, 1H), 7.22-7.17 (m, 1H), 7.14 (dd, J=8.2, 0.9 Hz, 1H), 7.05 (d, J=7.8 Hz, 1H), 6.79 (s, 1H), 6.60 (d, J=7.8 Hz, 1H), 4.97 (s, 1H), 4.51 (br s, 1H), 3.79 (ddd, J=17.1, 6.0, 2.4 Hz, 1H), 3.64 (ddd, J=17.4, 6.0, 2.3 Hz, 1H), 3.33-3.25 (m, 1H), 3.24-3.16 (m, 1H). [α]$_D$=−22.9° (c 1.0, MeOH).

Example 257

3-[(R)-hydroxy(pyridin-2-yl)methyl]-3-[3-(trifluoromethoxy)phenyl]-cyclobutanone Mixture of enantiomers of Example 237 (10.2 g, 30.2 mmol) was separated on a Chiralpak AD-H column (3 cm ID×25 cm, 5 micron) and eluted with 10% EtOH in hexanes at 45 mL/min. The sample was injected at 100 mg in 0.5 mL 1:1 EtOH-hexanes per run. The second eluting peak was collected and concentrated to provide the title compound (4.1 g, 12.16 mmol) as a yellow solid. MS (ESI+): m/z 338 (M+H). $^1$H NMR (400 MHz, CD$_3$CN) δ 8.43 (ddd, J=4.8, 1.8, 0.9 Hz, 1H), 7.49 (td, J=7.7, 1.7 Hz, 1H), 7.34 (t, J=8.0 Hz, 1H), 7.19 (ddd, J=7.5, 4.9, 1.0 Hz, 1H), 7.16-7.10 (m, 1H), 7.05 (ddd, J=7.7, 1.8, 0.9 Hz, 1H), 6.79 (s, 1H), 6.60 (d, J=7.9 Hz, 1H), 4.97 (s, 1H), 4.49 (br s, 1H), 3.79 (ddd, J=17.1, 6.0, 2.4 Hz, 1H), 3.64 (ddd, J=17.4, 6.0, 2.4 Hz, 1H), 3.29 (ddd, J=17.1, 3.6, 2.5 Hz, 1H), 3.20 (ddd, J=17.4, 3.5, 2.5 Hz, 1H). [α]$_D$=+19.9° (c 1.0, MeOH).

Example 258

3-(3-chloro-4-fluorophenyl)-3-[hydroxy(pyridin-2-yl)methyl]cyclobutanone

A solution of Example 255E (13.105 g, 37.5 mmol) in acetone (200 mL), water (20 mL) and 12N hydrochloric acid (25 mL) was stirred overnight at ambient temperature, and concentrated to the half of the original volume. To the mixture was added 3N sodium hydroxide (150 mL) and extracted twice with EtOAc (300 mL). The organic phase was washed with brine, dried over Na$_2$SO$_4$, filtered, and concentrated. The residue was chromatographed on silica (0-100% EtOAc in heptane) to give Example 258 (10.73 g, 35.1 mmol, 94% yield) as a yellow oil. MS (ESI+): m/z 306 (M+H). $^1$H NMR (400 MHz, CD$_3$CN) δ 8.47-8.41 (m, 1H), 7.53 (td, J=7.7, 1.8 Hz, 1H), 7.21 (ddd, J=7.5, 4.9, 1.0 Hz, 1H), 7.11-7.05 (m, 1H), 7.04 (dd, J=7.1, 2.4 Hz, 1H), 6.89 (ddd, J=8.6, 4.6, 2.4 Hz, 1H), 6.68 (d, J=7.9 Hz, 1H), 4.95 (s, 1H), 4.47 (br s, 1H), 3.76 (ddd, J=17.1, 6.0, 2.5 Hz, 1H), 3.61 (ddd, J=17.4, 6.0, 2.4 Hz, 1H), 3.26 (ddd, J=17.1, 3.6, 2.5 Hz, 1H), 3.18 (ddd, J=17.4, 3.6, 2.6 Hz, 1H.

Example 259 cis-3-[(S)-hydroxy(pyridin-2-yl)methyl]-3-[3-(trifluoromethyl)phenyl]-cyclobutanol Example 241 (1.525 g, 4.75 mmol) was dissolved in dichloromethane (30 mL) and MeOH (3 mL), followed by the addition of sodium borohydride (0.377 g, 9.97 mmol) to the colorless solution. The reaction was stirred overnight at ambient temperature. 1N sodium hydroxide (200 mL) was added and the mixture was extracted twice with EtOAc (200 mL). The combined organic phases was washed with brine, dried over Na$_2$SO$_4$, filtered, and concentrated. The residue was chromatographed on silica (0-10% MeOH in EtOAc) to give mixture of geometric isomers (1.42 g, 4.39 mmol, 93% yield) as a white solid. MS (ESI+): m/z 324 (M+H). This mixture (1.35 g, 4.18 mmol) was chromatographed on a Chiralpak AD-H column (3 cm ID×25 cm, 5 micron) and eluted with 5% (8:2 MeOH-EtOH) in hexanes (0.1% n-propylamine) at 45 mL/min. The sample was injected at 25 mg in 0.5 mL 1:1 EtOH-hexanes per run. The first eluting peak was collected and concentrated to provide Example 259 (0.458 g, 1.417 mmol) as a white solid. MS (ESI+): m/z 324 (M+H). $^1$H NMR (500 MHz, CD$_3$CN) δ 8.30 (d, J=4.8 Hz, 1H), 7.52 (td, J=7.7, 1.5 Hz, 1H), 7.44 (d, J=7.7 Hz, 1H), 7.34 (t, J=7.8 Hz, 1H), 7.27 (d, J=7.9 Hz, 1H), 7.14 (dd, J=7.4, 4.9 Hz, 1H), 7.11 (s, 1H), 6.79 (d, J=7.9 Hz, 1H), 4.86 (d, J=5.5 Hz, 1H), 4.33 (d, J=6.0 Hz, 1H), 3.92-3.82 (m, 1H), 3.26 (d, J=5.8 Hz, 1H), 2.74-2.61 (m, 3H), 2.48 (dd, J=11.3, 7.6 Hz, 1H). [α]$_D$=−45.6° (c 1.0, MeOH).

Example 260

[1-(4,4-difluorocyclohex-1-en-1-yl)cyclobutyl](pyridin-2-yl)methanol

Example 261 pyridin-2-yl{1-[5-(trifluoromethyl)cyclohex-1-en-1-yl]cyclobutyl}methanol

Example 262 cis-3-[(S)-hydroxy(pyridin-2-yl)methyl]-1-methyl-3-[3-(trifluoromethoxy)-phenyl]cyclobutanol Example 256 (2.0 g, 5.93 mmol) was dissolved in anhydrous 2-methyltetrahydrofuran (30 mL) and chilled with a dry ice/acetone bath. 1.6M Methyl lithium (9.0 mL, 14.4 mmol) in diethyl ether was added slowly, and the reaction was permitted to warm to ambient temperature overnight. The reaction was quenched with 1M aqueous KH$_2$PO$_4$ (50 mL), added water (200 mL), and extracted twice with EtOAc (200 mL). The combined organic phases was washed with brine, dried over Na$_2$SO$_4$, filtered, and concentrated. The residue was chromatographed on silica (0-10% MeOH in EtOAc) to give the two geometric isomers: Example 263 (0.174 g, 0.492 mmol, 8.3% yield) as a yellow oil (first peak) and Example 262 (0.943 g, 2.67 mmol, 45.0% yield) as a yellow oil (second peak). MS (ESI+): m/z 354 (M+H). $^1$H NMR (400 MHz, CD$_3$CN) δ 8.31 (ddd, J=4.9, 1.6, 1.0 Hz, 1H), 7.49 (td, J=7.7, 1.8 Hz, 1H), 7.24 (t, J=8.0 Hz, 1H), 7.14 (ddd, J=7.5, 4.9, 1.1 Hz, 1H), 7.07-7.01 (m, 1H), 6.95 (ddd, J=7.8, 1.5, 1.0 Hz, 1H), 6.71 (d, J=7.9 Hz, 1H), 6.66 (s, 1H), 4.91 (d, J=5.7 Hz, 1H), 4.48 (d, J=6.0 Hz, 1H), 3.40 (s, 1H), 2.94-2.86 (m, 1H), 2.78-2.71 (m, 1H), 2.44-2.36 (m, 2H), 0.99 (s, 3H). [α]$_D$=−43.7° (c 1.0, MeOH).

Example 263 trans-3-[(S)-hydroxy(pyridin-2-yl)methyl]-1-methyl-3-[3-(trifluoromethoxy)phenyl]cyclobutanol Example 256 (2.0 g, 5.93 mmol) was dissolved in anhydrous 2-methyltetrahydrofuran (30 mL) and chilled with a dry ice/acetone bath. 1.6M Methyl lithium (9.0 mL, 14.4 mmol) in diethyl ether was added slowly, and the reaction was permitted to warm to ambient temperature overnight. The reaction was quenched with 1M aqueous KH$_2$PO$_4$ (50 mL), added water (200 mL), and extracted twice with EtOAc (200 mL). The combined organic phases was washed with brine, dried over Na$_2$SO$_4$, filtered, and concentrated. The residue was chromatographed on silica (0-10% MeOH in EtOAc) to give the two geometric isomers: Example 263 (0.174 g, 0.492 mmol, 8.3% yield) as a yellow oil (first peak) and Example 262 (0.943 g, 2.67 mmol, 45.0% yield) as a yellow oil (second peak). MS (ESI+): m/z 354 (M+H). $^1$H NMR (400 MHz, CD$_3$CN) δ 8.32 (ddd, J=4.9, 1.6, 1.0 Hz, 1H), 7.49 (td, J=7.7, 1.8 Hz, 1H), 7.23 (t, J=8.0 Hz, 1H), 7.14 (ddd, J=7.6, 4.9, 1.1 Hz, 1H), 7.05-6.99 (m, 1H), 6.95-6.89 (m, 1H), 6.74 (d, J=7.9 Hz, 1H), 6.64 (s, 1H), 4.87 (d, J=5.1 Hz, 1H), 4.20 (d, J=5.7 Hz, 1H), 3.04-2.97 (m, 1H), 2.90-2.84 (m, 1H), 2.82 (s, 1H), 2.38-2.28 (m, 2H), 1.40 (s, 3H). [α]$_D$=−60.8° (c 1.0, MeOH).

Example 264 trans-3-[(S)-hydroxy(pyridin-2-yl)methyl]-3-[3-(trifluoromethyl)phenyl]-cyclobutanol The title compound (0.316 g, 0.977 mmol, beige solid) was collected as the second eluting peak from the chiral separation of the crude mixture obtained in Example 259. MS (ESI+): m/z 324 (M+H). $^1$H NMR (500 MHz, CD$_3$CN) δ 8.16 (d, J=4.8 Hz, 1H), 7.31 (td, J=7.7, 1.7 Hz, 1H), 7.23 (d, J=7.8 Hz, 1H), 7.14 (t, J=7.8 Hz, 1H), 6.97 (ddd, J=7.4, 4.9, 0.8 Hz, 1H), 6.89 (d, J=7.8 Hz, 1H), 6.75 (s, 1H), 6.57 (d, J=7.9 Hz, 1H), 4.61 (d, J=3.4 Hz, 1H), 4.05 (p, J=7.1 Hz, 1H), 3.97 (d, J=5.5 Hz, 1H), 3.02-2.89 (m, 2H), 2.84 (br s, 1H), 1.90 (ddd, J=11.6, 7.1, 4.2 Hz, 2H). [α]$_D$=−71.8° (c 1.0, MeOH).

Example 265 tert-butyl 3-{1-[hydroxy(pyridin-2-yl)methyl]cyclobutyl}pyrrolidine-1-carboxylate Example 266

[1-(1,3-benzothiazol-2-yl)cyclobutyl](pyridin-2-yl)methanol

Example 267

(S)-{3-(dimethylhydrazinylidene)-1-[4-(trifluoromethoxy)phenyl]-cyclobutyl}(pyridin-2-yl)methanol Example 251 (51 mg, 0.15 mmol), 1,1-dimethylhydrazine (15.5 μL, 0.20 mmol), and acetic acid (10 μL, 0.17 mmol) were heated in anhydrous tetrahydrofuran (300 μL) at 60° C. for three hours and then cooled to room temperature. The mixture was partitioned between CH$_2$Cl$_2$ and 1 M aqueous K$_2$HPO$_4$. The aqueous phase was separated and extracted with CH$_2$Cl$_2$. The combined organic phases were washed with brine, dried (Na$_2$SO$_4$), filtered, and concentrated. The residue was chromatographed on silica (10 to 100% CH$_3$CN/CH$_2$Cl$_2$, then to 5% 2 M NH$_3$ in MeOH/CH$_3$CN) to give title compound (39 mg). MS (ESI) m/z=380 (M+H)$^+$. $^1$H NMR (300 MHz, DMSO-d$_6$) δ 8.44-8.40 (m, 1H), 7.55-7.47 (m, 1H), 7.20-7.15 (m, 1H), 7.15-7.10 (m, 2H), 6.99-6.92 (m, 2H), 6.76-6.70 (m, 1H), 5.86-5.82 (m, 1H), 4.78 (d, J=4.7 Hz, 1H), 3.82-3.43 (m, 2H), 3.18-2.91 (m, 2H), 2.48-2.45 (m, 6H).

Example 268

3-(3-chloro-4-fluorophenyl)-3-[(S)-hydroxy(pyridin-2-yl)methyl]-cyclobutanone

Mixture of enantiomers of Example 258 (10.7 g, 35.0 mmol) was separated by chiral preparative SFC on a Chiralpak AD-H column (3 cm ID×25 cm, 5 micron), eluted with 15% isopropanol in supercritical CO$_2$ (100 bar) at 100 mL/min. The sample was injected at 100 mg in 1.0 mL isopropanol per run. The first eluting peak was collected and concentrated to provide Example 268 (4.02 g, 13.15 mmol) as a tan solid. MS (ESI+): m/z 306 (M+H). $^1$H NMR (500 MHz, CD$_3$CN) δ 8.24 (d, J=4.8 Hz, 1H), 7.33 (td, J=7.7, 1.7 Hz, 1H), 7.04-6.98 (m, 1H), 6.88 (t, J=9.0 Hz, 1H), 6.84 (dd, J=7.1, 2.3 Hz, 1H), 6.69 (ddd, J=8.5, 4.6, 2.4 Hz, 1H), 6.48 (d, J=7.9 Hz, 1H), 4.75 (d, J=5.5 Hz, 1H), 4.28 (d, J=5.9 Hz, 1H), 3.56 (ddd, J=17.1, 6.0, 2.4 Hz, 1H), 3.41 (ddd, J=17.4, 6.0, 2.4 Hz, 1H), 3.06 (ddd, J=17.1, 3.5, 2.5 Hz, 1H), 3.02-2.95 (m, 1H). [α]$_D$=−35.8° (c 1.0, MeOH).

Example 269

[1-(5,6-dihydro-2H-pyran-3-yl)cyclobutyl](pyridin-2-yl)methanol

Example 270

[1-(3,4-dihydro-2H-pyran-5-yl)cyclobutyl](pyridine-2-yl)methanol

Example 271

[1-(1,3-benzoxazol-2-yl)cyclobutyl](pyridin-2-yl)methanol

Example 272 cis-3-[(S)-hydroxy(pyridin-2-yl)methyl]-3-[3-(trifluoromethoxy)phenyl]-cyclobutanol Example 256 (1.32 g, 3.91 mmol) was dissolved in dichloromethane (30 mL) and MeOH (3 mL), followed by the addition of sodium borohydride (0.311 g, 8.22 mmol) to the colorless solution. The reaction was stirred overnight at ambient temperature, followed by the addition of 1N sodium hydroxide (200 mL) and extraction with EtOAc (2×200 mL). The combined organic phases was washed with brine, dried over Na$_2$SO$_4$, filtered, and concentrated. The residue was chromatographed on silica (0-10% MeOH in EtOAc) to give a mixture of geometrical isomers of diols (1.080 g, 3.18 mmol, 81% yield) as a white solid. MS (ESI$^+$): m/z 340 (M+H). The mixture (0.992 g, 2.92 mmol) was separated by chiral preparative SFC on a Chiralpak AD-H column (3 cm ID×25 cm, 5 micron) and eluting with 10% isopropanol (0.5% isopropylamine) in supercritical CO$_2$ (100 bar) at 100 mL/min. The sample was injected at 50 mg in 1.0 mL 1:1 EtOH-isopropanol per run. The first eluting peak was collected and concentrated to provide the title compound (0.242 g, 0.713 mmol) as a white solid. MS (ESI+): m/z 340 (M+H). $^1$H NMR (500 MHz, CD$_3$CN) δ 8.31 (d, J=4.8 Hz, 1H), 7.51 (td, J=7.7, 1.7 Hz, 1H), 7.25 (t, J=8.0 Hz, 1H), 7.16-7.12 (m, 1H), 7.05 (dd, J=7.8, 1.4 Hz, 2H), 6.80-6.74 (m, 2H), 4.83 (d, J=6.2 Hz, 1H), 4.37 (d, J=6.2 Hz, 1H), 3.92-3.83 (m, 1H), 3.24 (d, J=6.7 Hz, 1H), 2.67-2.59 (m, 3H), 2.46 (dd, J=12.3, 7.5 Hz, 1H). [α]$_D$=−39.4° (c 1.0, MeOH).

Example 273 trans-3-[(S)-hydroxy(pyridin-2-yl)methyl]-3-[3-(trifluoromethoxy)phenyl]-cyclobutanol The geometric isomers obtained during the synthesis of Example 272 (0.992 g, 2.92 mmol) were separated by chiral preparative SFC on a Chiralpak AD-H column (3 cm ID×25 cm, 5 micron) and eluted with 10% isopropanol (0.5% isopropylamine) in supercritical CO$_2$ (100 bar) at 100 mL/min. The sample was injected at 50 mg in 1.0 mL 1:1 EtOH-isopropanol per run. The second eluting peak was collected and concentrated to provide the title compound (0.419 g, 1.235 mmol) as a beige solid. MS (ESI): m/z 340 (M+H). $^1$H NMR (500 MHz, CD$_3$CN) δ 8.37 (d, J=4.7 Hz, 1H), 7.51 (td, J=7.7, 1.6 Hz, 1H), 7.25 (t, J=8.0 Hz, 1H), 7.17 (dd, J=7.4, 4.9 Hz, 1H), 7.04 (d, J=8.2 Hz, 1H), 6.87 (d, J=7.8 Hz, 1H), 6.76 (d, J=7.9 Hz, 1H), 6.60 (s, 1H), 4.79 (d, J=6.4 Hz, 1H), 4.30-4.22 (m, 1H), 4.20 (d, J=6.4 Hz, 1H), 3.15 (ddd, J=11.8, 7.3, 4.7 Hz, 1H), 3.09 (ddd, J=11.9, 7.3, 4.7 Hz, 1H), 3.02 (d, J=6.9 Hz, 1H), 2.07 (ddd, J=14.8, 11.8, 7.1 Hz, 2H). $[\alpha]_D$= −67.6° (c 1.0, MeOH).

Example 274

[1-(4,4-difluorocyclohexyl)cyclobutyl](pyridin-2-yl)methanol

Example 275

[1-(1-methyl-1H-benzimidazol-2-yl)cyclobutyl](pyridin-2-yl)methanol

Example 276

3-(3-chloro-4-fluorophenyl)-3-[(S)-hydroxy(pyridin-2-yl)methyl]-cyclobutanol

Example 268 (1.40 g, 4.58 mmol) was dissolved in dichloromethane (35 mL) and MeOH (3.5 mL), followed by the addition of sodium borohydride (0.364 g, 9.62 mmol) to the colorless solution. The reaction was stirred overnight at ambient temperature, followed by the addition of 1N sodium hydroxide (200 mL) and extraction with EtOAc (400 mL). The organic phase was washed with brine, and the organic layer extracted with 1N hydrochloric acid (100 mL). To the aqueous layer was added 1N sodium hydroxide (200 mL) and the resulting solution extracted with EtOAc (400 mL). The organic extracts were combined and concentrated to give Example 276 (1.393 g, 4.53 mmol, 99% yield) as a white solid. MS (ESI+): m/z 308 (M+H). $^1$H NMR (500 MHz, DMSO-$d_6$) δ 8.43 (ddd, J=4.8, 1.8, 0.9 Hz, 0.5H), 8.37 (d, J=4.7 Hz, 0.5H), 7.56 (td, J=7.7, 1.8 Hz, 0.5H), 7.54 (td, J=7.7, 1.7 Hz, 0.5H), 7.23-7.08 (m, 2H), 6.98 (dd, J=7.3, 2.2 Hz, 0.5H), 6.85 (ddd, J=8.5, 4.7, 2.2 Hz, 0.5H), 6.84-6.76 (m, 1H), 6.74 (d, J=7.9 Hz, 0.5H), 6.66 (ddd, J=8.5, 4.8, 2.2 Hz, 0.5H), 5.64 (d, J=2.7 Hz, 0.5H), 5.61 (d, J=4.3 Hz, 0.5H), 5.04 (d, J=6.1 Hz, 0.5H), 4.89 (d, J=6.7 Hz, 0.5H), 4.78 (s, 0.5H), 4.71 (d, J=4.2 Hz, 0.5H), 4.11-3.96 (m, 0.5H), 3.80-3.69 (m, 0.5H), 3.15-2.98 (m, 1H), 2.62-2.53 (m, 1H), 2.48-2.37 (m, 1H), 2.03-1.88 (m, 1H).

Example 277

3-[(S)-hydroxy(pyridin-2-yl)methyl]-3-[4-(trifluoromethyl)pyridin-2-yl]-cyclobutanone Example 277A 3-oxocyclobutanecarbonitrile To a solution of 3-methylenecyclobutanecarbonitrile (9.2 g, 99 mmol) in a mixture of dichloromethane (175 mL), CH$_3$CN (175 mL) and water (263 mL) was added ruthenium (III) chloride trihydrate (0.614 g, 2.348 mmol) in one portion at 0° C., followed by the addition of sodium periodate (86 g, 400 mmol) portionwise over 90 minutes, keeping the temp below 10° C. After the addition was completed, the reaction was diluted with dichloromethane (300 mL) and filtered to remove insoluble material. Organic phase was separated, and the aqueous phase was extracted with dichloromethane (200 mL×2). The organic layers were combined, dried over Na$_2$SO$_4$, filtered, and concentrated to give the title compound (8.4 g, 88 mmol, 89% yield) as a white solid. $^1$H NMR (400 MHz, CDCl$_3$): δ 3.49 (d, J=8.0 Hz, 4H), 3.17-3.22 (m, 1H).

Example 277B 5,8-dioxaspiro[3.4]octane-2-carbonitrile

To a solution of Example 277A (5.00 g, 52.6 mmol) in toluene (100 mL) was added ethane-1,2-diol (2.94 ml, 52.6 mmol) and p-toluenesulfonic acid (0.500 g, 2.63 mmol) at room temperature. The reaction was refluxed for 2 hours under a Dean-Stark trap. The reaction mixture was washed with saturated solution of NaHCO$_3$ (2×100 mL), dried over Na$_2$SO$_4$, filtered, and concentrated to give the title compound (5.6 g, 38.2 mmol, 72.7% yield) as a yellow oil. $^1$H NMR (400 MHz, CDCl$_3$): δ 3.84 (s, 4H), 2.70-2.84 (m, 1H), 2.64-2.68 (m, 4H).

Example 277C 2-(4-(trifluoromethyl)pyridin-2-yl)-5,8-dioxaspiro[3.4]octane-2-carbonitrile To a solution of Example 277B (15.13 g, 109 mmol) and 2-fluoro-4-(trifluoromethyl)-pyridine (17.95 g, 109 mmol) in toluene (100 mL) was added potassium hexamethyldisilazide (239 mL, 120 mmol), then the reaction was stirred at 60° C. for 4 hours. The reaction was quenched with water (100 mL) and extracted with EtOAc (100 mL×2). The combined organic layers were washed with brine (50 mL), dried over Na$_2$SO$_4$, filtered, and concentrated. The residue was purified by column chromatography on silica gel (petroleum ether/EtOAc=10/1) to give the title compound (20.8 g, 73.2 mmol, 67.3% yield) as a white solid. MS: 285.04 [M+H]$^+$; $^1$H NMR (400 MHz, CDCl$_3$): δ 8.78-8.79 (d, J=4.8 Hz, 1H), 7.78 (s, 1H), 7.43 (t, J=0.8 Hz, 1H), 3.96-4.00 (m, 2H), 3.84-3.90 (m, 2H), 3.24-3.27 (m, 2H), 3.06-3.11 (m, 2H).

Example 277D pyridin-2-yl(2-(4-(trifluoromethyl)pyridin-2-yl)-5,8-dioxaspiro[3.4]octan-2-yl)methanone To a solution of 2-bromopyridine (11.00 ml, 112.8 mmol) in ether (50 mL) was added a 1.6 M solution of n-BuLi (68.3 ml, 109 mmol) dropwise at −78° C. The reaction mixture was stirred at −78° C. for 1 hour. A solution of Example 277C (20.7 g, 72.8 mmol) in ether (120 mL) was added at −78° C. and the reaction was stirred for 2 hours at the same temperature. The progress of the reaction was monitored by LCMS. 3 M aqueous HCl (100 mL) was added dropwise slowly at −78° C. The biphasic mixture was warmed to room temperature and stirred for 0.5 hour, and then the mixture was basified with 3 M aqueous NaOH (150 mL). The aqueous phase was separated and extracted with EtOAc (150 mL×2), and the combined organic phases were washed with brine (50 mL), dried over Na$_2$SO$_4$, filtered, and concentrated. The residue was purified by column chromatography on silica gel (petroleum ether/EtOAc=5/1) to give the title compound (28.0 g, 46.1 mmol, 63.3% yield) as a white solid. MS: 365.1 [M+H]$^+$; $^1$H NMR (400 MHz, CDCl$_3$): δ 8.49 (d, J=5.2 Hz, 1H), 8.31 (t, J=2.2 Hz, 1H), 8.06 (d, J=8.0 Hz, 1H), 7.86 (s, 1H), 7.70 (d, J=1.6 Hz, 1H); 7.18-7.22 (m, 2H), 3.82-3.88 (m, 4H), 3.31-3.33 (m, 2H), 3.02-3.06 (m, 2H).

Example 277E pyridin-2-yl(2-(4-(trifluoromethyl)pyridin-2-yl)-5,8-dioxaspiro[3.4]octan-2-yl)methanol To a solution of Example 277D (28.5 g, 78.0 mmol) in dichloromethane (100 mL) and MeOH (10 mL) was added NaBH$_4$ (3.55 g, 94 mmol) in one portion, and then the reaction was stirred for 1 hour at room temperature. To the reaction mixture was added water (50 mL) and extracted with dichloromethane (80 mL×2). The combined organic phases were dried over Na$_2$SO$_4$, filtered. The residue was purified by column chromatography on silica gel (petroleum ether/EtOAc=2/1-1/1) to provide the title compound (28.6 g, 77 mmol, 98% yield) as a white solid. MS: 366.1 [M+H]$^+$; $^1$H NMR (400 MHz, CDCl$_3$): δ 8.51 (d, J=5.2 Hz, 1H), 8.24 (d, J=4.4 Hz, 1H), 7.38-7.44 (m, 1H), 7.21-7.22 (m, 1H), 7.07 (s, 1H), 7.00-7.04 (m, 1H), 6.77 (d, J=8.0 Hz, 1H), 5.10 (d, J=6.8 Hz, 1H), 4.68 (d, J=7.6 Hz, 1H), 3.86-3.92 (m, 2H), 3.75-3.82 (m, 2H), 3.06-3.12 (m, 2H), 2.80-2.84 (m, 1H), 2.65-2.70 (m, 1H).

Example 277F (S)-3-(hydroxy(pyridin-2-yl)methyl)-3-(4-(trifluoromethyl)pyridin-2-yl)-cyclobutanone To a solution of Example 277E (28.6 g, 78 mmol) in acetone (112 mL) was added 6N HCl (56 mL) at room temperature and the reaction was stirred overnight. The reaction mixture was basified with 3N NaOH (120 mL), extracted with EtOAc (200 mL×2) and the combined organic phases were washed with brine (100 mL), dried over Na$_2$SO$_4$, filtered, and concentrated to give an enantiomeric mixture of Example 278 and Example 277F (25 g, 76 mmol, 97% yield) as a white solid. This mixture was separated on a chiral column (Column: AD-H, 50×250 mm, 5 μm; CO$_2$/isopropanol/diethylamine=85/25/0.1; flow rate 160 g/min; sample solution: 37.7 g in 400 mL MeOH) to give Example 278 (10.2 g, 40% yield) and Example 277F (10.7 g, 43% yield) as a white solid. MS: 322.9 [M+H]$^+$; $^1$H NMR (400 MHz, CDCl$_3$): δ 8.65 (d, J=5.2 Hz, 1H), 8.40 (d, J=4.8 Hz, 1H), 7.36-7.40 (d, J=1.6 Hz, 1H), 7.33 (d, J=0.8 Hz, 1H), 7.15 (s, 1H), 7.08-7.12 (m, 1H), 6.38 (d, J=8.0 Hz, 1H), 5.10 (d, J=5.6 Hz, 1H), 4.86 (d, J=6.4 Hz, 1H), 3.78-3.86 (m, 1H), 3.58-3.64 (m, 1H), 3.40-3.46 (m, 1H), 3.22-3.29 (m, 1H). [α]$_D^{20}$=−21.8° (c=1.0, MeOH).

Example 278

3-[(R)-hydroxy(pyridin-2-yl)methyl]-3-[4-(trifluoromethyl)pyridin-2-yl]-cyclobutanone Chiral separation as described in Example 277F provided Example 278. MS: 322.9 [M+H]$^+$; $^1$H NMR (400 MHz, CDCl$_3$): δ 8.65 (d, J=5.2 Hz, 1H), 8.40 (d, J=4.8 Hz, 1H), 7.36-7.40 (d, J=1.6 Hz, 1H), 7.33 (d, J=0.8 Hz, 1H), 7.15 (s, 1H), 7.08-7.12 (m, 1H), 6.38 (d, J=8.0 Hz, 1H), 5.10 (d, J=5.6 Hz, 1H), 4.86 (d, J=6.4 Hz, 1H), 3.78-3.86 (m, 1H), 3.58-3.64 (m, 1H), 3.40-3.46 (m, 1H), 3.22-3.29 (m, 1H). [α]$_D^{20}$=+21.5° (c=1.0, MeOH).

Example 279 tert-butyl 4-{1-[hydroxy(pyridin-2-yl)methyl]cyclobutyl}piperidine-1-carboxylate

Example 280 pyridin-2-yl{1-[4-(trifluoromethyl)cyclohexyl]cyclobutyl}methanol

Example 281 pyridin-2-yl[1-(tetrahydro-2H-pyran-3-yl)cyclobutyl]methanol

Example 282 cis-3-[(S)-hydroxy(pyridin-2-yl)methyl]-3-[4-(trifluoromethyl)pyridin-2-yl]cyclobutanol To a solution of Example 277F (4.5 g, 13.96 mmol) in dichloromethane (30 mL) and MeOH (3.00 mL) was added NaBH$_4$ (0.634 g, 16.76 mmol) at 0° C., then the reaction was stirred at room temperature for 3 hours. To the reaction mixture was added water (10 mL) and extracted with dichloromethane (40 mL×2). The combined organic phases were dried over Na$_2$SO$_4$, filtered, and concentrated. The crude mixture was subjected to chiral separation (Column: AD-H, 50×250 mm, 5 μm; CO$_2$/isopropanol/diethylamine=85/25/0.1; flow rate 120 g/min; sample solution: 4.3 g in 62 mL MeOH) to give the title compound (1.7 g, 39% yield) and Example 283 (1.05 g, 24% yield) as white solids. MS: m/z 325.1 [M+H]$^+$; $^1$H NMR: (400 MHz, 400 MHz, CDCl$_3$): δ 8.68 (d, J=5.2 Hz, 1H), 8.41 (d, J=4.8 Hz, 1H), 7.30-7.40 (m, 2H), 7.11 (d, J=6.4 Hz, 2H), 6.35 (d, J=8.0 Hz, 1H), 5.23 (d, J=6.0 Hz, 1H), 5.03 (d, J=6.0 Hz, 1H), 4.15 (d, J=6.0 Hz, 1H), 2.95-2.98 (m, 1H), 2.75-2.80 (m, 2H), 2.56-2.60 (m, 1H). [α]$_D^{20}$=−32.6° (c=1.0, MeOH); >99.9% ee.

Example 283 trans-3-[(S)-hydroxy(pyridin-2-yl)methyl]-3-[4-(trifluoromethyl)pyridin-2-yl]cyclobutanol The title compound was obtained from the chiral separation described in Example 282. MS: m/z 325.1 [M+H]$^+$; $^1$H NMR: (400 MHz, 400 MHz, CDCl$_3$): δ 8.66 (d, J=5.2 Hz, 1H), 8.44 (d, J=4.0 Hz, 1H), 7.42-7.47 (td, J=2.0 Hz, 1H), 7.30-7.33 (dd, J$_1$=0.8 Hz, J$_2$=4.8 Hz, 1H), 7.10-7.16 (m, 1H), 7.06 (s, 1H), 6.59 (d, J=8.0 Hz, 1H), 4.98 (d, J=4.8 Hz, 1H), 4.82 (d, J=6.4 Hz, 1H), 4.36 (t, J=6.8 Hz, 1H), 3.12-3.25 (m, 2H), 2.23-2.41 (m, 2H). [α]$_D^{20}$=−53.9° (c=1.0, MeOH); >99.9% ee.

Example 284 pyridin-2-yl[1-(tetrahydrofuran-3-yl)cyclobutyl]methanol

Example 285 cis-3-[(S)-hydroxy(pyridin-2-yl)methyl]-1-methyl-3-[4-(trifluoromethyl)-pyridin-2-yl]cyclobutanol To a solution of Example 277F (2.0 g, 6.21 mmol) in THF (60 mL) was added methyllithium (4.76 mL, 14.27 mmol) at −78° C., then the reaction was stirred overnight. The reaction mixture was quenched with saturated KH$_2$PO$_4$ solution (30 mL), extracted with EtOAc (50 mL×2). The combined organic phases were washed with brine (50 mL), dried over MgSO$_4$, filtered, and concentrated. The crude mixture was separated on chiral column (Column: AD-H, 50×250 mm, 5 μm; CO$_2$/MeOH=80/20; flow rate: 120 g/min; sample solution: 10.2 g in 100 mL MeOH) to give the title compounds (2.06 g, 4.75 mmol, 77% yield) and Example 286 (2.08 g, 1.045 mmol, 16.84% yield) as white solids. MS: 339.0 [M+H]$^+$; $^1$H NMR: (400 MHz, 400 MHz, CDCl$_3$): δ 8.70 (d, J=4.8 Hz, 1H), 8.40 (d, J=4.4 Hz, 1H), 7.30-7.37 (m, 2H), 7.10-7.15 (m, 1H), 6.97 (s, 1H), 6.19 (d, J=7.6 Hz, 1H), 5.50 (brs, 1H), 5.05 (s, 1H), 3.90 (brs, 1H), 2.99 (d, J=2.0 Hz, 1H), 2.79 (d, J=2.0 Hz, 1H), 2.70 (d, J=1.2 Hz, 1H), 2.48 (d, J=1.2 Hz, 1H), 1.20 (s, 3H). [α]$_D^{20}$=−41.6° (c=1.0, MeOH); >99.9% ee.

Example 286 trans-3-[(S)-hydroxy(pyridin-2-yl)methyl]-3-[4-(trifluoromethyl)pyridin-2-yl]cyclobutanol The title compound was obtained from the chiral separation as described in Example 285. MS: 339.0 [M+H]$^+$; $^1$H NMR: (400 MHz, 400 MHz, CDCl$_3$): δ 8.60 (d, J=4.8 Hz, 1H), 8.43 (d, J=4.8 Hz, 1H), 7.49-7.50 (m, 1H), 7.25-7.30 (m, 2H), 7.14 (dd, J$_1$=4.8 Hz, J$_2$=7.2 Hz, 1H), 6.72 (d, J=8.0 Hz, 1H), 5.06 (s, 1H), 4.85 (br, 1H), 3.47 (s, 1H), 2.99 (d, J=13.2 Hz, 1H), 2.89 (d, J=13.2 Hz, 1H), 2.64 (dd, J$_1$=2.8 Hz, J$_2$=9.2 Hz, 1H), 2.48 (dd, J$_1$=2.8 Hz, J$_2$=9.2 Hz, 1H), 1.39 (s, 3H). [α]$_D^{20}$=−59.8° (c=1.0, MeOH); >99.9% ee.

Example 287

[1-(3,4-dichlorophenyl)cyclobutyl](5-methoxypyridin-2-yl) methanol

Example 288

(S)-pyridin-2-yl{1-[4-(trifluoromethoxy)phenyl] cyclobutyl}methyl acetate

Example 289

[1-(3,4-dichlorophenyl)cyclobutyl](4-methoxypyridin-2-yl) methanol

Example 290 cis-3-[(R)-hydroxy(pyridin-2-yl)methyl]-3-[4-(trifluoromethyl)pyridin-2-yl]cyclobutanol Example 278 (5.80 g, 18.0 mmol) was dissolved in anhydrous THF (90 mL) and chilled with a dry ice/acetone bath. The solution was treated slowly with 1.6 M methyl lithium in diethyl ether (20 mL, 32 mmol). At this point, the solution became a gelatinous mass and additional THF (50 mL) was added to restore efficient stirring. More 1.6 M methyl lithium in diethyl ether (20 mL, 32 mmol) was slowly added. The bath was permitted to slowly warm to 0° C., and it was kept at that temperature for another 30 minutes, then rechilled to −20° C. The reaction mixture was quenched slowly with 2 M aqueous HCl (30 mL) and the bath was removed. Hexanes (50 mL) was added and the aqueous phase was separated and extracted with EtOAc. The combined organic phases were washed with brine, dried (Na$_2$SO$_4$), filtered, and concentrated. The residue was chromatographed on silica (0 to 6% MeOH in 1:2 CH$_3$CN/CH$_2$Cl$_2$) to give 1.26 g of the title compound. MS (ESI) m/z=339 (M+H)$^+$. $^1$H NMR (300 MHz, DMSO-d$_6$) δ 8.60 (d, J=5.1 Hz, 1H), 8.28 (ddd, J=4.8, 1.7, 1.0 Hz, 1H), 7.54-7.45 (m, 2H), 7.22-7.20 (m, 1H), 7.12 (ddd, J=7.5, 4.8, 1.1 Hz, 1H), 6.72-6.67 (m, 1H), 5.76 (d, J=4.7 Hz, 1H), 4.95-4.91 (m, 2H), 2.84 (d, J=12.0 Hz, 1H), 2.76 (d, J=12.0 Hz, 1H), 2.57-2.49 (m, 1H), 2.45 (dd, J=12.0, 3.7 Hz, 1H), 0.84 (s, 3H).

Example 291

3-[(R)-hydroxy(pyridin-2-yl)methyl]-3-[6-methyl-4-(trifluoromethyl)-pyridin-2-yl]cyclobutanone The title compound was isolated from the chromatography described in Example 290. MS (ESI) m/z=337 (M+H)$^+$. $^1$H NMR (300 MHz, DMSO-d$_6$) δ 8.31 (ddd, J=4.8, 1.8, 0.9 Hz, 1H), 7.63 (ddd, J=7.9, 7.5, 1.8 Hz, 1H), 7.43 (s, 1H), 7.18 (ddd, J=7.5, 4.8, 1.1 Hz, 1H), 7.14 (s, 1H), 7.13-7.08 (m, 1H), 6.07 (d, J=5.0 Hz, 1H), 5.05 (d, J=5.0 Hz, 1H), 3.73-3.59 (m, 2H), 3.52-3.33 (m, 2H), 2.46 (s, 3H).

Example 292

[1-(6-chloro-1,3-benzothiazol-2-yl)cyclobutyl](pyridin-2-yl)methanol

Example 293

3-[hydroxy(pyridin-2-yl)methyl]-3-[4-(trifluoromethyl)pyridin-2-yl]-cyclobutanone To a solution of Example 277E (28.6 g, 78 mmol) in acetone (112 mL) was added 6N HCl (56 mL) at room temperature and the reaction was stirred overnight. The reaction mixture was basified with 3N NaOH (120 mL) and extracted with EtOAc (200 mL×2). The combined organic phases were washed with brine (100 mL), dried over Na$_2$SO$_4$, filtered, and concentrated to give the title compound (25 g, 76 mmol, 97% yield) as a white solid. $^1$H NMR: (400 MHz, CDCl$_3$): δ 8.65 (d, J=5.2 Hz, 1H), 8.40 (d, J=4.8 Hz, 1H), 7.36-7.40 (d, J=1.6 Hz, 1H), 7.33 (d, J=0.8 Hz, 1H), 7.15 (s, 1H), 7.08-7.12 (m, 1H), 6.38 (d, J=8.0 Hz, 1H), 5.10 (d, J=5.6 Hz, 1H), 4.86 (d, J=6.4 Hz, 1H), 3.78-3.86 (m, 1H), 3.58-3.64 (m, 1H), 3.40-3.46 (m, 1H), 3.22-3.29 (m, 1H).

Example 294

3-[(S)-hydroxy(pyridin-2-yl)methyl]-3-[4-(trifluoromethyl) pyridin-2-yl]-cyclobutanol To a solution of Example 277F (4.5 g, 13.96 mmol) in dichloromethane (30 mL) and MeOH (3.00 mL) was added NaBH$_4$ (0.634 g, 16.76 mmol) at 0° C., then the reaction was stirred at room temperature for 3 hours. To the reaction mixture was added water (10 mL) and extracted with dichloromethane (40 mL×2). The combined organic phases were dried over Na$_2$SO$_4$, filtered, and concentrated to give the title compound. MS: 325.1 [M+H]$^+$. $^1$H NMR: (400 MHz, CDCl$_3$): δ 8.65 (d, J=5.2 Hz, 1H), 8.40 (d, J=4.8 Hz, 1H), 7.36-7.40 (d, J=1.6 Hz, 1H), 7.33 (d, J=0.8 Hz, 1H), 7.15 (s, 1H), 7.08-7.12 (m, 1H), 6.38 (d, J=8.0 Hz, 1H), 5.10 (d, J=5.6 Hz, 1H), 4.86 (d, J=6.4 Hz, 1H), 3.78-3.86 (m, 1H), 3.58-3.64 (m, 1H), 3.40-3.46 (m, 1H), 3.22-3.29 (m, 1H). [α]$_D^{20}$=−21.8° C. (c=1.0, MeOH).

Example 295

3-[hydroxy(pyridin-2-yl)methyl]-3-[5-(trifluoromethyl)pyridin-3-yl]-cyclobutanone

Example 295A (5-(trifluoromethyl)pyridin-3-yl)methanol

To a solution of 5-(trifluoromethyl)nicotinic acid (10.0 g, 52.3 mmol) in THF (250 mL) was added triethyl amine (7.18 mL, 52.3 mmol) at room temperature, then ethyl chloroformate (4.98 mL, 52.3 mmol) was added dropwise at 5° C. slowly. The reaction was stirred for 1 hour to give ethyl [5-(trifluoromethyl)pyridin-3-yl]carbonyl carbonate. NaBH$_4$ (1.702 g, 45.0 mmol) was added to the mixture portionwise at −78° C. followed by addition of MeOH (100 mL) over 30 minutes. The reaction was warmed to 0° C. and stirred overnight. After removal of the solvent, the residue was purified by column chromatography on silica gel eluting with petroleum ether/ethyl acetate=2/1 to give the title compound (5.7 g, 62% yield) as a yellow oil. MS: 178.0 [M+H]$^+$; $^1$H NMR (400 MHz, CDCl$_3$): δ 8.73 (s, 1H), 8.70 (d, J=1.2 Hz, 1H), 7.92 (d, J=0.4 Hz, 1H), 4.77 (s, 2H), 2.34 (brs, 1H).

Example 295B (5-(trifluoromethyl)pyridin-3-yl)methyl methanesulfonate

To a solution of Example 295A (1.0 g, 4.91 mmol) and triethylamine (0.685 mL, 4.91 mmol) in dichloromethane (50 mL) at −20° C. under N$_2$ was added methanesulfonyl chloride (0.383 mL, 4.91 mmol) dropwise. After 45 minutes, the reaction was allowed to warm to room temperature and diluted with dichloromethane (75 mL). The reaction mixture was washed with water (75 mL), saturated NaHCO$_3$ (75 mL), and brine (75 mL). Concentration in vacuo afforded the title compound (0.825 g, 2.263 mmol, 46.1% yield) as a yellow oil. MS: 256.1 [M+H]$^+$ Example 295C 2-(5-(trifluoromethyl)pyridin-3-yl)acetonitrile To a solution of Example 295B (1.0 g, 3.92 mmol) in DMSO (10 mL) was added KCN (0.255 g, 3.92 mmol) in one portion at room temperature. The reaction mixture was stirred at room temperature overnight. The reaction mixture was diluted with EtOAc (50 mL) and the organic layer washed with H$_2$O (50 mL), dried over Na$_2$SO$_4$, filtered, and concentrated. The residue was purified by column chromatography eluting with petroleum ether: EtOAc=3:1 to give the title compound (460 mg, 61.2% yield) as a yellow oil. $^1$H NMR (400 MHz, CDCl$_3$): δ 8.89 (s, 1H), 8.81 (d, J=1.6 Hz, 1H), 7.96 (s, 1H), 3.88 (s, 2H).

Example 295D 3-hydroxy-1-(5-(trifluoromethyl)pyridin-3-yl)cyclobutanecarbonitrile To a solution of Example 295C (9.60 g, 51.6 mmol) in THF (200 mL) was added methyllithium (20.63 mL, 61.9 mmol) dropwise slowly at −78° C. during 0.5 h, then the reaction was stirred for 1 hour at −78° C. A solution of 2-(bromomethyl)oxirane (8.48 g, 61.9 mmol) in THF (20 mL) was added to the reaction mixture dropwise, then the reaction was stirred for additional 1 hour and methylmagnesium bromide (20.63 mL, 61.9 mmol) added slowly at −70° C. After the completion of addition, the reaction was warmed to room temperature and stirred overnight. A solution of saturated NH$_4$Cl solution (50 mL) was added and the mixture was extracted with EtOAc (300 mL×2). The combined organic phases were washed by brine (200 mL), dried over Na$_2$SO$_4$, filtered, and concentrated to provide crude title compound (13.2 g) as a dark oil which was used for the next step without further purification. MS: 243.1 [M+H]$^+$.

Example 295E 3-oxo-1-(5-(trifluoromethyl)pyridin-3-yl)cyclobutanecarbonitrile

To a solution of Example 295D (12.4 g, 51.2 mmol) in dichloromethane (150 mL) was added Dess-Martin periodinane (23.89 g, 56.3 mmol) portionwise at 0° C., then the reaction was stirred for 3 h at rt. The completion of the reaction was monitored by LCMS and TLC. Saturated Na$_2$S$_2$O$_3$ solution (115 g) was added and the aqueous layer extracted with dichloromethane (100 mL×2). The combined organic phases were dried over Na$_2$SO$_4$, filtered, and concentrated. The residue was purified by column chromatography on silica gel (petroleum ether/EtOAc=15/1-10/1) to give the title compound (3.3 g, 13.74 mmol, 26.8% yield) as a pale yellow solid. MS: 241.1 [M+H]$^+$; $^1$H NMR (400 MHz, CDCl$_3$): δ 8.95 (d, J=2.4 Hz, 1H), 8.89 (d, J=1.2 Hz, 1H), 7.96 (s, 1H), 4.14-4.23 (m, 2H), 3.70-3.75 (m, 2H).

Example 295F 2-(5-(trifluoromethyl)pyridin-3-yl)-5,8-dioxaspiro[3.4]octane-2-carbonitrile To a solution of Example 295E (1.28 g, 5.33 mmol) in dichloromethane (20 mL) was added ethane-1,2-diol (2.71 mL, 53.3 mmol) and chlorotrimethylsilane (2.32 g, 21.32 mmol), then the reaction was stirred at room temperature overnight. After addition of saturated NaHCO$_3$ solution (20 mL), the aqueous layer was extracted with dichloromethane (30 mL×2). The combined organic phases were washed with brine (50 mL), dried over MgSO$_4$, filtered, and concentrated. The residue was purified by column chromatography on silica gel (petroleum ether/EtOAc=5/1) to give title compound (970 mg, 3.34 mmol, 62.8% yield) as a yellow oil. MS: 285.0 [M+H]$^+$; $^1$H NMR (400 MHz, CDCl$_3$): δ 8.98 (d, J=2.0 Hz, 1H), 8.81 (d, J=0.8 Hz, 1H), 8.03 (s, 1H), 3.88-9.99 (m, 4H), 3.25-3.33 (dd, J$_1$=4.8, J$_2$=10.8, 2H), 2.92-2.96 (dd, J$_1$=4.8, J$_2$=10.8, 2H).

Example 295G pyridin-2-yl(2-(5-(trifluoromethyl)pyridin-3-yl)-5,8-dioxaspiro[3.4]octan-2-yl)methanone To a solution of 2-bromopyridine (1.896 g, 12.00 mmol) in diethyl ether (3 mL) was added n-butyllithium (7.26 ml, 11.61 mmol) dropwise at −78° C., then the reaction was stirred for 1 hour. A solution of Example 295F (2.2 g, 7.74 mmol) in diethyl ether (4 mL) was added to the reaction dropwise. After the completion of addition, the mixture was warmed to −30° C. and stirred for additional 3 hours. The mixture was acidified with 3N HCl solution to pH=4, stirred for 0.5 hour, basified with 5% NaOH solution, and extracted with EtOAc (30 mL×2). The combined organic phases were washed with brine (50 mL), dried over MgSO$_4$, and filtered. After removal of solvent, the residue was purified by column chromatography on silica gel (petroleum ether/EtOAc=5/1) to provide the title compound (1.34 g) as a colorless oil. MS: 365.1 [M+H]$^+$.

Example 295H pyridin-2-yl(2-(5-(trifluoromethyl)pyridin-3-yl)-5,8-dioxaspiro[3.4]octan-2-yl)methanol To a mixture of crude Example 295G (1.94 g, 5.33 mmol) in dichloromethane (40 mL) and MeOH (4.00 mL) was added NaBH$_4$ (0.302 g, 7.99 mmol) in one portion. The reaction was stirred at room temperature overnight. After addition of H$_2$O (15 mL), the aqueous layer was extracted with dichloromethane (30 mL×2). The combined organic phases were washed with brine (50 mL), dried over MgSO$_4$, filtered, and concentrated. The residue was purified by column chromatography on silica gel (Petroleum ether/EtOAc=4:1) to give the title compound (780 mg, 2.129 mmol, 40.0% yield). MS: 367.1 [M+H]$^+$

Example 295I

3-[hydroxy(pyridin-2-yl)methyl]-3-[5-(trifluoromethyl)pyridin-3-yl]-cyclobutanone To a solution of Example 295H (960 mg, 2.62 mmol) in acetone (5 mL) was added 6N HCl (2.5 mL), then the reaction was stirred at 30° C. overnight. The reaction was basified with 3N NaOH solution to pH=9 and extracted with EtOAc (20 mL×2). The combined organic phases were washed by brine (20 mL), dried over MgSO$_4$, filtered, and concentrtated to obtain title compound (850 mg, 2.453 mmol, 94% yield). MS: 323.0 [M+H]$^+$; $^1$H NMR (400 MHz, CDCl$_3$): δ 8.77 (s, 1H), 8.46 (d, J=4.8 Hz, 1H), 8.41 (d, J=2.0 Hz, 1H), 7.51-7.55 (m, 1H), 7.37 (s, 1H), 7.21-7.26 (m, 1H), 6.54 (d, J=8.0 Hz, 1H), 4.96 (d, J=6.0 Hz, 1H), 4.67 (d, J=6.4 Hz, 1H), 3.78-3.95 (m, 2H), 3.20-3.40 (m, 2H).

Example 296

3-[(S)-hydroxy(pyridin-2-yl)methyl]-3-[5-(trifluoromethyl)pyridin-3-yl]-cyclobutanone Chiral resolution of Example 295I (Column: AD-H, 30×250 mm, 5 micron; mobile phase CO$_2$/EtOH=80/20 at flow rate of 80 g/minute; sample solution: 850 mg in 50 mL MeOH) provided the title compound. MS: 322.9 [M+H]$^+$. $^1$H NMR (400 MHz, CDCl$_3$): δ 8.76 (m, 1H), 8.46 (d, J=7.2 Hz, 1H), 8.41 (d, J=2.0 Hz, 1H), 7.50-7.55 (m, 1H), 7.37 (s, 1H), 7.21-7.26 (m, 1H), 6.55 (d, J=8.0 Hz, 1H), 4.96 (s, 1H), 4.69 (brs, 1H), 3.78-3.95 (m, 2H), 3.22-3.41 (m, 2H). [α]$_D^{20}$= −63.52° (c=1.0, MeOH); >95.0% ee.

Example 297 pyridin-2-yl{2-[2-(trifluoromethyl)pyridin-4-yl]-5,8-dioxaspiro[3.4]oct-2-yl}methanol

Example 297A 2-(2-(trifluoromethyl)pyridin-4-yl)-5,8-dioxaspiro[3.4]octane-2-carbonitrile To a solution of 4-chloro-2-(trifluoromethyl)pyridine (10.0 g, 55.1 mmol) and Example 277B (11.57 g, 83 mmol) in THF (100 mL) was added lithium hexamethyl-disilazide (83 mL, 82.6 mmol) dropwise at −78° C. and the reaction was stirred overnight. The reaction solution was quenched with saturated NH$_4$Cl solution (30 mL) and the aqueous layer was extracted with EtOAc (100 mL). The organic layer was dried over Na$_2$SO$_4$, filtered, and concentrated. The residue was purified by column chromatography (petroleum ether/EtOAc=3:1) to give the title compound (12.4 g, 43.2 mmol, 78% yield) as a yellow oil. MS: 285.0 [M+H]$^+$; $^1$H NMR (400 MHz, CDCl$_3$): δ 8.79 (d, J=5.2 Hz, 1H), 7.91 (d, J=0.8 Hz, 1H), 7.74 (dd, J$_1$=1.6 Hz, J$_2$=5.2 Hz, 1H), 3.91-4.06 (m, 4H), 3.36 (dd, J$_1$=3.2 Hz, J$_2$=10.8 Hz, 2H), 2.99 (dd, J$_1$=3.2 Hz, J$_2$=11.2 Hz, 2H).

Example 297B pyridin-2-yl(2-(2-(trifluoromethyl)pyridin-4-yl)-5,8-dioxaspiro[3.4]octan-2-yl)methanone To a solution of 2-bromopyridine (25.5 g, 161 mmol) in THF (50 mL) was added n-butyllithium (95 mL, 152 mmol) dropwise at −78° C. and the reaction was stirred for 30 minutes. Example 297A (27.8 g, 98 mmol) in diethyl ether (120 mL) was added and the reaction was stirred for 4 hours at −78° C. After acidification by the addition of 2N HCl to the reaction until pH=4, the reaction was stirred for 15 minutes and extracted twice with EtOAc (100 mL×2). The combined organic phases was washed with brine (200 mL), dried over MgSO$_4$, filtered, and concentrated. The residue was purified by column chromatography (petroleum ether/EtOAc=4:1) to give the title compound (34.0 g, 84 mmol, 86% yield) as a yellow oil. MS: 364.9 [M+H]$^+$.

Example 297C pyridin-2-yl{2-[2-(trifluoromethyl)pyridin-4-yl]-5,8-dioxaspiro[3.4]oct-2-yl}methanol To a solution of Example 297B (34.0 g, 93 mmol) in dichloromethane (50 mL) and MeOH (5 mL) was added NaBH$_4$ (5.30 g, 140 mmol) and the reaction was stirred at room temperature for 3 h. After addition of water (35 mL), the reaction mixture was extracted with dichloromethane (60 mL×2). The organic phase was separated, washed with brine (200 mL), dried over MgSO$_4$ and concentrated. The residue was purified by column chromatography (petroleum ether/EtOAc=2:1 to 1:1) to give title compound (20.6 g, 56.2 mmol, 60.3% yield) as a colorless oil. MS: 367.1 [M+H]$^+$; $^1$H NMR (400 MHz, CDCl$_3$): δ 8.49 (d, J=5.2 Hz, 1H), 8.26 (d, J=4.8 Hz, 1H), 7.55-7.61 (m, 1H), 7.13-7.17 (m, 1H), 6.99-7.04 (m, 2H), 6.94 (s, 1H), 5.13 (d, J=6.4 Hz, 1H), 4.43 (d, J=7.2 Hz, 1H), 3.97-4.01 (m, 2H), 3.84-3.89 (m, 2H), 3.09-3.23 (m, 2H), 2.64-2.71 (m, 2H).

Example 298

3-[hydroxy(pyridin-2-yl)methyl]-3-[2-(trifluoromethyl)pyridin-4-yl]-cyclobutanone To a solution of Example 297C (20.1 g, 54.9 mmol) in acetone (100 mL) was added 6N HCl (50.0 mL) and the reaction was stirred overnight. The reaction was basified with 3N NaOH till pH=8 and extracted with EtOAc (60 mL×2). The combined organic phases was washed with brine (100 mL), dried over MgSO$_4$, filtered, and concentrated to give the title compound (17.0 g, 50.6 mmol, 92.0% yield) as a yellow solid. MS: 323.0 [M+H]$^+$; $^1$H NMR: (400 MHz, CDCl$_3$): δ 8.62 (t, J=3.6 Hz, 1H), 8.47 (d, J=4.8 Hz, 1H), 7.48-7.53 (m, 1H), 7.14-7.25 (m, 1H), 7.14 (t, J=1.6 Hz, 2H), 6.51 (d, J=8.0 Hz, 1H), 4.97 (s, 1H), 4.75 (brs, 1H), 3.88-3.94 (m, 1H), 3.74-3.81 (m, 1H), 3.30-3.60 (m, 1H), 3.17-3.23 (m, 1H).

Example 299

3-[(S)-hydroxy(pyridin-2-yl)methyl]-3-[2-(trifluoromethyl)pyridin-4-yl]-cyclobutanone Chiral HPLC separation (Column: AD-H, 30×250 mm, 5 micron; mobile phase: CO$_2$/EtOH/diethylamine=90/10/0.1; flow rate: 70 g/min; sample solution: 26 g in 230 mL MeOH) of Example 298 gave title compound (5.0 g, 29% yield) as a white solid. MS: 323.0 [M+H]$^+$; $^1$H NMR: (400 MHz, CDCl$_3$): δ 8.62 (t, J=3.6 Hz, 1H), 8.47 (d, J=4.8 Hz, 1H), 7.48-7.53 (m, 1H), 7.14-7.25 (m, 1H), 7.14 (t, J=1.6 Hz, 2H), 6.51 (d, J=8.0 Hz, 1H), 4.97 (s, 1H), 4.75 (brs, 1H), 3.88-3.94 (m, 1H), 3.74-3.81 (m, 1H), 3.30-3.60 (m, 1H), 3.17-3.23 (m, 1H). [α]$_D^{20}$=−42.4° (c=1.0. MeOH).

Example 300

[1-(6-fluoro-1,3-benzothiazol-2-yl)cyclobutyl](pyridin-2-yl)methanol

Example 301

[1-(6-chloro-1,3-benzoxazol-2-yl)cyclobutyl](pyridin-2-yl)methanol

Example 302 cis-3-[(S)-hydroxy(pyridin-2-yl)methyl]-1-methyl-3-[2-(trifluoromethyl)-pyridin-4-yl]cyclobutanol To a solution of Example 299 (2.8 g, 8.69 mmol) in THF (50 mL) was added methyllithium (6.37 ml, 19.11 mmol) dropwise at −78° C. and then the reaction was stirred overnight allowing temperature to become ambient. The reaction mixture was quenched with saturated $KH_2PO_4$ solution (30 mL), extracted with EtOAc (50 mL×2). The combined organic phases were washed by brine (50 mL), dried over $MgSO_4$, filtered, and concentrated. The crude mixture was resolved by chiral HPLC (AD-H, 30×250 mm, 5 μm; mobile phase: $CO_2$/EtOH/hexanes/diethylamine=85/7.5/7.5/0.1; flow rate 80 g/min; sample solution: 2 g in 40 mL MeOH) to give the title compound (600 mg, 1.77 mmol, 21% yield) and Example 307 (100 mg, 0.30 mmol, 3.4% yield) as white solids. MS: 339 $[M+H]^+$; $^1H$ NMR: (400 MHz, 400 MHz, $CDCl_3$): δ 8.49 (d, J=4.8 Hz, 1H), 8.32 (d, J=4.4 Hz, 1H), 7.35-7.40 (m, 1H), 7.09-7.12 (m, 1H), 6.93-6.97 (m, 2H), 6.31 (d, J=8.0 Hz, 1H), 4.83 (s, 1H), 2.79-2.97 (dd, $J_1$=12.8 Hz, $J_2$=59.2 Hz, 2H), 2.30-2.48 (dd, $J_1$=12.8 Hz, $J_2$=58.4 Hz, 2H), 1.14 (s, 3H).

Example 303 cis-3-[(S)-hydroxy(pyridin-2-yl)methyl]-3-[5-(trifluoromethyl)pyridin-3-yl]cyclobutanol To a solution of Example 296 (80 mg, 0.248 mmol) in dichloromethane (5 mL) and MeOH (0.5 mL) was added $NaBH_4$ (9.39 mg, 0.248 mmol). The reaction was stirred at room temperature for 3 hours. After addition of $H_2O$ (5 mL), the mixture was extracted with dichloromethane (15 mL×2). The combined organic phases was washed with brine (20 mL), dried over $MgSO_4$, and filtered. After removal of solvent, the residue (80 mg, 99% yield) was resolved by chiral HPLC (AD-H, 30×250 mm, 5 μm; mobile phase: $CO_2$/EtOH/diethylamine=85/15/0.1; flow rate: 80 g/min; sample solution: 80 mg in 10 mL MeOH) to give the title compound (40 mg, 50% yield) and Example 304 (10 mg, 12.5% yield) as white solids. MS: 325$[M+H]^+$; $^1H$ NMR: (400 MHz, 400 MHz, $CDCl_3$): δ 8.57 (s, 1H), 8.27 (d, J=1.6 Hz, 1H), 8.24 (d, J=4.8 Hz, 1H), 7.42-7.47 (m, 1H), 7.22 (s, 1H), 7.07 (dd, $J_1$=4.8 Hz, $J_2$=2.0 Hz, 1H), 6.61 (d, J=8.0 Hz, 1H), 4.87 (s, 1H), 4.03-4.09 (m, 1H), 2.64-2.73 (m, 4H).

Example 304 trans-3-[(S)-hydroxy(pyridin-2-yl)methyl]-3-[5-(trifluoromethyl)pyridin-3-yl]cyclobutanol Chiral separation as described for Example 303 also provided the title compound (10 mg, 12.5% yield) as a white solid. MS: 325 $[M+H]^+$; $^1H$ NMR: (400 MHz, 400 MHz, $CDCl_3$): δ 8.55 (s, 1H), 8.29 (d, J=4.4 Hz, 1H), 8.14 (d, J=1.6 Hz, 1H), 7.45-7.49 (m, 1H), 7.08-7.13 (m, 2H), 6.68 (d, J=7.6 Hz, 1H), 4.74 (s, 1H), 4.48 (t, J=7.2 Hz, 1H), 3.12-3.19 (m, 2H), 2.12-2.21 (m, 2H).

Example 305 cis-3-[(S)-hydroxy(pyridin-2-yl)methyl]-3-[2-(trifluoromethyl)pyridin-4-yl]-cyclobutanol To a solution of Example 299 (500 mg, 1.551 mmol) in dichloromethane (15 mL) and MeOH (1.5 mL) was added $NaBH_4$ (70.4 mg, 1.862 mmol) and the reaction was stirred overnight allowing the temperature to become ambient. After water (5 mL) was added, the reaction mixture was extracted with dichloromethane (20 mL×2). The combined organic phases was washed with brine (20 mL), dried over $MgSO_4$, filtered, and concentrated. The crude mixture was resolved by chiral HPLC (OZ—H, 30×250 mm, 5 μm; mobile phase: $CO_2$/isopropanol/deiethylamine=80/20/0.1; flow rate 80 g/min; sample solution: 1.5 g in 220 mL MeOH) to provide the title compound (240 mg, 48% yield) and Example 306. MS: 325 $[M+H]^+$; $^1H$ NMR: (400 MHz, $CDCl_3$): δ 8.48 (d, J=5.2 Hz, 1H), 8.30 (d, J=4.8 Hz, 1H), 7.40-7.45 (m, 1H), 7.04-7.11 (m, 1H), 7.00-7.02 (m, 2H), 6.48 (d, J=7.6 Hz, 1H), 4.94 (brs, 1H), 4.81 (s, 1H), 4.05-4.08 (m, 1H), 3.41 (s, 1H), 2.71-2.74 (m, 2H), 2.56-2.67 (m, 2H).

Example 306 trans-3-[(S)-hydroxy(pyridin-2-yl)methyl]-3-[2-(trifluoromethyl)pyridin-4-yl]cyclobutanol Chiral separation as described for Example 305 provided also the title compound (200 mg, 40%) as a white solid. MS: 325 $[M+H]^+$; $^1H$ NMR: (400 MHz, 400 MHz, $CDCl_3$): δ 8.45 (d, J=2.4 Hz, 1H), 8.32 (d, J=4.8 Hz, 1H), 7.43-7.48 (m, 1H), 7.08-7.13 (m, 1H), 6.92 (d, J=2.0 Hz, 2H), 6.62 (d, J=7.6 Hz, 1H), 5.22 (s, 1H), 4.71 (s, 1H), 4.42-4.47 (m, 2H), 3.11-3.16 (m, 2H), 2.08-2.20 (m, 2H).

Example 307 trans-3-[(S)-hydroxy(pyridin-2-yl)methyl]-1-methyl-3-[2-(trifluoromethyl)-pyridin-4-yl]cyclobutanol Chiral HPLC separation as described in Example 302 also provided the title compound (100 mg, 3.4%) as a white solid. MS: 339 $[M+H]^+$; $^1H$ NMR: (400 MHz, $CDCl_3$): δ 8.44 (d, J=5.2 Hz, 1H), 8.24 (d, J=4.8 Hz, 1H), 7.45-7.50 (m, 1H), 7.07-7.11 (m, 1H), 6.96-7.00 (m, 2H), 6.69 (d, J=8.0 Hz, 1H), 4.80 (d, J=6.0 Hz, 1H), 4.48 (d, J=6.4 Hz, 1H), 2.92-2.97 (m, 2H), 2.35-2.41 (m, 2H), 1.47 (s, 3H).

Example 308 cis-3-[(S)-hydroxy(pyridin-2-yl)methyl]-1-methyl-3-[5-(trifluoromethyl)-pyridin-3-yl]cyclobutanol To a solution of Example 296 (200 mg, 0.621 mmol) in THF (10 mL) was added methyllithium (0.455 mL, 1.365 mmol) dropwise at −78° C. The reaction was stirred for 1 hour and warmed to room temperature overnight. After addition of saturated solution of $NH_4Cl$ (10 mL), the aqueous layer was extracted with EtOAc (15 mL×2). The combined organic phases were washed with brine (20 mL), dried over $Na_2SO_4$, and filtered. After the removal of solvent, the residue was resolved by chiral HPLC separation (AD-H, 20×250 mm, 5 μm; mobile phase: $CO_2$/MeOH/diethylamine=85/15/0.1; flow rate: 80 g/min; sample solution: 200 mg in 22 mL MeOH) to provide the title compound (50 mg, 0.148 mmol, 23.81% yield) and Example 309 (10 mg, 0.030 mmol, 4.76% yield). MS: 339$[M+H]^+$; $^1H$ NMR: (400 MHz, $CDCl_3$): δ 8.62 (s, 1H), 8.32 (d, J=4.8 Hz, 1H), 8.21 (d, J=1.6 Hz, 1H), 7.37-7.41 (m, 1H), 7.08-7.16 (m, 2H), 6.63 (d, J=8.0 Hz, 1H), 5.23 (s, 1H), 5.08 (d, J=5.2 Hz, 1H), 4.85 (d, J=3.6 Hz, 1H), 3.27 (s, 1H), 2.94-2.97 (m, 1H), 2.81-2.85 (m, 1H), 2.49-2.52 (m, 1H), 2.34-2.37 (m, 1H), 1.15 (s, 3H).

Example 309 trans-3-[(S)-hydroxy(pyridin-2-yl)methyl]-1-methyl-3-[5-(trifluoromethyl)-pyridin-3-yl]cyclobutanol Chiral separation as described for Example 308 also provided the title compound (10 mg, 4.76%). MS: 339 [M+H]$^+$; $^1$H NMR: (400 MHz, CDCl$_3$): δ 8.49 (s, 1H), 8.17-8.22 (m, 2H), 7.46-7.50 (m, 1H), 7.16 (s, 1H), 7.05-7.09 (m, 1H), 6.76 (d, J=8.0 Hz, 1H), 4.83 (s, 1H), 4.47 (brs, 1H), 2.95 (t, J=11.6 Hz, 2H), 2.41 (t, J=10.0 Hz, 2H), 1.47 (s, 3H).

Example 310 trans-3-((S)-hydroxy(pyrimidin-2-yl)methyl)-1-methyl-3-(4-(trifluoromethoxy)phenyl)cyclobutanol

Example 310A trans-3-((tert-butyldimethylsilyl)oxy)-3-methyl-1-(4-(trifluoromethoxy)-phenyl)cyclobutyl)(pyrimidin-2-yl)methanol To a solution of 2-iodopyrimidine (391 mg, 1.90 mmol), trans-3-((tert-butyldimethylsilyl)oxy)-3-methyl-1-(4-(trifluoromethoxy)phenyl)cyclobutanecarbaldehyde (492 mg, 1.27 mmol) and lithium bromide (2.11 mL, 3.17 mmol, 1.5 M in THF) in anhydrous THF (15 mL) at −95° C. was added n-butyl lithium (1.19 mL, 1.90 mmol, 1.6 M in hexanes) dropwise over about 8-10 minutes. After 60 minutes the mixture was quenched with saturated aqueous NH$_4$Cl (3 mL), warmed to ambient temperature, and extracted with dichloromethane (50 mL). The organic extract was washed with saturated aqueous NH$_4$Cl, dried (Na$_2$SO$_4$), filtered, and concentrated. Purification by chromatography (SiO$_2$, 0-25% ethyl acetate/heptane gradient) provided the title compound (489 mg, 1.04 mmol, 82% yield). MS (DCI$^+$) M/Z 469 (M+H)$^+$.

Example 310B (S)-((trans)-3-(tert-butyldimethylsilyloxy)-3-methyl-1-(4-(trifluoromethoxy)phenyl)cyclobutyl)(pyrimidin-2-yl)methanol and

Example 310C (R)-((trans)-3-((tert-butyldimethylsilyl)oxy)-3-methyl-1-(4-(trifluoromethoxy)phenyl)cyclobutyl)(pyrimidin-2-yl)methanol The mixture from Example 310A was separated by SFC using a CHIRALPAK OD-H column, 5-50% MeOH/CO$_2$ gradient, 70 mL/minute flow rate, 150 barr, to provide Example 310B as the first eluting isomer and Example 310C as the second eluting isomer. MS (DCI$^+$) M/Z 469 (M+H)$^+$ for both isomers.

Example 310D (trans)-3-((S)-hydroxy(pyrimidin-2-yl)methyl)-1-methyl-3-(4-(trifluoromethoxy)phenyl)cyclobutanol To a solution of methanol (0.68 mL, 1.67 mmol) at 0° C. was added acetyl chloride (0.026 mL, 0.37 mmol). The methanolic HCl solution was added to a room temperature solution of Example 310B (87 mg, 0.19 mmol) in MTBE (3 mL). The mixture was stirred for 60 minutes then diluted with MTBE (10 mL) and washed with 2N NaOH (2 mL), brine (10 mL), dried over Na$_2$SO$_4$ and concentrated. Purification by flash chromatography (SiO$_2$, 0-50% EtOAc/heptanes gradient) afforded the title compound (62 mg, 0.18 mmol, 94% yield). $^1$H NMR (300 MHz, DMSO-d$_6$) δ 8.64-8.57 (m, 2H), 7.31 (t, J=4.9 Hz, 1H), 7.08-7.00 (m, 2H), 6.89-6.82 (m, 2H), 5.02 (d, J=6.2 Hz, 1H), 4.83 (d, J=6.2 Hz, 1H), 4.65 (s, 1H), 3.20-3.03 (m, 1H), 2.97 (d, J=11.4 Hz, 1H), 2.37-2.26 (m, 2H), 1.57 (s, 3H). MS (DCI$^+$) M/Z 355 (M+H)$^+$.

Example 311

(trans)-3-((R)-hydroxy(pyrimidin-2-yl)methyl)-1-methyl-3-(4-(trifluoromethoxy)phenyl)cyclobutanol The title compound was prepared as described in Example 310D, substituting Example 310C for Example 310B. $^1$H NMR (300 MHz, DMSO-d$_6$) δ 8.63-8.57 (m, 2H), 7.31 (t, J=4.9 Hz, 1H), 7.05 (d, J=1.1 Hz, 1H), 7.08-7.01 (m, 2H), 6.89-6.82 (m, 1H), 5.02 (d, J=6.2 Hz, 1H), 4.83 (d, J=6.2 Hz, 1H), 4.65 (s, 1H), 3.20-3.03 (m, 1H), 2.97 (d, J=11.5 Hz, 1H), 2.37-2.26 (m, 2H), 2.02 (s, 3H). MS (DCI$^+$) M/Z 355 (M+H)$^+$.

Example 312

(trans)-3-(3,4-dichlorophenyl)-3-((S)-hydroxy(pyrimidin-2-yl)methyl)-cyclobutanol

Example 312A ((trans)-3-((tert-butyldimethylsilyl)oxy)-1-(3,4-dichlorophenyl)cyclobutyl)-(pyrimidin-2-yl)methanol The title compound was prepared as described in Example 310A, substituting (trans)-3-((tert-butyldimethylsilyl)oxy)-1-(3,4-dichlorophenyl)cyclobutane-carbaldehyde for (trans)-3-((tert-butyldimethylsilyl)oxy)-3-methyl-1-(4-(trifluoromethoxy)phenyl)cyclobutanecarbaldehyde. MS (DCI$^+$) M/Z 439, 441 (M+H)$^+$.

Example 312B (S)-((trans)-3-((tert-butyldimethylsilyl)oxy)-1-(3,4-dichlorophenyl)-cyclobutyl)(pyrimidin-2-yl)methanol and

Example 312C (R)-((trans)-3-((tert-butyldimethylsilyl)oxy)-1-(3,4-dichlorophenyl)-cyclobutyl)(pyrimidin-2-yl)methanol The title compounds were separated by chiral SFC as described in Examples 310A and 310B with Example 312B. Example 312B was isolated as the first eluting isomer and Example 312C as the second eluting isomer. MS (DCI$^+$) M/Z 439, 441 (M+H)$^+$ for both isomers.

Example 312D (trans)-3-(3,4-dichlorophenyl)-3-((S)-hydroxy(pyrimidin-2-yl)methyl)-cyclobutanol The title compound was prepared as described in Example 310D, substituting Example 312B for Example 310B. $^1$H NMR (300 MHz, DMSO-d$_6$) δ 8.68 (d, J=4.9 Hz, 2H), 7.34 (m, 2H), 6.93 (d, J=2.1 Hz, 1H), 6.69 (dd, J=8.3, 2.1 Hz, 1H), 5.25 (d, J=6.4 Hz, 1H), 4.89 (d, J=6.8 Hz, 1H), 4.75 (d, J=6.3 Hz, 1H), 4.12-3.97 (m, 1H), 3.23-3.13 (m, 2H), 2.05-1.97 (m, 2H). MS (ESI$^+$) M/Z 325 (M+H)$^+$.

Example 313

(trans)-3-(3,4-dichlorophenyl)-3-((R)-hydroxy(pyrimidin-2-yl)methyl)-cyclobutanol The title compound was prepared as described in Example 310D, substituting Example 312C for Example 310B. $^1$H NMR (300 MHz, DMSO-$d_6$) δ 8.67 (s, 2H), 7.35 (dd, J=9.2, 4.5 Hz, 2H), 6.93 (d, J=2.1 Hz, 1H), 6.69 (dd, J=8.4, 2.1 Hz, 1H), 5.25 (s, 1H), 4.89 (d, J=6.5 Hz, 1H), 4.75 (s, 1H), 4.16-3.86 (m, 1H), 3.24-3.02 (m, 2H), 2.05-1.97 (m, 2H). MS (ESI$^+$) M/Z 325 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

The invention claimed is:

1. A compound according to Formula (I):

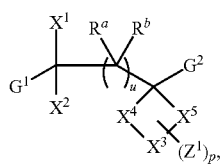

(I)

or a salt thereof, wherein:
R$^a$ and R$^b$ are each absent;
u is 0;
X$^3$ is CH$_2$;
X$^4$ is (CH$_2$)$_m$;
X$^5$ is (CH$_2$)$_n$;
m and n are each 1;
each Z$^1$ group is a substituent on the X$^3$ carbon atom of the ring containing X$^3$, X$^4$, and X$^5$ and is independently halogen oxo C$_1$-C$_4$-alkyl, or —OR$^c$; or two Z$^1$ groups that are situated on the X$^3$ carbon atom, together with the carbon atom to which they are attached, form a 5-membered monocyclic heterocycle ring comprising two oxygen ring atoms;
R$^c$ is hydrogen C$_1$-C$_4$-alkyl;
p is 1 or 2;
X$^1$ is —OH and X$^2$ is hydrogen;
G$^1$ is pyridinyl or pyrimidinyl; each of which is optionally substituted with 1, 2, or 3 substituents independently selected from the group consisting of halogen C$_1$-C$_6$-alkyl, C$_1$-C$_6$-haloalkyl, and N(R$^{gc}$)$_2$;
R$^{gc}$ is hydrogen or C$_1$-C$_6$-alkyl;
G$^2$ is G$^{2d}$;
G$^{2d}$ is phenyl, pyridinyl, or pyrimidinyl; each of which is optionally substituted with 1, 2, or 3 substituents independently selected from the group consisting of halogen, —CN, C$_1$-C$_6$-alkyl, C$_1$-C$_6$-haloalkyl, and —OR$^f$; and
R$^f$ is C$_1$-C$_6$-alkyl or C$_1$-C$_6$-haloalkyl.

2. The compound according to claim 1, or a salt thereof, wherein
the compound has the configuration of Formula (I-i-a):

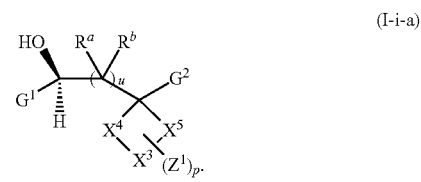

(I-i-a)

3. The compound according to claim 1, or a salt thereof, wherein:
G$^1$ is pyridinyl; which is optionally substituted with 1 or 2 substituents independently selected from the group consisting of halogen, C$_1$-C$_4$-alkyl, C$_1$-C$_4$-haloalkyl, and N(R$^{gc}$)$_2$;
R$^{gc}$ is hydrogen or C$_1$-C$_4$alkyl;
G$^{2d}$ is phenyl or pyridinyl; each of which is optionally substituted with 1, 2, or 3 substituents independently selected from the group consisting of halogen, C$_1$-C$_4$-alkyl, C$_1$-C$_4$-haloalkyl, and —OR$^f$; and
R$^f$ is C$_1$-C$_4$-alkyl or C$_1$-C$_4$-haloalkyl.

4. The compound according to claim 1, or a salt thereof, wherein
G$^1$ is unsubstituted pyridinyl;
G$^{2d}$ is phenyl or pyridinyl; each of which is optionally substituted with 1, 2, or 3 substituents independently selected from the group consisting of halogen, C$_1$-C$_4$-alkyl, C$_1$-C$_4$-haloalkyl, and —OR$^f$; and
R$^f$ is C$_1$-C$_4$alkyl or C$_1$-C$_4$-haloalkyl.

5. The compound according to claim 3, or a salt thereof, wherein:
G$^1$ is unsubstituted pyridin-2-yl;
G$^{2d}$ is phenyl or pyridinyl; each of which is optionally substituted with 1, 2, or 3 substituents independently selected from the group consisting of halogen, C$_1$-C$_3$-alkyl, C$_1$-C$_3$-haloalkyl, and —OR$^f$; and
R$^f$ is C$_1$-C$_3$-alkyl or C$_1$-C$_3$-haloalkyl.

6. The compound according to claim 5, or a salt thereof, wherein:
G$^{2d}$ is phenyl which is optionally substituted with 1, 2, or 3 substituents independently selected from the group consisting of halogen, C$_1$-C$_3$-alkyl, C$_1$-C$_3$-haloalkyl, and —OR$^f$; and
R$^f$ is C$_1$-C$_3$-alkyl or C$_1$-C$_3$-haloalkyl.

7. The compound according to claim 5, or a salt thereof, wherein:
G$^{2d}$ is pyridinyl which is optionally substituted with 1, 2, or 3 substituents independently selected from the group consisting of halogen, C$_1$-C$_3$-alkyl or C$_1$-C$_3$-haloalkyl haloalkyl, and —OR$^f$; and
R$^f$ is C$_1$-C$_3$alkyl or C$_1$-C$_3$-haloalkyl.

8. The compound according to claim 2, or a salt thereof, wherein:
p is 2;
the two Z$^1$ groups are situated on the X$^3$ carbon atom and, together with the carbon atom to which they are attached, form an unsubstituted 5-membered monocyclic heterocycle ring comprising two oxygen ring atoms;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

9. The compound according to claim 2, or a salt thereof, wherein:
each $Z^1$ group is independently halogen, oxo, $C_1$-$C_3$-alkyl, or —$OR^c$;
$R^c$ is hydrogen or $C_1$-$C_3$-alkyl;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

10. The compound according to claim 2, or a salt thereof, wherein:
p is 1;
$Z^1$ is oxo;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

11. The compound according to claim 2, or a salt thereof, wherein:
each $Z^1$ group is independently halogen, $C_1$-$C_3$-alkyl, or —$OR^c$;
$R^c$ is hydrogen or $C_1$-$C_3$-alkyl;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl and $C_1$-$C_3$-haloalkyl.

12. The compound according to claim 2, or a salt thereof, wherein:
p is 1;
$Z^1$ is halogen, $C_1$-$C_3$-alkyl, or —$OR^c$;
$R^c$ is hydrogen or $C_1$-$C_3$-alkyl;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

13. The compound according to claim 12, or a salt thereof, wherein $Z^1$ is $C_1$-$C_3$-alkyl.

14. The compound according to claim 12, or a salt thereof, wherein $Z^1$ is methyl.

15. The compound according to claim 12, or a salt thereof, wherein:
$Z^1$ is —$OR^c$; and
$R^c$ is hydrogen.

16. The compound according to claim 12, or a salt thereof, wherein:
$Z^1$ is —$OR^c$; and
$R^c$ is $C_1$-$C_3$-alkyl.

17. The compound according to claim 12, or a salt thereof, wherein:
$Z^1$ is —$OR^c$; and
$R^c$ is methyl.

18. The compound according to claim 2, or a salt thereof, wherein:
p is 2;
each $Z^1$ group is independently halogen, $C_1$-$C_3$-alkyl, or —$OR^c$;
$R^c$ is hydrogen or $C_1$-$C_3$-alkyl;
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

19. The compound according to claim 2, or a salt thereof, wherein:
p is 2;
each $Z^1$ group is independently halogen, $C_1$-$C_3$-alkyl, or —$OR^c$;
$R^c$ is hydrogen or $C_1$-$C_3$-alkyl, or —$OR^c$;
$G^1$ is unsubstituted pyridin-2-yl;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

20. The compound according to claim 2, or a salt thereof, wherein:
p is 2;
each $Z^1$ group is independently halogen, $C_1$-$C_3$-alkyl, or —$OR^c$;
$R^c$ is hydrogen or $C_1$-$C_3$-alkyl;
$G^1$ is unsubstituted pyridin-2-yl;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

21. The compound according to claim 18, or a salt thereof, wherein both $Z^1$ groups are halogen.

22. The compound according to claim 18, or a salt thereof, wherein both $Z^1$ groups are $C_1$-$C_3$-alkyl.

23. The compound according to claim 18, or a salt thereof, wherein both $Z^1$ groups are methyl.

24. The compound according to claim 18, or a salt thereof, wherein both $Z^1$ groups are —$OR^c$ wherein $R^c$ is $C_1$-$C_3$-alkyl.

25. The compound according to claim 18, or a salt thereof, wherein both $Z^1$ groups are —$OR^c$ wherein $R^c$ is methyl.

26. The compound according to claim 18, or a salt thereof, wherein one $Z^1$ group is $C_1$-$C_3$-alkyl and the other $Z^1$ group is —$OR^c$ wherein $R^c$ is hydrogen.

27. The compound according to claim 18, or a salt thereof, wherein one $Z^1$ group is methyl and the other $Z^1$ group is —$OR^c$ wherein $R^c$ is hydrogen.

28. The compound according to claim 27, or a salt thereof, wherein the substituent containing $X^1$ and the —$OR^c$ substituent have a cis configuration.

29. The compound according to claim 27, or a salt thereof, wherein the substituent containing $X^1$ and the —$OR^c$ substituent have a trans configuration.

30. The compound according to claim 1, or a salt thereof, selected from the group consisting of:
[1-(3,4-dichlorophenyl)-3,3-difluorocyclobutyl](pyridin-2-yl)methanol;
(S)-[1-(3,4-dichlorophenyl)-3,3-difluorocyclobutyl](pyridin-2-yl)methanol;
{3,3-difluoro-1-[4-(trifluoromethoxy)phenyl]cyclobutyl}(pyridin-2-yl)methanol;

{3,3-difluoro-1-[3-(trifluoromethyl)phenyl]cyclobutyl}(pyridin-2-yl)methanol;
{3,3-difluoro-1-[3-(trifluoromethoxy)phenyl]cyclobutyl}(pyridin-2-yl)methanol;
3-(3,4-dichlorophenyl)-3-[(S)-hydroxy(pyridin-2-yl)methyl]cyclobutanone;
(trans)-3-(3,4-dichlorophenyl)-3-[(S)-hydroxy(pyridin-2-yl)methyl]cyclobutanol;
(cis)-3-(3,4-dichlorophenyl)-3-[(S)-hydroxy(pyridin-2-yl)methyl]cyclobutanol;
(R)-{3,3-difluoro-1-[4-(trifluoromethyl)pyridin-2-yl]cyclobutyl}(pyridin-2-yl)-methanol;
(S)-{3,3-difluoro-1-[4-(trifluoromethyl)pyridin-2-yl]cyclobutyl}(pyridin-2-yl)-methanol;
(S)-{3,3-difluoro-1-[4-(trifluoromethoxy)phenyl]cyclobutyl}(pyridin-2-yl)-methanol;
{3,3-dimethoxy-1-[4-(trifluoromethoxy)phenyl]cyclobutyl}(pyridin-2-yl)methanol;
cis-3-[(S)-hydroxy(pyridin-2-yl)methyl]-3-[4-(trifluoromethoxy)phenyl]-cyclobutanol;
(trans)-3-[(S)-hydroxy(pyridin-2-yl)methyl]-3-[4-(trifluoromethoxy)phenyl]-cyclobutanol;
{3,3-difluoro-1-[4-(trifluoromethyl)phenyl]cyclobutyl}(pyridin-2-yl)methanol;
cis-3-[(S)-hydroxy(pyridin-2-yl)methyl]-1-methyl-3-[4-(trifluoromethoxy)phenyl]-cyclobutanol;
{3,3-difluoro-1-[5-(trifluoromethyl)pyridin-2-yl]cyclobutyl}(pyridin-2-yl)-methanol;
{1-[4-chloro-3-(trifluoromethyl)phenyl]-3,3-difluorocyclobutyl}(pyridin-2-yl)-methanol;
{3,3-difluoro-1-[4-fluoro-3-(trifluoromethyl)phenyl]cyclobutyl}(pyridin-2-yl)-methanol;
(S)-[cis-1-(3,4-dichlorophenyl)-3-methoxycyclobutyl](pyridin-2-yl)methanol;
(S)-[1-(3,4-dichlorophenyl)-3-methoxycyclobutyl](pyridin-2-yl)methanol;
(S)-{3,3-difluoro-1-[4-(trifluoromethyl)phenyl]cyclobutyl}(pyridin-2-yl)methanol;
(R)-{3,3-difluoro-1-[4-(trifluoromethoxy)phenyl]cyclobutyl}(pyridin-2-yl)-methanol;
3-[hydroxy(pyridin-2-yl)methyl]-3-[4-(trifluoromethyl)phenyl]cyclobutanone;
pyridin-2-yl{2-[4-(trifluoromethyl)phenyl]-5,8-dioxaspiro[3.4]oct-2-yl}methanol;
3-[(S)-hydroxy(pyridin-2-yl)methyl]-3-[4-(trifluoromethyl)phenyl]cyclobutanone;
3-[(R)-hydroxy(pyridin-2-yl)methyl]-3-[4-(trifluoromethyl)phenyl]cyclobutanone;
3-[(S)-hydroxy(pyridin-2-yl)methyl]-3-[4-(trifluoromethyl)phenyl]cyclobutanol;
3-[(R)-hydroxy(pyridin-2-yl)methyl]-3-[4-(trifluoromethyl)phenyl]cyclobutanol;
cis-3-[(S)-hydroxy(pyridin-2-yl)methyl]-3-[4-(trifluoromethyl)phenyl]cyclobutanol;
trans-3-[(S)-hydroxy(pyridin-2-yl)methyl]-3-[4-(trifluoromethyl)phenyl]-cyclobutanol;
pyridin-2-yl{2-[4-(trifluoromethoxy)phenyl]-5,8-dioxaspiro[3.4]oct-2-yl}methanol;
trans-3-[(S)-hydroxy(pyridin-2-yl)methyl]-1-methyl-3-[4-(trifluoromethoxy)-phenyl]-cyclobutanol;
cis-3-[(S)-hydroxy(pyridin-2-yl)methyl]-1-methyl-3-[4-(trifluoromethyl)phenyl]-cyclobutanol;
trans-3-[(S)-hydroxy(pyridin-2-yl)methyl]-1-methyl-3-[4-(trifluoromethyl)phenyl]-cyclobutanol;
pyridin-2-yl{2-[3-(trifluoromethoxy)phenyl]-5,8-dioxaspiro[3.4]oct-2-yl}methanol;
cis-3-[(S)-hydroxy(pyridin-2-yl)methyl]-1-methyl-3-[3-(trifluoromethyl)phenyl]-cyclobutanol;
3-[hydroxy(pyridin-2-yl)methyl]-3-[3-(trifluoromethoxy)phenyl]cyclobutanone;
3-[(S)-hydroxy(pyridin-2-yl)methyl]-3-[3-(trifluoromethyl)phenyl]cyclobutanone;
pyridin-2-yl{2-[3-(trifluoromethyl)phenyl]-5,8-dioxaspiro[3.4]oct-2-yl}methanol;
3-[(R)-hydroxy(pyridin-2-yl)methyl]-3-[3-(trifluoromethyl)phenyl]cyclobutanone;
trans-3-[(S)-hydroxy(pyridin-2-yl)methyl]-1-methyl-3-[3-(trifluoromethyl)phenyl]-cyclobutanol;
3-[hydroxy(pyridin-2-yl)methyl]-3-[3-(trifluoromethyl)phenyl]cyclobutanone;
cis-3-(3,4-dichlorophenyl)-3-[(R)-hydroxy(pyridin-2-yl)methyl]cyclobutanol;
cis-3-[(R)-hydroxy(pyridin-2-yl)methyl]-1-methyl-3-[4-(trifluoromethoxy)phenyl]-cyclobutanol;
3-[(S)-hydroxy(pyridin-2-yl)methyl]-3-[4-(trifluoromethoxy)phenyl]cyclobutanone;
[2-(3-chloro-4-fluorophenyl)-5,8-dioxaspiro[3.4]oct-2-yl](pyridin-2-yl)methanol;
3-[(S)-hydroxy(pyridin-2-yl)methyl]-3-[3-(trifluoromethoxy)phenyl]cyclo-butanone;
3-[(R)-hydroxy(pyridin-2-yl)methyl]-3-[3-(trifluoromethoxy)phenyl]cyclo-butanone;
3-(3-chloro-4-fluorophenyl)-3-[hydroxy(pyridin-2-yl)methyl]cyclobutanone;
cis-3-[(S)-hydroxy(pyridin-2-yl)methyl]-3-[3-(trifluoromethyl)phenyl]cyclobutanol;
cis-3-[(S)-hydroxy(pyridin-2-yl)methyl]-1-methyl-3-[3-(trifluoromethoxy)phenyl]-cyclobutanol;
trans-3-[(S)-hydroxy(pyridin-2-yl)methyl]-1-methyl-3-[3-(trifluoromethoxy)-phenyl]cyclobutanol;
trans-3-[(S)-hydroxy(pyridin-2-yl)methyl]-3-[3-(trifluoromethyl)phenyl]-cyclobutanol;
3-(3-chloro-4-fluorophenyl)-3-[(S)-hydroxy(pyridin-2-yl)methyl]cyclobutanone;
cis-3-[(S)-hydroxy(pyridin-2-yl)methyl]-3-[3-(trifluoromethoxy)phenyl]-cyclobutanol;
trans-3-[(S)-hydroxy(pyridin-2-yl)methyl]-3-[3-(trifluoromethoxy)phenyl]-cyclobutanol;
3-(3-chloro-4-fluorophenyl)-3-[(S)-hydroxy(pyridin-2-yl)methyl]cyclobutanol;
3-[(S)-hydroxy(pyridin-2-yl)methyl]-3-[4-(trifluoromethyl)pyridin-2-yl]cyclo-butanone;
3-[(R)-hydroxy(pyridin-2-yl)methyl]-3-[4-(trifluoromethyl)pyridin-2-yl]-cyclobutanone;
cis-3-[(S)-hydroxy(pyridin-2-yl)methyl]-3-[4-(trifluoromethyl)pyridin-2-yl]-cyclobutanol;
trans-3-[(S)-hydroxy(pyridin-2-yl)methyl]-3-[4-(trifluoromethyl)pyridin-2-yl]-cyclobutanol;
cis-3-[(S)-hydroxy(pyridin-2-yl)methyl]-1-methyl-3-[4-(trifluoromethyl)pyridin-2-yl]cyclobutanol;
trans-3-[(S)-hydroxy(pyridin-2-yl)methyl]-3-[4-(trifluoromethyl)pyridin-2-yl]-cyclobutanol;
cis-3-[(R)-hydroxy(pyridin-2-yl)methyl]-3-[4-(trifluoromethyl)pyridin-2-yl]-cyclobutanol;
3-[(R)-hydroxy(pyridin-2-yl)methyl]-3-[6-methyl-4-(trifluoromethyl)pyridin-2-yl]-cyclobutanone;
3-[hydroxy(pyridin-2-yl)methyl]-3-[4-(trifluoromethyl)pyridin-2-yl]cyclobutanone;
3-[(S)-hydroxy(pyridin-2-yl)methyl]-3-[4-(trifluoromethyl)pyridin-2-yl]cyclo-butanol;
3-[hydroxy(pyridin-2-yl)methyl]-3-[5-(trifluoromethyl)pyridin-3-yl]cyclobutanone;

3-[(S)-hydroxy(pyridin-2-yl)methyl]-3-[5-(trifluoromethyl)pyridin-3-yl]cyclobutanone;
pyridin-2-yl{2-[2-(trifluoromethyl)pyridin-4-yl]-5,8-dioxaspiro[3.4]oct-2-yl}-methanol;
3-[hydroxy(pyridin-2-yl)methyl]-3-[2-(trifluoromethyl)pyridin-4-yl]cyclobutanone;
3-[(S)-hydroxy(pyridin-2-yl)methyl]-3-[2-(trifluoromethyl)pyridin-4-yl]-cyclobutanone;
cis-3-[(S)-hydroxy(pyridin-2-yl)methyl]-1-methyl-3-[2-(trifluoromethyl)pyridin-4-yl]cyclobutanol;
cis-3-[(S)-hydroxy(pyridin-2-yl)methyl]-3-[5-(trifluoromethyl)pyridin-3-yl]-cyclobutanol;
trans-3-[(S)-hydroxy(pyridin-2-yl)methyl]-3-[5-(trifluoromethyl)pyridin-3-yl]-cyclobutanol;
cis-3-[(S)-hydroxy(pyridin-2-yl)methyl]-3-[2-(trifluoromethyl)pyridin-4-yl]-cyclobutanol;
trans-3-[(S)-hydroxy(pyridin-2-yl)methyl]-3-[2-(trifluoromethyl)pyridin-4-yl]-cyclobutanol;
trans-3-[(S)-hydroxy(pyridin-2-yl)methyl]-1-methyl-3-[2-(trifluoromethyl)pyridin-4-yl]cyclobutanol;
cis-3-[(S)-hydroxy(pyridin-2-yl)methyl]-1-methyl-3-[5-(trifluoromethyl)pyridin-3-yl]cyclobutanol;
trans-3-[(S)-hydroxy(pyridin-2-yl)methyl]-1-methyl-3-[5-(trifluoromethyl)pyridin-3-yl]cyclobutanol;
(trans)-3-((S)-hydroxy(pyrimidin-2-yl)methyl)-1-methyl-3-(4-(trifluoromethoxy)-phenyl)-cyclobutanol;
(trans)-3-((R)-hydroxy(pyrimidin-2-yl)methyl)-1-methyl-3-(4-(trifluoromethoxy)-phenyl)-cyclobutanol;
(trans)-3-(3,4-dichlorophenyl)-3-((S)-hydroxy(pyrimidin-2-yl)methyl)cyclobutanol;
(trans)-3-(3,4-dichlorophenyl)-3-((R)-hydroxy(pyrimidin-2-yl)methyl)cyclobutanol; and
salts thereof.

31. The compound, or a salt thereof, of claim 1, wherein the salt is a pharmaceutically acceptable salt.

32. A pharmaceutical composition comprising a therapeutically effective amount of a compound of Formula (I) according to claim 1, or a pharmaceutically acceptable salt thereof, in combination with a pharmaceutically acceptable carrier.

33. The compound according to claim 2, or a salt thereof, wherein:
$G^1$ is pyridinyl; which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

34. The compound according to claim 2, or a salt thereof, wherein
$G^1$ is unsubstituted pyridinyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$- -$C_4$-haloalkyl.

35. The compound according to claim 33, or a salt thereof, wherein:
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

36. The compound according to claim 35, or a salt thereof, wherein:
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

37. The compound according to claim 35, or a salt thereof, wherein:
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

38. The compound or salt of claim 1 that is cis-3-[(S)-hydroxy(pyridin-2-yl)methyl]-1-methyl-3-[4-(trifluoromethoxy)-phenyl]cyclobutanol, or a pharmaceutically acceptable salt thereof.

39. The pharmaceutical composition of claim 32, wherein the compound or salt is cis-3-[(S)-hydroxy(pyridin-2-yl)methyl]-1-methyl-3-[4-(trifluoromethoxy)-phenyl]cyclobutanol, or a pharmaceutically acceptable salt thereof.

40. The compound or salt of claim 1 that is cis-3-[(S)-hydroxy(pyridin-2-yl)methyl]-3-[4-(trifluoromethyl)pyridin-2-yl]cyclobutanol, or a pharmaceutically acceptable salt thereof.

41. The pharmaceutical composition of claim 32, wherein the compound or salt is cis-3-[(S)-hydroxy(pyridin-2-yl)methyl]-3-[4-(trifluoromethyl)pyridin-2-yl]cyclobutanol, or a pharmaceutically acceptable salt thereof.

42. The compound or salt of claim 1 that is trans-3-[(S)-hydroxy(pyridin-2-yl)methyl]-3-[4-(trifluoromethyl)pyridin-2-yl]cyclobutanol, or a pharmaceutically acceptable salt thereof.

43. The pharmaceutical composition of claim 32, wherein the compound or salt is trans-3-[(S)-hydroxy(pyridin-2-yl)methyl]-3-[4-(trifluoromethyl)pyridin-2-yl]cyclobutanol, or a pharmaceutically acceptable salt thereof.

44. The compound or salt of claim 1 that is cis-3-[(S)-hydroxy(pyridin-2-yl)methyl]-1-methyl-3-[4-(trifluoromethyl)-pyridin-2-yl]cyclobutanol, or a pharmaceutically acceptable salt thereof.

45. The pharmaceutical composition of claim 32, wherein the compound or salt is cis-3-[(S)-hydroxy(pyridin-2-yl)methyl]-1-methyl-3-[4-(trifluoromethyl)-pyridin-2-yl]cyclobutanol, or a pharmaceutically acceptable salt thereof.

* * * * *